US007875700B2

(12) United States Patent
Radhakrishnan et al.

(10) Patent No.: US 7,875,700 B2
(45) Date of Patent: *Jan. 25, 2011

(54) CATION COMPLEXES OF INSULIN COMPOUND CONJUGATES, FORMULATION AND USES THEREOF

(75) Inventors: Balasingam Radhakrishnan, Chapel Hill, NC (US); Diti Aggarwal, Raleigh, NC (US); Michelle Ferro, Raleigh, NC (US); Kenneth D. James, Mebane, NC (US); Navdeep B. Malkar, Cary, NC (US); Mark A. Miller, Raleigh, NC (US); Monica Puskas, Spring Hope, NC (US); Nnochiri N. Ekwuribe, Cary, NC (US)

(73) Assignee: Biocon Limited (IN)

( * ) Notice: Subject to any disclaimer, the term of this patent is extended or adjusted under 35 U.S.C. 154(b) by 989 days.

This patent is subject to a terminal disclaimer.

(21) Appl. No.: 11/184,668

(22) Filed: Jul. 19, 2005

(65) Prior Publication Data
US 2006/0019874 A1    Jan. 26, 2006

Related U.S. Application Data

(60) Provisional application No. 60/589,058, filed on Jul. 19, 2004, provisional application No. 60/619,153, filed on Oct. 15, 2004, provisional application No. 60/632,578, filed on Dec. 2, 2004, provisional application No. 60/655,838, filed on Feb. 24, 2005, provisional application No. 60/655,803, filed on Feb. 24, 2005.

(51) Int. Cl.
*A61K 38/28* (2006.01)
(52) U.S. Cl. ................ 530/304; 530/303; 530/345; 514/2; 514/3; 514/4
(58) Field of Classification Search ................ 514/2–4; 530/303, 345, 304
See application file for complete search history.

(56) References Cited

U.S. PATENT DOCUMENTS

| | | | |
|---|---|---|---|
| 2,626,228 A | 1/1953 | Petersen |
| 2,789,080 A | 4/1957 | Christensen |
| 2,799,622 A | 7/1957 | Schlichtkrull et al. |
| 2,819,999 A | 1/1958 | Schlichtkrull et al. |
| 2,849,370 A | 8/1958 | Petersen et al. |
| 2,882,203 A | 4/1959 | Petersen et al. |
| 2,920,014 A | 1/1960 | Petersen et al. |
| 3,014,842 A | 12/1961 | Schlichtkrull |
| 3,058,885 A | 10/1962 | Schlichtkrull |
| 3,060,093 A | 10/1962 | Poulsen et al. |
| 3,091,573 A | 5/1963 | Schlichtkrull |
| 3,102,077 A | 8/1963 | Christensen |
| 3,256,153 A | 6/1966 | Heimlick |
| 3,868,356 A | 2/1975 | Smyth |
| 3,919,411 A | 11/1975 | Glass et al. |
| 3,950,517 A | 4/1976 | Lindsay et al. |
| 4,003,792 A | 1/1977 | Mill et al. |
| 4,044,196 A | 8/1977 | Huper et al. |
| 4,087,390 A | 5/1978 | Shields |
| 4,093,574 A | 6/1978 | Shields |
| 4,100,117 A | 7/1978 | Shields |
| 4,179,337 A | 12/1979 | Davis et al. |
| 4,223,163 A | 9/1980 | Guilloty |
| 4,229,438 A | 10/1980 | Fujino et al. |
| 4,253,998 A | 3/1981 | Sarantakis |
| 4,277,394 A | 7/1981 | Fujino et al. |
| 4,338,306 A | 7/1982 | Kitao et al. |
| 4,348,387 A | 9/1982 | Brownlee et al. |
| 4,410,547 A | 10/1983 | Ueno et al. |
| 4,469,681 A | 9/1984 | Brownlee et al. |
| 4,472,382 A | 9/1984 | Labrie et al. |
| 4,476,113 A | 10/1984 | Young et al. |
| 4,554,101 A | 11/1985 | Hopp |
| 4,579,730 A | 4/1986 | Kidron et al. |
| 4,585,745 A | 4/1986 | Tunooka et al. |
| 4,602,043 A | 7/1986 | Geho |

(Continued)

FOREIGN PATENT DOCUMENTS

DE    196 32 440 A1    2/1998

(Continued)

OTHER PUBLICATIONS

Brange J., (Diabetic medicine : A Journal of the British Diabetic Association 3(6), 532-536, 1986).*

(Continued)

*Primary Examiner*—David Lukton
(74) *Attorney, Agent, or Firm*—Marianne Fuierer; Moore & Van Allen, PLLC

(57) ABSTRACT

The invention provides a complex including a cation and an insulin compound conjugate. The insulin compound conjugate includes insulin compound, such as human insulin or an analog thereof, conjugated to a modifying moiety, such as a polyethylene glycol moiety. The invention also includes solids and pharmaceutical compositions including such complexes, methods of making such complexes, and methods of using such complexes in the treatment of insulin compound deficiencies and other ailments. Further, the invention includes novel insulin compound conjugates and modifying moieties for use in making novel insulin compound conjugates. The invention also includes fatty acid compositions for administration of pharmaceutical agents, such as the novel insulin compound conjugates, and/or the cation-insulin compound conjugate complexes of the invention.

82 Claims, 42 Drawing Sheets

U.S. PATENT DOCUMENTS

| | | |
|---|---|---|
| 4,622,392 A | 11/1986 | Hong et al. |
| 4,654,324 A | 3/1987 | Chance et al. |
| 4,662,872 A | 5/1987 | Cane |
| 4,684,524 A | 8/1987 | Eckenhoff et al. |
| 4,698,264 A | 10/1987 | Steinke |
| 4,704,394 A | 11/1987 | Geho |
| 4,717,566 A | 1/1988 | Eckenhoff et al. |
| 4,744,976 A | 5/1988 | Snipes et al. |
| 4,761,287 A | 8/1988 | Geho |
| 4,764,592 A | 8/1988 | Massey et al. |
| 4,772,471 A | 9/1988 | Vanlerberghe et al. |
| 4,797,288 A | 1/1989 | Sharma et al. |
| 4,801,575 A | 1/1989 | Pardridge |
| 4,822,337 A | 4/1989 | Newhouse et al. |
| 4,839,341 A | 6/1989 | Massey et al. |
| 4,840,799 A | 6/1989 | Appelgren et al. |
| 4,849,405 A | 7/1989 | Ecanow |
| 4,863,896 A | 9/1989 | Geho et al. |
| 4,917,888 A | 4/1990 | Katre et al. |
| 4,935,246 A | 6/1990 | Ahrens |
| 4,946,828 A | 8/1990 | Markussen |
| 4,957,910 A | 9/1990 | Sutton et al. |
| 4,963,367 A | 10/1990 | Ecanow |
| 4,963,526 A | 10/1990 | Ecanow |
| 4,994,439 A | 2/1991 | Longenecker et al. |
| 5,013,556 A | 5/1991 | Woodle et al. |
| 5,055,300 A | 10/1991 | Gupta |
| 5,055,304 A | 10/1991 | Makino et al. |
| 5,089,261 A | 2/1992 | Nitecki et al. |
| 5,093,198 A | 3/1992 | Speaker et al. |
| 5,157,021 A | 10/1992 | Balschmidt et al. |
| 5,162,430 A | 11/1992 | Rhee et al. |
| 5,164,366 A | 11/1992 | Balschmidt et al. |
| 5,177,058 A | 1/1993 | Dorschug |
| 5,202,415 A | 4/1993 | Jonassen et al. |
| 5,206,219 A | 4/1993 | Desai |
| 5,283,236 A | 2/1994 | Chiou |
| 5,286,637 A | 2/1994 | Veronese et al. |
| 5,292,802 A | 3/1994 | Rhee et al. |
| 5,298,410 A | 3/1994 | Phillips et al. |
| 5,304,473 A | 4/1994 | Belagaje et al. |
| 5,308,889 A | 5/1994 | Rhee et al. |
| 5,312,808 A | 5/1994 | Shorr et al. |
| 5,320,094 A | 6/1994 | Laube et al. |
| 5,321,009 A | 6/1994 | Baeder et al. |
| 5,324,775 A | 6/1994 | Rhee et al. |
| 5,328,955 A | 7/1994 | Rhee et al. |
| 5,349,052 A | 9/1994 | Delgado et al. |
| 5,359,030 A | 10/1994 | Ekwuribe |
| 5,364,838 A | 11/1994 | Rubsamen |
| 5,405,621 A | 4/1995 | Sipos |
| 5,405,877 A | 4/1995 | Greenwald et al. |
| 5,413,791 A | 5/1995 | Rhee et al. |
| 5,415,872 A | 5/1995 | Sipos |
| 5,420,108 A | 5/1995 | Shohet |
| 5,438,040 A | 8/1995 | Ekwuribe |
| 5,444,041 A | 8/1995 | Owen et al. |
| 5,446,091 A | 8/1995 | Rhee et al. |
| 5,457,066 A | 10/1995 | Frank et al. |
| 5,461,031 A | 10/1995 | De Felippis |
| 5,468,478 A | 11/1995 | Saifer et al. |
| 5,468,727 A | 11/1995 | Phillips et al. |
| 5,474,978 A | 12/1995 | Bakaysa et al. |
| 5,504,188 A | 4/1996 | Baker et al. |
| 5,506,203 A | 4/1996 | Backstrom et al. |
| 5,518,998 A | 5/1996 | Backstrom et al. |
| 5,523,348 A | 6/1996 | Rhee et al. |
| 5,529,915 A | 6/1996 | Phillips et al. |
| 5,534,488 A | 7/1996 | Hoffmann |
| 5,545,618 A | 8/1996 | Buckley et al. |
| 5,550,188 A | 8/1996 | Rhee et al. |
| 5,567,422 A | 10/1996 | Greenwald |
| 5,597,797 A | 1/1997 | Clark |
| 5,606,038 A | 2/1997 | Regen |
| 5,612,460 A | 3/1997 | Zalipsky |
| 5,631,347 A | 5/1997 | Baker et al. |
| 5,637,749 A | 6/1997 | Greenwald |
| 5,643,575 A | 7/1997 | Martinez et al. |
| 5,646,242 A | 7/1997 | Baker et al. |
| 5,650,388 A | 7/1997 | Shorr et al. |
| 5,650,486 A | 7/1997 | De Felippis |
| 5,658,878 A | 8/1997 | Backstrom et al. |
| 5,681,567 A | 10/1997 | Martinez et al. |
| 5,681,811 A | 10/1997 | Ekwuribe |
| 5,693,609 A | 12/1997 | Baker et al. |
| 5,693,769 A | 12/1997 | Kahne et al. |
| 5,700,904 A | 12/1997 | Baker et al. |
| 5,704,910 A | 1/1998 | Humes |
| 5,707,648 A | 1/1998 | Yiv |
| 5,714,519 A | 2/1998 | Cincotta et al. |
| 5,738,846 A | 4/1998 | Greenwald et al. |
| 5,747,445 A | 5/1998 | Backstrom et al. |
| 5,747,642 A | 5/1998 | De Felippis |
| 5,750,497 A | 5/1998 | Havelund et al. |
| 5,763,396 A | 6/1998 | Weiner et al. |
| 5,766,620 A | 6/1998 | Heiber et al. |
| 5,773,581 A | 6/1998 | Camble et al. |
| 5,824,638 A | 10/1998 | Burnside et al. |
| 5,830,853 A | 11/1998 | Backstrom et al. |
| 5,830,918 A | 11/1998 | Sportsman et al. |
| 5,843,866 A | 12/1998 | Parker et al. |
| 5,849,860 A | 12/1998 | Hakimi et al. |
| 5,853,748 A | 12/1998 | New |
| 5,854,208 A | 12/1998 | Jones et al. |
| 5,856,451 A | 1/1999 | Olsen et al. |
| 5,866,538 A | 2/1999 | Norup et al. |
| 5,866,584 A | 2/1999 | Cincotta et al. |
| 5,874,111 A | 2/1999 | Maitra et al. |
| 5,889,153 A | 3/1999 | Suzuki et al. |
| 5,898,028 A * | 4/1999 | Jensen et al. .................. 514/4 |
| 5,902,588 A | 5/1999 | Greenwald et al. |
| 5,905,140 A | 5/1999 | Hansen |
| 5,907,030 A | 5/1999 | Shen et al. |
| 5,922,675 A | 7/1999 | Baker et al. |
| 5,932,462 A | 8/1999 | Harris et al. |
| 5,942,248 A | 8/1999 | Barnwell |
| 5,948,751 A | 9/1999 | Kimer et al. |
| 5,952,008 A | 9/1999 | Backstrom et al. |
| 5,952,297 A | 9/1999 | De Felippis et al. |
| 5,952,461 A | 9/1999 | Kim et al. |
| 5,955,459 A | 9/1999 | Bradley et al. |
| 5,962,267 A | 10/1999 | Shin et al. |
| 5,968,549 A | 10/1999 | New et al. |
| 5,969,040 A | 10/1999 | Hallahan et al. |
| 5,981,709 A | 11/1999 | Greenwald et al. |
| 5,985,263 A | 11/1999 | Lee et al. |
| 5,997,848 A | 12/1999 | Patton et al. |
| 6,004,574 A | 12/1999 | Backstrom et al. |
| 6,011,008 A | 1/2000 | Domb et al. |
| 6,025,325 A | 2/2000 | Campfiled et al. |
| 6,034,054 A | 3/2000 | DeFelippis et al. |
| 6,042,822 A | 3/2000 | Gilbert et al. |
| 6,043,214 A * | 3/2000 | Jensen et al. .................. 514/3 |
| 6,051,551 A | 4/2000 | Hughes et al. |
| 6,057,292 A | 5/2000 | Cunningham et al. |
| 6,063,761 A | 5/2000 | Jones et al. |
| 6,068,993 A | 5/2000 | Filho et al. |
| 6,093,391 A | 7/2000 | Kabanov et al. |
| 6,113,906 A | 9/2000 | Greenwald et al. |
| 6,147,108 A | 11/2000 | Hauptman |
| 6,165,976 A | 12/2000 | Backstrom et al. |
| 6,174,856 B1 | 1/2001 | Langballe et al. |
| 6,177,087 B1 | 1/2001 | Greenwald et al. |
| 6,191,105 B1 | 2/2001 | Ekwuribe et al. |

| | | | |
|---|---|---|---|
| 6,200,602 | B1 | 3/2001 | Watts et al. |
| 6,211,144 | B1 | 4/2001 | Havelund |
| 6,221,837 | B1 | 4/2001 | Ertl et al. |
| 6,248,363 | B1 | 6/2001 | Patel et al. |
| 6,251,856 | B1 | 6/2001 | Markussen et al. |
| 6,258,377 | B1 | 7/2001 | New et al. |
| 6,268,335 | B1 | 7/2001 | Brader |
| 6,268,355 | B1 | 7/2001 | Mizobuchi et al. |
| 6,306,440 | B1 | 10/2001 | Backstrom et al. |
| 6,309,633 | B1 | 10/2001 | Ekwuribe et al. |
| 6,310,038 | B1 | 10/2001 | Havelund |
| 6,323,311 | B1 | 11/2001 | Liu et al. |
| 6,335,316 | B1 | 1/2002 | Hughes et al. |
| 6,342,225 | B1 | 1/2002 | Jones et al. |
| 6,444,641 | B1 | 9/2002 | Flora |
| 6,451,970 | B1 | 9/2002 | Schaffer et al. |
| 6,451,974 | B1 | 9/2002 | Hansen |
| 6,465,426 | B2 | 10/2002 | Brader |
| RE37,971 | E | 1/2003 | Baker et al. |
| 6,506,730 | B1 | 1/2003 | Lee et al. |
| 6,531,448 | B1 | 3/2003 | Brader |
| 6,551,992 | B1 | 4/2003 | DeFelippis et al. |
| 6,566,490 | B1 | 5/2003 | Manique et al. |
| 6,620,780 | B2 | 9/2003 | Markussen et al. |
| 6,652,885 | B2 | 11/2003 | Steiner et al. |
| 6,685,967 | B1 | 2/2004 | Patton et al. |
| 6,686,177 | B1 | 2/2004 | Ertl et al. |
| 7,192,919 | B2 * | 3/2007 | Tzannis et al. .................. 514/3 |
| 2001/0031726 | A1 | 10/2001 | Van Antwerp et al. |
| 2001/0036916 | A1 | 11/2001 | Brader |
| 2001/0041786 | A1 * | 11/2001 | Brader et al. ............... 530/300 |
| 2002/0045731 | A1 | 4/2002 | Schaffer et al. |
| 2002/0082199 | A1 | 6/2002 | Brader |
| 2002/0160938 | A1 | 10/2002 | Brandenburg et al. |
| 2003/0004304 | A1 | 1/2003 | Ekwuribe et al. |
| 2003/0027995 | A1 | 2/2003 | Ekwuribe et al. |
| 2003/0050228 | A1 | 3/2003 | Ekwuribe et al. |
| 2003/0060606 | A1 | 3/2003 | Ekwuribe et al. |
| 2003/0069170 | A1 | 4/2003 | Soltero et al. |
| 2003/0083232 | A1 | 5/2003 | Soltero et al. |
| 2003/0087808 | A1 | 5/2003 | Soltero et al. |
| 2003/0144468 | A1 | 7/2003 | Ekwuribe et al. |
| 2003/0153488 | A1 | 8/2003 | May et al. |
| 2004/0077528 | A1 | 4/2004 | Steiner et al. |

FOREIGN PATENT DOCUMENTS

| | | |
|---|---|---|
| EP | 0 031 567 A2 | 7/1981 |
| EP | 0 511 903 B1 | 10/1996 |
| EP | 0 597 007 B1 | 10/1996 |
| EP | 0 797 615 B1 | 1/1999 |
| EP | 0 822 218 B1 | 10/2000 |
| EP | 0835129 B1 | 10/2003 |
| EP | 1 044 023 B1 | 5/2005 |
| EP | 1 148 873 B1 | 7/2005 |
| WO | WO 93/01802 | 2/1993 |
| WO | WO 95/30641 | 11/1995 |
| WO | WO 97/14740 | 4/1997 |
| WO | WO 98/07745 A2 | 2/1998 |
| WO | WO 98/07745 A3 | 2/1998 |
| WO | WO 99/26661 | 6/1999 |
| WO | 00/29013 | 5/2000 |
| WO | WO 00/44361 | 8/2000 |
| WO | WO 01/12230 A1 | 2/2001 |
| WO | WO 03/086361 A1 | 10/2003 |
| WO | 2004/004779 A1 | 1/2004 |
| WO | 2004/004780 A1 | 1/2004 |
| WO | 2004/004781 A1 | 1/2004 |
| WO | WO 2004/060347 A2 | 7/2004 |

OTHER PUBLICATIONS

Surendrakumar, K. (Journal of Controlled Release 91(3), 385-394, 2003).*

H. Paul Neubauer et al.; Influence of Polyethylene Glycol Insulin on lipid Tissues of Experimental Animals; Diabetes; (1983), vol. 32, 953-958; Germany.

A.J. Bone et al.; Successful Treatment of an Insulin Dependent Rat Model of Human Type 1 Diabetes with Orally Active Insulin; Department of Pharmacy, University of Brighton and Protein Delivery, Inc., Durham, North Carolina, USA.

Samuel Zalipsky et al.; Peptide Attachment to Extremities of Liposomal Surface Grafted PEG Chains: Preparation of the Long-Circulating Form of Laminin Pentapeptide, YIGSR; Bioconjugate Chem.; (1995), 6, 705-708; American Chemical Society.

S. Salipsky et al., Attachment of Drugs to Polyethylene Glycols; Eur. Polym. Journal; (1983), vol. 19, No. 12, 1177-1183; Great Britain.

Takashi Uchio et al.; Site-Specific Insulin Conjugates with Enhanced Stability and Extended Action Profile; Advanced Drug Delivery Reviews; (1999), 35, 289-306; Elsevier Science B.V.

Jens Brange et al.; Chemical Stability of Insulin. 2. Formation of Higher Molecular Weight Transformation Products During Storage of Pharmaceutical Preparations; Pharmaceutical Research; (1992), vol. 9, No. 6, 727-734; Plenum Publishing Corporation.

Jens Brange et al.; Chemical Stability of Insulin. 1. Hydrolytic Degradation During Storage of Pharmaceutical Preparations; Pharmaceutical Research; (1992), vol. 9, No. 6, 715-726; Plenum Publishing Corporation.

Jens Brange et al.; Insulin Analogs with Improved Pharmacokinetic Profiles; Advanced Drug Delivery Reviews; (1999), 35, 307-335; Elsevier Science B.V.

J. Milton Harris; Laboratory Synthesis of Polyethylene Glycol Derivatives; JMS-Rev. Macromol. Chem. Phys.; (1985), C25(3), 325-373; Marcel Dekker, Inc.

Vikas Agarwal et al.; Polymethyacrylate Based Microparticulates of Insulin for Oral Delivery: Preparation and in vitro Dissolution Stability in the Presence of Enzyme Inhibitors; International Journal of Pharmaceutics; (2001), 225, 31-39; Elsevier Science B.V.

Minoru Akiyama et al.; The Synthesis of new Derivatives of 1-B-D-Arabinofuranosylcytosine; Chem. Pharm. Bull.; (1978), vol. 26, No. 3 981-984; Japan.

H. Allaudeen et al.; Orally Active Insulin: A Single Insulin Conjugate Selected for Future Studies; American Diabetes Association; Jun. 2000, Atlanta, GA, USA.

Soon H. Song et al.; Direct Measurement of Pulsatile Insulin Secretion from the Portal Vein in Human Subjects; The Journal of Clinical Endocrinology and Metabolism; (2000), vol. 85, No. 12, 4491-4499; The Endocrine Society, USA.

Steven M. Ansell et al.; Application of Oligo-(14-amino-3,6,9,12-tetraoxatetradecanoic acid) Lipid Conjugates as Steric Barrier Molecules in Liposomal Formulations; Bioconjugate Chem.; (1999), 10, 653-666; American Chemical Society.

Michiko Aoshima et al.; N4-Behenoyl-1-B-D-Arabinofuranosylcytosine as a potential New Antitumor Agent; Cancer Research; (1977), 37, 2481-2486; Japan.

Reto Stocklin et al.; A Stable Isotope Dilution Assay for the in vivo Determination of Insulin Levels in Humans by Mass Spectrometry; Diabetes; (1997), vol. 46, No. 1, p. 44(7), 1-8; American Diabetes Association.

David C. Baker et al.; Prodrugs of 9-B-D-Arabinofuranosyladenine. 1. Synthesis and Evaluation of Some 5'-(O-Acyl) Derivatives; Journal of Medicinal Chemistry; (9178), vol. 21, No. 12, 1218-1221; American Chemical Society.

Angel Guzman et al; Effects of Fatty Ethers and Stearic Acid on the Gastrointestinal Absorption of Insulin; PRHSJ; (1990), vol. 9, No. 2, 155-159; San Juan, PR.

D.G. Lindsay et al.; The Acetylation of Insulin; Biochem. J.; (1971), 121, 737-745; Great Britain.

T. Forst et al.; New Aspects on Biological Activity of C-peptide in IDDM Patients; Experimental and Clinical Endocrinology Diabetes; (1998), 106, 270-276; Johann Ambrosius Barth.

F.G. Banting et al.; Pancreatic Extracts in the Treatment of Diabetes Mellitus; The Canadian Medical Association Journal; (1922), 141-146; The Canadian Medical Association.

J. Gordon Still et al.; Effects of Orally Active Modified Insulin in Type 1 Diabetic Patients; 2001 Annual Meeting of the American Society for Clinical Pharmacology and Therapeutics; Orlando, Florida, USA.

M. Baudys, et al.; Stabilization and Intestinal Absorption of Human Calcitonin; Journal of Controlled Release; (1996), 39, 145-151; Elsevier Science B.V.

J.G. Still et al.; Magnitude and Variability of Pharmacokinetic and Glucodynamic Responses to Modified Human Insulin Administered Orally to Healthy Volunteers; Diabetes Research and Clinical Practice; (2002), vol. 56, Supp. 1, S77; USA.

Miroslav Baudys et al.; Synthesis and Characterization of Different Glycosylated Derivatives of Insulin; Proceed. Intern. Symp. Control. Rel. Bioact. Mater., (1992), 19, 210-211; Controlled Release Society, Inc.

E. Boccu et al.; Pharmacokinetic Properties of Polyethylene Glycol Derivatized Superoxide Dismutase; Pharmacological Research Communications; (1982), vol. 14, No. 2, 113-120.

N. Ekwuribe et al.; Oral Insulin Delivery: Hydrolyzable Amphiphilic Oligomer Conjugates Prolong Glucose Reduction; Proceed. Int'l. Symp. Control. Rel. Bioact. Mater.; (1999), 26, 147-148; Controlled Release Society, Inc.

B. Radha Krishnan et al.; Chemical Modification of Insulin with Amphiphilic Polymers Improves Intestinal Delivery; Proceed. Int'l. Symp. Control. Rel. Bioact. Mater.; (1998), 25, 124-125; Controlled Release Society, Inc.

Giovanni M. Pauletti et al.; Improvement of Oral Peptide Bioavailability: Peptidomimetics and Prodrug Strategies; Advanced Drug Delivery Reviews; (1997), 27, 235-256; Elsevier Science B.V.

J. Gordon Still et al.; Oral Insulin Development; Presentation made in London, England; (2000); Protein Delivery Incorporated, RTP, North Carolina, USA.

Christiane Damge et al.; Poly(alkyl cyanoacrylate) Nanospheres for Oral Administration of Insulin; Journal of Pharmaceutical Sciences; (1997), vol. 86, No. 12, 1403-1409; American Chemical Society and American Pharmaceutical Association.

David C. Pang; Bridging Gaps in Drug Discovery and Development; Pharmaceutical Technology; (1998), 22, 11, 82-94; USA.

Gerard Coudert et al.; A Novel, Unequivocal Synthesis of Polyethylene Glycols; Synthetic Communications; (1986), 16, 1, 19-26; Marcel Dekker, Inc.

Stephen Clement et al.; A Dose-Escalation Study of the Effects of Two Sequential Doses of Oral Modified Insulin on Blood Glucose Concentrations in Patients with Type 1 Diabetes Mellitus; American Diabetes Association Annual Meeting; (2001); USA.

Stephen Clement, et al.; A Dose-Escalation Study of the Effects of Two Sequential Doses of Oral Modified Insulin on Blood Glucose Concentrations in Patients with Type 1 Diabetes Mellitus; American Diabetes Association Meeting in Philadelphia Pennsylvania; (2001); USA.

Stephen Clement et al.; Effects of Multiple Doses of Orally Administered Hexyl Insulin M2 (HIM2) on Postprandial Blood Glucose (PPG) Concentrations in Type 1 diabetic (T1) Patients; American Diabetes Association Meeting in San Francisco, California; (2002); USA.

Mary L. Nucci et al.; The Therapeutic Value of Poly(ethylene glycol)-Modified Proteins; Advanced Drug Delivery Reviews; (1991), 6, 133-151; Elsevier.

C.T. Musabayane et al.; Orally Administered, Insulin-Loaded Amidated Pectin Hydrogel Beads Sustain Plasma Concentrations of Insulin in Streptozotocin-Diabetic Rats; Journal of Endocrinology; (2000), 164, 1-6; Society for Endocrinology, Great Britain.

Amir Moghaddam; Use of Polyethylene Glycol Polymers for Bioconjugations and Drug Development; (2001).

Michaela K. Marschutz et al.; Oral Peptide Drug Delivery: Polymer-Inhibitor Conjugates Protecting Insulin from Enzymatic Degradation in vitro; Biomaterial; (2000), 21, 1499-1507; Elesevier Science Ltd.

Mark Kipnes et al.; The Effects of an Oral Modified Insulin on Postprandial Blood Glucose Levels in Patients with Type 2 Diabetes; American Diabetes Association Annual Meeting; (2001); USA.

Stephen Clement et al.; Oral Insulin Product Hexyl-Insulin Monoconjugate 2 (HIM2) in Type 1 Diabetes Mellitus: The Glucose Stabilization Effects of HIM2; Diabetes Technology & Therapeutics; (2002), vol. 4, No. 4, 459-466; Mary Ann Liebert, Inc..

Robert A. Conradi et al.; The Influence of Peptide Structure on Transport Across Caco-2 Cells; Pharmaceutical Research; (1991), vol. 8, No. 12, 1453-1460; Plenum Publishing Corporation.

Mark Kipnes et al.; The Effects of an Oral Modified Insulin on Postprandial Blood Glucose Levels in Patients with Type 2 Diabetes Mellitus; American Diabetes Association Meeting in Philadelphia, Pennsylvania; (2001); Nobex Corporation; USA.

A.G.A. Coombes et al; Biodegradable Polymeric Microparticles for Drug Delivery and Vaccine Formulation: The Surface Attachment of Hydrophilic Species Using the Concept of Poly(ethylene glycol) anchoring segments; Biomaterials; (1997), vol. 18, No. 17, 1153-1161; Elsevier Science Limited, Great Britain.

Yiyan Chen et al.; Synthesis and Properties of ABA Amphiphiles; Journal of Organic Chemistry; (1999), vol. 64, No. 18, 6870-6873; American Chemical Society.

Mark Kipnes et al.; Control of Postprandial Plasma Glucose by an Oral Insulin Product (HIM2) in Patients with Type 2 Diabetes; Diabetes Care; (2003), vol. 26, No. 2, 421-426.

Wolfgang Kemmler et al.; Studies on the Conversion of Proinsulin to Insulin; The Journal of Biological Chemistry; (1971), vol. 245, No. 22, 6786-6791; USA.

Jens Brange; Galenics of Insulin; (1987), 18-100; Springer-Verlag Berlin-Heidelberg, Germany.

Ken Hinds et al.; Synthesis and Characterization of Poly(ethylene glycol)-Insulin Conjugates; Bioconjugate Chemistry; (2000), vol. 11, No. 2, 195-201; American Chemical Society.

Duane T. Gish et al.; Nucleic Acids. 11. Synthesis of 5'-Esters of 1-B-D-Arabinofuranosylcytosine Possessing Antileukemic and Immunosuppressive Activity; Journal of Medicinal Chemistry; (1971), vol. 14, No. 12, 1159-1162.

Jane P. Richards et al.; Self-Association Properties of Monomeric Insulin Analogs Under Formulation Conditions; Pharmaceutical Research; (1998), vol. 15, No. 9, 1434-1441; Plenum Publishing Corporation.

B. Radhakrishnan et al.; Structure-Activity Relationship of Insulin Modified with Amphiphilic Polymers; AAPS Annual Meeting in San Francisco, California; (1998); USA.

N. Santiago et al.; Oral Immunization of Rats with Influenza Virus M Protein (M1) Microspheres; Proceed. Intern. Symp. Control. Rel. Bioact. Mater.; (1992), 19, 116-117; Controlled Release Society, Inc.

Victoria Sluzky et al.; Kinetics of Insulin Aggregation in Aqueous Solutions Upon Agitation in the Presence of Hydrophobic Surfaces; Proc. Natl. Acad. Sci.; (1991), vol. 88, 9377-9381; Applied Biological Sciences.

Wei-Chiang Shen et al.; Enhancement of Polypeptide and Protein Absorption by Macromolecular Carriers Via Endocytosis and Transcytosis; Advanced Drug Delivery Reviews; (1992), 9, 92-113; Elsevier Science Publishers.

Lawrence H. Block; Pharmaceutical Emulsions and Microemulsions; Pharmaceutical Dosage Forms: Disperse Systems vol. 2; (1996), Chapter 2, 47-109; Marcel Dekker, Inc., USA.

Y. Pocker et al.; Conformational Dynamics of Insulin in Solution. Circular Dichroic Studies; Biochemistry; 1980; pp. 5043-5049; vol. 19, No. 22; American Chemical Society.

A. Wollmer et al.; Correlation of Structural Details of Insulin in the Crystal and in Solution; Insulin, Chemistry, Structure and Function of Insulin and Related Hormones; 1980; pp. 27-31; Walter de Gruyter & Co., New York.

Ling Xie et al.; Comparison of Secondary Structures of Insulin and Proinsulin by FTIR; Journal of Protein Chemistry; 1993; pp. 483-487; vol. 12, No. 4; Plenum Publishing Corporation.

Navdeep B. Malkar et al.; Characterization of Peptide—Amphiphiles Possessing Cellular Activation Sequences; Biomacromolecules; 2003; Published on the web by the American Chemical Society.

A.N. McLeod et al.; High-Performance Liquid Chromatography of Insulin Accessibility and Flexibility; Chrom. 22 076; 1990; Elsevier Science Publishers B.V.

Yuping Li et al.; Dissociation of Insulin Oligomers by Bile Salt Micelles and Its Effect on a-Chymotrypsin-Mediated Proteolytic Degradation; Pharmaceutical Research; 1992; pp. 864-869; vol. 9; No. 7; Plenum Publishing Corporation.

Mark L. Brader et al.; Hybrid Insulin Cocrystals for Controlled Release Delivery; Nature Biotechnology; 2002; pp. 800-804; vol. 20; http://biotech.nature.com.

Jean L. Whittingham et al.; Crystal Structure of a Prolonged-Acting Insulin with Albumin-Binding Properties; Biochemistry; 1997; pp. 2826-2831; vol. 36; No. 10; American Chemical Society.

Jose Goldman et al.; Zinc Binding, Circular Dichroism, and Equilibrium Sedimentation Studies on Insulin (Bovine) and Several of Its Derivatives; Biochemistry; 1974; pp. 4566-4574; vol. 13, No. 22; American Chemical Society.

Steven E. Shoelson et al.; Mutations at the Dimer, Hexamer, and Receptor-Binding Surfaces of Insulin Independently Affect Insulin-Insulin and Insulin-Receptor Interactions; Biochemistry; 1992; pp. 1757-1767; vol. 31; No. 6; American Chemical Society.

P.T. Grant et al.; Differences in the Nature of the Interaction of Insulin and Proinsulin with Zinc; Biochemistry; 1972; pp. 433-440; vol. 126; Great Britain.

Edgar Jacoby et al.; Structure and Dynamics of a Protein Assembly; J. Mol. Biol.; 1996; pp. 136-157; vol. 258; Academic Press Limited.

Allen H. Pekar et al.; Conformation of Proinsulin. A Comparison of Insulin and Proinsulin Self-Association at Neutral pH; Biochemistry; 1972; pp. 4013-4016; vol. 11; No. 22; American Chemical Society.

Michael A. Weiss et al.; Heteronuclear 2D NMR Studies of an Engineered Insulin Monomer: Assignment and Characterization of the Receptor-Binding Surface by Selective . . . ; Biochemistry; 1991; pp. 7373-7389; vol. 30; No. 30; American Chemical Society.

Mark L. Brader et al.; The T to R Transition in the Copper(II)-Substituted Insulin Hexamer. Anion Complexes of the R-State Species Exhibiting Type 1 and Type 2 Spectral Characteristics; Biochemistry; 1992; pp. 4691-4696; vol. 31; No. 19; American Chemical Society.

Wayne Genck; Crystal Clear—An Extremely Selective Process, Crystallization can be a Powerful Separation Tool. But, to Optimize product, you must clearly understand.; Filtration/Separation; 2003; pp. 63-67; www.chemicalprocessing.com.

Duane T. Birnbaum et al.; Hierarchial Modeling of Phenolic Ligand Binding to 2Zn-Insulin Hexamers; Biochemistry; 1996; vol. 35; No. 17; American Chemical Society.

Alan Dove; Seeking Purity in the Proteomic Era; Geonomics & Proteomics; 2004; pp. 20-24; www.genpromag.com.

Michael A. Weiss et al.; Two-Dimensional NMR and Photo-CIDNP Studies of the Insulin Monomer: Assignment of Aromatic Resonances with Application to Protein Folding, Structure, and Dynamics; Biochemistry; 1989; pp. 9855-9873; vol. 28; No. 23; American Chemical Society.

Anna Jen et al.; Diamonds in the Rough: Protein Crystals from a Formulation Perspective; Pharmaceutical Research; 2001; pp. 1483-1488; vol. 18, No. 11; Plenum Publishing Corporation.

Steven W. Dodd et al.; Reversible Adsorption of Soluble Hexameric Insulin onto the Surface of Insulin Crystals Cocrystallized iwth protamine: An Electrostatic Interaction; Pharmaceutical Research; 1995; pp. 60-68; vol. 12; No. 1; Plenum Publishing Corporation.

Wolfgang H. Fischer et al.; A Shortened Insulin with Full in vitro Potency; Biol. Chem. Hoppe-Seyler; 1985; pp. 521-525; vol. 366; Walter de Gruyter & Co., New York.

S. J. Wodak et al.; Simulation of Conformational Changes in 2 Zn Insulin; J. Mol. Biol.; 1984; pp. 317-322; vol. 181.

M.J. Adams et al.; Structure of Rhombohedral 2 Zinc Insulin Crystals; Nature; 1969; pp. 491-495; vol. 224.

Michael J. Pikal et al.; The Stability of Insulin in Crystalline and amorphous Solids: Observation of Greater Stability for the Amorphous Form; Pharmaceutical Research; 1997; pp. 1379-1387; vol. 19; No. 10; Plenum Publishing Corporation.

E.J. Dodson et al.; Structural Relationships in the Two-Zinc Insulin Hexamer; Can. J. Biochem.; 1979; vol. 57; National Research Council of Canada.

Graham Bentley et al.; Structure of Insulin in 4-Zinc Insulin; Nature; 1976; vol. 261.

J. Schlichtkrull; Insulin Crystals; Acta Chemica Scandinavica; 1956; pp. 1455-1459; vol. 10, No. 9.

G. Bentley et al.; Rhombohedral Insulin Crystal Transformation; J. Mol. Biol.; 1978; pp. 871-875; vol. 126.

Navdeep B. Malkar et al.; Conjugation of Peptide Therapeutics Using Small, Mono-Dispersed Amphiphilic Oligomers for Oral Delivery; AAPS-Biotech Conference; 2005; USA.

Labeling, Derivatization and Crosslinking Reagents for Biological and Related Materials with dPEG; Quanta Biodesign; 2003; p. 13; USA.

Oliver Seitz et al.; HYCRON, an Allylic Anchor for High-Efficiency Solid Phase Synthesis of Protected Peptides and Glycopeptides; J. Org. Chem.; 1997; pp. 813-826; vol. 62; No. 4; American Chemical Society.

Michael Alvarsson et al.; Beneficial Effects of Insulin Versus Sulphonylurea on Insulin Secretion and Metabolic Control in Recently Diagnosed Type 2 diabetic Patients; Diabetes Care; 2003; pp. 2231-2237; vol. 26, No. 8; USA.

Matthew C. Riddle; Making the Transition from Oral to Insulin Therapy; The American Journal of Medicine; 2005; pp. 14S-20S; vol. 118, No. 5A; Elsevier Inc.

Kenneth D. Hinds et al.; Effects of PEG Conjugation on Insulin Properties; Advanced Drug Delivery Reviews; 2002; pp. 505-530; vol. 54; Elsevier Science B.V.

P. Calceti et al.; Development and in vivo Evaluation of an Oral Insulin-PEG Delivery System; European Journal of Pharmaceutical Sciences; 2004; pp. 315-323; vol. 22; Elsevier B.V.

Nektar Advanced PEGylation—Polyethylene Glycol and Derivatives for Advanced PEGylation; Catalog 2004; USA.

Kang Choon Lee et al.; Isolation, Characterization, and Stability of Positional Isomers of Mono-PEGylated Salmon Calcitonins; Pharmaceutical Research; 1999; vol. 16, No. 6, pp. 813-818; Plenum Publishing Corporation.

Haeshin Lee et al.; Preparation and Characterization of Mono-PEGylated Epidermal Growth Factor: Evaluation of in Vitro Biologic Activity; Pharmaceutical Research; 2002; vol. 19, No. 6, pp. 845-851; Plenum Publishing Corporation.

Andrea Lucke et al.; Biodegradable poly(D,L-lactic acid)-poly(ethylene glycol)-monomethyl ether diblock copolymers: structures and surface properties relevant to their use as biomaterials; Biomaterials; 2000; 21, pp. 2361-2370; Elsevier Science Ltd.

Jong-Hoon Lee et al.; Polymeric nanoparticle composed of fatty acids and poly(ethylene glycol) as a drug carrier; International Journal of Pharmaceutics; 2003; 251, pp. 23-32; Elsevier Science B.V.

Praveen Tyler; Iontophoretic Devices for Drug Delivery; Pharmaceutical Research; (1986), vol. 3, No. 6, 318-326; Plenum Publishing Co., USA.

Jeffrey L. Cleland et al.; Emerging Protein Delivery Methods; Biochemical Engineering; (2001) pp. 212-219.

H. Paul Neubauer et al.; Influence of Polyethylene Glycol Insulin on lipid Tissues of Experimental Animals; Diabetes; (1983), vol. 32, 953-958; Germany.

Samuel Zalipsky et al.; Peptide Attachment to Extremities of Liposomal Surface Grafted PEG Chains: Preparation of the Long-Circulatin Form of Laminin Pentapeptide, YIGSR; Bioconjugate Chem.; (1995), 6, 705-708; American Chemical Society.

S. Salipsky et al.; Attachment of Drugs to Polyethylene Glycols; Eur. Polym. Journal; (1983), vol. 19, No. 12, 1177-1183; Great Britain.

Takashi Uchio et al.; Site-Specific Insulin Conjugates with Enhanced Stability and Extended Action Profile; Advanced Drug Delivery Reviews; (1999), 35, 289-306; Elsevier Science B.V.

Jens Brange et al.; Chemical Stability of Insulin. 2. Formation of Higher Molecular Weight Transformation Products During Storage of Pharmaceutical Preparations; Pharmaceutical Research; (1992), vol. 9, No. 6, 727-734; Plenum Publishing Corporation.

Jens Brange et al.; Chemical Stability of Insulin. 1. Hydrolylic Degradation During Storage of Pharmaceutical Preparations; Pharmaceutical Research; (1992), vol. 9, No. 6, 715-726; Plenum Publishing Corporation.

Jens Brange et al.; Insulin Analogs with Improved Pharmacokinetic Profiles; Advanced Drug Delivery Reviews; (1999), 35, 307-335; Elsevier Science B.V.

J. Milton Harris, Laboratory Synthesis of Polyethylene Glycol Derivatives; JMS-Rev. Macromol. Chem. Phys ; (1985), C25(3), 325-373; Marcel Dekker, Inc.

Vikas Agarwal et al.; Polymethyacrylate Based Microparticulates of Insulin for Oral Delivery: Preparation and in vitro Dissolution Stability in the Presence of Enzyme Inhibitors; International Journal of Pharmaceutics; (2001), 225, 31-39; Elsevier Science B.V.

Minoru Akiyama et al ; The Synthesis of new Derivatives of 1-B-D-Arabinoturanosylcytosine; Chem. Pharm. Bull ; (1978), vol. 26, No. 3 981-984; Japan.

H. Allaudeen et al.; Orally Active Insulin: A Single Insulin Conjugate Selected for Future Studies; American Diabetes Association; Jun. 2000, Atlanta, GA, USA.

Soon H. Song et al.; Direct Measurement of Pulsatile Insulin Secretion from the Portal Vein in Human Subjects; The Journal of Clinical Endocrinology and Metabolism; (2000), vol. 85, No. 12, 4491-4499; The Endocrine Society, USA.

Steven M. Ansell et al.; Application of Oligo-(14-amino-3,6,9,12-tetraoxatetradecanoic acid) Lipid Conjugates as Steric Barrier Molecules in Liposomal Formulations; Bioconjugate Chem.; (1999), 10, 653-666; American Chemical Society.

Michiko Aoshima et al.; N4-Behenoyl-1-B-D-Arabinofuranosylcytosine as a Potential New Antitumor Agent; Cancer Research; (1977), 37, 2481-2486; Japan.

Reto Stocklin et al.; A Stable Isotope Dilution Assay for the in vivo Determination of Insulin Levels in Humans by Mass Spectrometry; Diabetes; (1997), vol. 46, No. 1, p. 44(7), 1-8; American Diabetes Association.

David C. Baker et al.; Prodrugs of 9-B-D-Arabinofuranosyladenine. 1. Synthesis and Evaluation of Some 5'-(O-Acyl) Derivatives; Journal of Medicinal Chemistry; vol. 21, No. 12, 1218-1221; American Chemical Society, published Dec. 1987

Angel Guzman et al; Effects of Fatty Ethers and Stearic Acid on the Gastrointestinal Absorption of Insulin; PRHSJ; (1990), vol. 9, No. 2, 155-159; San Juan, PR.

D.G. Lindsay et al.; The Acetylation of Insulin; Biochem. J.; (1971), 121, 737-745; Great Britain.

T. Forst et al.; New Aspects on Biological Activity of C-peptide in IDDM Patients; Experimental and Clinical Endocrinology Diabetes; (1998), 106, 270-276; Johann Ambrosius Barth.

F.G. Banting et al.; Pancreatic Extracts in the Treatment of Diabetes Mellitus; The Canadian Medical Association Journal; (1922), 141-146; The Canadian Medical Association.

J. Gordon Still et al.; Effects of Orally Active Modified Insulin in Type 1 Diabetic Patients; 2001 Annual Meeting of the American Society for Clinical Pharmacology and Therapeutics; Orlando, Florida, USA.

M. Baudys, et al.; Stabilization and Intestinal Absorption of Human Calcitonin; Journal of Controlled Release; (1996), 39, 145-151; Elsevier Science B.V.

J.G. Still et al.; Magnitude and Variability of Pharmacokinetic and glucodynamic Responses to Modified Human Insulin Administered Orally to Healthy Volunteers; Diabetes Research and Clinical Practice, (2002), vol. 56, Supp. 1, S77; USA.

Miroslav Baudys et al.; Synthesis and Characterization of Different Glycosylated Derivatives of Insulin; Proceed. Intern. Symp. Control. Rel. Bioact. Mater., (1992), 19. 210-211; Controlled Release Society, Inc.

E. Boccu et al ; Pharmacokinetic Properties of Polyethylene Glycol Derivatized Superoxide Dismutase; Pharmacological Research Communications; (1982), vol. 14, No. 2, 113-120.

N. Ekwuribe et al.; Oral Insulin Delivery: Hydrolyzable Amphiphilic Oligomer Conjugates Prolong Glucose Reduction; Proceed. Int'l. Symp. Control. Rel. Bioact. Mater.; (1999), 26, 147-148; Controlled Release Society, Inc.

B. Radha Krishnan et al., Chemical Modification of Insulin with Amphiphilic Polymers Improves Intestinal Delivery; Proceed. Int'l. Symp. Control. Rel. Bioact. Mater.; (1996), 25, 124-125; Controlled Release Society, Inc.

Giovanni M. Pauletti et al.; Improvement of Oral Peptide Bioavailability: Peptidomimetics and Prodrug Strategies; Advanced Drug Delivery Reviews; (1997), 27, 235-256; Elsevier Science B.V.

J. Gordon Still et al.; Oral Insulin Development, Presentation made in London, England, (2000); Protein Delivery Incorporated, RTP, North Carolina, USA.

Christiane Damge et al.; Poly(alkyl cyanoacrylate) Nanospheres for Oral Administration of Insulin; Journal of Pharmaceutical Sciences; (1997), vol. 86, No. 12, 1403-1409; American Chemical Society and American Pharmaceutical Association.

David C. Pang; Bridging Gaps in Drug Discovery and Development; Pharmaceutical Technology; (1998), 22, 11, 82-94; USA.

Clement, Stephen et al.. "Oral Modified Insulin (HIM2) in Patients With Type 1 Diabetes Mellitus: Results From a Phase I/II Clinical Trial", 53(1):54-58 (Jan. 2004).

Abstract of Jiding Xia et al.; Effects of Polyoxyethylene Chain Length Distribution on the Interfacial Properties of Polyethylene Glycol n-dodecyl ether; Yingyong Huaxue (1985), 2(4), 59-65; China.

Abraham Abuchowski et al.; Soluble Polymer-Enzyme Adducts; Enzymes as Drugs; 1981; Chapter 13, 367-383; John Wiley & Sons, New York, US.

Abstract of Monica E. Puskas et al.; Investigation of Chymotrypsin Digestion Profile of Orally Active Insulin Conjugate Him2; AAPSPharmSci; (2001), vol. 3, No. 3, Arlington, VA, USA.

Abstract of Nnochiri Ekwuribe; Conjugation-Stabilized Polypeptide Compositions, Therapeutic Delivery and Diagnostic Formulations Compriisng Same, and Method of Making and Using the Same; Biotechnology Advances; (1996), vol. 14, Issue 4, 575-576; Elsevier Science Direct, USA.

Abstract of A.J. Bone et al. Successful Treatment of an Insulin Dependent Rat Model of Human Type 1 Diabetes with Orally Active Insulin; Department of Pharmacy, University of Brighton and Protein Delivery, Inc. Durham NC, USA . 1996.

Harry R. Allcock et al., Gel Permeation Chromatography; Contemporary Polymer Chemistry (2nd ed.) 1990 394-493, Prentice Hall, USA.

Tyle, et al. Iontophoretic Devices for Drug Delivery; Pharmaceutical Research, (1986) 3 (6) 318-326; Plenum Publishing Co USA.

* cited by examiner

Reaction 2 pH 5.2

Reaction 3 pH 5.0

Reaction cc2B B pH=5.2

Reaction cc3B pH=5.6

CATION COMPLEXES OF INSULIN COMPOUND CONJUGATES, FORMULATION AND USES THEREOF

1 RELATED APPLICATIONS

This application claims priority to and incorporates by reference the entire disclosures of U.S. Patent Application Nos. 60/589,058 filed Jul. 19, 2004, 60/619,153 filed Oct. 15, 2004, 60/632,578 filed Dec. 2, 2004, and 60/655,838 filed Feb. 24, 2005, and 60/655,803 filed Feb. 24, 2005. This application also incorporates by reference the following applications filed herewith on 19 Jul. 2005 by Radhakrishnan et al.: U.S. patent application Ser. No. 11/184,594, entitled "Insulin-oligomer conjugates, formulations and uses thereof"; U.S. patent application Ser. No. 11/184,528, entitled "Fatty acid formulations for oral delivery of proteins and peptides, and uses thereof"; International Patent Application No. PCT/US05/25644 entitled Insulin compound conjugates, cation complexes, formulations and uses thereof."

2 FIELD

The invention relates generally to complexes in which a metal cation is complexed with an insulin compound conjugate, and to the making and using of such complexes. The complexes may be provided as solids in a liquid or as dried solids, and may be provided as components of pharmaceutical formulations. The complexes exhibit various properties useful in the preparation of pharmaceuticals and in the treatment of insulin compound deficiencies. The invention also relates to novel modifying moieties for making drug conjugates and to novel protein conjugates, including insulin compound conjugates, employing such modifying moieties. Further, the invention relates to novel fatty acid formulations and to such formulations prepared for oral delivery of conjugated and unconjugated proteins and peptides, such as the insulin compound conjugates and complexes of the invention.

3 BACKGROUND

Zinc complexed insulin compound is commercially available, for example, under the trade names HUMULIN® and HUMALOG®. Zinc complexed insulin typically exists in a hexameric form.

Various methods have been described for the use of zinc in the crystallization of acylated insulin. For example, U.S. patent Publication 20010041786, published on 15 Nov. 2001, by Mark L. Brader et al., entitled "Stabilized acylated insulin formulations" describes a formulation with an aqueous solution for parenteral delivery, particularly as an injectable formulation, with a pH of 7.1 to 7.6, containing a fatty acid-acylated insulin or a fatty acid-acylated insulin analog and stabilized using zinc and preferably a phenolic compound. U.S. Pat. No. 6,451,970, issued on 17 Sep. 2002 to Schaffer et al., assigned to Novo Nordisk A/S, entitled "Peptide derivatives" describes derivatives of insulin compound and insulin analogs where the N-terminal amino group of the B-chain and/or the e-amino group of Lys in position B28, B29 or B30 is acylated using long chain hydrocarbon group having from 12 to 22 carbon atoms and zinc complexes thereof.

Protamines and phenolic compounds have been described for use in the crystallization of acylated insulin. U.S. Pat. No. 6,268,335 (31 Jul. 2001) and U.S. Pat. No. 6,465,426 (10 Oct. 2002) to Brader, both entitled "Insoluble insulin compositions," describe insoluble compositions comprised of acylated insulin a protamine complexing compound, a hexamer-stabilizing phenolic compound, and a divalent metal cation.

Existing approaches are especially tailored for crystallization of native insulin compound or insulin compound analogs or for acylated insulin compounds having increased lipophilicity relative to non-acylated insulin compounds. There is a need in the art for pharmaceutically acceptable complexes including derivatized insulin compounds, other than acylated insulin compound, such as hydrophilic and/or amphiphilic insulin compound derivatives, and for stabilizing non-acylated lipophilic insulin compound analogs. There is also a need in the art for new protein conjugates having increased bioavailability or other improved pharmaceutical attributes relative to existing conjugates. There is a need in the art for new formulations that facilitate oral delivery of proteins and protein conjugates. Finally, there is a need for a combined approach to improving the oral bioavailability of a protein, such as insulin compound, which incorporates an improved oral protein conjugate provided as a solid in an improved formulation to maximize the benefits for the oral delivery of proteins.

4 SUMMARY OF THE INVENTION

In general, the invention provides a complex including an insulin compound conjugate with an insulin compound conjugated to a modifying moiety, and a cation, where the insulin compound conjugate is complexed with the cation. The insulin compound may, for example, be a native insulin or an insulin analogs. Examples of insulin compounds include human insulin, lyspro insulin, des30 insulin, native proinsulin, artificial proinsulins, etc. The cation component may, for example, be a divalent metal cation selected from the group consisting of Zn++, Mn++, Ca++, Fe++, Ni++, Cu++, Co++ and Mg++.

The modifying moiety may be selected to render the insulin compound conjugate more, less or equally soluble as compared to the corresponding unconjugated insulin compound. The modifying moiety is preferably selected to render the insulin compound conjugate at least 1.05, 1.25, 1.5, 1.75, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 times more soluble than a corresponding unconjugated insulin compound in an aqueous solution at a pH of about 7.4. Preferably the modifying moiety is selected to render an insulin compound conjugate having an aqueous solubility that exceeds about 1 g/L, 2 g/L, 3 g/L, 4 g/L, 5 g/L, 10 g/L, 15 g/L, 20 g/L, 25 g/L, 50 g/L, 75 g/L, 100 g/L, 125 g/L, or 150 g/L at a pH of about 7.4. Further, the modifying moiety is selected to render the insulin compound conjugate equally or more soluble than a corresponding unconjugated insulin compound, and the water solubility of the insulin compound conjugate is decreased by the addition of zinc. In another embodiment, the modifying moiety is selected to render the insulin compound conjugate equally or more soluble than a corresponding unconjugated insulin compound; the water solubility of the insulin compound conjugate is decreased by the addition of zinc; and water solubility of the complex is greater than the water solubility of insulin compound. In still another embodiment, the relative lipophilicity of the insulin compound conjugate as compared to corresponding parent insulin compound ($k_{rel}$) is 1 or less than 1.

The invention also provides novel insulin compound conjugates having an insulin compound conjugated to a modifying moiety. For example, the invention provides insulin compounds coupled to a modifying moiety having a formula:

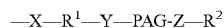  (Formula VI)

where,

X, Y and Z are independently selected linking groups and each is optionally present, and X, when present, is coupled to the insulin compound by a covalent bond, at least one of $R^1$ and $R^2$ is present, and is lower alkyl and may optionally include a carbonyl group, $R^2$ is a capping group, such as —$CH_3$, —H, tosylate, or an activating group, and PAG is a linear or branched carbon chain incorporating one or more alkalene glycol moieties (i.e., oxyalkalene moieties), and optionally incorporating one or more additional moieties selected from the group consisting of —S—, —O—, —N—, and —C(O)—, and where the modifying moiety has a maximum number of 3, 4, 5, 6, 7, 8, 9, 10, 11, 12, 13, 14, 15, 16, 17, 18, 19, 20, 21, 22, 23, 24, or 25 heavy atoms.

In embodiments of the invention, any one or more of X, Y and Z may be absent. Further, when present, X, Y and/or Z may be independently selected from —C(O)—, —O—, —S—, —C— and —N—. In one embodiment, Z is —C(O)—. In another embodiment, Z is not present.

In some embodiments, $R^1$ is lower alkyl, and $R^2$ is not present. In other embodiments, $R^2$ is lower alkyl, and $R^1$ is not present.

In another embodiment, the modifying moiety may include a linear or branched, substituted carbon chain moiety having a backbone of 3, 4, 5, 6, 7, 8, 9, 10, 11, 12, 13, 14, 15, 16, 17, 19, 19, 20, 21, 22, 23, 24 or 25 atoms selected from the group consisting of —C, —C—, —O—, =O, —S—, —N—, —Si—. The heavy atoms will typically include one or more carbon atoms and one or more non-carbon heavy atoms selected from the group consisting of —O—, —S—, —N—, and =O. The carbon atoms and non-carbon heavy atoms are typically present in a ratio of at least 1 carbon atom for every non-carbon heavy atom, preferably at least 2 carbon atoms for every non-carbon heavy atom, more preferably at least 3 carbon atoms for every non-carbon heavy atom. The carbon atoms and oxygen atoms are typically present in a ratio of at least 1 carbon atom for every oxygen atom, preferably at least 2 carbon atoms for every oxygen atom, more preferably at least 3 carbon atoms for every oxygen atom. The modifying moiety may include one or more capping groups, such as branched or linear $C_{1-6}$, branched or linear, or a carbonyl. The modifying moiety will typically include hydrogens, and one or more of the hydrogens may be substituted with a fluorine (which is a heavy atom but should not be counted as a heavy atom in the foregoing formula). The modifying moiety may in some cases specifically exclude unsubstituted alkyl moieties. The modifying moiety may, for example, be coupled to an available group on an amino acid, such as an amino group, a hydroxyl group or a free carboxyllic acid group the polypeptide, e.g., by a linking group, such as a carbamate, carbonate, ether, ester, amide, or secondary amine group, or by a disulfide bond. The molecules in the linking group are counted as part of the modifying moiety. In a preferred embodiment, the molecular weight of the modifying moiety is less than the molecular weight of the HIM2 modifying moiety.

The invention includes insulin compound conjugates having modifying moieties with a formula:

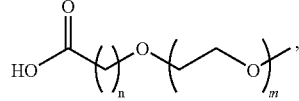

(Formula VII)

where n is 1, 2, 3 or 4, and m is 1, 2, 3, 4 or 5; and/or

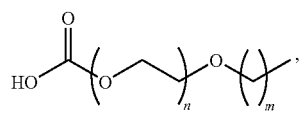

(Formula VIII)

where n is 1, 2, 3, 4 or 5, and m is 1, 2, 3 or 4.

It will be appreciated that the novel modifying moieties, as well as the use of such moities to modify insulin and other polypeptides are themselves aspects of the invention.

The invention also provides novel formulations including the insulin compound conjugates and/or cation-insulin compound conjugates of the invention. The inventors have surprisingly discovered that certain fatty acid compositions are particularly useful, especially for oral delivery of the polypeptides and polypeptide conjugates, such as insulin and insulin compound conjugates and/or oral delivery of the cation-insulin compound conjugate complexes of the invention. In one aspect, the invention provides fatty acid compositions with one or more saturated or unsaturated $C_4$, $C_5$, $C_6$, $C_7$, $C_8$, $C_9$ or $C_{10}$ fatty acids and/or salts of such fatty acids. Preferred fatty acids are caprylic, capric, myristic and lauric. Preferred fatty acid salts are sodium salts of caprylic, capric, myristic and lauric acid. The fatty acid content of the composition is typically within a range having as a lower limit of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0% w/w, and having as an upper limit of about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0% w/w. In yet another embodiment, the fatty acid content of the composition is within a range having as a lower limit about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0% w/w, and having as an upper limit about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0% w/w, and the fatty acid content of the composition is typically greater than about 90, 91, 92, 93, 94, 95, 96, 97, 98, 99, 99.5, 99.6, 99.7, 99.8, or 99.9% w/w a single fatty acid, preferably caprylic, capric, myristic or lauric, or a salt thereof.

The invention also provides method of treating insulin deficiencies or otherwise supplementing insulin in a subject using the insulin compound conjugates, cation-insulin compound conjugate complexes, and/or formulations of the invention. The methods generally include administering a therapeutically effective amount of one or more of the insulin compound conjugates, cation-insulin compound conjugate complexes, and/or formulations of the invention to a subject in need thereof.

5 BRIEF DESCRIPTION OF THE FIGURES

FIGS. 1-15B show photomicrographs of various crystalline solids of the invention. FIGS. 1 and 2 are photomicrographs taken using a Zeiss Axiovert microscope showing T-type Zn complex of HIM2 30 g/L concentration, crystals grown for 24 hours. FIG. 3 is a photomicrograph taken using a Zeiss Axiovert microscope showing T-type Zn complex of HIM2 30 g/L concentration, crystals grown for 5 days. FIG. 4 is a photomicrograph taken using a Zeiss Axiovert microscope showing R-type Zn complex of HIM2 at 30 g/L crystals grown for 4 days. FIG. 5 shows photomicrograph of R-type crystalline Zn complex of IN105 containing 30% organic. FIGS. 6A-10B show photomicrographs of various R-type Zn complexes of HIM2 made using organic solvent. FIGS. 11A-14B show photomicrographs of crystals of various R-type co-crystallized Zn complexes of HIM2 and IN105. FIGS. 15A-15B show photomicrographs of crystals of various R-type co-crystallized Zn complexes of HIM2 and human insulin. The invention includes crystals having the morphologies shown in any of FIGS. 1-15B.

FIGS. 16-20 show Mouse Blood Glucose Assay results for HIM2 and various Zn-HIM2 complexes. FIG. 16 shows MBGA biopotency profiles for HIM2. FIG. 17 shows MBGA biopotency profiles for Zn HIM2 insulin compound product R type. FIG. 18 shows MBGA biopotency profiles for Zn HIM2 insulin compound product T-type. FIG. 19 shows MBGA biopotency profiles for Zn HIM2 insulin compound product with protamine. FIG. 20 shows glucose lowering effect of R type protamine complex at 30 and 90 minutes post dose.

Figure 31:
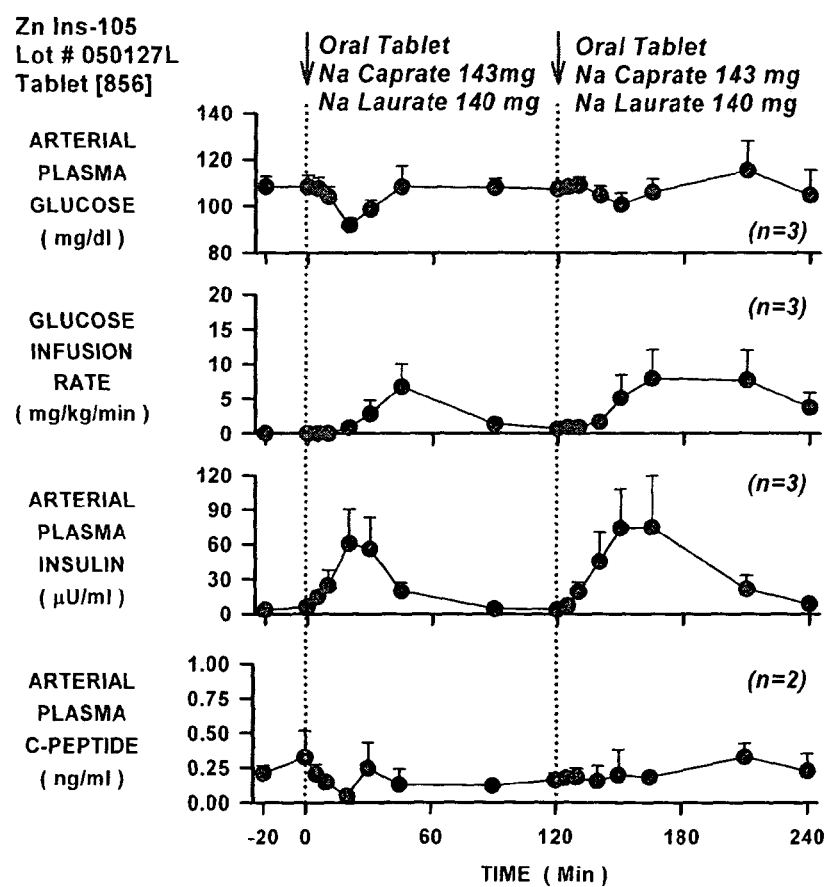
Figure 32:
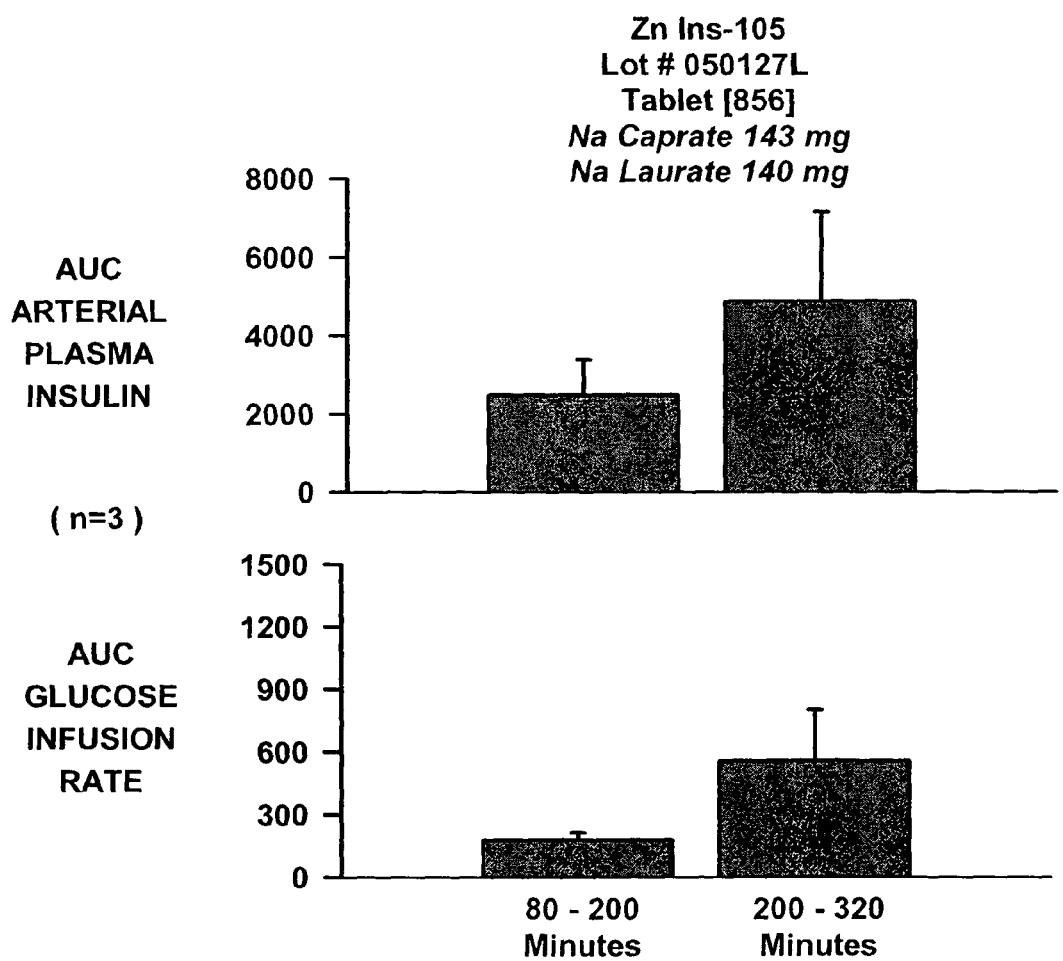
Figure 33:
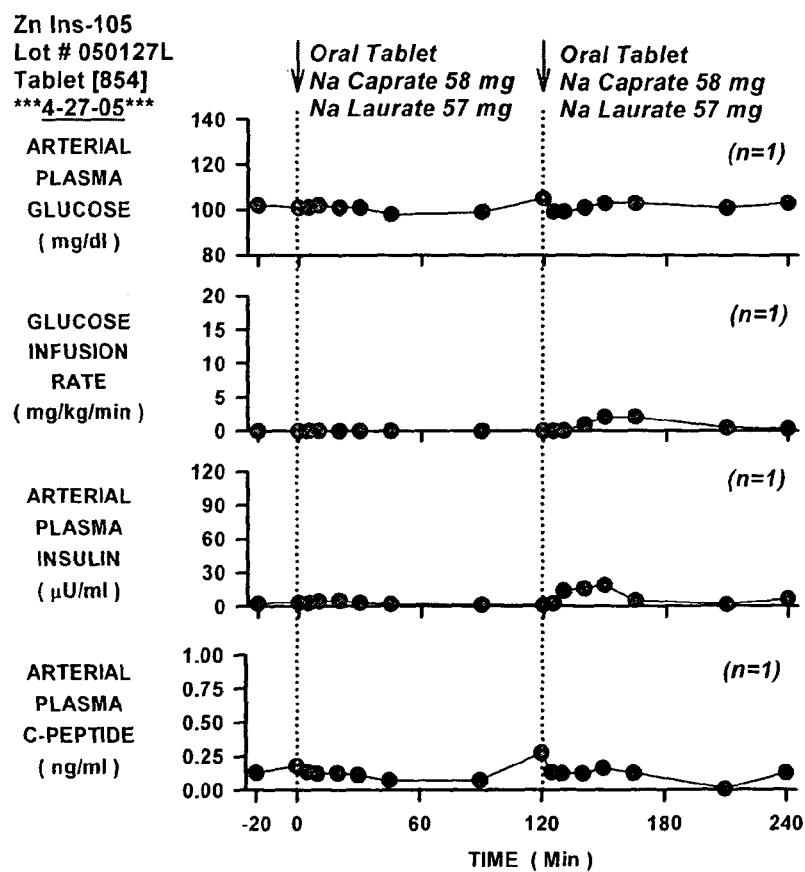
Figure 34:
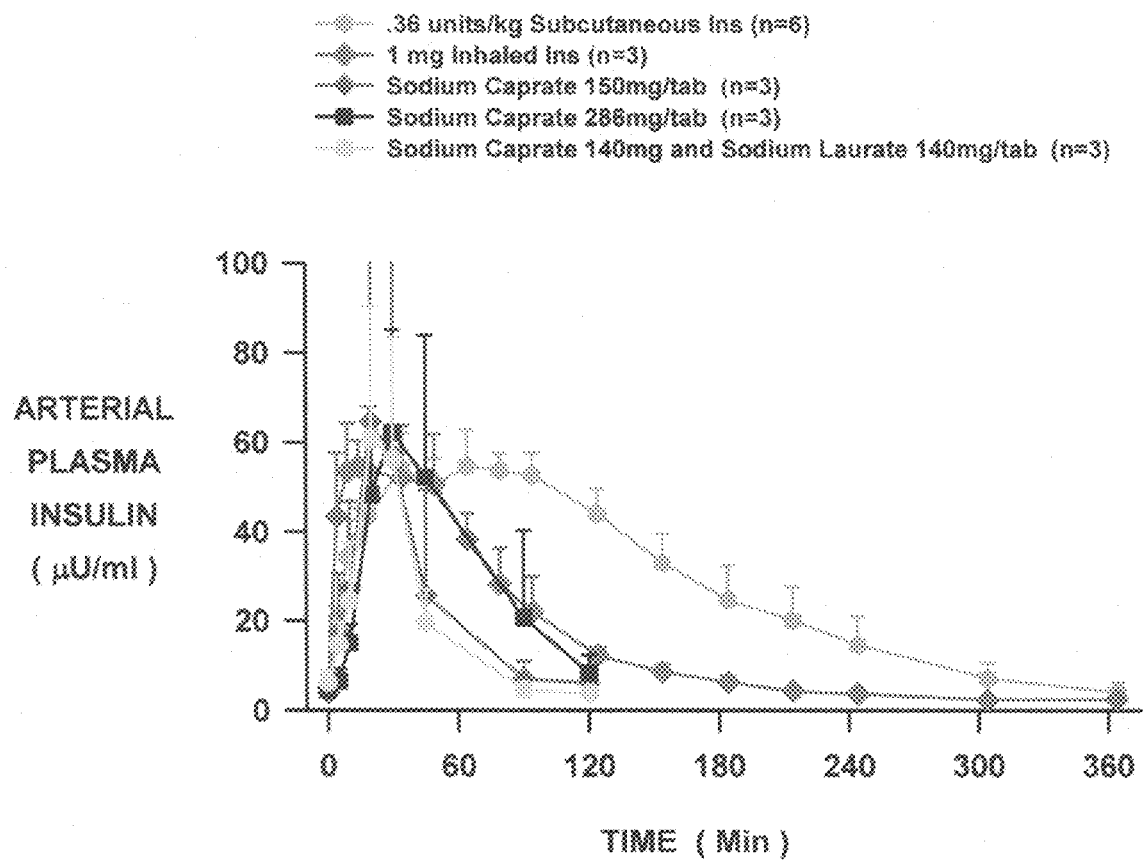
Figure 35:
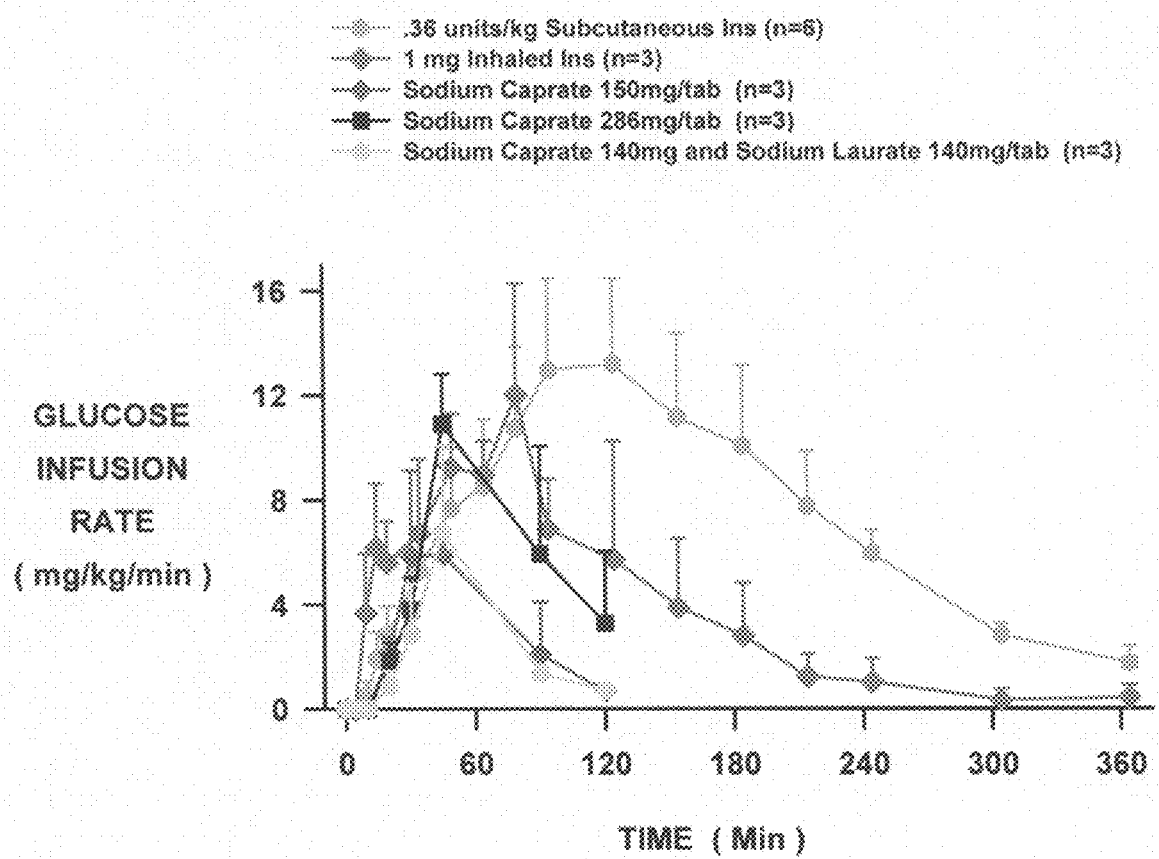
Figure 36:
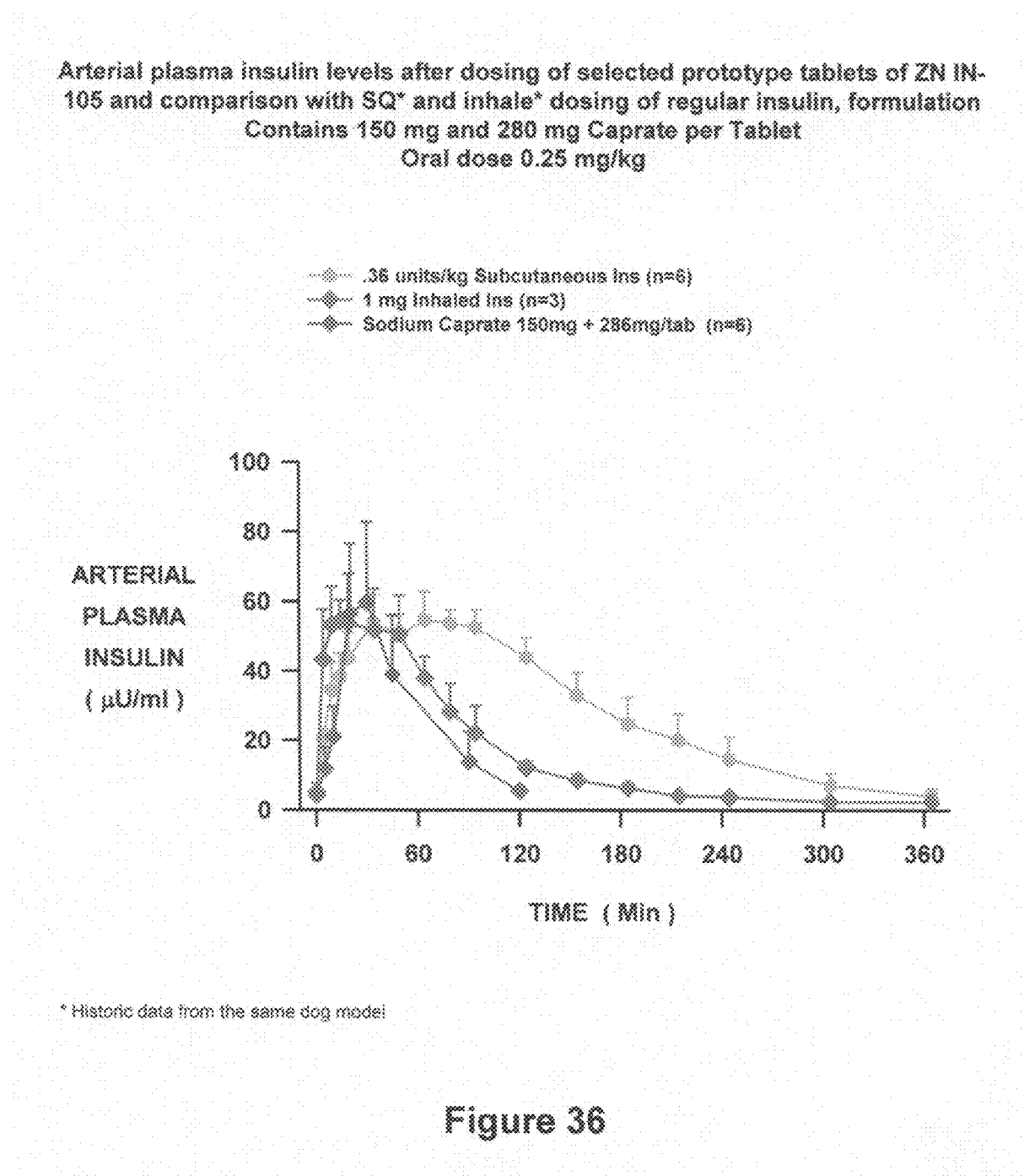
Figure 37:
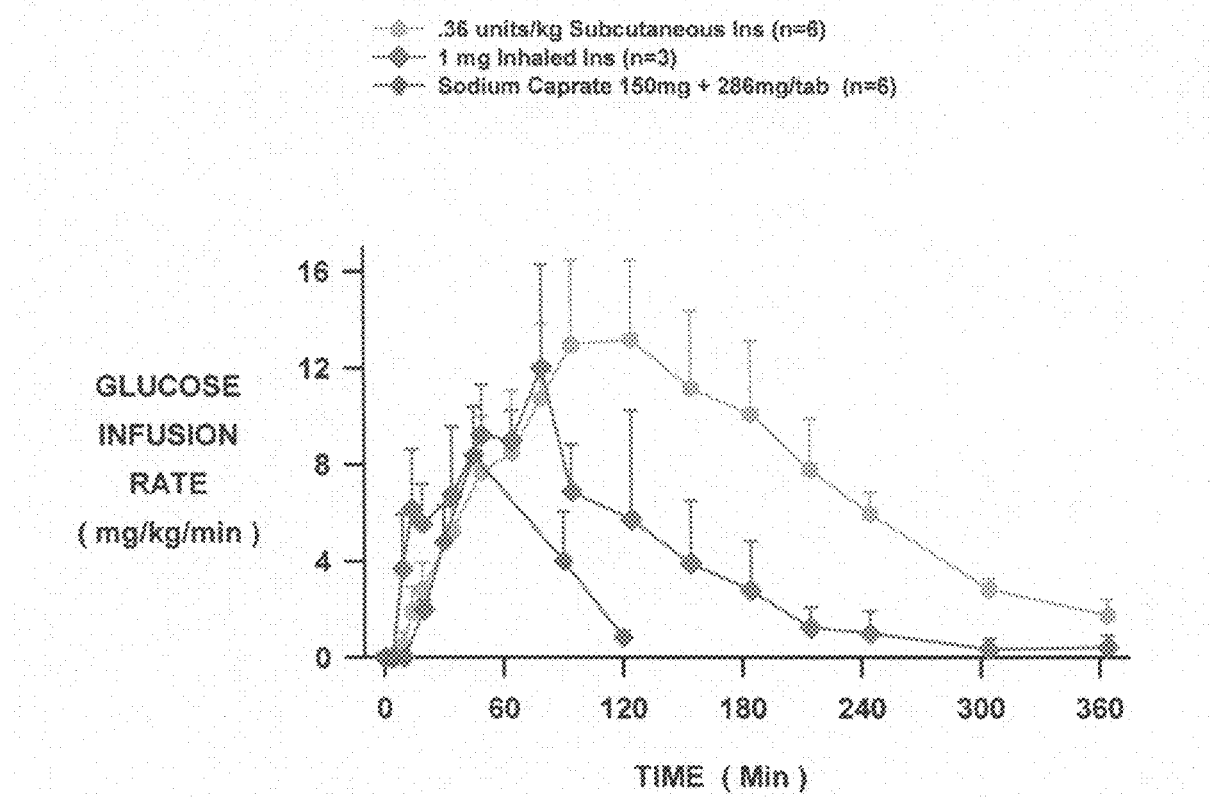
Figure 38:
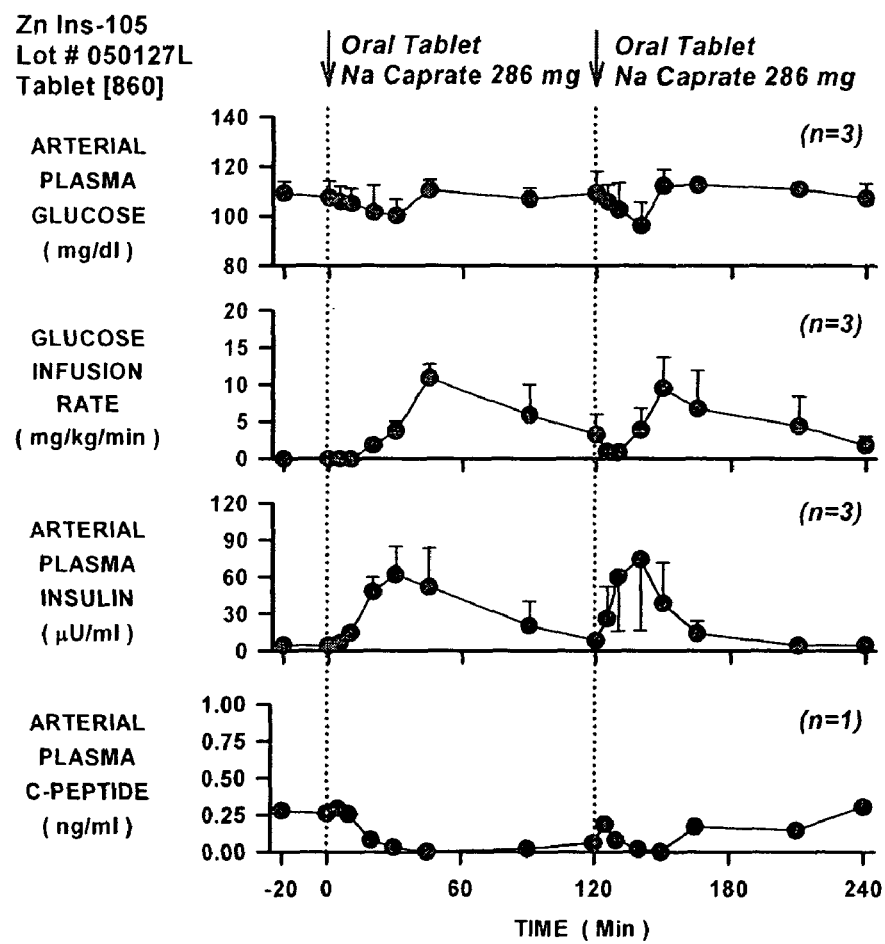
Figure 39:
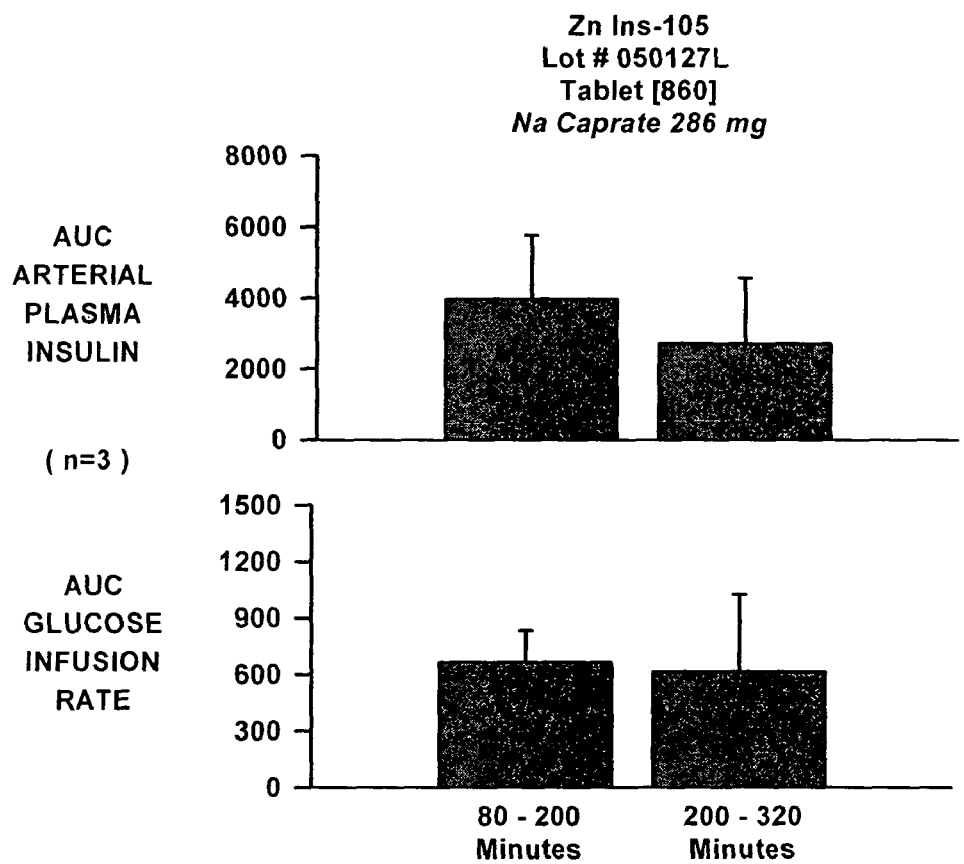
Figure 40:
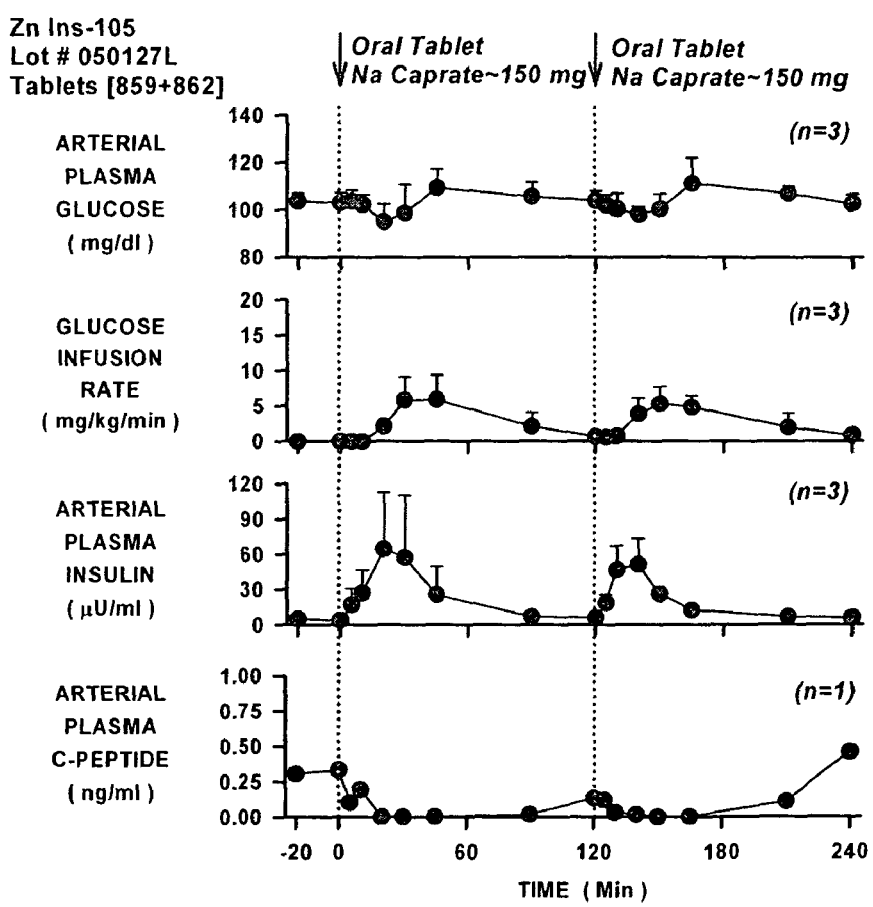
Figure 41:
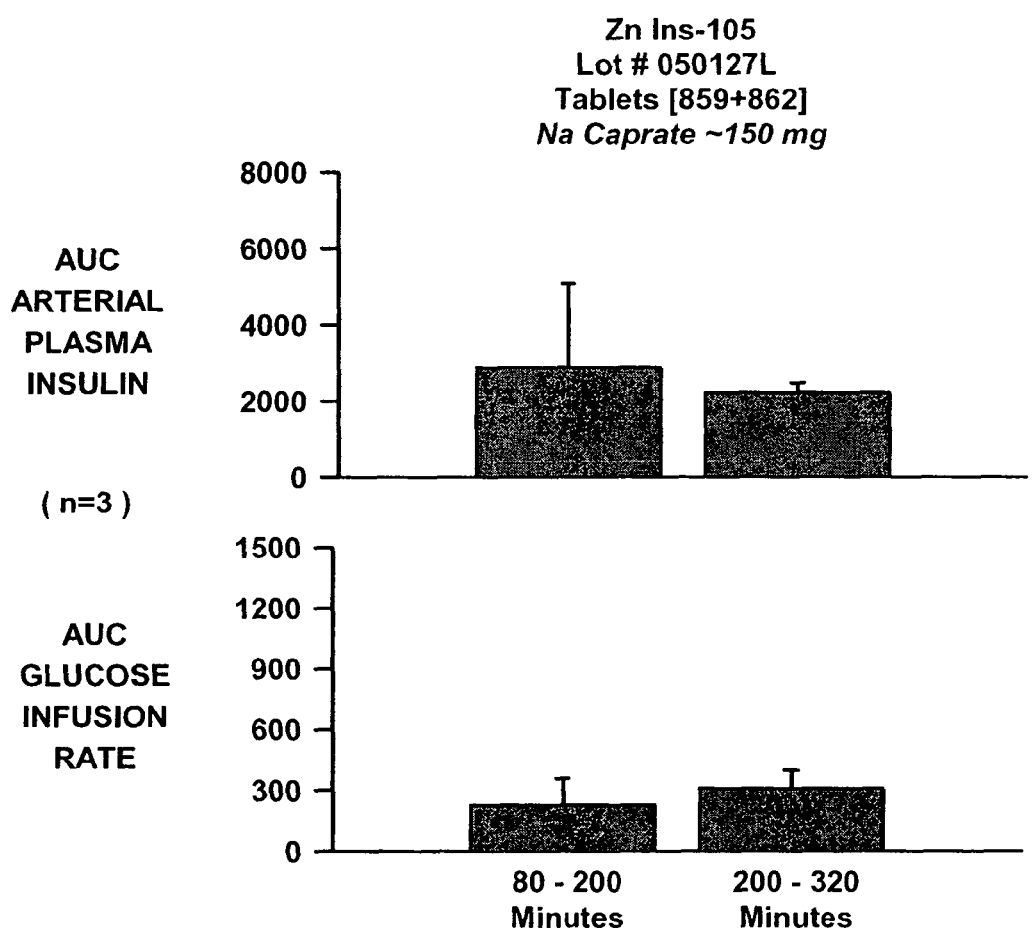
Figure 42:
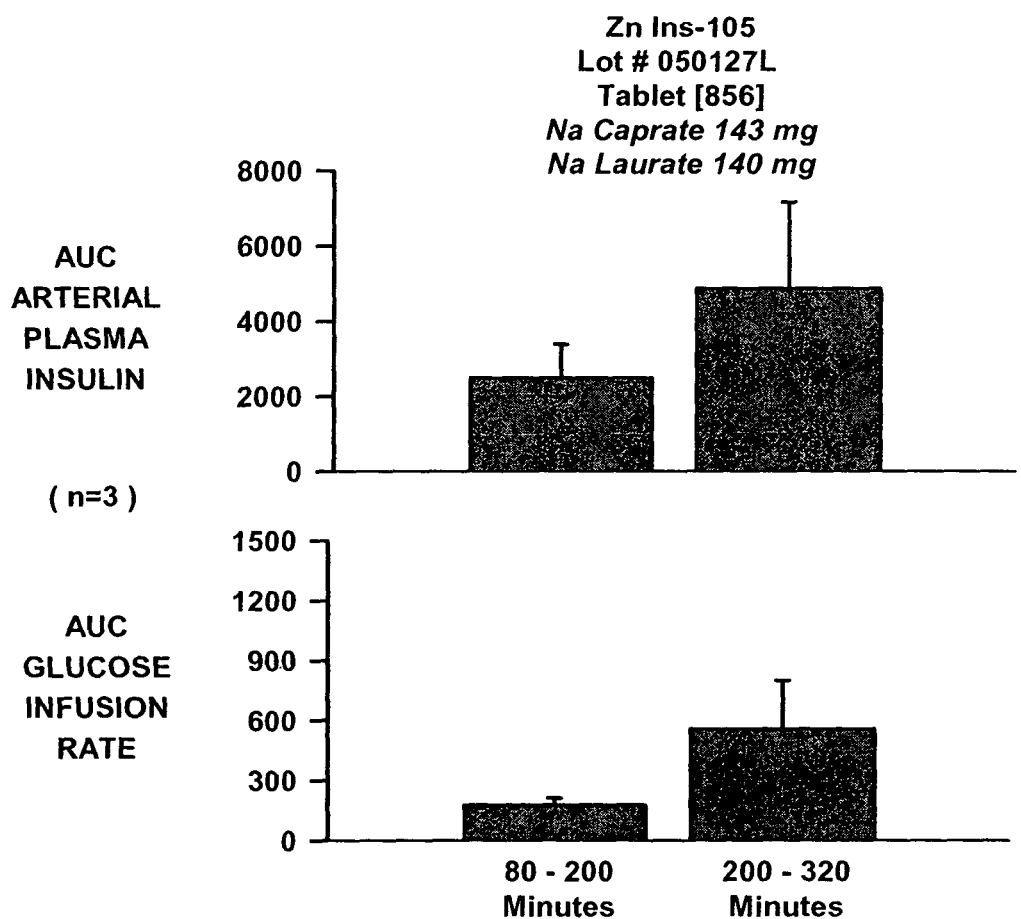

FIGS. 31-33 show dog clamp study results for dogs dosed with tablets containing 6 mg of IN105 and 150 mg Mannitol, 30 mg Exlotab with 143 mg Caparte with or with out 143 mg laurate.

FIGS. 34-37 show dog clamp study results for dogs dosed with prototype tablet 150 mg and 280 mg caprate tablets and with 140 mg/140 mg caprate/laurate tablets.

FIGS. 38-42 show dog clamp study results for additional dogs dosed with prototype tablet 150 mg and 280 mg caprate tablets and with 140 mg/140 mg caprate/laurate tablets.

6 DEFINITIONS

The following are definitions of the terms as used throughout this specification and claims. The definitions provided apply throughout the present specification unless otherwise indicated. Terms not defined herein have the meaning commonly understood in the art to which the term pertains.

"Addition," when used in reference to an amino acid sequence, includes extensions of one or more amino acids at either or both ends of the sequence as well as insertions within the sequence.

"Complex" refers to a molecular association in which one or more insulin compounds or insulin compound conjugates form coordinate bonds with one or more metal atoms or ions. Complexes may exist in solution or as a solid, such as a crystal, microcrystal, or an amorphous solid. "Complex mixture" means a mixture having two or more different complexes, whether in solution or in solid form. Complexes mixtures may, for example, include complexes with different insulin compounds, different insulin compound conjugates, different hybrid complexes, different cations, combinations of the foregoing, and the like. "Hybrid complex" means a cation-insulin compound conjugate complex having two or more different insulin compounds and/or insulin compound conjugates.

"Complexing agent" means a molecule that has a multiplicity of charges and that binds to or complexes with insulin compound conjugates. Examples of complexing agents suitable for use in the present invention include protamines, surfen, globin proteins, spermine, spermidine albumin, amino acids, carboxylic acids, polycationic polymer compounds, cationic polypeptides, anionic polypeptides, nucleotides, and antisense. See Brange, J., Galenics of Insulin compound, Springer-Verlag, Berlin Heidelberg (1987), the entire disclosure of which is incorporated herein by reference.

"Conservative" used in reference to an addition, deletion or substitution of an amino acid means an addition, deletion or substitution in an amino acid chain that does not completely diminish the therapeutic efficacy of the insulin compound, i.e., the efficacy may be reduced, the same, or enhanced, relative to the therapeutic efficacy of scientifically acceptable control, such as a corresponding native insulin compound.

"Hydrophilic" means exhibiting characteristics of water solubility, and the term "hydrophilic moiety" refers to a moiety which is hydrophilic and/or which when attached to another chemical entity, increases the hydrophilicity of such chemical entity. Examples include, but are not limited to, sugars and polyalkylene moieties such as polyethylene glycol. "Lipophilic" means exhibiting characteristics of fat solubility, such as accumulation in fat and fatty tissues, the ability to dissolve in lipids and/or the ability to penetrate, interact with and/or traverse biological membranes, and the term, "lipophilic moiety" means a moiety which is lipophilic and/or which, when attached to another chemical entity, increases the lipophilicity of such chemical entity. "Amphiphilic" means exhibiting characteristics of hydropilicity and lipophilicity, and the term "amphiphilic moiety" means a moiety which is amphiphilic and/or which, when attached to a polypeptide or non-polypeptide drug, increases the amphiphilicity (i.e., increases both the hydrophilicity and the amphiphilicity) of the resulting conjugate, e.g., certain PEG-fatty acid modifying moieties, and sugar-fatty acid modifying moieties.

"Lower alkyl" means substituted or unsubstituted, linear or branched alkyl moieties having from one to six carbon atoms, i.e., $C_1$, $C_2$, $C_3$, $C_4$, $C_5$ or $C_6$. "Higher alkyl" means substituted or unsubstituted, linear or branched alkyl moieties having six or more carbon atoms, e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, etc.

"Monodispersed" describes a mixture of compounds where about 100 percent of the compounds in the mixture have the same molecular weight. "Substantially monodispersed" describes a mixture of compounds where at least about 95 percent of the compounds in the mixture have the same molecular weight. "Purely monodispersed" describes a mixture of compounds where about 100 percent of the compounds in the mixture have the same molecular weight and have the same molecular structure. Thus, a purely monodispersed mixture is a monodispersed mixture, but a monodispersed mixture is not necessarily a purely monodispersed mixture. "Substantially purely monodispersed" describes a mixture of compounds where at least about 95 percent of the compounds in the mixture have the same molecular weight and same molecular structure. Thus, a substantially purely monodispersed mixture is a substantially monodispersed mixture, but a substantially monodispersed mixture is not necessarily a substantially purely monodispersed mixture. The insulin compound conjugate components of the cation-insulin compound conjugate compositions are preferably monodispersed, substantially monodispersed, purely monodispersed or substantially purely monodispersed, but may also be polydispersed. "Polydispersed" means having a dispersity that is not monodispersed, substantially monodispersed, purely monodispersed or substantially purely monodispersed.

"Native insulin compound" as specifically used herein means mammalian insulin compound (e.g., human insulin, bovine insulin compound, porcine insulin compound or whale insulin compound), provided by natural, synthetic, or genetically engineered sources. Human insulin is comprised of a twenty-one amino acid A-chain and a thirty-amino acid B-chain which are cross-linked by disulfide bonds. A properly cross-linked human insulin includes three disulfide bridges: one between A7 and B7, a second between A20 and B 19, and a third between A6 and A11. Human insulin possesses three free amino groups: B1-Phenylalanine, A1-Glycine, and B29-Lysine. The free amino groups at positions A1 and B1 are α-amino groups. The free amino group at position B29 is an e-amino group. "Insulin analog" means a polypeptide exhibiting some, all or enhanced activity relative to a corresponding native insulin or which is converted in in vivo or in vitro into a polypeptide exhibiting some, all or enhanced activity relative to a corresponding native insulin, e.g., a polypeptide having the structure of a human insulin with one or more conservative amino acid additions, deletions and/or substitutions. Insulin analogs can be identified using known techniques, such as those described in U.S. patent Publication No. 20030049654, "Protein design automation for protein libraries," filed 18 Mar. 2002 in the name of Dahiyat et al. Proinsulins, pre-proinsulins, insulin precursors, single chain insulin precursors of humans and non-human animals and analogs of any of the foregoing are also referred to herein as insulin analogs, as are non-mammalian insulins. Many insulin analogs are known in the art (see discussion below). Unless context specifically indicates otherwise (e.g., were a specific insulin is referenced, such as "human insulin" or the like), the term "insulin compound" is used broadly to include native insulins and insulin analogs.

"Polyalkylene glycol" or PAG refers to substituted or unsubstituted, linear or branched polyalkylene glycol polymers such as polyethylene glycol (PEG), polypropylene glycol (PPG), and polybutylene glycol (PBG), and combinations thereof (e.g., linear or branched polymers including combinations of two or more different PAG subunits, such as two or more different PAG units selected from PEG, PPG, PPG, and PBG subunits), and includes the monoalkylether of the polyalkylene glycol. The term PAG subunit means a single PAG unit, e.g., "PEG subunit" refers to a single polyethylene glycol unit, e.g., —(CH$_2$CH$_2$O)—, "PPG subunit" refers to a single polypropylene glycol unit, e.g., —(CH$_2$CH$_2$CH$_2$O)—, and "PBG subunit" refers to a single polypropylene glycol unit, e.g., —(CH$_2$CH$_2$CH$_2$CH$_2$O)—. PAGs and/or PAG subunits also include substituted PAGs or PAG subunits, e.g., PAGs including alkyl side chains, such as methyl, ethyl or propyl side chains, or carbonyl side chains, as well as PAGs including one or more branched PAG subunits, such as iso-PPG or iso-PBG.

"Proinsulin compound" means an insulin compound in which the C-terminus of the B-chain is coupled to the N-terminus of the A-chain via a natural or artificial C-peptide having 5 or more amino acids. "Preproinsulin compound" means a proinsulin compound further including a leader sequence coupled to the N-terminus of the B-chain, such as a sequence selected to promote excretion as a soluble protein, or a sequence selected to prevent conjugation of the N-terminus, or a sequence selected to enhance purification (e.g., a sequence with binding affinity to a purification column). "Single chain insulin compound precursor" or "miniproinsulin compound" means an insulin compound in which the C-terminus of the B-chain (or a truncated B-chain having 1, 2, 3 or 4 amino acids removed from the C-terminus) is coupled to the N-terminus of the A-chain or a truncated A-chain shortened at the N-terminus by 1, 2, 3 or 4 amino acids, without an intervening C-peptide, or via a shortened C-peptide having 1, 2, 3 or 4 amino acids.

"Protamine" refers to a mixture of strongly basic proteins obtained from natural (e.g., fish sperm) or recombinant sources. See Hoffmann, J. A., et al., Protein Expression and Purification, 1:127-133 (1990). The Protamine composition can be provided in a relatively salt-free preparation of the proteins, often called "protamine base" or in a preparation including salts of the proteins.

"Protein" "peptide" and "polypeptide" are used interchangeably herein to refer to compounds having amino acid sequences of at least two and up to any length.

"R-type" means a complex conformation formed in the presence of insulin compound conjugate, a cation and a stabilizing compound, such as phenol. "T-type" means a complex conformation formed in the presence of insulin compound conjugate and a cation without a stabilizing compound, such as phenol. A T-type or R-type complex may include or exclude protamine.

"Scientifically acceptable control" means an experimental control that is acceptable to a person of ordinary skill in the art of the subject matter of the experiment.

"Solid" means a state of matter in which there is three-dimensional regularity of structure; the term is used broadly herein to refer to both crystalline solids, amorphous solids, and combinations of crystalline solids and amorphous solids. "Cation-insulin compound conjugate solid," refers to a solid that includes a cation-insulin compound conjugate, preferably coordinated with a monovalent or multivalent cation. "Crystal" means a solid with a regular polyhedral shape. "Crystalline" refers to solids having the characteristics of crystals. "Microcrystal" means a solid that is comprised primarily of matter in a crystalline state that is microscopic in size, typically of longest dimension within the range 1 micron to 100 microns. In some cases, the individual crystals of a microcrystalline composition are predominantly of a single crystallographic composition. In some embodiments, the crystals of the invention are not microcrystals. The term "microcrystalline" refers to the state of being a microcrystal. "Amorphous" refers to a solid material that is not crystalline in form. The person of ordinary skill in the art can distinguish crystals from amorphous materials using standard techniques, e.g., using x-ray crystallographic techniques, scanning electron microscopy or optical microscopy. "Solid mixture" means a mixture of two different solids. "Crystal mixture" means a mixture of two different crystals. "Cocrystal" means a crystal having two or more different insulin compounds and/or insulin compound conjugates. The cation-insulin compound conjugate complexes of the invention may be provided in any of the foregoing forms or in mixtures of two or more of such forms.

"Substitution" means replacement of one or more amino acid residues within the insulin compound sequence with another amino acid. In some cases, the substituted amino acid acts as a functional equivalent, resulting in a silent alteration. Substitutions may be conservative; for example, conservative substitutions may be selected from other members of the class to which the substituted amino acid belongs. Examples of nonpolar (hydrophobic) amino acids include alanine, leucine, isoleucine, valine, proline, phenylalanine, tryptophan and methionine. Examples of polar neutral amino acids include glycine, serine, threonine, cysteine, tyrosine, asparagine, and glutamine. Examples of positively charged (basic) amino acids include arginine, lysine and histidine. Examples of negatively charged (acidic) amino acids include aspartic acid and glutamic acid.

"Water solubility" or "aqueous solubility" unless otherwise indicated, is determined in an aqueous buffer solution at a pH of 7.4.

7 DETAILED DESCRIPTION OF THE INVENTION

The invention provides cation-insulin compound conjugate complexes and various compositions including such complexes, as well as methods of making and using such complexes and compositions. The complexes are useful for administering insulin compound for the treatment of various medical conditions, such as conditions characterized by insulin compound deficiency. The complexes generally include a cation component and an insulin compound conjugate component. The insulin compound conjugate component generally includes an insulin compound coupled to a modifying moiety. Examples of other suitable components of the complexes and/or compositions include stabilizing agents, complexing agents, and other components known in the art for use in preparing cation-protein complexes. The invention also provides novel insulin compound conjugates and fatty acid formulations including such insulin compound conjugates and/or cation-insulin compound conjugate complexes.

7.1 Insulin Compound

The cation-insulin compound conjugate includes an insulin compound component. The insulin compound may, for example, be a mammalian insulin compound, such as human insulin, or an insulin compound analog.

A wide variety of insulin compound analogs are known in the art. Preferred insulin compound analogs are those which include a lysine, preferably a lysine within 5 amino acids of the C-terminus of the B chain, e.g., at position B26, B27, B28, B29 and/or B30. A set of suitable analogs is described in EP-A 1227000107 (the entire disclosure of which is incorporated herein by reference), having the sequence of insulin compound, except that the amino acid residue at position B28 is Asp, Lys, Leu, Val, or Ala; the amino acid residue at position B29 is Lys or Pro; the amino acid residue at position B10 is His or Asp; the amino acid residue at position B1 is Phe, Asp, or deleted alone or in combination with a deletion of the residue at position B2; the amino acid residue at position B30 is Thr, Ala, or deleted; and the amino acid residue at position B9 is Ser or Asp; provided that either position B28 or B29 is Lys.

Other examples of suitable insulin compound analogs include $Asp^{B28}$ human insulin, $Lys^{B28}$ human insulin, $Leu^{B28}$ human insulin, $Val^{B28}$ human insulin, $Ala^{B28}$ human insulin, $Asp^{B28}Pro^{B29}$ human insulin, $Lys^{B28}Pro^{B29}$ human insulin, $Leu^{B28}Pro^{B29}$ human insulin, $Val^{B28}Pro^{B29}$ human insulin, $Ala^{B28}Pro^{B29}$ human insulin, as well as analogs provided using the substitution guidelines described above. Insulin compound fragments include, but are not limited to, B22-B30 human insulin, B23-B30 human insulin, B25-B30 human insulin, B26-B30 human insulin, B27-B30 human insulin, B29-B30 human insulin, B1-B2 human insulin, B1-B3 human insulin, B1-B4 human insulin, B1-B5 human insulin, the A chain of human insulin, and the B chain of human insulin.

Still other examples of suitable insulin compound analogs can be found in U.S. patent Publication No. 20030144181A1, entitled "Insoluble compositions for controlling blood glucose," 31 Jul. 2003; U.S. patent Publication No. 20030104983A1, entitled "Stable insulin formulations," 5 Jun. 2003; U.S. patent Publication No. 20030040601A1, entitled "Method for making insulin precursors and insulin analog precursors," 27 Feb. 2003; U.S. patent Publication No. 20030004096A1, entitled "Zinc-free and low-zinc insulin preparations having improved stability," 2 Jan. 2003; U.S. Pat. No. 6,551,992B1, entitled "Stable insulin formulations," 22 Apr. 2003; U.S. Pat. No. 6,534,288B1, entitled "C peptide for improved preparation of insulin and insulin analogs," 18 Mar. 2003; U.S. Pat. No. 6,531,448B1, entitled "Insoluble compositions for controlling blood glucose," 11 Mar. 2003; U.S. Pat. No. RE37,971E, entitled "Selective acylation of epsilon-amino groups," 28 Jan. 2003; U.S. patent Publication No. 20020198140A1, entitled "Pulmonary insulin crystals," 26 Dec. 2002; U.S. Pat. No. 6,465,426B2, entitled "Insoluble insulin compositions," 15 Oct. 2002; U.S. Pat. No. 6,444,641B1, entitled "Fatty acid-acylated insulin analogs," 3 Sep. 2002; U.S. patent Publication No. 20020137144A1, entitled "Method for making insulin precursors and insulin precursor analogues having improved fermentation yield in yeast," 26 Sep. 2002; U.S. patent Publication No. 20020132760A1, entitled "Stabilized insulin formulations," 19 Sep. 2002; U.S. patent Publication No. 20020082199A1, entitled "Insoluble insulin compositions," 27 Jun. 2002; U.S. Pat. No. 6,335,316B1, entitled "Method for administering acylated insulin," 1 Jan. 2002; U.S. Pat. No. 6,268,335B1, entitled "Insoluble insulin compositions," 31 Jul. 2001; U.S. patent Publication No. 20010041787A1, entitled "Method for making insulin precursors and insulin precursor analogues having improved fermentation yield in yeast," 15 Nov. 2001; U.S. patent Publication No. 20010041786A1, entitled "Stabilized acylated insulin formulations," 15 Nov. 2001; U.S. patent Publication No. 20010039260A1, entitled "Pulmonary insulin crystals," 8 Nov. 2001; U.S. patent Publication No. 20010036916A1, entitled "Insoluble insulin compositions," 1 Nov. 2001; U.S. patent Publication No. 20010007853A1, entitled "Method for administering monomeric insulin analogs," 12 Jul. 2001; U.S. Pat. No. 6,051,551A, entitled "Method for administering acylated insulin," 18 Apr. 2000; U.S. Pat. No. 6,034,054A, entitled "Stable insulin formulations," 7 Mar. 2000; U.S. Pat. No. 5,970,973A, entitled "Method of delivering insulin lispro," 26 Oct. 1999; U.S. Pat. No. 5,952,297A, entitled "Monomeric insulin analog formulations," 14 Sep. 1999; U.S. Pat. No. 5,922,675A, entitled "Acylated Insulin Analogs," 13 Jul. 1999; U.S. Pat. No. 5,888,477A, entitled "Use of monomeric insulin as a means for improving the bioavailability of inhaled insulin," 30 Mar. 1999; U.S. Pat. No. 5,873,358A, entitled "Method of maintaining a diabetic patient's blood glucose level in a desired range," 23 Feb. 1999; U.S.

Pat. No. 5,747,642A, entitled "Monomeric insulin analog formulations," 5 May 98; U.S. Pat. No. 5,693,609A, entitled "Acylated insulin compound analogs," 2 Dec. 1997; U.S. Pat. No. 5,650,486A, entitled "Monomeric insulin analog formulations," 22 Jul. 1997; U.S. Pat. No. 5,646,242A, entitled "Selective acylation of epsilon-amino groups," 8 Jul. 1997; U.S. Pat. No. 5,597,893A, entitled "Preparation of stable insulin analog crystals," 28 Jan. 1997; U.S. Pat. No. 5,547,929A, entitled "Insulin analog formulations," 20 Aug. 1996; U.S. Pat. No. 5,504,188A, entitled "Preparation of stable zinc insulin compound analog crystals," 2 Apr. 1996; U.S. Pat. No. 5,474,978A, entitled "Insulin analog formulations," 12 Dec. 1995; U.S. Pat. No. 5,461,031A, entitled "Monomeric insulin analog formulations," 24 Oct. 1995; U.S. Pat. No. 4,421,685A, entitled "Process for producing an insulin," 20 Dec. 1983; U.S. Pat. No. 6,221,837, entitled "Insulin derivatives with increased zinc binding" 24 Apr. 2001; U.S. Pat. No. 5,177,058, entitled "Pharmaceutical formulation for the treatment of diabetes mellitus" 5 Jan. 1993 (describes pharmaceutical formulations including an insulin compound derivative modified with a base at B31 and having an isoelectric point between 5.8 and 8.5 and/or at least one of its physiologically tolerated salts in a pharmaceutically acceptable excipient, and a relatively high zinc content in the range from above 1 µg to about 200 µg of zinc/IU, including insulin compound-B31-Arg-OH and human insulin-B31-Arg-B32-Arg-OH). The entire disclosure of each of the foregoing patent documents is incorporated herein by reference, particularly for teaching about the making, using and compositions of various insulin compound analogs.

Insulin compound used to prepare the cation-insulin compound conjugates can be prepared by any of a variety of recognized peptide synthesis techniques, e.g., classical (solution) methods, solid phase methods, semi-synthetic methods, and recombinant DNA methods. For example, Chance et al., U.S. patent application Ser. No. 07/388,201, EPO383472, Brange et al., EPO214826, and Belagaje et al., U.S. Pat. No. 5,304,473 disclose the preparation of various proinsulin compound and insulin compound analogs and are herein incorporated by reference. The A and B chains of the insulin compound analogs may also be prepared via a proinsulin compound-like precursor molecule or single chain insulin compound precursor molecule using recombinant DNA techniques. See Frank at al., "Peptides: Synthesis-Structure-Function," *Proc. Seventh Am. Pept. Symp.*, Eds. D. Rich and E. Gross (1981); Bernd Gutte, *Peptides: Synthesis, Structures, and Applications*, Academic Press (Oct. 19, 1995); Chan, Weng and White, Peter (Eds.), *Fmoc Solid Phase Peptide Synthesis. A Practical Approach*, Oxford University Press (March 2000); the entire disclosures of which are incorporated herein by reference for their teachings concerning peptide synthesis, recombinant production and manufacture.

7.2 Modifying Moiety

The cation-insulin compound conjugate complexes include a modifying moiety coupled (e.g., covalently or ionically) to the insulin compound to provide the insulin compound conjugate. Modifying moieties are moieties coupled to the insulin compound that provide the insulin compound with desired properties as described herein. For example, the modifying moiety can reduce the rate of degradation of the insulin compound in various environments (such as the GI tract, and/or the bloodstream), such that less of the insulin compound is degraded in the modified form than would be degraded in the absence of the modifying moiety in such environments. Preferred modifying moieties are those which permit the insulin compound conjugate to retain a therapeutically significant percentage of the biological activity of the parent insulin compound. Further, preferred modifying moieties are those which are amphiphilic or hydrophilic, and/or which render the insulin compound conjugate amphiphilic or hydrophilic or less lipophilic than a scientifically acceptable control, such as a corresponding insulin compound, or a corresponding unconjugated insulin compound.

Examples of suitable modifying moieties and insulin compound conjugates useful in the cation-insulin compound conjugate compositions can be found in the following patents, the entire disclosures of which are incorporated herein by reference: U.S. Pat. No. 6,303,569, entitled "Trialkyl-lock-facilitated polymeric prodrugs of amino-containing bioactive agents," 16 Oct. 2001; U.S. Pat. No. 6,214,330, "Coumarin and related aromatic-based polymeric prodrugs," 10 Apr. 2001; U.S. Pat. No. 6,113,906, entitled "Water-soluble non-antigenic polymer linkable to biologically active material," 5 Sep. 2000; U.S. Pat. No. 5,985,263, entitled "Substantially pure histidine-linked protein polymer conjugates," 16 Nov. 1999; U.S. Pat. No. 5,900,402, entitled "Method of reducing side effects associated with administration of oxygen-carrying proteins," Apr. 5, 1999; U.S. Pat. No. 5,681,811, "Conjugation-stabilized therapeutic agent compositions, delivery and diagnostic formulations comprising same, and method of making and using the same" 28 Oct. 1997; U.S. Pat. No. 5,637,749, entitled "Aryl imidate activated polyalkylene oxides," 10 Jun. 1997; U.S. Pat. No. 5,612,460, entitled "Active carbonates of polyalkylene oxides for modification of polypeptides," 18 Mar. 1997; U.S. Pat. No. 5,567,422, entitled "Azlactone activated polyalkylene oxides conjugated to biologically active nucleophiles," 22 Oct. 1996; U.S. Pat. No. 5,405,877, entitled "Cyclic imide thione activated polyalkylene oxides," 11 Apr. 1995; and U.S. Pat. No. 5,359,030, entitled "Conjugation-stabilized polypeptide compositions, therapeutic delivery and diagnostic formulations comprising same, and method of making and using the same," 25 Oct. 1994. Additional examples of conjugated polypeptides useful in the formulations of the instant invention can be found in the following U.S. patent applications, the entire specifications of which are incorporated herein by reference: U.S. patent application Ser. No. 09/134,803, filed 14 Aug. 1998; Ser. No. 10/018,879, filed 19 Dec. 2001; 10/235,381, filed 5 Sep. 2002; Ser. No. 10/235,284, filed 5 Sep. 2002; and Ser. No. 09/873,797, filed 4 Jun. 2001. The entire disclosure of each of the foregoing patents and patent applications is incorporated herein by reference for their teachings concerning moieties used to modify polypeptides.

The modifying moieties may include weak or degradable linkages in their backbones. For example, the PAGs can include hydrolytically unstable linkages, such as lactide, glycolide, carbonate, ester, carbamate and the like, which are susceptible to hydrolysis. This approach allows the polymers to be cleaved into lower molecular weight fragments. Examples of such polymers are described, for example, in U.S. Pat. No. 6,153,211, entitled, to Hubbell et al., the entire disclosure of which is incorporated herein by reference. See also U.S. Pat. No. 6,309,633, to Ekwuribe et al., the entire disclosure of which is incorporated herein by reference.

The modifying moiety can include any hydrophilic moieties, lipophilic moieties, amphiphilic moieties, salt-forming moieties, and combinations thereof. Representative hydrophilic, amphiphilic, and lipophilic polymers and modifying moieties are described in more detail below.

7.2.1 Hydrophilic Moieties

Examples of suitable hydrophilic moieties include PAG moieties, other hydrophilic polymers, sugar moieties, polysorbate moieties, and combinations thereof.

7.2.2 Polyalkylene Glycol Moieties

PAGs are compounds with repeat alkylene glycol units. In some embodiments, the units are all identical (e.g., PEG or PPG). In other embodiments, the alkylene units are different (e.g., polyethylene-co-propylene glycol, or PLURONICS®). The polymers can be random copolymers (for example, where ethylene oxide and propylene oxide are co-polymerized) or branched or graft copolymers.

PEG is a preferred PAG, and is useful in biological applications because it has highly desirable properties and is generally regarded as safe (GRAS) by the Food and Drug Administration. PEG generally has the formula $H-(CH_2CH_2O)_n-H$, where n can range from about 2 to about 4000 or more, though the capping moieties may vary, e.g., mono-methoxy or di-hydroxy. PEG typically is colorless, odorless, water-soluble or water-miscible (depending on molecular weight), heat stable, chemically inert, hydrolytically stable, and generally nontoxic. PEG is also biocompatible, and typically does not produce an immune response in the body. Preferred PEG moieties include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more PEG subunits.

The PEG may be monodispersed, substantially monodispersed, purely monodispersed or substantially purely monodispersed (e.g., as previously described by the applicants in U.S. patent Ser. No. 09/873,731 and U.S. patent Ser. No. 09/873,797, both filed 4 Jun. 2001, the entire disclosures of which are incorporated herein by reference) or polydispersed. One advantage of using the relatively low molecular weight, monodispersed polymers is that they form easily defined conjugate molecules, which can facilitate both reproducible synthesis and FDA approval.

The PEG can be linear with a hydroxyl group at each terminus (before being conjugated to the remainder of the insulin compound). The PEG can also be an alkoxy PEG, such as methoxy-PEG (or mPEG), where one terminus is a relatively inert alkoxy group (e.g., linear or branched $OC_{1-6}$), while the other terminus is a hydroxyl group (that is coupled to the insulin compound).

The PEG can also be branched, which can in one embodiment be represented as $R(-PEG-_nOH)_m$ in which R represents a central (typically polyhydric) core agent such as pentaerythritol, sugar, lysine or glycerol, n represents the number of PEG subunits and can vary for each arm and is typically 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 and m represents the number of arms, and ranges from 2 to the maximum number of attachment sitesz on the core agent. Each branch can be the same or different and can be terminated, for example, with ethers and/or esters. The number of arms m can range from three to a hundred or more, and one or more of the terminal hydroxyl groups can be coupled to the remainder of the insulin compound, or otherwise subject to chemical modification.

Other branched PEGs include those represented by the formula $(CH_3O-PEG-)_pR-Z$, where p equals 2 or 3, R represents a central core such as lysine or glycerol, and Z represents a group such as carboxyl that is subject to ready chemical activation. Still another branched form, the pendant PEG, has reactive groups, such as carboxyls, along the PEG backbone rather than, or in addition to, the end of the PEG chains. Forked PEG can be represented by the formula $PEG(-LCHX_2)_n$, where L is a linking group and X is an activated terminal group.

7.2.3 Sugar Moieties

The modifying moieties described herein can include sugar moieties. In general, the sugar moiety is a carbohydrate product of at least one saccharose group. Representative sugar moieties include, but are not limited to, glycerol moieties, mono-, di-, tri-, and oligosaccharides, and polysaccharides such as starches, glycogen, cellulose and polysaccharide gums. Specific monosaccharides include $C_6$ and above (preferably $C_6$ to $C_8$) sugars such as glucose, fructose, mannose, galactose, ribose, and sedoheptulose; di- and trisaccharides include moieties having two or three monosaccharide units (preferably $C_5$ to $C_8$) such as sucrose, cellobiose, maltose, lactose, and raffinose. Conjugation using sugar moieties is described in U.S. Pat. Nos. 5,681,811, 5,438,040, and 5,359,030, the entire disclosures of which are incorporated herein by reference.

7.2.4 Polysorbate Moieties

The modifying moieties may include one or more polysorbate moieties. Examples include sorbitan esters, and polysorbate derivatized with polyoxyethylene. Conjugation using polysorbate moieties is described in U.S. Pat. Nos. 5,681,811, 5,438,040, and 5,359,030, the entire disclosures of which are incorporated herein by reference.

7.2.5 Biocompatible Water-Soluble Polycationic Moieties

In some embodiments, biocompatible water-soluble polycationic polymers can be used. Biocompatible water-soluble polycationic polymers include, for example, any modifying moiety having protonated heterocycles attached as pendant groups. "Water soluble" in this context means that the entire modifying moiety is soluble in aqueous solutions, such as buffered saline or buffered saline with small amounts of added organic solvents as cosolvents, at a temperature between 20 and 37° C. In some embodiments, the modifying moiety itself is not sufficiently soluble in aqueous solutions per se but is brought into solution by grafting with water-soluble polymers such as PEG chains. Examples include polyamines having amine groups on either the modifying moiety backbone or the modifying moiety side chains, such as poly-L-Lys and other positively charged polyamino acids of natural or synthetic amino acids or mixtures of amino acids, including poly(D-Lys), poly(ornithine), poly(Arg), and poly(histidine), and nonpeptide polyamines such as poly (aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly (aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan.

7.2.6 Other Hydrophilic Moieties

The modifying moieties may also include other hydrophilic polymers. Examples include poly(oxyethylated polyols) such as poly(oxyethylated glycerol), poly(oxyethylated sorbitol), and poly(oxyethylated glucose); poly(vinyl alcohol) ("PVA"); dextran; carbohydrate-based polymers and the like. The polymers can be homopolymers or random or block copolymers and terpolymers based on the monomers of the above polymers, linear chain or branched.

Specific examples of suitable additional polymers include, but are not limited to, poly(oxazoline), difunctional poly (acryloylmorpholine) ("PAcM"), and poly(vinylpyrrolidone) ("PVP"). PVP and poly(oxazoline) are well known polymers in the art and their preparation will be readily apparent to the skilled artisan. PAcM and its synthesis and use are described in U.S. Pat. No. 5,629,384 and U.S. Pat. No. 5,631,322, the disclosures of which are incorporated herein by reference in their entirety.

7.2.7 Bioadhesive Polyanionic Moieties

Certain hydrophilic polymers appear to have potentially useful bioadhesive properties. Examples of such polymers are found, for example, in U.S. Pat. No. 6,197,346, to Mathiowitz, et al. Those polymers containing carboxylic groups (e.g., poly(acrylic acid)) exhibit bioadhesive properties, and are also readily conjugated with the insulin compounds described herein. Rapidly bioerodible polymers that expose carboxylic acid groups on degradation, such as poly(lactide-co-glycolide), polyanhydrides, and polyorthoesters, are also bioadhesive polymers. These polymers can be used to deliver the insulin compounds to the gastrointestinal tract. As the polymers degrade, they can expose carboxylic acid groups to enable them to adhere strongly to the gastrointestinal tract, and can aid in the delivery of the insulin compound conjugates.

7.2.8 Lipophilic Moieties

In some embodiments, the modifying moieties include one or more lipophilic moieties. The lipophilic moiety may be various lipophilic moieties as will be understood by those skilled in the art including, but not limited to, alkyl moieties, alkenyl moieties, alkynyl moieties, aryl moieties, arylalkyl moieties, alkylaryl moieties, fatty acid moieties, adamantantyl, and cholesteryl, as well as lipophilic polymers and/or oligomers.

The alkyl moiety can be a saturated or unsaturated, linear, branched, or cyclic hydrocarbon chain. In some embodiments, the alkyl moiety has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more carbon atoms. Examples include saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. In other embodiments, the alkyl moiety is a lower alkyl moiety. In still other embodiments, the alkyl moiety is a $C_1$ to $C_3$ lower alkyl moiety. In some embodiments, the modifying moiety specifically does not consist of an alkyl moiety, or specifically does not consist of a lower alkyl moiety, or specifically does not consist of an alkane moiety, or specifically does not consist of a lower alkane moiety.

The alkyl groups can either be unsubstituted or substituted with one or more substituents, and such substituents preferably either do not interfere with the methods of synthesis of the conjugates or eliminate the biological activity of the conjugates. Potentially interfering functionality can be suitably blocked with a protecting group so as to render the functionality non-interfering. Each substituent may be optionally substituted with additional non-interfering substituents. The term "non-interfering" characterizes the substituents as not eliminating the feasibility of any reactions to be performed in accordance with the process of this invention.

The lipophilic moiety may be a fatty acid moiety, such as a natural or synthetic, saturated or unsaturated, linear or branched fatty acid moiety. In some embodiments, the fatty acid moiety has 2, 3, 4, 5, 6, 7, 8, 9, 10, 11, 12, 13, 14, 15, 16, 17, 18, 19, 20, 21, 22, 23, 24, or more carbon atoms. In some embodiments, the modifying moiety specifically does not consist of a fatty acid moiety; or specifically does not consist of a fatty acid moiety having 2, 3, 4, 5, 6, 7, 8, 9, 10, 11, 12, 13, 14, 15, 16, 17, 18, 19, 20, 21, 22, 23, 24 or more carbon atoms.

When the modifying moiety includes an aryl ring, the ring can be functionalized with a nucleophilic functional group (such as OH, or SH) that is positioned so that it can react in an intramolecular fashion with the carbamate moiety and assist in its hydrolysis. In some embodiments, the nucleophilic group is protected with a protecting group capable of being hydrolyzed or otherwise degraded in vivo, with the result being that when the protecting group is deprotected, hydrolysis of the conjugate, and resultant release of the parent insulin compound, is facilitated.

Other examples of suitable modifying moieties include —C(CH$_2$OH)$_3$; —CH(CH$_2$OH)$_2$; —C(CH$_3$)$_3$; —CH(CH$_3$)$_2$.

7.2.9 Amphiphilic Moieties

In some embodiments, the modifying moiety includes an amphiphilic moiety. Many polymers and oligomers are amphiphilic. These are often block co-polymers, branched copolymers or graft co-polymers that include hydrophilic and lipophilic moieties, which can be in the form of oligomers and/or polymers, such as linear chain, branched, or graft polymers or co-polymers.

The amphiphilic modifying moieties may include combinations of any of the lipophilic and hydrophilic moieties described herein. Such modifying moieties typically include at least one reactive functional group, for example, halo, hydroxyl, amine, thiol, sulfonic acid, carboxylic acid, isocyanate, epoxy, ester, and the like, which is often at a terminal end of the modifying moiety. These reactive functional groups can be used to attach a lipophilic linear or branched chain alkyl, alkenyl, alkynyl, arylalkyl, or alkylaryl group, or a lipophilic polymer or oligomer, thereby increasing the lipophilicity of the modifying moiety (and thereby rendering them generally amphiphilic).

The lipophilic groups can, for example, be derived from mono- or di-carboxylic acids, or where appropriate, reactive equivalents of carboxylic acids such as anhydrides or acid chlorides. Examples of suitable precursors for the lipophilic groups are acetic acid, propionic acid, butyric acid, valeric acid, isobutyric acid, trimethylacetic acid, caproic acid, caprylic acid, heptanoic acid, capric acid, pelargonic acid, lauric acid, myristic acid, palmitic acid, stearic acid, behenic acid, lignoceric acid, ceratic acid, montanoic acid, isostearic acid, isononanoic acid, 2-ethylhexanoic acid, oleic acid, ricinoleic acid, linoleic acid, linolenic acid, erucic acid, soybean fatty acid, linseed fatty acid, dehydrated castor fatty acid, tall oil fatty acid, tung oil fatty acid, sunflower fatty acid, safflower fatty acid, acrylic acid, methacrylic acid, maleic anhydride, orthophthalic anhydride, terephthalic acid, isophthalic acid, adipic acid, azelaic acid, sebacic acid, tetrahydrophthalic anhydride, hexahydrophthalic anhydride, succinic acid and polyolefin carboxylic acids.

The terminal lipophilic groups need not be equivalent, i.e., the resulting copolymers can include terminal lipophilic groups that are the same or different. The lipophilic groups can be derived from more than one mono or di-functional alkyl, alkenyl, alkynyl, cycloalkyl, arylalkyl or alkylaryl group as defined above.

7.2.10 PAG-alkyl Modifying Moieties

The modifying moiety may be a linear or branched polymeric moiety having one or more linear or branched PAG moieties and/or one or more linear or branched, substituted or unsubstituted alkyl moieties. In certain cases, such moieties are considered amphiphilic; however, the PAG and alkyl moieties may be varied to render such moieties more lipophilic or more hydrophilic. In certain embodiments, the modifying moiety specifically does not consist of an alkyl moiety and in other embodiments, the modifying moiety specifically does not consist of an alkane moiety.

The PAG moieties in some embodiments include 1, 2, 3, 4, 5, 6, 7, 8, 9, 10, 11, 12, 13, 14, 15, 16, 17, 18, 19, 20, 21, 22, 23, 24, or 25 PAG subunits arranged in linear or branched form. The PAG moieties in some embodiments include PEG, PPG and/or PBG subunits. The alkyl moieties in some embodiments preferably have 2, 3, 4, 5, 6, 7, 8, 9, 10, 11, 12, 13, 14, 15, 16, 17, 18, 19, or 20 carbon atoms. The alkyl moieties are preferably alkane moieties. The modifying moiety may include a capping moiety, such as —OCH$_3$. Further, the modifying moiety may include a hydrophobic group, such as a pivaloyl group.

In one embodiment, the modifying moiety has a formula:

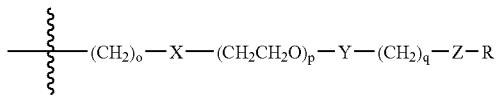

(Formula I)

where o, p and q are independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and at least one of o, p and q is at least 2. X, Y and Z are independently selected from —C—, —O—, —C(O)—, —C(O)O—, —OC(O)—, —NH—, —NHC(O)—, and —C(O)NH—, and R is H or an alkyl, preferably a lower alkyl, more preferably methyl. The variables o, p and q are preferably selected to yield a hydrophilic or amphiphilic modifying moiety, and are preferably selected in relation to the insulin compound to yield a hydrophilic or amphiphilic insulin compound conjugate, preferably a monoconjugate, diconjugate or triconjugate. In one preferred embodiment for an insulin compound conjugate which is to be used for basal insulin compound maintenance, o, p and q are selected to yield a PAG which is proximal to the insulin compound and an alkyl moiety which is distal to the insulin compound. Alternatively, O, P and Q may be selected to yield a PAG which is distal to the insulin compound and an alkyl which is proximal to the insulin. In an alternative embodiment, R is a pivaloyl group or an alkyl-pivaloyl group.

In a related embodiment, the modifying moiety has a formula:

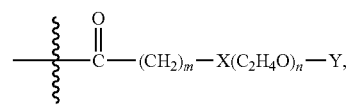

(Formula II)

where m is 1, 2, 3, 4, 5, 6, 7, 8, 9, 10, 11, 12, 13, 14, 15, 16, 17, 18, 19, 20, 21, 22, 23, 24, or 25 and n is from 2 to 100, preferably 2 to 50, more preferably 2, 3, 4, 5, 6, 7, 8, 9, 10, 11, 12, 13, 14, 15, 16, 17, 18, 19, 20, 21, 22, 23, 24 or 25, X is —C—, —O—, —C(O)—, —NH—, —NHC(O)—, or —C(O)NH—, and Y is lower alkyl or —H. X is preferably O and Y is preferably —CH$_3$. In some cases the carbonyl group (—C(O)—) may be absent, and the —(CH2)- moiety may be coupled to an available group on an amino acid, such as a hydroxyl group or a free carboxyllic acid group.

In a preferred embodiment, the modifying moiety has a structure selected from the following:

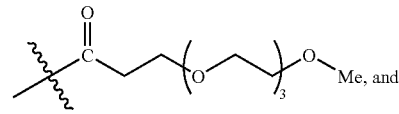

(when the immediately preceding modifying moiety is coupled to human insulin at B29, the resulting monoconjugate is referred to as IN105).

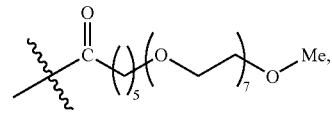

(when the immediately preceding modifying moiety is coupled to human insulin at B29, the resulting monoconjugate is referred to as HIM2). Any of the foregoing moieties may, for example, be coupled to human insulin at a nucleophilic residue, e.g., A1, B1 or B29. In some cases the carbonyl group (—C(O)—) may be absent or replaced with an alkyl moiety, preferably a lower alkyl moiety, and the —(CH$_2$)— moiety may be coupled to an available group on an amino acid, such as a hydroxyl group or a free carboxyllic acid group.

In another embodiment, the modifying moiety has a formula:

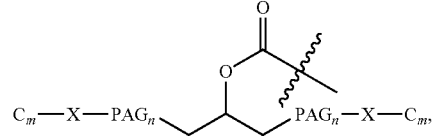

(Formula III)

where each C is independently selected and is an alkyl moiety having m carbons and m is 1, 2, 3, 4, 5, 6, 7, 8, 9, 10, 11, 12, 13, 14, 15, 16, 17, 18, 19, or 20; and each PAG is independently selected and is a PAG moiety having n subunits and n is 1, 2, 3, 4, 5, 6, 7, 8, 9, 10, 11, 12, 13, 14, 15, 16, 17, 18, 19, 20, 21, 22, 23, 24, or 25; each X is independently selected and is a linking moiety coupling PAG to C, and is preferably —C—, —O—, —C(O)—, —NH—, —NHC(O)—, or —C(O)NH—. In some embodiments the $C_m$—X moiety is absent, and the $PAG_n$ moiety is terminated with an —OH moiety or an —OCH$_3$ moiety. For example, the PAG may be methoxy-terminated or hydroxy-terminated PAG, having 1, 2, 3, 4, 5, 6, 7, 8, 9, 10, 11, 12, 13, 14, 15, 16, 17, 18, 19 or 20 PAG subunits, including PEG, PPG, and/or PBG subunits. In some cases the carbonyl group (—C(O)—) may be replaced with an alkyl moiety, preferably a lower alkyl moiety, which may be coupled to an available group on an amino acid, such as a hydroxyl group or a free carboxyllic acid group.

The modifying moiety may, for example, have a formula:

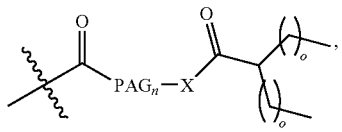

(Formula IV)

where each C is independently selected and is an alkyl moiety having m carbons and m is 1, 2, 3, 4, 5, 6, 7, 8, 9, 10, 11, 12, 13, 14, 15, 16, 17, 18, 19 or 20; and each PAG is independently selected and is a PAG moiety having n subunits and n is 1, 2, 3, 4, 5, 6, 7, 8, 9, 10, 11, 12, 13, 14, 15, 16, 17, 18, 19, 20, 21, 22, 23, 24 or 25; X is —O—, or —NH—; each o is independently selected and is 1, 2, 3, 4, 5, 6, 7, 8, 9, 10, 11, 12, 13, 14 or 15. For example, the PAG may have 1, 2, 3, 4, 5, 6, 7, 8, 9, 10, 11, 12, 13, 14, 15, 16, 17, 18, 19 or 20 PAG subunits, including PEG, PPG, and/or PBG subunits. In some cases the carbonyl group (—C(O)—) proximal to the point of attachment may be absent or replaced with an alkyl moiety, preferably a lower alkyl moiety, and the —(CH2)- moiety may be coupled to an available group on an amino acid, such as a hydroxyl group or a free carboxyllic acid group.

The modifying moiety may, for example, have a formula:

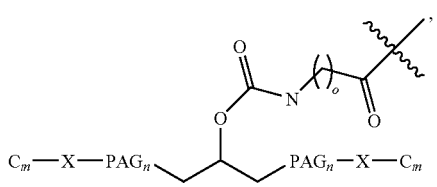

(Formula V)

where each C is independently selected and is an alkyl moiety having m carbons and m is 1, 2, 3, 4, 5, 6, 7, 8, 9, 10, 11, 12, 13, 14, 15, 16, 17, 18, 19 or 20; and each PAG is independently selected and is a PAG moiety having n subunits and n is 1, 2, 3, 4, 5, 6, 7, 8, 9, 10, 11, 12, 13, 14, 15, 16, 17, 18, 19, 20, 21, 22, 23, 24 or 25; each X is independently selected and is a linking moiety coupling PAG to C, and is preferably —C—, —O—, —C(O)—, —NH—, —NHC(O)—, or —C(O)NH—; each o is independently selected and is 1, 2, 3, 4, 5, 6, 7, 8, 9, 10, 11, 12, 13, 14 or 15. In some embodiments the Cm—X moiety is absent, and the $PAG_n$ moiety is terminated with an —OH moiety or an —OCH$_3$ moiety. For example, the PAG may be methoxy-terminated or hydroxy-terminated PAG, having 1, 2, 3, 4, 5, 6, 7, 8, 9, 10, 11, 12, 13, 14, 15, 16, 17, 18, 19 or 20 PAG subunits, including PEG, PPG, and/or PBG subunits. In some cases the carbonyl group (—C(O)—) proximal to the point of attachment may be absent, and the —(CH2)- moiety may be coupled to an available group on an amino acid, such as a hydroxyl group or a free carboxyllic acid group.

In another embodiment, the modifying moiety may have a formula:

  —X—R$^1$—Y—PAG-Z—R$^2$ (Formula VI)

where,

X, Y and Z are independently selected linking groups and each is optionally present, and X, when present, is coupled to the insulin compound by a covalent bond, at least one of R$^1$ and R$^2$ is present, and is lower alkyl and may optionally include a carbonyl group, R$^2$ is a capping group, such as —CH$_3$, —H, tosylate, or an activating group, and PAG is a linear or branched carbon chain incorporating one or more alkalene glycol moieties (i.e., oxyalkalene moieties), and optionally incorporating one or more additional moieties selected from the group consisting of —S—, —O—, —N—, and —C(O)—, and where the modifying moiety has a maximum number of 3, 4, 5, 6, 7, 8, 9, 10, 11, 12, 13, 14, 15, 16, 17, 18, 19, 20, 21, 22, 23, 24, or 25 heavy atoms.

In embodiments of the invention, any one or more of X, Y and Z may be absent. Further, when present, X, Y and/or Z may be independently selected from —C(O)—, —O—, —S—, —C— and —N—. In one embodiment, Z is —C(O)—. In another embodiment, Z is not present.

In some embodiments, R$^1$ is lower alkyl, and R$^2$ is not present. In other embodiments, R$^2$ is lower alkyl, and R$^1$ is not present.

In another embodiment, the modifying moiety may include a linear or branched, substituted carbon chain moiety having a backbone of 3, 4, 5, 6, 7, 8, 9, 10, 11, 12, 13, 14, 15, 16, 17, 18, 19, 20, 21, 22, 23, 24 or 25 atoms selected from the group consisting of —C—, —C—, —O—, =O, —S—, —N—, —Si—. The heavy atoms will typically include one or more carbon atoms and one or more non-carbon heavy atoms selected from the group consisting of —O—, —S—, —N—, and =O. The carbon atoms and non-carbon heavy atoms are typically present in a ratio of at least 1 carbon atom for every non-carbon heavy atom, preferably at least 2 carbon atoms for every non-carbon heavy atom, more preferably at least 3 carbon atoms for every non-carbon heavy atom. The carbon atoms and oxygen atoms are typically present in a ratio of at least 1 carbon atom for every oxygen atom, preferably at least 2 carbon atoms for every oxygen atom, more preferably at least 3 carbon atoms for every oxygen atom. The modifying moiety may include one or more capping groups, such as branched or linear $C_{1-6}$, branched or linear, or a carbonyl. The modifying moiety will typically include hydrogens, and one or more of the hydrogens may be substituted with a fluorine (which is a heavy atom but should not be counted as a heavy atom in the foregoing formula). The modifying moiety may in some cases specifically exclude unsubstituted alkyl moieties. The modifying moiety may, for example, be coupled to an available group on an amino acid, such as an amino group, a hydroxyl group or a free carboxyllic acid group the polypeptide, e.g., by a linking group, such as a carbamate, carbonate, ether, ester, amide, or secondary amine group, or by a disulfide bond. The molecules in the linking group are counted as part of the modifying moiety. In a preferred embodiment, the molecular weight of the modifying moiety is less than the molecular weight of the HIM2 modifying moiety.

The invention includes modifying moieties having a formula:

(Formula VII)

where n is 1, 2, 3 or 4, and m is 1, 2, 3, 4 or 5.

The invention includes modifying moieties having a formula:

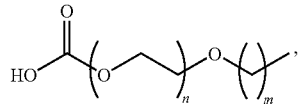
(Formula VIII)

where n is 1, 2, 3, 4 or 5, and m is 1, 2, 3 or 4.

The invention includes modifying moieties having a formula:

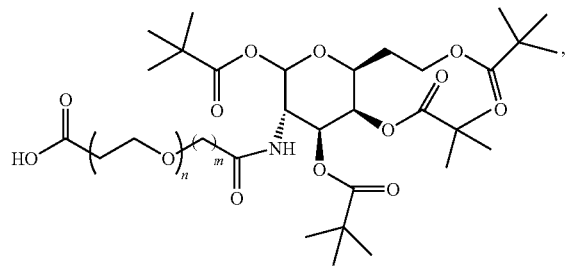
(Formula IX)

where m is 1, 2, 3, 4, 5, 6, 7, 8, 9, 10, 11, 12, 13, 14, 15, 16, 17, 18, 19 or 20 and n is 1, 2, 3, 4, 5, 6, 7, 8, 9, 10, 11, 12, 13, 14, 15, 16, 17, 18, 19 or 20.

The invention also includes modifying moieties having a formula:

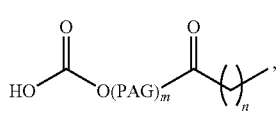
(Formula X)

where PAG is a PAG moiety having m subunits and m is 1, 2, 3, 4, 5, 6, 7, 8, 9, 10, 11, 12, 13, 14, 15, 16, 17, 18, 19 or 20 and n is 1, 2, 3, 4, 5, 6, 7, 8, 9, 10, 11, 12, 13, 14, 15, 16, 17, 18, 19 or 20.

Other preferred modifying moieties include:

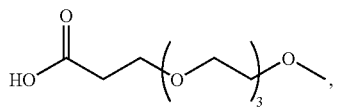

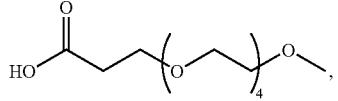

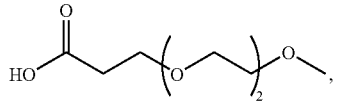

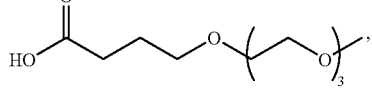

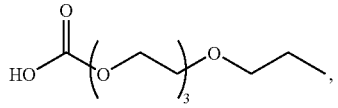

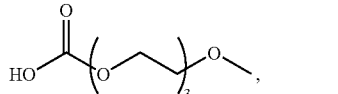

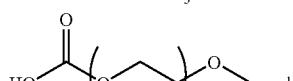, and

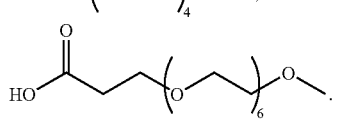.

The following modifying moieties can be particularly preferred for use in a basal insulin compound replacement regimen.

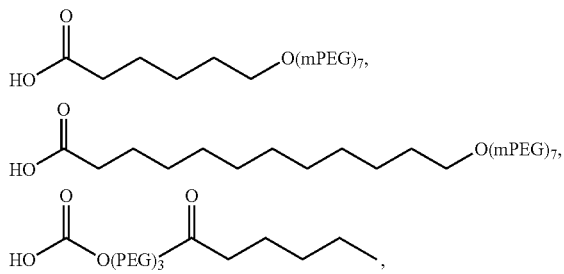

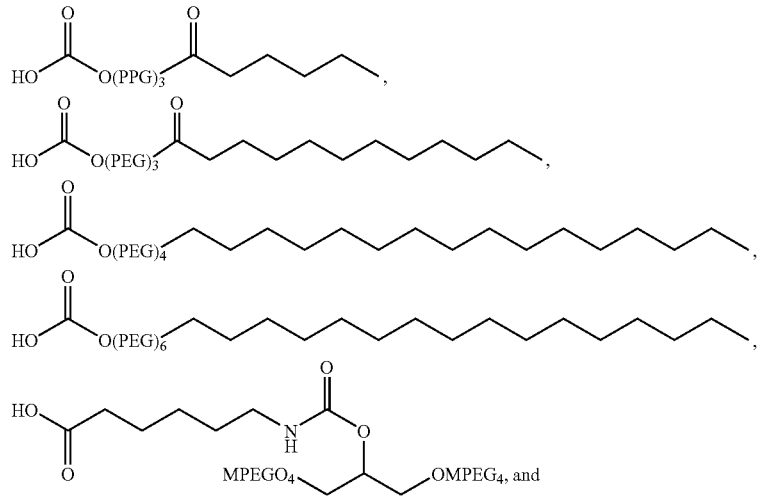

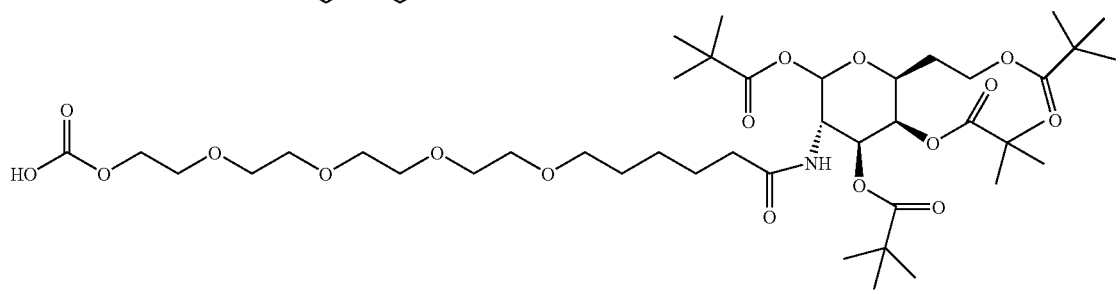

Still other modifying moieties include the following:
R—CH₂—CH₂—CH₂—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—CH₂—O—CH₂—O—CH₃,
R—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₃,
R—CH₂—CH₂—CH₂—CH₂—CH₂—CH₂—CH₂—CH₃,
R—CH₂—CH₂—CH₂—CH₂—CH₂—CH₂—CH₂—CH₂—O—CH₂—CH₂—CH₂—CH₂—CH₃,
R—CH₂—CH₂—CH₂—CH₂—CH₂—CH₂—CH₂—CH₂—O—CH₂—CH₂—CH₂—CH₃,
R—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—O—CH₂—CH₂—O—CH₃,
R—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—O—CH₂—CH₂—O—CH₂—CH₃,
R—CH₂—CH₂—CH₂—CH₂—CH₂—CH₂—CH₂—CH₂—O—CH₂—CH₂—O—CH₃,
R—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—O—CH₃,
R—CH₂—CH₂—CH₂—CH₂—CH₂—CH₂—CH₂—CH₃,
R—CH₂—CH₂—CH₂—CH₂—CH₂—CH₂—CH₂—CH₂—O—CH₂—CH₂—CH₂—CH₂—CH₃,
R—CH₂—O—CH₂—CH₂—CH₂—CH₂—CH₃, R—CH$_2$—CH$_2$—CH$_2$—CH$_2$—CH$_2$—CH$_2$—CH$_2$—CH$_2$—O—CH$_2$—CH$_2$—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—O—CH$_3$,
R—CH$_2$—CH$_2$—CH$_2$—CH$_2$—CH$_2$—CH$_2$—CH$_2$—CH$_2$—O—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—O—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—O—CH$_3$,
R—CH$_2$—CH$_2$—CH$_2$—CH$_2$—CH$_2$—CH$_2$—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_3$,
R—CH$_2$—CH$_2$—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—O—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—CH$_2$—O—CH$_3$,
R—CH$_2$—CH$_2$—CH$_2$—CH$_2$—CH$_2$—CH$_2$—CH$_2$—CH$_2$—O—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—O—CH$_2$—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—O—CH$_2$—CH$_2$—O—CH$_3$,
R—CH$_2$—CH$_2$—CH$_2$—CH$_2$—CH$_2$—CH$_2$—CH$_2$—CH$_2$—O—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_2$—CH$_2$—O—CH$_3$,
R—CH$_2$—CH$_2$—CH$_2$—CH$_2$—CH$_2$—CH$_2$—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_2$—CH$_3$,
R—CH$_2$—CH$_2$—CH$_2$—CH$_2$—CH$_2$—CH$_2$—CH$_2$—CH$_2$—O—CH$_3$,
R—CH$_2$—CH$_2$—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—O—CH$_2$—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—O—CH$_2$—CH$_2$—CH$_2$—CH$_2$—CH$_2$—CH$_3$,
R—CH$_2$—CH$_2$—CH$_2$—CH$_2$—CH$_2$—CH$_2$—CH$_2$—O—CH$_2$—CH$_2$—CH$_2$—CH$_2$—CH$_3$, R—CH$_2$—CH$_2$—CH$_2$—CH$_2$—CH$_2$—CH$_2$—O—CH$_2$—CH$_2$—CH$_2$—CH$_2$—CH$_3$,
R—CH$_2$—CH$_2$—CH$_2$—CH$_2$—CH$_2$—CH$_2$—O—CH$_2$—CH$_2$—CH$_2$—CH$_3$,
R—CH$_2$—CH$_2$—CH$_2$—CH$_2$—CH$_2$—CH$_2$—O—CH$_2$—CH$_2$—O—CH$_2$—CH$_2$—CH$_2$—CH$_3$,
R—CH$_2$—CH$_2$—CH$_2$—CH$_2$—CH$_2$—CH$_2$—O—CH$_2$—CH$_2$—O—CH$_2$—CH$_2$—CH$_3$,
R—CH$_2$—CH$_2$—CH$_2$—CH$_2$—CH$_2$—CH$_2$—O—CH$_2$—CH$_2$—O—CH$_2$—CH$_2$—O—CH$_3$,
R—CH$_2$—CH$_2$—CH$_2$—CH$_2$—CH$_2$—CH$_2$—O—CH$_2$—CH$_2$—CH$_3$,
R—CH$_2$—CH$_2$—CH$_2$—CH$_2$—CH$_2$—CH$_2$—O—CH$_2$—CH$_2$—O—CH$_2$—CH$_2$—CH$_3$,
R—CH$_2$—CH$_2$—CH$_2$—CH$_2$—CH$_2$—CH$_2$—O—CH$_2$—CH$_2$—O—CH$_2$—CH$_3$,
R—CH$_2$—CH$_2$—CH$_2$—CH$_2$—CH$_2$—CH$_2$—O—CH$_2$—CH$_2$—CH$_2$—O—,
R—CH$_2$—CH$_2$—CH$_2$—CH$_2$—CH$_2$—CH$_2$—O—CH$_2$—CH$_2$—CH$_3$,
R—CH$_2$—CH$_2$—CH$_2$—CH$_2$—CH$_2$—CH$_2$—O—CH$_2$—CH$_2$—CH$_2$—O—CH$_2$—CH$_3$,
R—CH$_2$—CH$_2$—CH$_2$—CH$_2$—CH$_2$—CH$_2$—O—CH$_2$—CH$_2$—O—CH$_3$,
R—CH$_2$—CH$_2$—CH$_2$—CH$_2$—CH$_2$—CH$_2$—O—CH$_2$—CH$_3$,
R—CH$_2$—CH$_2$—CH$_2$—CH$_2$—CH$_2$—CH$_2$—O—CH$_3$,
R—CH$_2$—CH$_2$—CH$_2$—CH$_2$—CH$_2$—CH$_2$—O—CH$_2$—CH$_3$,
R—CH$_2$—CH$_2$—CH$_2$—CH$_2$—CH$_2$—O—CH$_3$,
R—CH$_2$—CH$_2$—CH$_2$—CH$_2$—CH$_2$—CH$_3$,
R—CH$_2$—CH$_2$—CH$_2$—CH$_2$—CH$_2$—O—CH$_2$—CH$_2$—CH$_2$—CH$_2$—CH$_2$—CH$_3$,
R—CH$_2$—CH$_2$—CH$_2$—CH$_2$—CH$_2$—O—CH$_2$—CH$_2$—CH$_2$—CH$_2$—CH$_3$,
R—CH$_2$—CH$_2$—CH$_2$—CH$_2$—CH$_2$—O—CH$_2$—CH$_2$—CH$_2$—CH$_3$,
R—CH$_2$—CH$_2$—CH$_2$—CH$_2$—CH$_2$—O—CH$_2$—CH$_2$—CH$_2$—CH$_3$,
R—CH$_2$—CH$_2$—CH$_2$—CH$_2$—CH$_2$—O—CH$_2$—CH$_2$—O—CH$_2$—CH$_3$,
R—CH$_2$—CH$_2$—CH$_2$—CH$_2$—CH$_2$—O—CH$_2$—CH$_2$—O—CH$_3$,
R—CH$_2$—CH$_2$—CH$_2$—CH$_2$—CH$_2$—O—CH$_2$—CH$_2$—CH$_3$,
R—CH$_2$—CH$_2$—CH$_2$—CH$_2$—CH$_2$—O—CH$_2$—CH$_2$—O—CH$_2$—CH$_3$,
R—CH$_2$—CH$_2$—CH$_2$—CH$_2$—CH$_2$—O—CH$_2$—CH$_2$—O—CH$_3$,
R—CH$_2$—CH$_2$—CH$_2$—CH$_2$—CH$_2$—O—CH$_2$—CH$_3$,
R—CH$_2$—CH$_2$—CH$_2$—CH$_2$—CH$_2$—O—CH$_3$,
R—CH$_2$—CH$_2$—CH$_2$—CH$_2$—CH$_2$—O—CH$_2$—CH$_3$,
O—CH$_2$—CH$_2$—CH$_2$—CH$_2$—CH$_2$—CH$_3$, R—CH₂—CH₂—CH₂—CH₂—CH₂—O—CH₂—CH₂—O—CH₂—CH₂—CH₂—CH₂—CH₃,
R—CH₂—CH₂—CH₂—CH₂—CH₂—O—CH₂—CH₂—O—CH₂—CH₂—CH₂—CH₃,
R—CH₂—CH₂—CH₂—CH₂—CH₂—O—CH₂—CH₂—O—CH₂—CH₂—CH₂—O—CH₂—CH₃,
R—CH₂—CH₂—CH₂—CH₂—CH₂—O—CH₂—CH₂—O—CH₂—CH₂—CH₂—O—CH₃,
R—CH₂—CH₂—CH₂—CH₂—CH₂—O—CH₂—CH₂—O—CH₂—CH₂—CH₃,
R—CH₂—CH₂—CH₂—CH₂—CH₂—O—CH₂—CH₂—O—CH₂—CH₂—CH₃,
R—CH₂—CH₂—CH₂—CH₂—CH₂—O—CH₂—CH₂—O—CH₂—CH₂—O—CH₂—CH₂—CH₃,
R—CH₂—CH₂—CH₂—CH₂—CH₂—O—CH₂—CH₂—O—CH₂—CH₂—O—CH₂—CH₃,
R—CH₂—CH₂—CH₂—CH₂—CH₂—O—CH₂—CH₂—O—CH₂—CH₂—O—CH₃,
R—CH₂—CH₂—CH₂—CH₂—CH₂—O—CH₂—CH₂—O—CH₂—CH₃,
R—CH₂—CH₂—CH₂—CH₂—CH₂—O—CH₂—CH₂—O—CH₃,
R—CH₂—CH₂—CH₂—CH₂—CH₂—O—CH₂—CH₃,
R—CH₂—CH₂—CH₂—CH₂—CH₂—O—CH₃,
R—CH₂—CH₂—CH₂—CH₂—O—CH₂—CH₂—,
R—CH₂—CH₂—CH₂—CH₂—O—CH₂—CH₂—CH₂—CH₂—CH₂—CH₂—CH₂—CH₃,
R—CH₂—CH₂—CH₂—CH₂—O—CH₂—CH₂—CH₂—CH₂—CH₂—CH₂—CH₃,
R—CH₂—CH₂—CH₂—CH₂—O—CH₂—CH₂—CH₂—CH₂—CH₂—CH₃,
R—CH₂—CH₂—CH₂—CH₂—O—CH₂—CH₂—CH₂—CH₂—CH₃,
R—CH₂—CH₂—CH₂—CH₂—O—CH₂—CH₂—CH₂—CH₃,
R—CH₂—CH₂—CH₂—CH₂—O—CH₂—CH₂—CH₂—CH₃,
R—CH₂—CH₂—CH₂—CH₂—O—CH₂—CH₂—CH₃,
R—CH₂—CH₂—CH₂—CH₂—O—CH₂—CH₂—O—CH₂—CH₂—CH₂—CH₂—CH₂—CH₃,
R—CH₂—CH₂—CH₂—CH₂—O—CH₂—CH₂—O—CH₂—CH₂—CH₂—CH₂—CH₃,
R—CH₂—CH₂—CH₂—CH₂—O—CH₂—CH₂—O—CH₂—CH₂—CH₂—CH₃,
R—CH₂—CH₂—CH₂—CH₂—O—CH₂—CH₂—O—CH₂—CH₂—CH₃,
R—CH₂—CH₂—CH₂—CH₂—O—CH₂—CH₂—O—CH₂—CH₂—O—CH₃,
R—CH₂—CH₂—CH₂—CH₂—O—CH₂—CH₂—O—CH₂—CH₃,
R—CH₂—CH₂—CH₂—CH₂—O—CH₂—CH₂—O—CH₃,
R—CH₂—CH₂—CH₂—CH₂—O—CH₂—CH₃,
R—CH₂—CH₂—CH₂—CH₂—O—CH₂—CH₂—O—CH₂—CH₂—CH₂—CH₂—CH₂—CH₃,
R—CH₂—CH₂—CH₂—CH₂—O—CH₂—CH₂—O—CH₂—CH₂—CH₂—CH₂—CH₃,
R—CH₂—CH₂—CH₂—CH₂—O—CH₂—CH₂—O—CH₂—CH₂—CH₂—CH₃, R—CH₂—CH₂—CH₂—CH₂—O—CH₂—CH₂—O—CH₂—CH₂—CH₂—CH₃,
R—CH₂—CH₂—CH₂—CH₂—O—CH₂—CH₂—O—CH₂—CH₂—CH₃,
R—CH₂—CH₂—CH₂—CH₂—O—CH₂—CH₂—O—CH₂—CH₂—CH₃,
R—CH₂—CH₂—CH₂—CH₂—O—CH₂—CH₂—O—CH₂—CH₂—O—CH₂—CH₂—CH₂—CH₃,
R—CH₂—CH₂—CH₂—CH₂—O—CH₂—CH₂—O—CH₂—CH₂—CH₂—CH₃,
R—CH₂—CH₂—CH₂—CH₂—O—CH₂—CH₂—O—CH₂—CH₂—O—CH₂—CH₂—O—CH₃,
R—CH₂—CH₂—CH₂—CH₂—O—CH₂—CH₂—O—CH₂—CH₂—O—CH₂—CH₃,
R—CH₂—CH₂—CH₂—CH₂—O—CH₂—CH₂—O—CH₂—CH₂—O—CH₃,
R—CH₂—CH₂—CH₂—CH₂—O—CH₂—CH₂—O—CH₂—CH₃,
R—CH₂—CH₂—CH₂—CH₂—O—CH₂—CH₂—O—CH₃,
R—CH₂—CH₂—CH₂—CH₂—O—CH₂—CH₂—CH₂—CH₂—CH₂—CH₂—CH₃,
R—CH₂—CH₂—CH₂—O—CH₂—CH₂—CH₂—CH₂—CH₂—CH₂—CH₃,
R—CH₂—CH₂—CH₂—O—CH₂—CH₂—CH₂—CH₂—CH₂—CH₃,
R—CH₂—CH₂—CH₂—O—CH₂—CH₂—CH₂—CH₂—CH₃,
R—CH₂—CH₂—CH₂—O—CH₂—CH₂—CH₂—CH₂—CH₃,
R—CH₂—CH₂—CH₂—O—CH₂—CH₂—CH₂—CH₂—CH₃,
R—CH₂—CH₂—CH₂—O—CH₂—CH₂—CH₂—CH₃,
R—CH₂—CH₂—CH₂—O—CH₂—CH₂—CH₂—CH₃,
R—CH₂—CH₂—CH₂—O—CH₂—CH₂—CH₂—,
R—CH₂—CH₂—CH₂—O—CH₂—CH₂—CH₂—CH₂—,
R—CH₂—CH₂—CH₂—O—CH₂—CH₂—CH₂—CH₂—O—CH₂—CH₂—O—CH₂—,
R—CH₂—CH₂—CH₂—O—CH₂—CH₂—CH₂—O—CH₂—CH₃,
R—CH₂—CH₂—CH₂—O—CH₂—CH₂—CH₂—O—CH₃,
R—CH₂—CH₂—CH₂—O—CH₂—CH₂—CH₃,
R—CH₂—CH₂—CH₂—O—CH₂—CH₂—CH₂—O—CH₂—CH₂—CH₂—CH₂—CH₂—CH₂—CH₃,
R—CH₂—CH₂—CH₂—O—CH₂—CH₂—CH₂—O—CH₂—CH₂—CH₂—CH₂—CH₂—CH₃,
R—CH₂—CH₂—CH₂—O—CH₂—CH₂—CH₂—O—CH₂—CH₂—CH₂—CH₂—CH₃,
R—CH₂—CH₂—CH₂—O—CH₂—CH₂—CH₂—O—CH₂—CH₂—CH₂—CH₃,
R—CH₂—CH₂—CH₂—O—CH₂—CH₂—O—CH₂—CH₂—CH₂—CH₃, R—CH₂—CH₂—CH₂—O—CH₂—CH₂—CH₂—O—CH₂—CH₂—O—CH₂—CH₂—CH₃,
R—CH₂—CH₂—CH₂—O—CH₂—CH₂—CH₂—O—CH₂—CH₂—O—CH₂—CH₂—O—CH₃,
R—CH₂—CH₂—CH₂—O—CH₂—CH₂—CH₂—O—CH₂—CH₂—O—CH₂—CH₃,
R—CH₂—CH₂—CH₂—O—CH₂—CH₂—CH₂—O—CH₂—CH₂—O—CH₃,
R—CH₂—CH₂—CH₂—O—CH₂—CH₂—CH₂—O—CH₂—CH₃,
R—CH₂—CH₂—CH₂—O—CH₂—CH₂—CH₂—O—CH₃,
R—CH₂—CH₂—CH₂—O—CH₂—CH₂—CH₃,
R—CH₂—CH₂—CH₂—O—CH₂—CH₂—O—CH₂—CH₂—CH₂—CH₂—CH₂—CH₂—CH₂—CH₃,
R—CH₂—CH₂—CH₂—O—CH₂—CH₂—O—CH₂—CH₂—CH₂—CH₂—CH₂—CH₃,
R—CH₂—CH₂—CH₂—O—CH₂—CH₂—O—CH₂—CH₂—CH₂—CH₂—CH₃,
R—CH₂—CH₂—CH₂—O—CH₂—CH₂—O—CH₂—CH₂—CH₂—CH₃,
R—CH₂—CH₂—CH₂—O—CH₂—CH₂—O—CH₂—CH₂—CH₃,
R—CH₂—CH₂—CH₂—O—CH₂—CH₂—O—CH₂—CH₂—O—CH₂—CH₂—CH₂—CH₃,
R—CH₂—CH₂—CH₂—O—CH₂—CH₂—O—CH₂—CH₂—O—CH₂—CH₂—CH₃,
R—CH₂—CH₂—CH₂—O—CH₂—CH₂—O—CH₂—CH₂—O—CH₂—CH₂—O—CH₃,
R—CH₂—CH₂—CH₂—O—CH₂—CH₂—O—CH₂—CH₂—O—CH₂—CH₃,
R—CH₂—CH₂—CH₂—O—CH₂—CH₂—O—CH₂—CH₂—O—CH₃,
R—CH₂—CH₂—CH₂—O—CH₂—CH₂—O—CH₂—CH₃,
R—CH₂—CH₂—CH₂—O—CH₂—CH₂—O—CH₂—CH₃,
R—CH₂—CH₂—CH₂—O—CH₂—CH₂—O—CH₂—CH₂—O—CH₂—CH₂—CH₂—CH₂—CH₃,
R—CH₂—CH₂—CH₂—O—CH₂—CH₂—O—CH₂—CH₂—O—CH₂—CH₂—CH₂—CH₃,
R—CH₂—CH₂—CH₂—O—CH₂—CH₂—O—CH₂—CH₂—O—CH₂—CH₂—CH₃,
R—CH₂—CH₂—CH₂—O—CH₂—CH₂—O—CH₂—CH₂—O—CH₂—CH₂—O—CH₂—CH₃,
R—CH₂—CH₂—CH₂—O—CH₂—CH₂—O—CH₂—CH₂—O—CH₂—CH₂—O—CH₃,
R—CH₂—CH₂—CH₂—O—CH₂—CH₂—O—CH₂—CH₂—O—CH₂—CH₃,
R—CH₂—CH₂—CH₂—O—CH₂—CH₂—O—CH₂—CH₂—O—CH₃,
R—CH₂—CH₂—CH₂—O—CH₂—CH₂—O—CH₂—CH₃,
R—CH₂—CH₂—CH₂—O—CH₂—CH₂—O—CH₃,
R—CH₂—CH₂—CH₂—O—CH₂—CH₂—CH₂—CH₃,
R—CH₂—CH₂—CH₂—O—CH₂—CH₂—CH₃,
R—CH₂—CH₂—CH₂—O—CH₂—CH₃,
R—CH₂—CH₂—CH₂—O—CH₃,
R—CH₂—CH₂—O—CH₂—CH₂—CH₂—CH₂—CH₂—CH₂—CH₂—CH₂—CH₂—CH₂—CH₂—CH₂—CH₃,
R—CH₂—CH₂—O—CH₂—CH₂—CH₂—CH₂—CH₂—CH₂—CH₂—CH₂—CH₂—CH₂—CH₃,
R—CH₂—CH₂—O—CH₂—CH₂—CH₂—CH₂—CH₂—CH₂—CH₂—CH₂—CH₂—CH₃,
R—CH₂—CH₂—O—CH₂—CH₂—CH₂—CH₂—CH₂—CH₂—CH₂—CH₂—CH₃, R—CH₂—CH₂—O—CH₂—CH₂—CH₂—CH₂—CH₂—CH₂—CH₂—CH₃,
R—CH₂—CH₂—O—CH₂—CH₂—CH₂—CH₂—CH₂—CH₂—CH₃,
R—CH₂—CH₂—O—CH₂—CH₂—CH₂—CH₂—CH₂—CH₃,
R—CH₂—CH₂—O—CH₂—CH₂—CH₂—CH₂—CH₃,
R—CH₂—CH₂—O—CH₂—CH₂—CH₂—CH₂—O—CH₂—CH₂—CH₂—CH₂—CH₃,
R—CH₂—CH₂—O—CH₂—CH₂—CH₂—CH₂—O—CH₂—CH₂—CH₂—CH₃,
R—CH₂—CH₂—O—CH₂—CH₂—CH₂—CH₂—O—CH₂—CH₂—CH₃,
R—CH₂—CH₂—O—CH₂—CH₂—CH₂—CH₂—O—CH₃,
R—CH₂—CH₂—O—CH₂—CH₂—CH₂—CH₂—O—CH₂—CH₃,
R—CH₂—CH₂—O—CH₂—CH₂—CH₂—CH₂—O—CH₂—CH₂—O—CH₂—CH₃,
R—CH₂—CH₂—O—CH₂—CH₂—CH₂—CH₂—O—CH₂—CH₂—O—CH₃,
R—CH₂—CH₂—O—CH₂—CH₂—CH₂—CH₂—CH₃,
R—CH₂—CH₂—O—CH₂—CH₂—CH₂—CH₂—CH₃,
R—CH₂—CH₂—O—CH₂—CH₂—O—CH₂—CH₂—CH₂—CH₂—CH₂—CH₂—CH₃,
R—CH₂—CH₂—O—CH₂—CH₂—O—CH₂—CH₂—CH₂—CH₂—CH₂—CH₃,
R—CH₂—CH₂—O—CH₂—CH₂—O—CH₂—CH₂—CH₂—CH₂—CH₃,
R—CH₂—CH₂—O—CH₂—CH₂—O—CH₂—CH₂—CH₂—CH₃,
R—CH₂—CH₂—O—CH₂—CH₂—O—CH₂—CH₂—CH₃,
R—CH₂—CH₂—O—CH₂—CH₂—O—CH₂—CH₂—CH₃,
R—CH₂—CH₂—O—CH₂—CH₂—O—CH₂—CH₂—CH₃,
R—CH₂—CH₂—O—CH₂—CH₂—O—CH₂—CH₃, R—CH₂—CH₂—O—CH₂—CH₂—O—CH₂—CH₂—CH₂—O—CH₂—CH₂—CH₂—CH₂—CH₃,
R—CH₂—CH₂—O—CH₂—CH₂—O—CH₂—CH₂—CH₂—O—CH₂—CH₂—CH₂—CH₃,
R—CH₂—CH₂—O—CH₂—CH₂—O—CH₂—CH₂—CH₂—O—CH₂—CH₂—CH₃,
R—CH₂—CH₂—O—CH₂—CH₂—O—CH₂—CH₂—CH₂—O—CH₂—CH₂—O—CH₂—CH₃,
R—CH₂—CH₂—O—CH₂—CH₂—O—CH₂—CH₂—CH₂—O—CH₂—CH₂—O—CH₃,
R—CH₂—CH₂—O—CH₂—CH₂—O—CH₂—CH₂—CH₂—O—CH₂—CH₃,
R—CH₂—CH₂—O—CH₂—CH₂—O—CH₂—CH₂—CH₂—O—CH₃,
R—CH₂—CH₂—O—CH₂—CH₂—O—CH₂—CH₂—CH₃,
R—CH₂—CH₂—O—CH₂—CH₂—O—CH₂—CH₂—CH₃,
R—CH₂—CH₂—O—CH₂—CH₂—O—CH₂—CH₂—O—CH₂—CH₂—CH₂—CH₂—CH₂—CH₃,
R—CH₂—CH₂—O—CH₂—CH₂—O—CH₂—CH₂—O—CH₂—CH₂—CH₂—CH₂—CH₃,
R—CH₂—CH₂—O—CH₂—CH₂—O—CH₂—CH₂—O—CH₂—CH₂—CH₂—CH₃,
R—CH₂—CH₂—O—CH₂—CH₂—O—CH₂—CH₂—O—CH₂—CH₂—CH₃,
R—CH₂—CH₂—O—CH₂—CH₂—O—CH₂—CH₂—O—CH₂—CH₂—O—CH₂—CH₂—CH₃,
R—CH₂—CH₂—O—CH₂—CH₂—O—CH₂—CH₂—O—CH₂—CH₂—O—CH₂—CH₃,
R—CH₂—CH₂—O—CH₂—CH₂—O—CH₂—CH₂—O—CH₂—CH₂—O—CH₃,
R—CH₂—CH₂—O—CH₂—CH₂—O—CH₂—CH₂—O—CH₂—CH₃,
R—CH₂—CH₂—O—CH₂—CH₂—O—CH₂—CH₂—O—CH₃,
R—CH₂—CH₂—O—CH₂—CH₂—O—CH₂—CH₃,
R—CH₂—CH₂—O—CH₂—CH₂—O—CH₃,
R—CH₂—CH₂—O—CH₂—CH₂—CH₃,
R—CH₂—CH₂—O—CH₃,
R—CH₂—O—CH₂—CH₂—CH₂—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₂—O—CH₃,
R—CH₂—O—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—O—CH₂—CH₃,
R—CH₂—O—CH₂—CH₂—CH₂—CH₂—CH₂—CH₂—CH₂—O—CH₃,
R—CH₂—O—CH₂—CH₂—CH₂—CH₂—CH₂—CH₂—CH₂—CH₃,
R—CH₂—O—CH₂—CH₂—CH₂—CH₂—CH₂—CH₂—O—CH₂—CH₂—CH₃,
R—CH₂—O—CH₂—CH₂—CH₂—CH₂—CH₂—CH₂—O—CH₃,
R—CH₂—O—CH₂—CH₂—CH₂—CH₂—CH₂—CH₂—CH₂—O—CH₂—CH₂—CH₂—CH₂—CH₃, R—CH₂—O—CH₂—CH₂—CH₂—CH₂—CH₂—CH₂—O—CH₂—CH₂—CH₂—CH₃,
R—CH₂—O—CH₂—CH₂—CH₂—CH₂—CH₂—CH₂—O—CH₂—CH₂—CH₃,
R—CH₂—O—CH₂—CH₂—CH₂—CH₂—CH₂—O—CH₃,
R—CH₂—O—CH₂—CH₂—CH₂—CH₂—CH₂—CH₂—CH₂—CH₃,
R—CH₂—O—CH₂—CH₂—CH₂—CH₂—CH₂—O—CH₂—CH₂—CH₂—CH₂—CH₃,
R—CH₂—O—CH₂—CH₂—CH₂—CH₂—CH₂—O—CH₂—CH₂—CH₂—CH₃,
R—CH₂—O—CH₂—CH₂—CH₂—CH₂—CH₂—O—CH₂—CH₂—CH₂—O—CH₃,
R—CH₂—O—CH₂—CH₂—CH₂—CH₂—CH₂—O—CH₂—CH₂—CH₃,
R—CH₂—O—CH₂—CH₂—CH₂—CH₂—CH₂—O—CH₂—O—CH₂—CH₃,
R—CH₂—O—CH₂—CH₂—CH₂—CH₂—CH₂—O—CH₂—O—CH₂—CH₃,
R—CH₂—O—CH₂—CH₂—CH₂—CH₂—CH₂—CH₂—O—CH₂—CH₂—CH₃,
R—CH₂—O—CH₂—CH₂—CH₂—CH₂—O—CH₂—CH₃,
R—CH₂—O—CH₂—CH₂—CH₂—CH₂—O—CH₂—O—CH₂—CH₃,
R—CH₂—O—CH₂—CH₂—CH₂—CH₂—O—CH₂—O—CH₃,
R—CH₂—O—CH₂—CH₂—CH₂—CH₂—O—CH₂—CH₃,
R—CH₂—O—CH₂—CH₂—CH₂—CH₂—O—CH₃,
R—CH₂—O—CH₂—CH₂—CH₂—CH₂—CH₃,
R—CH₂—O—CH₂—CH₂—CH₂—O—CH₂—CH₂—CH₂—CH₂—CH₂—CH₂—CH₃,
R—CH₂—O—CH₂—CH₂—O—CH₂—CH₂—CH₂—CH₂—CH₂—CH₃,
R—CH₂—O—CH₂—CH₂—O—CH₂—CH₂—CH₂—CH₂—CH₃,
R—CH₂—O—CH₂—CH₂—O—CH₂—CH₂—CH₂—CH₃,
R—CH₂—O—CH₂—CH₂—O—CH₂—CH₂—CH₃,
R—CH₂—O—CH₂—CH₂—O—CH₂—CH₃,
R—CH₂—O—CH₂—CH₂—O—CH₂—CH₂—CH₃,
R—CH₂—O—CH₂—CH₂—O—CH₂—CH₂—CH₃, R—CH₂—O—CH₂—CH₂—CH₂—O—CH₂—CH₂—O—CH₂—CH₂—CH₂—CH₂—CH₂—CH₃,
R—CH₂—O—CH₂—CH₂—CH₂—O—CH₂—CH₂—O—CH₂—CH₂—CH₂—CH₂—CH₃,
R—CH₂—O—CH₂—CH₂—CH₂—O—CH₂—CH₂—O—CH₂—CH₂—CH₂—CH₃,
R—CH₂—O—CH₂—CH₂—CH₂—O—CH₂—CH₂—O—CH₂—CH₂—CH₃,
R—CH₂—O—CH₂—CH₂—CH₂—O—CH₂—CH₂—O—CH₂—CH₂—O—CH₂—CH₂—CH₃,
R—CH₂—O—CH₂—CH₂—CH₂—O—CH₂—CH₂—O—CH₂—CH₂—O—CH₂—CH₃,
R—CH₂—O—CH₂—CH₂—CH₂—O—CH₂—CH₂—O—CH₂—CH₂—O—CH₃,
R—CH₂—O—CH₂—CH₂—CH₂—O—CH₂—CH₂—O—CH₂—CH₃,
R—CH₂—O—CH₂—CH₂—CH₂—O—CH₂—CH₂—O—CH₃,
R—CH₂—O—CH₂—CH₂—CH₃,
R—CH₂—O—CH₂—CH₂—O—CH₂—CH₂—,
R—CH₂—O—CH₂—CH₂—O—CH₂—CH₂—CH₂—CH₂—CH₂—CH₂—CH₂—CH₂—CH₃,
R—CH₂—O—CH₂—CH₂—O—CH₂—CH₂—CH₂—CH₂—CH₂—CH₂—CH₂—CH₃,
R—CH₂—O—CH₂—CH₂—O—CH₂—CH₂—CH₂—CH₂—CH₂—CH₂—CH₃,
R—CH₂—O—CH₂—CH₂—O—CH₂—CH₂—CH₂—CH₂—CH₂—CH₃,
R—CH₂—O—CH₂—CH₂—O—CH₂—CH₂—CH₂—CH₂—CH₃,
R—CH₂—O—CH₂—CH₂—O—CH₂—CH₂—CH₂—CH₃,
R—CH₂—O—CH₂—CH₂—O—CH₂—CH₂—CH₂,
R—CH₂—O—CH₂—CH₂—O—CH₂—CH₂—CH₃,
R—CH₂—O—CH₂—CH₂—O—CH₂—CH₂—CH₂—CH₃,
R—CH₂—O—CH₂—CH₂—O—CH₂—CH₂—CH₃,
R—CH₂—O—CH₂—CH₂—O—CH₂—CH₂—CH₂—O—CH₂—CH₂—CH₂—CH₂—CH₂—CH₃,
R—CH₂—O—CH₂—CH₂—O—CH₂—CH₂—CH₂—O—CH₂—CH₂—CH₂—CH₂—CH₃,
R—CH₂—O—CH₂—CH₂—O—CH₂—CH₂—CH₂—O—CH₂—CH₂—CH₂—CH₃,
R—CH₂—O—CH₂—CH₂—O—CH₂—CH₂—CH₂—O—CH₂—CH₂—CH₃,
R—CH₂—O—CH₂—CH₂—O—CH₂—CH₂—CH₂—O—CH₂—CH₂—O—CH₂—CH₂—CH₃,
R—CH₂—O—CH₂—CH₂—O—CH₂—CH₂—CH₂—O—CH₂—CH₂—O—CH₂—CH₃,
R—CH₂—O—CH₂—CH₂—O—CH₂—CH₂—CH₂—O—CH₂—CH₂—O—CH₃,
R—CH₂—O—CH₂—CH₂—O—CH₂—CH₂—CH₂—O—CH₂—CH₃,
R—CH₂—O—CH₂—CH₂—O—CH₂—CH₂—CH₂—O—CH₃,
R—CH₂—O—CH₂—CH₂—O—CH₂—CH₂—CH₃,
R—CH₂—O—CH₂—CH₂—O—CH₂—CH₂—O—CH₂—CH₂—CH₂—CH₃,
R—CH₂—O—CH₂—CH₂—O—CH₂—CH₂—O—CH₂—CH₂—CH₂—CH₂—CH₃,
R—CH₂—O—CH₂—CH₂—O—CH₂—CH₂—O—CH₂—CH₂—CH₂—CH₂—CH₂—CH₃,
R—CH₂—O—CH₂—CH₂—O—CH₂—CH₂—O—CH₂—CH₂—CH₂—CH₃,
R—CH₂—O—CH₂—CH₂—O—CH₂—CH₂—O—CH₂—CH₂—CH₃,
R—CH₂—O—CH₂—CH₂—O—CH₂—CH₂—O—CH₂—CH₂—O—CH₂—CH₂—CH₃,
R—CH₂—O—CH₂—CH₂—O—CH₂—CH₂—O—CH₂—CH₂—O—CH₂—CH₃,
R—CH₂—O—CH₂—CH₂—O—CH₂—CH₂—O—CH₂—CH₂—O—CH₃,
R—CH₂—O—CH₂—CH₂—O—CH₂—CH₂—O—CH₂—CH₃,
R—CH₂—O—CH₂—CH₂—O—CH₂—CH₂—O—CH₃,
R—CH₂—O—CH₂—CH₂—O—CH₂—CH₂—O—CH₂—CH₂—O—CH₂—CH₂—O—CH₃,
R—CH₂—O—CH₂—CH₂—O—CH₂—CH₂—O—CH₃,
R—CH₂—O—CH₂—CH₃,
R—CH₂—O—CH₃, where R is —H, —OH, —CH₂OH, —CH(OH)₂, —C(O)OH, —CH₂C(O)OH, or an activating moiety, such as a carbodiimide, a mixed anhydride, or an N-hydroxysuccinimide, or a capping group. The invention also includes such moieties attached to a protein or peptide, preferably to an insulin compound. Specific conjugation strategies are discussed in more detail below. Of these modifying moieties, preferred moieties are those which render the insulin compound less lipophilic and/or more hydrophilic than the corresponding unconjugated insulin compound. The invention includes such modifying moieties further including one or more carbonyl groups, preferably 1, 2, 3, 4, or 5 carbonyl groups; the carbonyl groups may be inserted into the modifying moiety, or an —O— or —CH₂— may be replaced with a carbonyl. Further, any of the —CH₂— or —CH₃ moieties may be substituted, e.g., with a lower alkyl or an —OH or a PAG chain having 1, 2, 3, 4, or 5 PAG subunits, which may be the same or different. Preferably R is selected so that each —O— is separated from the nearest —O— by at least 2 carbons. The invention also includes branched modifying moieties in which two or more of the moieties are attached to a branching moiety, such as a lysine.

The pharmaceutical characteristics, such as hydrophilicity/lipophilicity of the conjugates according to embodiments of the invention, can be varied by, for example, adjusting the lipophilic and hydrophilic portions of the modifying moieties, e.g., by increasing or decreasing the number of PAG monomers, the type and length of alkyl chain, the nature of the PAG-peptide linkage, and the number of conjugation sites. The exact nature of the modifying moiety-peptide linkage can be varied such that it is stable and/or sensitive to hydrolysis at physiological pH or in plasma. The invention also includes any of the foregoing modifying moieties coupled to a polypeptide, preferably to insulin compound. Preferably, the modifying moiety renders the polypeptide more soluble than a corresponding unconjugated polypeptide, e.g., by a multiplier of at least 1.05, 1.25. 1.5, 1.75, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15. A modifying moiety of the invention may be coupled, for example, to an insulin compound, such as a human insulin, at any available point of attachment. A preferred point of attachment is a nucleophilic residue, e.g., A1, B1 and/or B29.

Moreover, it will be appreciated that one aspect of the invention includes novel modifying moieties, such as but not limited to the moieties of Formulas VII and VIII, in a carboxylic acid form. Further, where the modifying moiety includes a carboxyl group, it can be converted to a mixed anhydride and reacted with an amino group of a peptide to create a conjugate containing an amide bond. In another procedure, the carboxyl group can be treated with water-soluble carbodiimide and reacted with the peptide to produce conjugates containing amide bonds. Consequently, the invention includes activated forms of the novel moieties presented herein, such as activated forms of the modifying moieties of Formulas VII and VIII and other novel oligomers of the invention, such as carbodiimides, mixed anhydrides, or N-hydroxysuccinimides.

In some cases, the modifying moiety may be coupled to the polypeptide via an amino acid or series of 2 or more amino acids coupled to the C-terminus, or a side chain of the polypeptide. For example, in one embodiment, the modifying moiety is coupled at the —OH or —C(O)OH of Thr, and the mm-modified Thr is coupled to a polypeptide at the carboxy terminus. For example, in one embodiment, the modifying moiety is coupled at the —OH or —C(O)OH of Thr, and the modified Thr is coupled to the B29 amino acid (e.g., a B29 Lys for human insulin) of des-Thr insulin compound. In another example, the mm is coupled at the —OH or —C(O)OH of Thr of a terminal octapeptide from the insulin compound B-chain, and the mm-modified octapeptide is coupled to the B22 amino acid of des-octa insulin compound. Other variations will be apparent to one skilled in the art in light of this specification.

7.2.11 Salt-Forming Moieties

In some embodiments, the modifying moiety comprises a salt-forming moiety. The salt-forming moiety may be various suitable salt-forming moieties as will be understood by those skilled in the art including, but not limited to, carboxylate and ammonium. In some embodiments where the modifying moiety includes a salt forming moiety, the insulin compound conjugate is provided n salt form. In these embodiments, the insulin compound conjugate is associated with a suitable pharmaceutically acceptable counterion as will be understood by those skilled in the art including, but not limited to, negative ions such as chloro, bromo, iodo, phosphate, acetate, carbonate, sulfate, tosylate, and mesylate, or positive ions such as sodium, potassium, calcium, lithium, and ammonium.

The foregoing examples of modifying moieties are intended as illustrative and should not be taken as limiting in any way. One skilled in the art will recognize that suitable moieties for conjugation to achieve particular functionality will be possible within the bounds of the chemical conjugation mechanisms disclosed and claimed herein. Accordingly, additional moieties can be selected and used according to the principles as disclosed herein.

7.3 Conjugation Strategies

Factors such as the degree of conjugation with modifying moieties, selection of conjugation sites on the molecule and selection of modifying moieties may be varied to produce a conjugate which, for example, is less susceptible to in vivo degradation, and thus, has an increased plasma half life. For example, the insulin compounds may be modified to include a modifying moiety at one, two, three, four, five, or more sites on the insulin compound structure at appropriate attachment (i.e., modifying moiety conjugation) sites suitable for facilitating the association of a modifying moiety thereon. By way of example, such suitable conjugation sites may comprise an amino acid residue, such as a lysine amino acid residue.

In some embodiments, the insulin compound conjugates are monoconjugates. In other embodiments, the insulin compound conjugates are multi-conjugates, such as di-conjugates, tri-conjugates, tetra-conjugates, penta-conjugates and the like. The number of modifying moieties on the insulin compound is limited only by the number of conjugation sites on the insulin compound. In still other embodiments, the insulin compound conjugates are a mixture of mono-conjugates, di-conjugates, tri-conjugates, tetra-conjugates, and/or penta-conjugates.

Preferred conjugation strategies are those which yield a conjugate relating some or all of the bioactivity of the parent insulin compound.

Preferred attachment sites include A1 N-terminus, B1 N-terminus, and B29 lysine side chain. The B29 monoconjugate and B1, B29 diconjugates are highly preferred. Another preferred point of attachment is an amino functionality on a C-peptide component or a leader peptide component of the insulin compound.

One or more modifying moieties (i.e., a single or a plurality of modifying moiety structures) may be coupled to the insulin compound. The modifying moieties in the plurality are preferably the same. However, it is to be understood that the modifying moieties in the plurality may be different from one another, or, alternatively, some of the modifying moieties in the plurality may be the same and some may be different. When a plurality of modifying moieties are coupled to the insulin compound, it may be preferable to couple one or more of the modifying moieties to the insulin compound with hydrolyzable bonds and couple one or more of the modifying moieties to the insulin compound with non-hydrolyzable bonds. Alternatively, all of the bonds coupling the plurality of modifying moieties to the insulin compound may be hydrolyzable but have varying degrees of hydrolyzability such that, for example, one or more of the modifying moieties may be relatively rapidly removed from the insulin compound by hydrolysis in the body and one or more of the modifying moieties is more slowly removed from the insulin compound by hydrolysis in the body.

7.3.1 Coupling of Modifying Moiety to Insulin Compound

The modifying moiety is preferably covalently coupled to the insulin compound. More than one moiety on the modifying moiety may be covalently coupled to the insulin compound. Coupling may employ hydrolyzable or non-hydrolyzable bonds or mixtures of the two (i.e., different bonds at different conjugation sites).

In some embodiments, the insulin compound is coupled to the modifying moiety using a hydrolyzable bond (e.g., an ester, carbonate or hydrolyzable carbamate bond). Use of a hydrolyzable coupling will provide an insulin compound conjugate that acts as a prodrug. A prodrug approach may be desirable where the insulin compound-modifying moiety conjugate is inactive (i.e., the conjugate lacks the ability to affect the body through the insulin compound's primary mechanism of action), such as when the modifying moiety conjugation site is in a binding region of insulin compound. Use of a hydrolyzable coupling can also provide for a time-release or controlled-release effect, administering the insulin compound over a given time period as one or more modifying moieties are cleaved from their respective insulin compound-modifying moiety conjugates to provide the active drug.

In other embodiments, the insulin compound is coupled to the modifying moiety utilizing a non-hydrolyzable bond (e.g., a non-hydrolyzable carbamate, amide, or ether bond).

Use of a non-hydrolyzable bond may be preferable when it is desirable to allow therapeutically significant amounts of the insulin compound conjugate to circulate in the bloodstream for an extended period of time, e.g., at least 2 hours post administration. Bonds used to covalently couple the insulin compound to the modifying moiety in a non-hydrolyzable fashion are typically selected from the group consisting of covalent bond(s), ester moieties, carbonate moieties, carbamate moieties, amide moieties and secondary amine moieties.

The modifying moiety may be coupled to the insulin compound at various nucleophilic residues, including, but not limited to, nucleophilic hydroxyl functions and/or amino functions. Nucleophilic hydroxyl functions may be found, for example, at serine and/or tyrosine residues, and nucleophilic amino functions may be found, for example, at histidine and/or Lys residues, and/or at the one or more N-terminus of the A or B chains of the insulin compound. When a modifying moiety is coupled to the N-terminus of the natriuretic peptide, coupling preferably forms a secondary amine.

The modifying moiety may be coupled to the insulin compound at a free —SH group, e.g., by forming a thioester, thioether or sulfonate bond.

The modifying moiety may be coupled to the insulin compound via one or more amino groups. Examples in human insulin include the amino groups at A1, B1 and B29. In one embodiment, a single modifying moiety is coupled to a single amino group on the insulin compound. In another embodiment, two modifying moieties are each connected to a different amino group on the insulin compound. Where there are two modifying moieties coupled to two amino groups, a preferred arrangement is coupling of at B1 and B29. Where there are multiple polymers, the polymers may all be the same or one or more of the polymers may be different from the others. Various methods and types of coupling of polymers to insulin compounds are described in U.S. patent application Ser. No. 09/873,899, entitled "Mixtures of insulin compound conjugates comprising polyalkylene glycol, uses thereof, and methods of making same," filed on 4 Jun. 2001, the entire disclosure of which is incorporated herein by reference.

In still other embodiments, a partial prodrug approach may be used, in which a portion of the modifying moiety is hydrolyzed. For example, see U.S. Pat. No. 6,309,633 to Ekwuribe et al. (the entire disclosure of which is incorporated herein by reference), which describes modifying moieties having hydrophilic and lipophilic components in which the lipophilic components hydrolyze in vivo to yield a micropegylated conjugate.

7.3.2 Selection of Modifying Moiety and Properties of the Insulin-Compound Conjugate and Complexes Thereof The modifying moiety may be selected to provide desired attributes to the insulin compound conjugate and complexes thereof. Preferred modifying moieties are selected to render the insulin compound more soluble in an aqueous solution than the aqueous solubility of the insulin compound in the absence of the modifying moiety, preferably at least 1.05, 1.25, 1.5, 1.75, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 times more soluble than the parent insulin compound (i.e., the corresponding unconjugated insulin compound) in an aqueous solution. For example, uncomplexed native human insulin has a solubility of ~18 mg/ml at a pH of about 7.4. The inventors have surprisingly discovered a method of complexing human insulin conjugates that are more soluble than human insulin by a multiplier of at least 1.05, 1.25, 1.5, 1.75, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15.

In certain embodiments, the modifying moiety is selected to render an insulin compound conjugate having an aqueous solubility that exceeds 1 g/L, 2 g/L, 3 g/L, 4 g/L, 5 g/L, 20 g/L, 50 g/L, 100 g/L, or even 150 g/L at a pH ranging from about 4 to about 8, preferably a pH ranging from about 5 to about 7.5, ideally pH of about 7.4.

The insulin compound conjugate can be more orally bioavalable in a mammal than a scientifically acceptable control, such as a corresponding unconjugated insulin compound. In other embodiments, the insulin compound conjugate is more orally bioavalable in a human than a scientifically acceptable control, such as a corresponding unconjugated insulin compound. In certain embodiments, absorption of the insulin compound conjugate, e.g., as measured by plasma levels of the conjugate, is at least 1.5, 2, 2.5, 3, 3.5, or 4 times greater that the absorption of an unconjugated insulin compound control.

It will be appreciated that while in some aspects of the invention the modifying moiety is selected to render the insulin compound conjugate more soluble than a corresponding unconjugated insulin compound, in other aspects the modifying moiety may also or alternatively be selected to render the insulin compound conjugate equally or more hydrophilic than a corresponding unconjugated insulin compound. Further, the modifying moiety may be selected to render the insulin compound conjugate more amphiphilic than a corresponding unconjugated insulin compound.

In some embodiments, the cation-insulin compound conjugate complex is equally as water soluble or more water soluble than (a) a corresponding uncomplexed insulin compound conjugate, (b) a corresponding uncomplexed and unconjugated insulin compound, and/or (c) a corresponding complexed but unconjugated insulin compound.

In a preferred embodiment, the water solubility of the insulin compound conjugate is decreased by the addition of $Zn^{++}$. In some embodiments, the modifying moiety is selected to render the insulin compound conjugate equally or more soluble than a corresponding unconjugated insulin compound, and the water solubility of the insulin compound conjugate is decreased by the addition of zinc. In other embodiments, the modifying moiety is selected to render the insulin compound conjugate equally or more soluble than a corresponding unconjugated insulin compound, the water solubility of the insulin compound conjugate is decreased by the addition of zinc, and the water solubility of the cation complex is greater than the water solubility of insulin compound. In another aspect, the insulin compound conjugate is a fatty acid acylated insulin compound, the cation is zinc, and the water solubility of the insulin compound conjugate is decreased by the addition of the zinc. In still another embodiment, the insulin compound conjugate is a fatty acid acylated insulin compound that is equally or more water soluble than a corresponding unconjugated insulin compound, the cation is zinc, and the water solubility of the insulin compound conjugate is decreased by the addition of the zinc.

In certain preferred embodiments, the lipophilicity of the insulin compound conjugate relative to the corresponding parent insulin compound is 1 or less than 1. The relative lipophilicity of the insulin compound conjugate as compared to corresponding parent insulin compound ($k_{rel}$) can, for example, be determined as follows: $k_{rel}=(t_{conjugate}-t_0)/(t_{human}-t_0)$, where relative lipophilicity is measured on an LiChroSorb RP18 (5 µm, 250×4 mm) high performance liquid chromatography column by isocratic elution at 40° C. The following mixtures can be used as eluents: 0.1M sodium phosphate buffer at pH 7.3 containing 10% acetonitrile, and 50% acetonitrile in water. Void time ($t_0$) is identified by injecting 0.1 mM sodium nitrate. Retention time for human insulin is adjusted to at least 2 $t_0$ by varying the ration between the mixtures of (c)(i) and (c)(ii). Preferably, in these embodiments, the relative lipophilicity is about equal to 1 or is less than 1 or substantially less than 1. In a preferred embodiment, the insulin compound is human insulin, and the relative lipophilicity is less than 1. Preferably the relative lipophilicity is less than about 0.99, 0.98, 0.97, 0.96, 0.95, 0.94, 0.93, 0.92, 0.91, or 0.90. Discussion of techniques for determining solubility and/or lipophilicity of insulin and insulin conjugates are set forth in the U.S. Pat. No. 5,750,499 entitled "Acylated insulin" issued to Harelund et al., on 12 May 1998, the entire disclosure of which is incorporated herein by reference.

In one embodiment, the relative lipophilicity is as described above and the modifying moiety is a carbon chain having 5, 6, 7, 8, 9, 10, 11, 12, 13, 14, 15, 16, 17 or 18 carbons, wherein the carbon chain comprises 2, 3, 4, 5, 6, 7, 8, 9, or 10 oxy groups inserted therein. In another embodiment, the relative lipophilicity is as described above and the modifying moiety is a carbon chain having 5, 6, 7, 8, 9 or 10 carbons, wherein the carbon chain comprises 2, 3 or 4 oxy groups inserted therein. In a related embodiment, the relative lipophilicity is as described above and the modifying moiety comprises 2, 3, 4, 5, 6, 7, 8, 9 or 10 polyalkalene glycol units. In another related embodiment, relative lipophilicity is as described above and the modifying moiety comprises 1, 2 or 3 polyethylene glycol units and 1, 2 or 3 polypropylene glycol units.

7.4 Metal Cation Component and Characteristics of Complexes

The cation-insulin compound conjugate complexes include a metal cation. Suitable metal cations for use as the cation component include any metal cation capable of complexing, aggregating, or crystallizing with the insulin compound conjugate. It is preferred that the metal cation be complexed to the insulin compound conjugate. Single or multiple cations can be used. The cation is preferably not significantly oxidizing to the insulin compound conjugate, i.e., not oxidizing to the extent that the complexes are rendered useless for their intended purpose.

In some embodiments, the metal cation is biocompatible. A metal cation is biocompatible if the cation presents no unduly significant deleterious effects on the recipient's body, such as a significant immunological reaction at the injection site. However, it will be appreciated that in some circumstances, the risks of toxicity and other deleterious effects may be outweighed by the benefits of the cation-insulin compound conjugate composition, and therefore may be acceptable under such circumstances.

The suitability of metal cations for stabilizing biologically active agents and the ratio of metal cation to biologically active agent needed can be determined by one of ordinary skill in the art by performing a variety of tests for stability such as polyacrylamide gel electrophoresis, isoelectric focusing, reverse phase chromatography, and HPLC analysis on particles of metal cation-stabilized biologically active agents prior to and following particle size reduction and/or encapsulation.

The metal cation component suitably includes one or more monovalent, divalent, or trivalent metal cations, or combinations thereof In a preferred embodiment, the metal cation is a Group II or transition metal cation. Examples of suitable divalent cations include $Zn^{++}$, $Mn^{++}$, $Ca^{++}$, $Fe^{++}$, $Ni^{++}$, $Cu^{++}$, $Co^{++}$ and/or $Mg^{++}$. Where a monovalent cation is included, it is preferably $Na^+$, $Li^+$, or $K^+$. The cation is preferably added as a salt, such as a chloride or acetate salt, most preferred are $ZnCl_2$ and ZnAc.

The molar ratio of insulin compound conjugate to cation is typically between about 1:1 and about 1:100 preferably between about 1:2 and about 1:12, and more preferably between about 1:2 and about 1:7 or about 1:2, 1:3, 1:4, 1:5, 1:6, or 1:7. In a particular embodiment, $Zn^{++}$ is used as the cation component, is provided at a zinc cation component to insulin compound conjugate molar ratio of about 1:1 and about 1:100, preferably between about 1:2 and about 1:12, and more preferably between about 1:2 and about 1:7 or about 1:2, 1:3, 1:4, 1:5, 1:6, or 1:7.

The cation component is preferably greater than about 90% a single cation, such as $Zn^{++}$. Preferably, the cation is greater than about 95%, 99%, or 99.9% $Zn^{++}$.

Preferably resistance of the complexed insulin compound conjugate to chymotrypsin degradation is greater than the chymotrypsin degradation of the corresponding uncomplexed insulin compound conjugate. Preferably resistance of the complexed insulin compound conjugate to chymotrypsin degradation is greater than the chymotrypsin degradation of the corresponding complexed but unconjugated insulin compound.

The complexed insulin compound conjugate can be more orally bioavalable in a mammal than a scientifically acceptable control, such as a corresponding uncomplexed insulin compound conjugate. In other embodiments, the complexed insulin compound conjugate is more orally bioavalable in a human than a scientifically acceptable control, such as a corresponding uncomplexed insulin compound conjugate. In certain embodiments, absorption of the complexed insulin compound conjugate, e.g., as measured by plasma levels of the conjugate, is at least 1.5, 2, 2.5, 3, 3.5, or 4 times greater that the absorption of an uncomplexed insulin compound conjugate.

The complexed insulin compound conjugate can be more orally bioavalable in a mammal than a scientifically acceptable control, such as a corresponding complexed but unconjugated insulin compound. In other embodiments, the complexed insulin compound conjugate is more orally bioavalable in a human than a scientifically acceptable control, such as a corresponding complexed but unconjugated insulin compound. In certain embodiments, absorption of the complexed insulin compound conjugate, e.g., as measured by plasma levels of the conjugate, is at least 1.5, 2, 2.5, 3, 3.5, or 4 times greater that the absorption of an complexed but unconjugated insulin compound.

7.5 Complexing Agents

In some embodiments, the cation-insulin compound conjugatecompositions include one or more complexing agents. Examples of complexing agents suitable for use in the present invention include protamines, surfen, globin proteins, spermine, spermidine albumin, amino acids, carboxyllic acids; polycationic polymer compounds, cationic polypeptides, anionic polypeptides, nucleotides, and antisense. See Brange, J., Galenics of Insulin compound, Springer-Verlag, Berlin Heidelberg (1987), the entire disclosure of which is incorporated herein by reference. The suitability of complexing agents for stabilizing the compositions can be determined by one of ordinary skill in the art in the light of the present disclosure. In some embodiments, the cation-insulin compound conjugatecompositions specifically exclude or are substantially devoid of a complexing agent.

A preferred complexing agent is protamine. In a solid form, the protamine will preferably be present in about 3:1 to about 1:3 molar ratio of insulin compound to protamine, more preferably about 2:1 to about 1:2 molar ratio, ideally about 1:1 molar ratio. In some embodiments, the cation-insulin compound conjugatecompositions specifically exclude or are substantially devoid of protamine.

Amino acids may also be used as complexing agents, e.g., glycine, alanine, valine, leucine, isoleucine, serine threonine, phenyl alanine, proline, tryptophan, asparagine, glutamic acid, and histidine, and oligopeptides, such as diglycine.

Carboxylic acids are also suitable for use as complexing agents; examples include acetic acid, and hydroxycarboxylic acids, such as citric acid, 3-hydroxybutyric acid, and lactic acid.

7.6 Stabilizing Agents

In some embodiments, the cation-insulin compound conjugate compositions include one or more stabilizing agents. Preferred stabilizing agents include phenolic compounds and aromatic compounds. Preferred phenolic compounds are phenol, m-cresol and m-paraben or mixtures thereof. The stabilizing agent may be provided in any amount that improves stability of the cation-insulin compound conjugate compositions relative to a scientifically acceptable control, such as a corresponding cation-insulin compound conjugate composition in the absence of the stabilizing agent.

7.7 Presentation of Complexes

The complexes may be provided as a dry solid, such as a substantially pure powder of cation-insulin compound conjugate, or a powder including a cation-insulin compound conjugate solid along with other pharmaceutically acceptable components. The complexes may also be provided in a dissolved state in aqueous or organic medium, and/or as undissolved solids in such mediums.

7.7.1 Solid Compositions

The cation-insulin compound conjugate complex may be provided as a solid. The solid may, for example be in a dried state or in an undissolved state in an aqueous solution, organic solvent, emulsion, microemulsion, or other non-dried form.

In one embodiment, the cation-insulin compound conjugate complex is provided as a pure processed solid composition. In a pure processed solid composition, the molar ratio of insulin compound conjugate to cation is typically about 3:4 to about 3:0.5 (insulin compound conjugate:cation), about 3:3.5 to about 3:1, or ideally about 3:1.

In a processed pure solid T-type composition (with cation, insulin compound conjugate and without protamine), the molar ratio of insulin compound conjugate to cation is typically about is typically about 3:4 to about 3:0.5 (insulin compound conjugate:cation), about 3:3.5 to about 3:1, or ideally about 3:1. In a processed pure solid T-type protamine composition (with cation, insulin compound conjugate and protamine), the molar ratio of insulin compound conjugate to cation is typically about 3:6 to about 3:0.5 (insulin compound conjugate:cation), about 3:5 to about 3:1, or ideally about 3:2.

In a processed pure solid R-type (lente) composition (with cation, insulin compound and stabilizing compound (e.g., a phenolic compound), and without protamine), the molar ratio of insulin compound conjugate to cation can typically range from about 3:4.5 to about 3:0.9, preferably about 3:3.9 to about 3:2.4. In a processed pure solid R-type (ultralente) composition (with cation, insulin compound and stabilizing compound (e.g., a phenolic compound), and without protamine), the molar ratio of insulin compound conjugate to cation can typically range from about 3:12 to greater than about 3:4.5, preferably about 3:9 to about 3:4.8, more preferably about 3:6 to about 3:5.4. In a processed pure solid R-type protamine composition (with cation, insulin compound and stabilizing compound (e.g., a phenolic compound), and protamine), the molar ratio of insulin compound conjugate to cation can typically range from about 3:12 to about 3:3, preferably about 3:9 to about 3:4.5, more preferably about 3:6.9 to about 3:5.4.

For a monovalent cation, such as $Na^+$, the solid would be expected to have an insulin compound conjugate to cation ratio of about 3:6 to about 3:3.

Solid compositions of the invention may, for example, include compositions, such as powders, including insulin compound conjugates and/or cation-insulin compound conjugate complexes of the invention. Preferably the solid compositions are provided at a pharmaceutically acceptable level of purity, i.e., free of contaminants which would unacceptably diminish the suitability of the compositions for use in humans.

In some embodiments, compositions are provided in which the cation-insulin compound conjugate component is greater than about 90% crystalline, preferably greater than about 95% crystalline, more preferably greater than about 99% crystalline. In other embodiments, compositions are provided in which the cation-insulin compound conjugate component is greater than about 90% amorphous solids, preferably greater than about 95% amorphous solids, more preferably greater than about 99% amorphous solids.

In still other embodiments, compositions are provided in which the cation-insulin compound conjugate component is present in a mixture of amorphous solids and crystalline solids. For example, the ratio of amorphous solid to crystalline solid may be from about 1:10 to about 10:1, or about 1:9 to about 9:1, or about 1:8 to about 8:1, or about 1:7 to about 7:1, or about 1:6 to about 6:1, or about 1:5 to about 5:1, or about 1:4 to about 4:1, or about 1:3 to about 3:1, or about 1:2 to about 2:1, or about 1:1.

Furthermore, compositions can be provided using mixtures of cation-insulin compound solids having different insulin compounds, such as a solid including native insulin compound with a solid including insulin compound conjugates, or solids including one insulin compound conjugate with a solid including a different insulin compound conjugate.

Moreover, the solid type and insulin compound/insulin compound conjugate component may all vary. For example, compositions can be provided which include Zn-insulin compound crystals using native insulin compound and amorphous insulin compound conjugates, or compositions can be provided which include amorphous Zn-insulin compound solids using native insulin compound and crystalline Zn-insulin compound conjugates. Such mixtures may be used to achieve variations in physical characteristics, such as dissolution profile and/or variations in pharmacokinetic profile.

The average particle size of the solids are preferably in the range of about 0.1 to about 100 microns, more preferably 1-50 microns, still more preferably 1-25 microns, ideally 1-15 microns. Small particle sizes may be obtained by microcrystallization conditions, spray drying, milling, vacuum drying, freeze drying and the like.

In one embodiment the composition, when dried, contains greater than about 96% w/w insulin compound conjugate and from about 0.05, 0.1, 0.15, or 0.2 to about 4% w/w zinc. In another embodiment the composition, when dried, contains greater than about 91% w/w insulin compound conjugate, from about 0.05, 0.1, 0.15, or 0.2 to about 4% w/w zinc, and from about 0.2 to about 5% w/w phenol. In yet another embodiment the composition, when dried, contains greater than about 82% w/w insulin compound conjugate, from about 0.05, 0.1, 0.15, or 0.2 to about 4% w/w zinc, from about 0.2 to about 14% w/w protamine. In yet another embodiment the composition, when dried, contains greater than about 71% w/w insulin compound conjugate, from about 0.05, 0.1, 0.15, or 0.2 to about 4% w/w zinc, from about 0.2 to about 14% w/w protamine, and from about 0.2 to about 15% w/w phenol.

In another embodiment the composition, when dried, includes from about 0.1 to about 2% w/w $Zn^{++}$, and from about 0.08 to about 1% w/w phenol, preferably from about 0.5 to about 1.3% w/w $Zn^{++}$, and from about 0.1 to about 0.7% w/w phenol, more preferably from greater than or equal to 1 to about 3.5% w/w $Zn^{++}$, and from about 0.1 to about 3% w/w phenol, and still more preferably from greater than or equal to 1.3 to about 2.2% w/w $Zn^{++}$, and from about 0.4 to about 2% w/w phenol.

The complexes can be provided in a lente-type preparation. For example, in a preferred dried lente-type preparation, Zn is provided in an amount ranging from about 0.1 to about 2% w/w and phenol is present in an amount ranging from about 0.08 to about 1% w/w, with the remaining % w/w being insulin compound conjugate. Ideally, for a dried lente-type preparation, Zn is provided in an amount ranging from about 0.5 to about 1.3% w/w and phenol is present in an amount ranging from about 0.1 to about 0.7% w/w, with the remaining % w/w being insulin compound conjugate.

The complexes can be provided in an ultralente-type preparation. For example, in a preferred dried ultralente-type preparation, Zn is provided in an amount ranging from greater than or equal to 1 to about 3.5% w/w, and phenol is present in an amount ranging from about 0.1 to about 3% w/w, with the remaining % w/w being insulin compound conjugate. Ideally, for a dried ultralente-type preparation, Zn is provided in an amount ranging from greater than or equal to 1.3 to about 2.2% w/w, and phenol is present in an amount ranging from about 0.4 to about 2% w/w, with the remaining % w/w being insulin compound conjugate.

7.7.2 Liquid Compositions

The cation-insulin compound conjugate complexes may be provided as components undissolved components of a liquid. For example, the liquid may be an aqueous solution including a cation-insulin compound conjugate as a precipitate, or the cation-insulin compound conjugate may be provided as a component of a suspension, emulsion or microemulsion. The liquid may also include dissolved components or complexes, along with the undissolved components.

7.7.3 Mixtures and Co-Crystals

The compositions of the invention may, for example, include complex mixtures, solid mixtures, hybrid complexes and co-crystals.

Thus, for example, the invention provides compositions which include two or more insulin compound conjugates and/or unconjugated insulin compounds. Further, where the compositions include solids, the solids may have different forms. Thus, for example, on solid may be crystalline and another solid may be an amorphous solid. As noted elsewhere, the solids may be provided in a dried form or may be provided as solid components of a liquid mixture. In a preferred embodiment, the mixture of the invention includes two or more different insulin compound conjugates, and the different insulin compound conjugates have different solubilities. In one embodiment, one of the complexes comprises a lipophilic insulin compound conjugate and the other comprises a hydrophilic insulin compound conjugate. In still another embodiment, the complexes may include different insulin compound conjugates, where one ore more of the complexes has a circulation half-life of from about 1 to about 4 hours, and one or more the complexes has a circulation half-life that is significantly greater than the circulation half-life of the first complex. In a related embodiment, one of the complexes has a rapid-acting profile and another of the complexes has a medium-to-long acting profile. Furthermore, one of the complexes may have profile suitable for basal insulin compound control while another has a profile suitable for post-prandial glucose control. Preferred mixtures are mixtures of HIM2 and insulin, mixtures of HIM2 and IN105, mixtures of IN105 and insulin compound, mixtures of IN105 and fatty acid acylated insulin, mixtures of HIM2 and fatty acid acylated insulin. Suitable fatty acid acylated insulins are described in the following U.S. patents, the entire disclosures of which are incorporated herein by reference: U.S. Pat. No. 6,531,448, entitled "Insoluble compositions for controlling blood glucose," issued 11 Mar. 2003; U.S. Pat. No. RE37,971, entitled "Selective acylation of epsilon-amino groups," issued 28 Jan. 2003; U.S. Pat. No. 6,465,426, entitled "Insoluble insulin compositions," issued 15 Oct. 2002; U.S. Pat. No. 6,444,641, entitled "Fatty acid-acylated insulin analogs." issued 3 Sep. 2002; U.S. Pat. No. 6,335,316, entitled "Method for administering acylated insulin," issued 1 Jan. 2002; U.S. Pat. No. 6,268,335, entitled "Insoluble insulin compositions," issued 31 Jul. 2001; U.S. Pat. No. 6,051,551, entitled "Method for administering acylated insulin," issued 18 Apr. 2000; U.S. Pat. No. 5,922,675, entitled "Acylated Insulin Analogs," issued 13 Jul. 1999; U.S. Pat. No. 5,700,904, entitled "Preparation of an acylated protein powder," issued 23 Dec. 1997; U.S. Pat. No. 5,693,609, entitled "Acylated insulin analogs Granted," issued 2 Dec. 1997; U.S. Pat. No. 5,646,242, entitled "Selective acylation of epsilon-amino groups," issue 8 Jul. 1997; U.S. Pat. No. 5,631,347, entitled "Reducing gelation of a fatty acid-acylated protein," issued 20 May 1997; U.S. Pat. No. 6,451,974, entitled "Method of acylating peptides and novel acylating agents," issued 17 Sep. 2002; U.S. Pat. No. 6,011,007, entitled "Acylated insulin," issued 4 Jan. 2000; U.S. Pat. No. 5,750,497, entitled "Acylated insulin Granted: 12 May 1998; U.S. Pat. No. 5,905,140, entitled "Selective acylation method," issued May 18, 1999; U.S. Pat. No. 6,620,780, entitled "Insulin derivatives," issued Sep. 16, 2003; U.S. Pat. No. 6,251,856, entitled "Insulin derivatives," issued Jun. 26, 2001; U.S. Pat. No. 6,211,144, entitled "Stable concentrated insulin preparations for pulmonary delivery," issued Apr. 3, 2001; U.S. Pat. No. 6,310,038, entitled "Pulmonary insulin crystals," issued Oct. 30, 2001; and U.S. Pat. No. 6,174,856, entitled "Stabilized insulin compositions," issued Jan. 16, 2001. Especially preferred mono-fatty acid acylated insulins having 12, 13, 14, 15, or 16-carbon fatty acids covalently bound to Lys(B29) of human insulin.

In one embodiment, the invention provides a co-crystal having two different insulin compounds and/or insulin compound conjugates. Preferably the co-crystal exhibits one or more of the following characteristics: substantially homogenous dissolution, a single in vivo dissolution curve, and/or a single peak pharmacodynamic profile. Preferred co-crystals are co-crystals of HIM2 and insulin, co-crystals of HIM2 and IN105, co-crystals of IN105 and insulin compound.

In one embodiment, the co-crystal includes human insulin, and co-crystallization with human insulin reduces the solubility of the crystal relative to the solubility of a corresponding crystal of the insulin compound conjugate. In another embodiment, the co-crystal includes human insulin, and co-crystallization with human insulin decreases the solubility of the crystal relative to the solubility of a corresponding crystal of the insulin compound conjugate.

In another embodiment, the co-crystal includes a rapid acting, rapid clearing, and/or highly potent insulin compound conjugate, and a long-acting, slow clearing, and/or poorly potent insulin compound conjugate. Preferably the co-crystal has a PK/PD profile suitable for post-prandial glucose control or for overnight basal insulin compound control.

In another embodiment, the invention provides a mixture or co-crystal in which an insulin compound conjugate is included with human insulin or lyspro insulin. The mixtures of the invention may include two different insulin compound conjugates. The mixtures may include an insulin compound conjugate and an unconjugated insulin compound. The mixtures may include different insulin compound conjugates with different insulin compounds.

Further, the invention provides complexes having two different insulin compound conjugates and/or an insulin compound conjugate and an unconjugated insulin compound. The invention provides hybrid co-crystals of two, three or more different insulin compound conjugates. The invention provides a complex having an insulin compound conjugate with an unconjugated insulin compound. The invention provides a co-crustal with two or more different hydrophilic insulin compound conjugates; two or more different hydrophobic insulin compound conjugates; two or more different amphiphilic insulin compound conjugates; a hydrophilic insulin compound conjugate and a lipophilic insulin compound conjugate; a hydrophilic insulin compound conjugate and an unconjugated insulin compound; HIM2 together with an unconjugated insulin compound; IN105 together with an unconjugated insulin compound; HIM2 together with IN105; HIM2 together with insulin compound and IN105; and other combinations of the foregoing elements. As mentioned elsewhere, the complexes may be provided as dried solids, as dissolved complexes in solution and/or as undissolved complexes in solution. Various combinations may, for example, be employed to provide a complex or co-crystal having an extended profile.

7.8 Solubility of Complexes of the Invention

Preferably the aqueous solubility of the cation-insulin compound conjugate complex at a pH of about 7.4 is from about 1/15, 1/14, 1/13, 1/12, 1/11, 1/10, 1/9, 1/8, 1/7, 1/6, 1/5 up to about 0, 1, 2, 3, 4, 5, 6, 7, 8, 9, or <10 times the aqueous solubility of the uncomplexed insulin compound conjugate. Any combination of the foregoing upper and lower limits is within the scope of the invention. However, a preferred range is from about 1/15 to <5, more preferred is about 1/10 to about 2, ideal is about 1/10 to <0. In a particularly surprising aspect of the invention, the aqueous solubility of the cation-insulin compound conjugate in solution at a pH of about 7.4 is often substantially less than the aqueous solubility of the insulin compound conjugate in solution at a pH of about 7.4. However, it will be appreciated that in certain embodiments, the aqueous solubility of the cation-insulin compound conjugate in solution at a pH of about 7.4 may be the same as, greater than, or substantially greater than, the aqueous solubility of the insulin compound conjugate in solution at a pH of about 7.4.

In one surprising embodiment, the aqueous solubility of the cation-insulin compound conjugate complex at a pH of about 7.4 is substantially less than the solubility of the corresponding uncomplexed insulin compound conjugate in solution at a pH of about 7.4, and the cation-insulin compound conjugate complex remains soluble at greater than about 1, 2, 3, 4, 5, 6, 7, 8, 9, 10, 11, 12, 13, 14, 15, 16, 17, 18, 19, 20, 30, 40, 50, 60, 70, 80, 90, 100, 110, 120 or 130 g/L in aqueous solution across a pH range beginning at about 5.5, 5.6, 5.7, 5.8, 5.9, 6, 6.1, 6.2, 6.3, 6.4, 6.5, 6.6, 6.7, 6.1, or 6.9 and ending at about 7.5, 7.6, 7.7, 7.8, 7.9, 8, 8.1, 8.2, 8.3, 8.4, 8.5, 8.6, 8.7, 8.8, or 8.9. In yet another embodiment, the aqueous solubility of the cation-insulin compound conjugate complex at a pH of about 7.4 is substantially less than the solubility of the corresponding insulin compound conjugate in solution at a pH of about 7.4, and the cation-insulin compound conjugate complex remains soluble at greater than about 1, 2, 3, 4, 5, 6, 7, 8, 9, 10, 11, 12, 13, 14, 15, 16, 17, 18, 19, 20, 30, 40, 50, 60, 70, 80, 90, 100, 110, 120 or 130 g/L in aqueous solution across a pH range from about 5.8 to about 8.5, preferably across a pH range from about 6.5 to about 8, more preferably across a pH range from about 6.9 to about 7.8. [QUESTION: Is the g/L solubility measured using the weight of the complex or the weight of the insulin compound conjugate?]

Preferably the insulin compound conjugates of the invention are selected to produce crystals in aqueous solution at a pH which is equal to pI+/−about 2.5, where the concentration of insulin compound conjugate is from about 0.5 mg/ml to about 50 mg/ml, preferably about 5 mg/ml to about 30 mg/ml, more preferably about 15 mg/ml to about 30 mg/ml, and the crystal formulation begins to occur at about 3, 4 or 5% w/w/ cation to insulin compound conjugate, where the cation is preferable $Z^{++}$. Preferably crystals are present for a monoconjugate without protamine in an aqueous solution at a pH ranging from about 4, 4.1, 4.2, 4.3 or 4.4 to about 5.2., 5.3, 5.4, 5.5, 5.6, 5.7 or 5.8, preferably at pH of about 4 to <6.5, preferably about 4 to <5.8, preferably about 4.2 to about 5.5, more preferably about 4.4 to about 5.2. Preferably crystals are present for a diconjugate without protamine at pH of about 3.5 to <5.8, preferably about 3.8 to about 5.5, more preferably about 4.0 to about 5.2. Preferably crystals are present for a triconjugate without protamine at pH of about 3 to <5.5, preferably about 3.3 to about 5, more preferably about 3.8 to about 4.8.

7.8.1 R-Type Complexes

Preferably the aqueous solubility of the R type Zn complex of the insulin compound conjugate at a pH of about 7.4 has a range of about 10 to about 150 g/L, more preferably about 20 to about 130 g/L, more preferably about 30 to about 110 g/L, more preferably about 35 to about 60 g/L.

Preferably the aqueous solubility of the R type Zn complex of the insulin compound conjugate with protamine at a pH of about 7.4 has a range of about 10 to about 110 g/L, more preferably about 20 to about 85 g/L, more preferably about 30 to about 70 g/L.

7.8.2 T-Type Complexes

Preferably the aqueous solubility of the T-type Zn complex of the insulin compound conjugate at a pH of about 7.4 has a range of about 30 to about 175 g/L, more preferably about 50 to about 160 g/L, more preferably about 70 to about 150 g/L.

Preferably the aqueous solubility of the T-type Zn complex of the insulin compound conjugate with protamine at a pH of about 7.4 has a range of about 10 to about 150 g/L, more preferably about 20 to about 130 g/L, more preferably about 30 to about 110 g/L, more preferably about 35 to about 60 g/L.

7.8.3 NPH-Type Complexes

Preferably the aqueous solubility of the NPH-type complex, of the insulin compound conjugate at a pH of about 7.4 has a range of about 1 to about 150 g/L, more preferably about 5 to about 120 g/L, still more preferably about 10 to about 90 g/L.

7.9 Pharmaceutical Properties

Complexation of the insulin compound conjugate with cation generally results in improved pharmaceutical properties of the insulin compound conjugate, relative to a scientifically acceptable control, such as a corresponding uncomplexed insulin compound conjugate.

In some cases, the complexed insulin compound conjugate will exhibit an extended or otherwise altered pK profile relative to a scientifically acceptable control, such as a corresponding uncomplexed insulin compound conjugate. In certain cases, the pK profile will exhibit a lispro-like profile. pK profile can be assessed using standard in vivo experiments, e.g., in mice, rats, dogs, or humans. Assays described herein for assessing the attributes of cation-insulin compound conjugate complexes are an aspect of the invention.

The complexes may exhibit improved chemical stability. Various attributes of stability can be assessed by exposing the complex to various assay conditions such as the presence of plasma, the presence of proteases, the presence of liver homogenate, the presence of acidic conditions, and the presence of basic conditions. Stability is improved relative to uncomplexed insulin compound conjugate when stability of the complexed insulin compound conjugate in any one or more of these assay conditions is greater than stability of the uncomplexed insulin compound conjugate in the same conditions. A preferred assay for determining stability in an acidic environment involves exposing the complexed insulin compound conjugate to a solution having a pH of 2 for at least 2 hours, where decreased degradation of the complexed insulin compound conjugate relative to a scientifically acceptable control, such as a corresponding uncomplexed insulin compound conjugate, is indicative of improved stability. In vivo assays can also be used to test stability. For example, stability of the complexed insulin compound conjugate can be tested by exposure to the gastrointestinal tract of a subject and comparison with an appropriate control.

7.10 Method of Making

The invention also provides a method of making cation-insulin compound conjugate compositions described herein. The method generally involves contacting one or more insulin compound conjugates, as described herein, with one or more cations, as described herein, to form a solid.

For a divalent cation, such as $Zn^{++}$, the molar ratio of insulin compound conjugate to cation used to make the composition in an aqueous solution with an insulin compound concentration ranging from about 2 mg/ml to about 50 mg/ml can typically range from about 1:15 (insulin compound conjugate:cation) to about 1:0.4, preferably about 1:9 to about 1:2.

To make T-type solid (with cation and insulin compound conjugate and without protamine) in the aqueous solution conditions described above, the molar ratio of insulin compound conjugate to cation is preferably about 1:1.5 to 1:3, ideally about 1:2. To make R-type solid (with cation, insulin compound and stabilizing compound (e.g., a phenolic compound), and without protamine) in the aqueous solution conditions described above, the molar ratio of insulin compound conjugate to cation is preferably about 1:4 to 1:9, preferably about 1:7 to about 1:9 ideally about 1:8.

To make T-type protamine solid (with cation and insulin compound conjugate and protamine) in the aqueous solution conditions described above, the molar ratio of insulin compound conjugate to cation is preferably about 1:1.5 to 1:9, ideally about 1:2. To make R-type protamine solid (with cation, insulin compound and stabilizing compound (e.g., a phenolic compound), and protamine) in the aqueous solution conditions described above, the molar ratio of insulin compound conjugate to cation is preferably about 1:2 to 1:15, preferably about 1:7 to about 1:9 ideally about 1:8.

The insulin compound conjugate is preferably added to the buffer in an amount which is calculated to achieve a concentration in the range of from greater than 2 to about 100 g/L, preferably from about 3, 4, 5, 6, 7, 8, 9 or 10 to about 40 g/L, more preferably from about 10 to about 30 g/L.

Where the cation is divalent (e.g., $Zn^{++}$, $Ca^{++}$), it is preferably added in an amount which calculated to achieve a concentration in the range of from about 0.04 to about 10 g/L, preferably from about 0.1 to about 5 g/L, more preferably from about 0.2 to about 4 g/L. For T-type crystals or T-type protamine crystals, the cation concentration is preferably in the range of from about 0.04 to about 1 g/L, more preferably about 0.1 to about 0.3 g/L. For R-type crystals or R-type protamine crystals, the cation concentration is preferably in the range of from about 1 to about 5 g/L, more preferably about 1.5 to about 4 g/L.

Where the cation is monovalent, it is preferably added in an amount which calculated to achieve a concentration in the range of from about 0.08 to about 40 g/L, preferably from about 0.4 to about 20 g/L, more preferably from about 0.8 to about 16 g/L.

The method may further include combining a stabilizing agent with the cation and insulin compound conjugate. Preferred stabilizing agents are described above. When used, the stabilizing agent is added in an amount sufficient to provide a greater degree of solid formation than is achieved using the same reagents and reaction conditions in the absence of the stabilizing agent. Where the stabilizing agent is a phenolic compound (e.g., phenol, m-cresol, m-paraben), can be added in an amount ranging from about 10 to about 50% w/w, more preferably from about 20 to about 40% w/w, still more preferably from about 25 to about 35% w/w. In a more preferred embodiment, the stabilizing agent is a phenolic compound (e.g., phenol, m-cresol, m-paraben), can be added in an amount ranging from about 0.01 to about 10% w/w, more preferably 0.01 to about 5% w/w, still more preferably 0.01 to about 1% w/w. Thus, in one embodiment, the method involves combining insulin compound conjugate, a cation and a stabilizing agent in an aqueous solution to yield the cation-insulin compound conjugate composition, where the combination may yield solubilized complexes and/or crystalline or non-crystalline solids.

The method may further include the use of a complexing agent, such as protamine, which is combined with the cation and insulin compound conjugate, and optionally also includes a stabilizing agent.

To prepare a solid in an aqueous solution having a pH in the range of about 5 to about 8, protamine is preferably provided in an amount relative to insulin compound conjugate of about 4 to about 45% w/w (protamine/insulin compound), preferably about 8 to about 25% w/w, more preferably about 9 to about 20% w/w, ideally about 10 to about 12% w/w. For T-type solids, a preferred pH range is from about 5 to about 6, more preferably about 5 to about 5.5, still more preferably about 5.1 to about 5.3, ideally about 5.2. For R-type solids, a preferred pH range is from about 6 to about 7, more preferably about 6.2 to about 6.8, still more preferably about 6.4 to about 6.6, ideally about 6.5.

The inventors have surprisingly discovered that T-type complexes can be converted to protamine T-type complexes in the absence of a stabilizing agent, such as phenol. The T-type complex is made by complexing Zn with the insulin compound molecule in aqueous solution in the absence of phenol. Protamine is then added to convert the T-type complex into a protamine T-type complex. Amounts and pH ranges are as described above.

Thus, in one embodiment, the method involves combining insulin compound conjugate, a cation and a complexing agent in an aqueous solution to yield the cation-insulin compound conjugate composition, where the combination may yield solubilized complexes and/or crystalline or amorphous solids. In another embodiment, the method involves combining insulin compound conjugate, a cation, a complexing agent, and a stabilizing agent in an aqueous solution to yield the cation-insulin compound conjugate composition, where the combination may yield solubilized complexes and/or crystalline or amorphous solids.

In some embodiments, the compositions can include preservatives. Examples of suitable preservatives include benzyl alcohol, p-hydroxybenzoic acid esters, glycerol. Stabilizing agents, such as phenol, m-cresol, and m-paraben, can also be used as preservatives. Glycerol and phenol are suitably added together to enhance antimicrobial effectiveness.

Other components useful in preparing the solids include isotonic agents, such as NaCl, glycerol, and monosaccharides.

The cation insulin compound conjugate solids can typically be formed relatively quickly. For example, solid formation is typically complete within three days, often within 24 hours. It may be desirable in some instances to slow the reaction down in order to improve crystal formation.

In one embodiment of the invention, the solids are formed at room temperature (25° C.) without requiring temperature reduction for inducing precipitation of solids. For example, room temperature is effective for R-type and T-type crystals. The temperature for solid formation is preferably about 0 to about 40° C., preferably about 17 to about 30° C., and more preferably about 22 to about 27° C., ideally about 25° C.

In one embodiment, the method includes combining in an aqueous solution an insulin compound conjugate and a metal cation to provide a crystalline or amorphous solid. The aqueous solution containing the insulin compound conjugate to which the cation will be added is preferably a buffered solution having a pH in the range of pI of the insulin compound conjugate+/−about 1.5, preferably pI+/−about 1, more preferably pI+/−about 0.75. These ranges also apply to T-type, R-type and protamine complexes. However, for neutral protamine complexes (NPH-type), the preferred pH is about 7 to about 8.5, more preferably about 7.5 to about 8. Once the metal cation is added, the pH may change slightly, and the pH may be adjusted to target the pH ranges described above. With phenolic compounds, there may be a minor pH change, and an acid or base can be used to adjust to the preferred ranges.

pI values for insulin compound conjugates typically require a pH of less than about 7, preferably less than about 6, more preferably less than about 5.5. Human insulin monoconjugates with neutral modifying moieties typically have a pI range of about 4.75+/−0.25. For human insulin diconjugates, the pI range is typically 4.25+/−0.25. For human insulin triconjugates, the pI range is typically 3.5+/−0.25.

Examples of suitable buffer systems include ammonium acetate buffer, sodium phosphate buffer, tris buffer, mixture of sodium phosphate and ammonium acetate, sodium acetate buffer, mixture of sodium acetate and ammonium acetate, and citric acid buffer, and any of the foregoing buffer systems [A] also containing ethanol and/or acetonitrile [B] (e.g., at percent ratio of A:B of about 1:1 to about 10:1). It is a surprising aspect of the invention that the cation-insulin compound conjugate solid can be formed in an aqueous mixture containing an organic solvent, such as ethanol or acetonitrile.

One unique feature of the invention is that in addition to providing useful cation-insulin compound conjugate complexes, the invention also provides a method of separating cation-insulin compound conjugates from unconjugated insulin compound in the manufacturing process. In this process, the cation-insulin compound conjugates can be precipitated out of solution and the solubilized unconjugated insulin compound can be removed by filtration, for example. This feature eliminates 2 steps in the manufacture of insulin compound conjugates: the concentration step and the lyophilization step.

Processed pure solid composition may be formed using standard techniques, such as centrifugation and/or filtration, followed by washing (e.g., with ethanol/water), and lyophilization or vacuum drying. Multiple washings may be used to adjust phenol and/or cation content.

7.11 Formulation

The complexes may be formulated for administration in a pharmaceutical carrier in accordance with known techniques. See, e.g., Alfonso R. Gennaro, *Remington: The Science and Practice of Pharmacy*, Lippincott Williams & Wilkins Publishers (June 2003), and Howard C. Ansel, *Pharmaceutical Dosage Forms and Drug Delivery Systems*, Lippincott Williams & Wilkins Publishers, 7th ed. (October 1999), the entire disclosures of which are incorporated herein by reference for their teachings concerning the selection, making and using of pharmaceutical dosage forms.

The complexes, typically in the form of an amorphous or crystalline solid, can be combined with a pharmaceutically acceptable carrier. The carrier must be acceptable in the sense of being compatible with any other ingredients in the pharmaceutical composition and should not be unduly deleterious to the subject, relative to the benefit provided by the active ingredient(s). The carrier may be a solid or a liquid, or both. It is preferably formulated as a unit-dose formulation, for example, a tablet. The unit dosage form may, for example, contain from about 0.01 or 0.5% to about 95% or 99% by weight of the cation-insulin compound complex. The pharmaceutical compositions may be prepared by any of the well known techniques of pharmacy including, but not limited to, admixing the components, optionally including one or more accessory ingredients.

Examples of suitable pharmaceutical compositions include those made for oral, rectal, inhalation (e.g., via an aerosol) buccal (e.g., sub-lingual), vaginal, parenteral (e.g., subcutaneous, intramuscular, intradermal, intraarticular, intrapleural, intraperitoneal, inracerebral, intraarterial, or intravenous), topical, mucosal surfaces (including airway surfaces), nasal surfaces, and transdermal administration. The most suitable route in any given case will depend on the nature and severity of the condition being treated and on the nature of the particular cation-insulin compound complexes being used. Preferred oral compositions are compositions prepared for ingestion by the subject. Ideally, the oral compositions are prepared to survive or substantially survive passage through the stomach and to completely or substantially completely dissolve in the intestine for delivery of the active ingredient. Examples of suitable transdermal systems include ultrasonic, iontophoretic, and patch delivery systems.

In one aspect, the invention provides fatty acid compositions comprising one or more saturated or unsaturated $C_4$, $C_5$, $C_6$, $C_7$, $C_8$, $C_9$ or $C_{10}$ fatty acids and/or salts of such fatty acids. Preferred fatty acids are caprylic, capric, myristic and lauric. Preferred fatty acid salts are sodium salts of caprylic, capric, myristic and lauric acid.

Preferred fatty acid compositions include a single fatty acid or a single fatty acid salt and do not include substantial amounts of other fatty acids or fatty acid salts. In one aspect of the invention, the fatty acid content of the composition is greater than about 90, 91, 92, 93, 94, 95, 96, 97, 98, 99, 99.5, 99.6, 99.7, 99.8, or 99.9% w/w a single fatty acid. In another embodiment, the fatty acid content of the composition is within a range having as a lower limit of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0% w/w, and having as an upper limit of about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0% w/w. In yet another embodiment, the fatty acid content of the composition is within a range having as a lower limit about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0% w/w, and having as an upper limit about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0% w/w, and the fatty acid content of the composition is greater than about 90, 91, 92, 93, 94, 95, 96, 97, 98, 99, 99.5, 99.6, 99.7, 99.8, or 99.9% w/w a single fatty acid.

Active components of these formulations may include conjugated or unconjugated, complexed or uncomplexed proteins and/or peptides. Preferred proteins and/or peptides are those described herein. Preferred conjugates are those described herein. Preferred complexes are those described herein. Preferred oral compositions are compositions prepared for ingestion by the subject. Ideally, the oral compositions are prepared to survive or substantially survive passage through the stomach and to completely or substantially completely dissolve in the intestine for delivery of the active ingredient. The formulation may in some cases include an enteric coating, and in some cases, the formulation will specifically exclude an enteric coating. The composition is preferably provided as a tablet, powder, hard gelatin capsule, or soft gelatin capsule, though other forms described herein are suitable as well.

The fatty acid compositions of the invention may include fatty acid acylated insulins. Examples of suitable fatty acid acylated insulins are described in the following U.S. patents, the entire disclosures of which are incorporated herein by reference: U.S. Pat. No. 6,531,448, entitled "Insoluble compositions for controlling blood glucose," issued 11 Mar. 2003; U.S. Pat. No. RE37,971, entitled "Selective acylation of epsilon-amino groups," issued 28 Jan. 2003; U.S. Pat. No 6,465,426, entitled "Insoluble insulin compositions," issued 15 Oct. 2002; U.S. Pat. No. 6,444,641, entitled "Fatty acid-acylated insulin analogs." issued 3 Sep. 2002; U.S. Pat. No. 6,335,316, entitled "Method for administering acylated insulin," issued 1 Jan. 2002; U.S. Pat. No. 6,268,335, entitled "Insoluble insulin compositions," issued 31 Jul. 2001; U.S. Pat. No. 6,051,551, entitled "Method for administering acylated insulin," issued 18 Apr. 2000; U.S. Pat. No. 5,922,675, entitled "Acylated Insulin Analogs," issued 13 Jul. 1999; U.S. Pat. No. 5,700,904, entitled "Preparation of an acylated protein powder," issued 23 Dec. 1997; U.S. Pat. No. 5,693,609, entitled "Acylated insulin analogs Granted," issued 2 Dec. 1997; U.S. Pat. No. 5,646,242, entitled "Selective acylation of epsilon-amino groups," issue 8 Jul. 1997; U.S. Pat. No. 5,631,347, entitled "Reducing gelation of a fatty acid-acylated protein," issued 20 May 1997; U.S. Pat. No. 6,451,974, entitled "Method of acylating peptides and novel acylating agents," issued 17 Sep. 2002; U.S. Pat. No. 6,011,007, entitled "Acylated insulin," issued 4 Jan. 2000; U.S. Pat. No. 5,750,497, entitled "Acylated insulin Granted: 12 May 1998; U.S. Pat. No. 5,905,140, entitled "Selective acylation method," issued May 18, 1999; U.S. Pat. No. 6,620,780, entitled "Insulin derivatives," issued Sep. 16, 2003; U.S. Pat. No. 6,251,856, entitled "Insulin derivatives," issued Jun. 26, 2001; U.S. Pat. No. 6,211,144, entitled "Stable concentrated insulin preparations for pulmonary delivery," issued Apr. 3, 2001; U.S. Pat. No. 6,310,038, entitled "Pulmonary insulin crystals," issued Oct. 30, 2001; and U.S. Pat. No. 6,174,856, entitled "Stabilized insulin compositions," issued Jan. 16, 2001. Especially preferred are mono-fatty acid acylated insulins having 12, 13, 14, 15, or 16-carbon fatty acids covalently bound to Lys(B29) of human insulin.

Pharmaceutical compositions suitable for oral administration may be presented in discrete units, such as capsules, cachets, lozenges, or tables, each containing a predetermined amount of the mixture of insulin compound conjugates; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the mixture of insulin compound conjugates and a suitable carrier (which may contain one or more accessory ingredients as noted above). Formulations may include suspensions of solids, complexed cation-insulin compound conjugates, uncomplexed active ingredient (e.g., native insulin compound, insulin compound conjugates), and mixtures of the foregoing.

In general, the pharmaceutical compositions of the invention are prepared by uniformly and intimately admixing the complexes with a liquid or solid carrier, or both, and then, if necessary, shaping the resulting mixture. For example, a tablet may be prepared by compressing or molding a powder or granules containing the mixture of insulin compound conjugates, optionally with one or more accessory ingredients. Compressed tablets may be prepared by compressing, in a suitable machine, the mixture in a free-flowing form, such as a powder or granules optionally mixed with a binder, lubricant, inert diluent, and/or surface active/dispersing agent(s). Molded tablets may be made by molding, in a suitable machine, the powdered composition moistened with an inert liquid binder.

Pharmaceutical compositions suitable for buccal (sub-lingual) administration include lozenges comprising the mixture of insulin compound conjugates in a flavoured base, usually sucrose and acacia or tragacanth; and pastilles comprising the mixture of insulin compound conjugates in an inert base such as gelatin and glycerin or sucrose and acacia. Examples of suitable formulations can be found in U.S. patent Publication Nos. 20030229022 ("Pharmaceutical formulation"); 20030236192 ("Method of modifying the release profile of sustained release compositions"); 20030096011 ("Method of producing submicron particles of a labile agent and use thereof"); 20020037309 ("Process for the preparation of polymer-based sustained release compositions"); 20030118660 ("Residual solvent extraction method and microparticles produced thereby"); as well as U.S. Pat. No. 6,180,141 ("Composite gel microparticles as active principle carriers"); U.S. Pat. No. 6,737,045 ("Methods and compositions for the pulmonary delivery insulin compound"); U.S. Pat. No. 6,730,334 ("Multi-arm block copolymers as drug delivery vehicles"); U.S. Pat. No. 6,685,967 ("Methods and compositions for pulmonary delivery of insulin compound"); U.S. Pat. No. 6,630,169 ("Particulate delivery systems and methods of use"); U.S. Pat. No. 6,589,560 ("Stable glassy state powder formulations; U.S. Pat. No. 6,592,904 ("Dispersible macromolecule compositions and methods for their preparation and use"); U.S. Pat. No. 6,582,728 ("Spray drying of macromolecules to produce inhaleable dry powders"); U.S. Pat. No. 6,565,885 ("Methods of spray drying pharmaceutical compositions"); U.S. Pat. No. 6,546,929 ("Dry powder dispersing apparatus and methods for their use"); U.S. Pat. No. 6,543,448 ("Apparatus and methods for dispersing dry powder medicaments"); U.S. Pat. No. 6,518,239 ("Dry powder compositions having improved dispersivity"); U.S. Pat. No. 6,514,496 ("Dispersible antibody compositions and methods for their preparation and use"); U.S. Pat. No. 6,509,006 ("Devices compositions and methods for the pulmonary delivery of aerosolized medicaments"); U.S. Pat. No. 6,433,040 ("Stabilized bioactive preparations and methods of use"); U.S. Pat. No. 6,423,344 ("Dispersible macromolecule compositions and methods for their preparation and use"); U.S. Pat. No. 6,372,258 ("Methods of spray-drying a drug and a hydrophobic amino acid"); U.S. Pat. No. 6,309,671 ("Stable glassy state powder formulations"); U.S. Pat. No. 6,309,623 ("Stabilized preparations for use in metered dose inhalers"); U.S. Pat. No. 6,294,204 ("Method of producing morphologically uniform microcapsules and microcapsules produced by this method"); U.S. Pat. No. 6,267,155 ("Powder filling systems, apparatus and methods"); U.S. Pat. No. 6,258,341 ("Stable glassy state powder formulations"); U.S. Pat. No. 6,182,712 ("Power filling apparatus and methods for their use"); U.S. Pat. No. 6,165,463 ("Dispersible antibody compositions and methods for their preparation and use"); U.S. Pat. No. 6,138,668 ("Method and device for delivering aerosolized medicaments"); U.S. Pat. No. 6,103,270 ("Methods and system for processing dispersible fine powders"); U.S. Pat. No. 6,089,228 ("Apparatus and methods for dispersing dry powder medicaments"); U.S. Pat. No. 6,080,721 ("Pulmonary delivery of active fragments of parathyroid hormone"); U.S. Pat. No. 6,051,256 ("Dispersible macromolecule compositions and methods for their preparation and use"); U.S. Pat. No. 6,019,968 ("Dispersible antibody compositions and methods for their preparation and use"); U.S. Pat. No. 5,997,848 ("Methods and compositions for pulmonary delivery of insulin compound"); U.S. Pat. No. 5,993,783 ("Method and apparatus for pulmonary administration of dry powder.alpha.1-antitrypsin"); U.S. Pat. No. 5,922,354 ("Methods and system for processing dispersible fine powders"); U.S. Pat. No. 5,826,633 ("Powder filling systems, apparatus and methods"); U.S. Pat. No. 5,814,607 ("Pulmonary delivery of active fragments of parathyroid hormone"); U.S. Pat. No. 5,785,049 ("Method and apparatus for dispersion of dry powder medicaments"); U.S. Pat. No. 5,780,014 ("Method and apparatus for pulmonary administration of dry powder alpha 1-antitrypsin"); U.S. Pat. No. 5,775,320 ("Method and device for delivering aerosolized medicaments"); U.S. Pat. No. 5,740,794 ("Apparatus and methods for dispersing dry powder medicaments"); U.S. Pat. No. 5,654,007 ("Methods and system for processing dispersible fine powders"); U.S. Pat. No. 5,607,915 ("Pulmonary delivery of active fragments of parathyroid hormone"); U.S. Pat. No. 5,458,135 ("Method and device for delivering aerosolized medicaments"); U.S. Pat. No. 6,602,952 ("Hydrogels derived from chitosan and poly(ethylene glycol) or related polymers"); and U.S. Pat. No. 5,932,462 ("Multiarmed, monofunctional, polymer for coupling to molecules and surfaces"). Further, Suitable sustained release formulations are described in Cardinal Health's U.S. Pat. No. 5,968,554, entitled "A sustained release pharmaceutical preparation," issued 19 Oct. 1999, the entire disclosure of which is incorporated herein by reference. Suitable microparticle formulations are described in Spherics, Inc.'s International Patent Publication WO/2003-049,701, entitled "Methods and products useful in the formation and isolation of microparticles," published 30 Oct. 2003. Suitable bioadhesive formulations are described in Spherics, Inc.'s International Patent Publication WO/2003-051,304, entitled "Bioadhesive drug delivery system with enhanced gastric retention", published 6 May 2004.

Pharmaceutical compositions according to embodiments of the invention suitable for parenteral administration comprise sterile aqueous and non-aqueous injection solutions of the complexes, which preparations are preferably isotonic with the blood of the intended recipient. These preparations may contain anti-oxidants, buffers, bacteriostats and solutes which render the composition isotonic with the blood of the intended recipient. Aqueous and non-aqueous sterile suspensions may include suspending agents and thickening agents. The compositions may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, an injectable, stable, sterile composition with a mixture of complexes in a unit dosage form in a sealed container may be provided. The mixture of complexes can be provided in the form of a lyophilizate which is capable of being reconstituted with a suitable pharmaceutically acceptable carrier to form a liquid composition suitable for injection into a subject. The parenteral unit dosage form typically comprises from about 1 microgram to about 10 mg of the mixture of complexes. When the complexes are substantially water-insoluble, a sufficient amount of emulsifying agent which is physiologically acceptable may be employed in sufficient quantity to emulsify the complexes in an aqueous carrier. One such useful emulsifying agent is phosphatidyl choline.

A solid dosage form for oral administration typically includes from about 2 mg to about 500 mg, preferably about 10 mg to about 250 mg, ideally about 20 mg to about 110 mg of the complexes.

Pharmaceutical compositions suitable for rectal administration are preferably presented as unit dose suppositories. These may be prepared by admixing the complexes with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, PEGs, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6): 318 (1986)) and typically take the form of an optionally buffered aqueous solution of the mixture of insulin compound conjugates. Suitable formulations comprise citrate or bis/tris buffer (pH 6) or ethanol/water and contain from 0.1 to 0.2M active ingredient.

In a preferred embodiment, the complexes are administered as components of solid fatty acid formulations as described in U.S. patent application No. 60/494,821, filed on 13 Aug. 2003, by Opawale et al., the entire disclosure of which is incorporated herein by reference.

In certain embodiments, the insulin compound conjugate may be provided separately from the cation and/or other components needed to form the solids. For example, the insulin compound conjugate may be provided as a dried solid, and the buffer solution including the cation, stabilizing agent, preservative and/or other component may be provided separately, so that the user may combine the separate components to produce the cation-insulin compound conjugate complexes.

7.12 Methods of Treatment

The cation-insulin compound conjugate compositions and formulations thereof are useful in the treatment of conditions in which increasing the amount of circulating insulin compound (relative to the amount provided by the subject in the absence of administration of insulin compound from an exogenous source) yields a desirable therapeutic or physiological effect. For example, the condition treated may be Type I oR-type II diabetes, prediabetes and/or metabolic syndrome. In one embodiment, the compositions are administered to alleviate symptoms of diabetes. In another embodiment, the compositions are administered to a prediabetic subject in order to prevent or delay the onset of diabetes.

The effective amount of the cation-insulin compound conjugate composition for administration according to the methods of the invention will vary somewhat from mixture to mixture, and subject to subject, and will depend upon factors such as the age and condition of the subject, the route of delivery and the condition being treated. Such dosages can be determined in accordance with routine pharmacological procedures known to those skilled in the art.

As a general proposition, an oral dosage from about 0.025 to about 10 mg/kg of active ingredient (i.e., the conjugate) will have therapeutic efficacy, with all weights being calculated based upon the weight of the mixture of insulin compound conjugates. A more preferred range is about 0.06 to about 1 mg/kg, and an even more preferred range is about 0.125 to about 0.5 mg/kg A parenteral dosage typically ranges from about 0.5 μg/kg to about 0.5 mg/kg, with all weights being calculated based upon the weight of the mixture of insulin compound conjugates. A more preferred range is about 1 μg/kg to about 100 μg/kg.

The frequency of administration is usually one, two, or three times per day or as necessary to control the condition. Alternatively, the cation-insulin compound conjugate compositions may be administered by continuous infusion. The duration of treatment depends on the type of insulin compound deficiency being treated and may be for as long as the life of the subject. The complexes may, for example, be administered within 0 to 30 minutes prior to a meal. The complexes may, for example, be administered within 0 to 2 hours prior to bedtime.

8 SYNTHESIS EXAMPLES

The following examples are presented to illustrate and explain the invention.

8.1 Synthesis of protected MPEG$_6$C$_3$ oligomer (3-{2-[2-(2-{2-[2-(2-Methoxy-ethoxy)-ethoxy]-ethoxy}-ethoxy)-ethoxy]-ethoxy}-propionic acid tert-butyl ester)

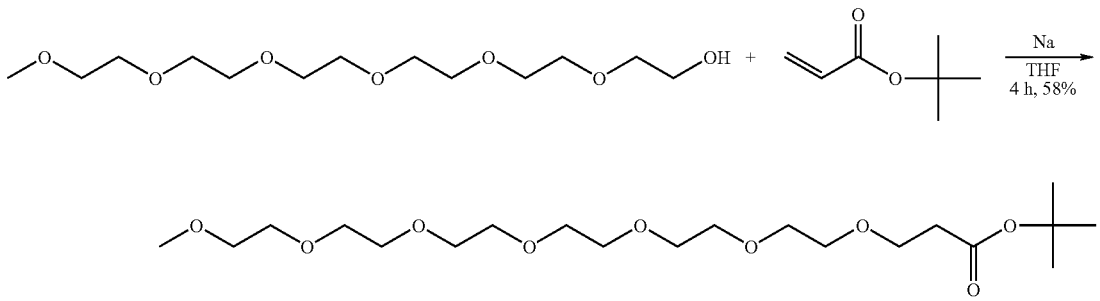

Methyl hexaethylene glycol (1.0 g, 3.37 mmol) and tert-butyl acrylate (0.216 g, 1.69 mmol) were dissolved in dry THF (10 mL). Sodium metal 0.4 mg, 0.016 mmol) was added to the solution. After stirring for 4 h at room temperature, the reaction mixture was quenched by the addition of 1 M HCl (15 mL). The quenched reaction mixture was then extracted with CH$_2$Cl$_2$ (1×50 mL, 1×25 mL). The organic layer was dried (MgSO$_4$) and concentrated. After purification by silica gel chromatography (ethyl acetate as eluent), the product was obtained as an oil (0.832 g, 58%).

8.2 Synthesis of the MPEG$_6$C$_3$ oligomer acid (3-{2-[2-(2-{2-[2-(2-Methoxy-ethoxy)-ethoxy]-ethoxy}-ethoxy)-ethoxy]-ethoxy}-propionic acid)

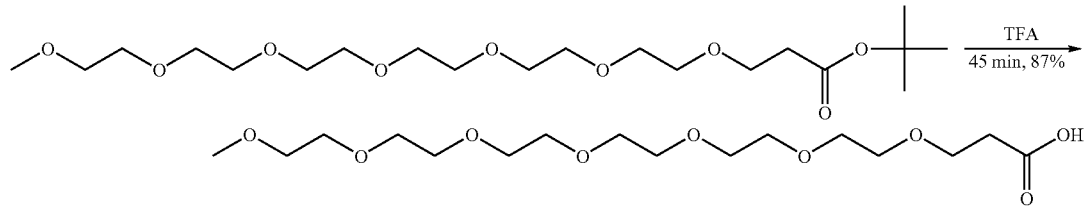

The tert-butyl ester (0.165 g, 0.0389 mmol) was deprotected by stirring at room temperature in trifluoroacetic acid (2.0 mL). The contents were then concentrated to a constant weight (0.125 g, 87%).

8.3 Synthesis of the activated MPEG$_6$C$_3$ oligomer (3-{2-[2-(2-{2-[2-(2-Methoxy-ethoxy)-ethoxy]-ethoxy}-ethoxy)-ethoxy]-ethoxy}-propionic acid 2,5-dioxo-pyrrolidin-1-yl ester)

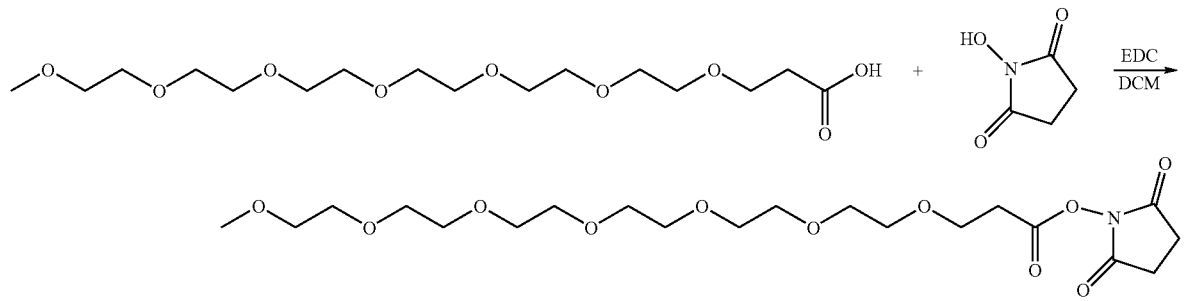

The acid (0.660 g, 1.79 mmol) and N-hydroxysuccinimide (0.2278 g, 1.97 mmol) were dissolved in dry CH$_2$Cl$_2$ (15 mL). Ethyl dimethylaminopropyl carbodiimide hydrochloride (EDC, 0.343 g, 1.79 mmol) was added. After stirring at room temperature overnight, the reaction mixture was diluted with CH$_2$Cl$_2$ and was washed with water (2×45 mL). The organic layer was dried (MgSO$_4$) and concentrated to a constant weight. The product was an oil (0.441 g, 53%).

8.4 Synthesis of the protected MPEG$_4$C$_3$ oligomer (3-(2-{2-[2-(2-Methoxy-ethoxy)-ethoxy]-ethoxy}-ethoxy)-propionic acid tert-butyl ester)

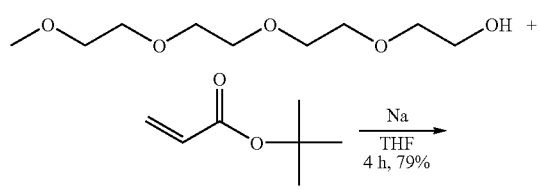

Methyl tetraethylene glycol (1.0 g, 4.80 mmol) and tert-butyl acrylate (0.308 g, 2.40 mmol) were dissolved in dry THF (10 mL). Sodium metal 0.6 mg, 0.024 mmol) was added to the solution. After stirring for 4 h at room temperature, the reaction mixture was quenched by the addition of 1 M HCl (15 mL). The quenched reaction mixture was then extracted with CH$_2$Cl$_2$ (1×50 mL, 1×25 mL). The organic layer was dried (MgSO$_4$) and concentrated. After purification by silica gel chromatography (ethyl acetate as eluent), the product was obtained as an oil (1.28 g, 79%).

8.5 Synthesis of the MPEG$_6$C$_3$ oligomer acid (3-(2-{2-[2-(2-Methoxy-ethoxy)-ethoxy]-ethoxy}-ethoxy)-propionic acid)

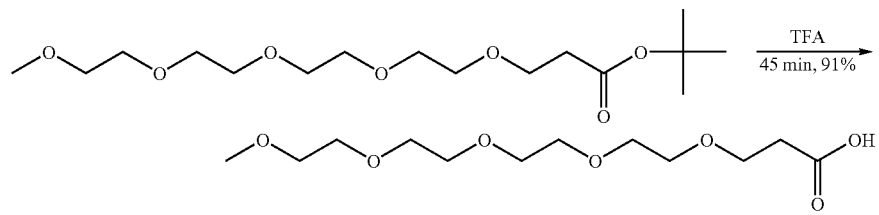

The tert-butyl ester (1 g, 3.42 mmol) was deprotected by stirring at room temperature in trifluoroacetic acid (6.0 mL). The contents were then concentrated to a constant weight (0.87 g, 91%).

8.6 Synthesis of the activated MPEG$_4$C$_3$ oligomer (3-(2-{2-[2-(2-Methoxy-ethoxy)-ethoxy]-ethoxy}-ethoxy)-propionic acid 2,5-dioxo-pyrrolidin-1-yl ester)

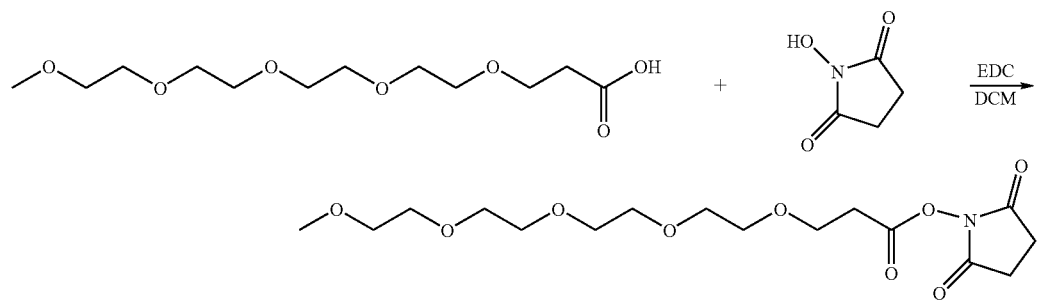

The acid (0.6 g, 2.14 mmol) and N-hydroxysuccinimide (0.271 g, 2.35 mmol) were dissolved in dry CH$_2$Cl$_2$ (20 mL). Ethyl dimethylaminopropyl carbodiimide hydrochloride (EDC, 0.409 g, 2.14 mmol) was added. After stirring at room temperature overnight, the reaction mixture was diluted with CH$_2$Cl$_2$ and was washed with water (2×45 mL). The organic layer was dried (MgSO$_4$) and concentrated to a constant weight. The product was an oil (0.563 g, 69%).

8.7 Synthesis of the protected MPEG$_4$C$_3$ oligomer (3-(2-Methoxy-ethoxy)-propionic acid tert-butyl ester)

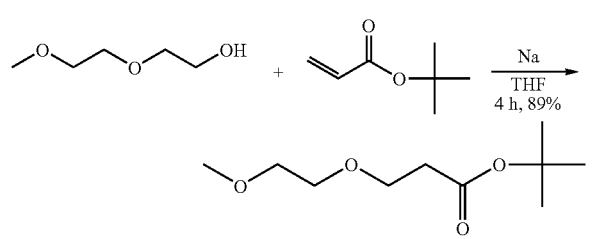

Methyl tetraethylene glycol (5.0 g, 41.6 mmol) and tert-butyl acrylate (2.66 g, 20.8 mmol) were dissolved in dry THF (20 mL). Sodium metal 0.47 mg, 20.8 mmol) was added to the solution. After stirring for 4 h at room temperature, the reaction mixture was quenched by the addition of 1 M HCl (30 mL). The quenched reaction mixture was then extracted with CH$_2$Cl$_2$ (1×100 mL, 1×50 mL). The organic layer was dried (MgSO$_4$) and concentrated. After purification by silica gel chromatography (ethyl acetate as eluent), the product was obtained as an oil (7.5 g, 89%).

8.8 Synthesis of the MPEG$_6$C$_3$ oligomer acid (3-[2-(2-Methoxy-ethoxy)-ethoxy]-propionic acid)

The tert-butyl ester (1 g, 4.90 mmol) was deprotected by stirring at room temperature in trifluoroacetic acid (6.0 mL). The contents were then concentrated to a constant weight (0.652 g, 89%).

8.9 Synthesis of 2-[2-(2-Propoxy-ethoxy)-ethoxy]-ethanol (1)

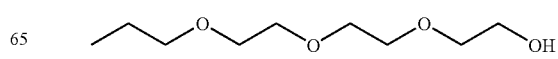

Triethylene glycol (19.5 g, 0.13 mol) was dissolved in tetrahydrofuran (150 mL) and sodium hydride (2.60 g, 0.065 mol) was added portion wise over 0.5 h and the reaction was stirred for an additional 1 h. Then 1-bromopropanol (8.0 g, 0.065 mol) dissolved in tetrahydrofuran (30 mL) was added dropwise via addition funnel and the reaction was stirred overnight at room temperature. Crude reaction mixture was filtered through Celite, washed $CH_2Cl_2$, and evaporated to dryness. The resultant oil was dissolved in $CH_2Cl_2$ (250 mL), washed sat. NaCl (250 mL), $H_2O$ (250 mL), dried $MgSO_4$, and evaporated to dryness. Column chromatography (Silica, ethyl acetate) afforded 1 a yellowish oil (2.24 g, 18% yield).

8.10 Synthesis of carbonic acid 4-nitro-phenyl ester 2-[2-(2-propoxy-ethoxy)-ethoxy]-ethyl ester

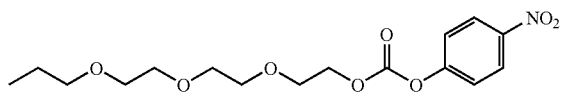

4-Nitrochloroformate (3.45 g, 17.1 mmol) and 1 (2.2 g, 11.4 mmol) were dissolved in $CH_2Cl_2$ (20 mL). After stirring for 10 min, TEA (2.1 mL, 15 mmol) was added and reaction stirred overnight at room temperature. Crude reaction was diluted with $CH_2Cl_2$ (50 mL), washed 1M HCl (50 mL), $H_2O$ (50 mL), dried $MgSO_4$, and evaporated to dryness. Column chromatography (silica, ethyl acetate/hexanes, 3:2) afforded 2 a yellowish oil (2.57 g, 63% yield).

8.11 Synthesis of carbonic acid 2,5-dioxo-pyrrolidin-1-yl ester 2-[2-(2-methoxy-ethoxy)-ethoxy]-ethyl ester

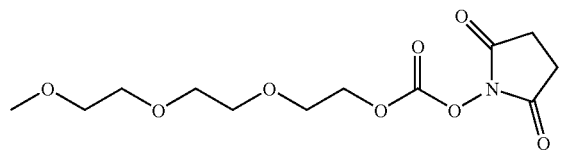

Triethylene glycol monomethyl ether (1.0 g, 6.1 mmol) and N,N'-disuccinimidyl carbonate (1.87 g, 7.3 mmol) were dissolved in acetonitrile (10 mL). Then triethylamine (1.3 mL, 9.15 mmol) was added and the reaction stirred overnight at room temperature. Crude reaction was evaporated to dryness, dissolved in sat. $NaHCO_3$ (50 mL), washed ethyl acetate (2×50 mL), dried $MgSO_4$, and evaporated to dryness. Column chromatography (Silica, ethyl acetate) afforded 1 a clear oil (0.367 g, 20% yield).

8.12 Synthesis of carbonic acid 2,5-dioxo-pyrrolidin-1-yl ester 2-{2-[2-(2-methoxy-ethoxy)-ethoxy]-ethoxy}-ethyl ester (1)

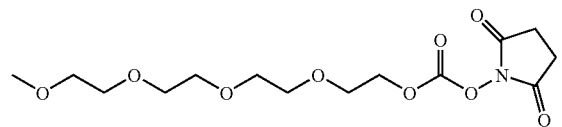

Tetraethylene glycol monomethyl ether (1.0 g, 4.8 mmol) and N,N'-disuccinimidyl carbonate (1.48 g, 5.8 mmol) were dissolved in acetonitrile (10 mL). Then triethylamine (1.0 mL, 7.2 mmol) was added and the reaction stirred overnight at room temperature. Crude reaction was evaporated to dryness, dissolved in sat. $NaHCO_3$ (30 mL), washed ethyl acetate (2×30 mL), dried $MgSO_4$, and evaporated to dryness. Column chromatography (Silica, ethyl acetate/MeOH, 20:1) afforded 1 a clear oil (0.462 g, 28% yield).

8.13 Synthesis of but-3-enoic acid ethyl ester

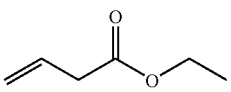

Vinylacetic acid (10.0 g, 0.12 mol) was dissolved in ethanol (200 mL) and conc. sulfuric acid (0.75 mL, 0.014 mol) was added. The reaction was heated to reflux for 4 h. Crude reaction was diluted with ethyl acetate (200 mL), washed $H_2O$ (200 mL), sat. $NaHCO_3$ (200 mL), dried $MgSO_4$, and evaporated to dryness to afford 1 a clear oil (3.17 g, 23%).

8.14 Synthesis of 4-{2-[2-(2-Methoxy-ethoxy)-ethoxy]-ethoxy}-butyric acid ethyl ester

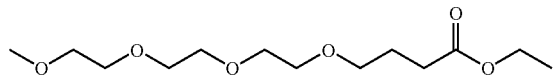

Triethylene glycol monomethyl ether (4.27 g, 0.026 mol) and But-3-enoic acid ethyl ester (1.5 g, 0.013 mol) were dissolved in tetrahydrofuran (10 mL). Then lump $Na^0$ (0.030 g, 0.013 mol) was added and the reaction was stirred for 4 h. Crude reaction was quenched with 1M HCl (20 mL), washed ethyl acetate (3×20 mL). Organic layers were combined and washed with $H_2O$ (2×10 mL), dried $MgSO_4$, and evaporated to dryness to afford 2 a yellowish oil (1.07 g, 30% yield).

8.15 Synthesis of 4-{2-[2-(2-Methoxy-ethoxy)-ethoxy]-ethoxy}-butyric acid

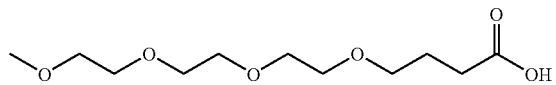

4-{2-[2-(2-Methoxy-ethoxy)-ethoxy]-ethoxy}-butyric acid ethyl ester (1.07 g, 4.0 mmol) was dissolved in 1M NaOH (10 mL) and the reaction was stirred for 2 h. Crude reaction was diluted with sat. NaCl (40 mL), acidified to pH ~2 with conc. HCl, washed $CH_2Cl_2$ (2×50 mL), dried $MgSO_4$, and evaporated to dryness to afford 3 a clear oil (0.945 g, 94% yield).

8.16 Synthesis of 4-{2-[2-(2-Methoxy-ethoxy)-ethoxy]-ethoxy}-butyric acid 2,5-dioxo-pyrrolidin-1-yl ester

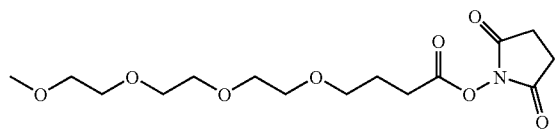

N-hydroxysuccinimide (0.55 g, 4.8 mmol) and EDCl (1.15 g, 6.0 mmol) were dissolved in $CH_2Cl_2$ (7 mL). Then 4-{2-[2-(2-Methoxy-ethoxy)-ethoxy]-ethoxy}-butyric acid (0.940 g, 3.8 mmol), dissolved in $CH_2Cl_2$ (2 mL), was added. Reaction stirred overnight at room temperature. Crude reaction was diluted with $CH_2Cl_2$ (21 mL), washed 1M HCl (30 mL), $H_2O$ (30 mL), dried $MgSO_4$, and evaporated to dryness. Column chromatography (Silica, ethyl acetate) afforded 4, a clear oil (0.556 g, 43% yield).

9 PREPARATION OF COMPLEXES

Methods were investigated for the preparation of zinc complexes of insulin compound conjugates. New methods, exceptional to published methods used for complexation/crystallization of insulin compound and insulin compound analogs, were developed to make zinc complex of HIM2. HIM2 is a human insulin monoconjugate with a modifying moiety coupled at B29, where the modifying moiety has the following structure:

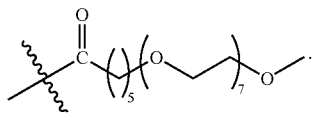

Further complexes were prepared using IN105, a human insulin monoconjugate with a modifying moiety coupled at B29, where the modifying moiety has the following structure:

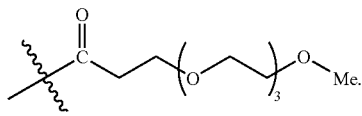

The methods provided three main types, "T-type" and "R-type" and "protamine" cation complexes of insulin compound conjugate solids.

9.1 Preparation and Analysis of T-Type Solids

9.1.1 Attempted Preparation of T-Type Zn Complex of HIM2 (2 g/L)

A HIM2 solution at approximately 2 g/L was prepared having a final pH ~3 with 10% HCl. Glacial acetic acid was added to a 10 mL aliquot (20 mg protein) of the above solution to a final concentration of 0.25M. Twenty (or forty) µL of a 2% w/w $ZnCl_2$ solution was added to the sample. The pH was adjusted to 5.1 (or 5.5) with concentrated ammonium hydroxide. The solution stirred for 15 minutes at room temperature (or +5° C.) and then stood for one day at room temperature (or +5° C.) to allow solid formation. No crystals or precipitation formed after allowing the reaction to stand one day at room temperature (or at +5° C.). See Example 2 of U.S. Pat. No. 5,504,188, entitled "Preparation of stable zinc insulin compound analog crystals."

9.1.2 T-Type Zn Complex of HIM2 (10 g/L Concentration)

A HIM2 solution at approximately 10 g/L was prepared having a final pH ~3 with 10% HCl. Glacial acetic acid was added to a 10 mL (100 mg protein) aliquot of the above solution to a final concentration of 0.25M. Forty µL of a 10% w/w ZnCl2 solution was added to the sample. The pH was adjusted to 5.20 with concentrated ammonium hydroxide. The solution was stirred for 15 minutes at +5° C. and then allowed to stand for five days at +5° C. to allow solid formation.

The reaction mixture was transferred to a centrifuge tube and centrifuged at 2000 RPM for 10 minutes. The solution was decanted and the solid was washed with 5 mL cold DI water. This solution was centrifuged at 2000 RPM for 10 minutes before the water was decanted and the solids were washed with another 5 mL cold DI water. Again, the sample was centrifuged at about 2000 RPM for about 10 minutes before the $H_2O$ was decanted. The sample was washed with 5 mL 200 proof cold EtOH and centrifuged at 2000 RPM for 10 minutes before the EtOH was decanted. The sample was dried in a lyophilizer to provide white solid.

9.1.3 T-Type Zn Complex of HIM2 (20 g/L Concentration)

A HIM2 solution at approximately 20 g/L was prepared having a final pH ~3 with 10% HCl. Glacial acetic acid was added to a 10 mL (200 mg protein) aliquot of the above solution to a final concentration of 0.25 M. Eighty µL of a 10% w/w $ZnCl_2$ solution was added to the sample. The pH was adjusted to 5.37 with concentrated ammonium hydroxide. The solution stirred for 15 minutes at +5° C. and then stood for four days at +5° C. to allow solid formation.

The reaction mixture was transferred to a centrifuge tube and centrifuged at 2600 RPM for 20 minutes. The solution was decanted and the solid was washed with 5 mL cold DI water. This solution was centrifuged at 2600 RPM for 20 minutes before the water was decanted and the solids were washed with another 5 mL cold DI water. Again, the sample was centrifuged at about 2600 RPM for about 20 minutes before the $H_2O$ was decanted. The sample was washed with 5 mL 200 proof cold EtOH and centrifuged at 2600 RPM for 20 minutes before the EtOH was decanted. The sample was dried in a lyophilizer to provide white solid.

9.1.4 T-Type Zn Complex of HIM2 (30 g/L Concentration)

A HIM2 solution at approximately 30 g/L is prepared having a final pH ~3 with 10% HCl. Glacial acetic acid was added to a 50 mL (1.5 g protein) aliquot of the above solution to a final concentration of 0.25 M. Six hundred µL of a 10% w/w $ZnCl_2$ solution was added to the sample.

The pH was adjusted to 5.34 with concentrated ammonium hydroxide. The solution stood at +5° C. for five days to allow solid formation.

The reaction mixture was transferred to a centrifuge tube and centrifuged at 2800 RPM for 15 minutes. The solution was decanted and the solid was washed three times with 10 mL cold DI water, centrifuging and decanting the $H_2O$ each wash. The sample was then washed three times with 10 mL 200 proof cold EtOH. It was centrifuged at 2800 RPM for 15 minutes and decanted after each wash. The sample was dried in a lyophilizer to provide white solid.

Figure 1:
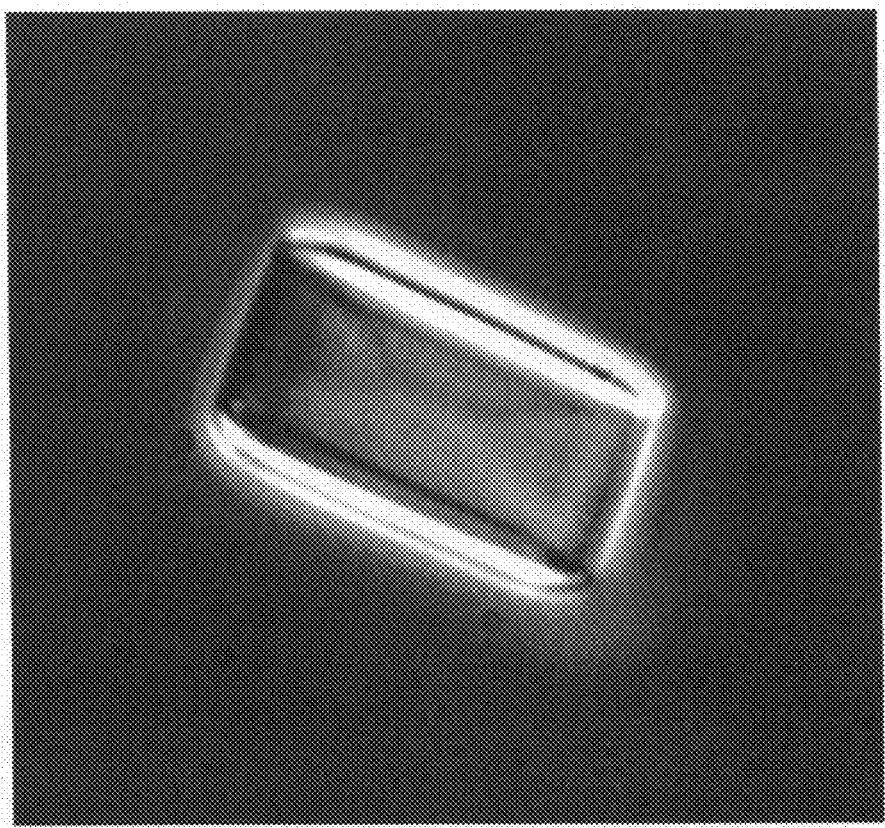
Figure 2:
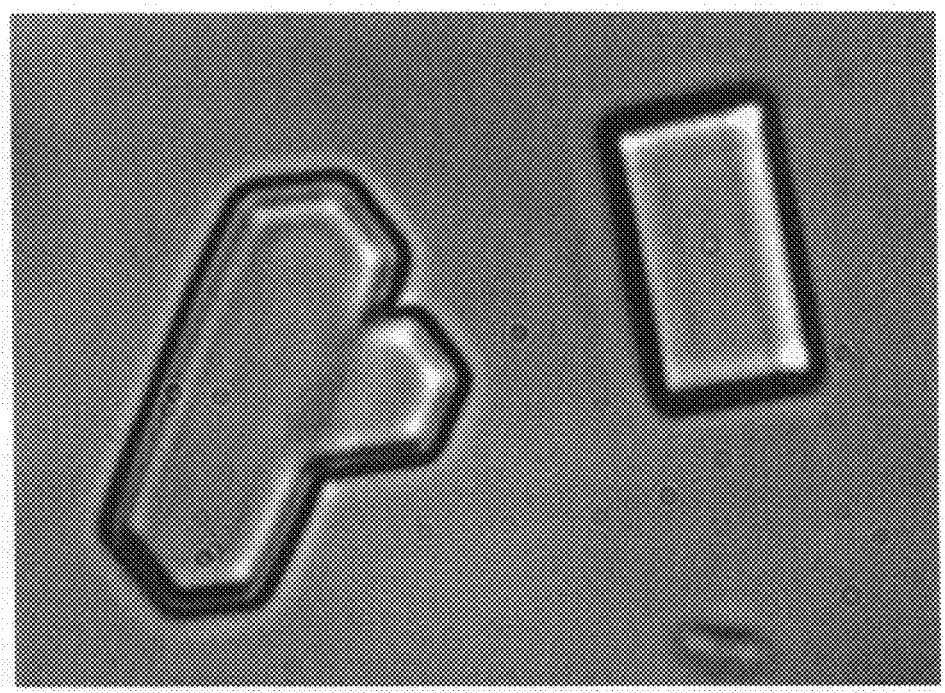
Figure 3:
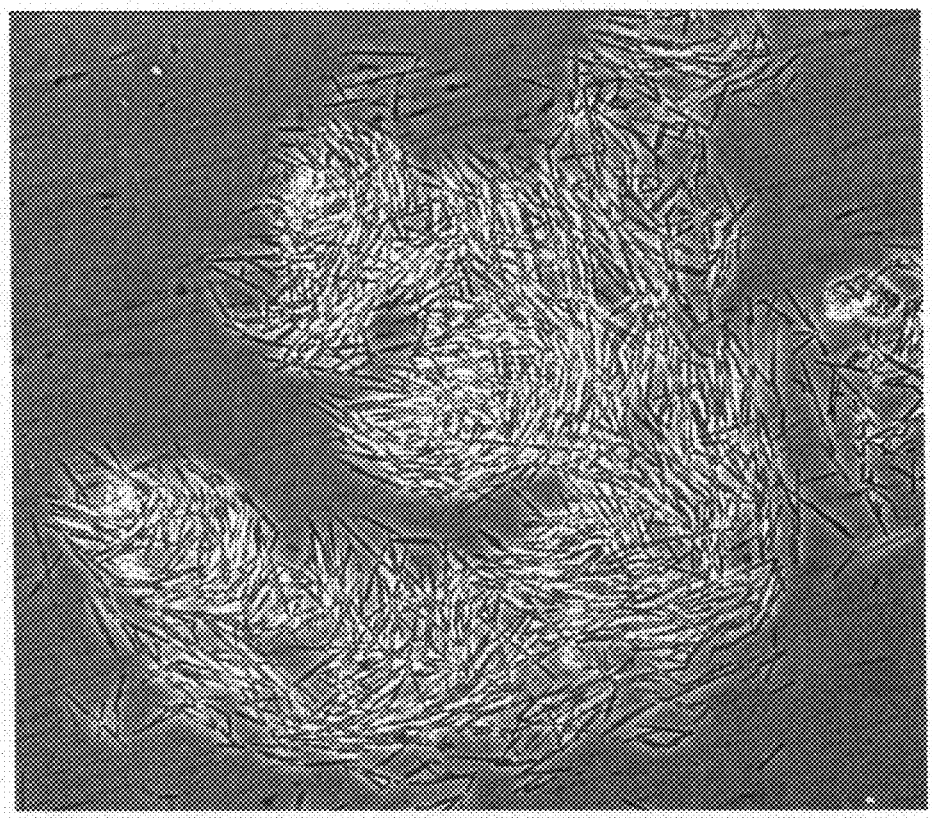

FIGS. 1 and 2 are photomicrographs taken using a Zeiss Axiovert microscope showing crystals grown for 24 hours. In FIG. 1, the crystal size is approximately 11.3 µM in length and approximately 5.3 µM in diameter. In FIG. 2, the size of the crystal on the left is approximately 15.1 µM in length and approximately 5.9 µM in diameter, and the size of the crystal on the right is approximately 9.1 µM in length and approximately 5.3 µM in diameter. FIG. 3 is a photomicrograph taken using a Zeiss Axiovert microscope showing crystals grown for 5 days. In one aspect, the invention includes crystals having a morphology as shown in FIG. 1, 2 or 3.

9.1.5 T-Type Zn Complex of HIM2 (50 g/L Concentration)

A HIM2 solution at approximately 50 g/L was prepared to a final pH ~3 with 10% HCl. Glacial acetic acid was added to a 10 mL aliquot of the above solution to a final concentration of 0.25 M. Two hundred µL of a 10% $ZnCl_2$ solution was added to the sample. The pH was adjusted to 5.23 with concentrated ammonium hydroxide. The solution was stirred at +5° C. for 15 minutes and then stood at +5° C. for four days to allow solid formation to occur.

The reaction mixture was transferred to a centrifuge tube and centrifuged at 2600 RPM for 20 minutes. The solution was decanted and the solid was washed with 5 mL cold DI $H_2O$. This solution was centrifuged at 2600 RPM for 20 minutes before the $H_2O$ was decanted and the solid was washed with another 5 mL cold DI $H_2O$. Again, the sample was centrifuged at 2600 RPM for 20 minutes before the $H_2O$ was decanted. The sample was washed with 5 mL 200 proof cold EtOH and centrifuged at 2600 RPM for 20 minutes before the EtOH was decanted. The sample was dried in a lyophilizer for three days.

9.1.6 T-Type Zn Complex of HIM2 (1 g Scale)

A HIM2 solution at approximately 10 g/L was prepared to a final pH ~3 with 10% HCl. Glacial acetic acid was added to a 50 mL (500 mg protein) aliquot of the above solution to a final concentration of 0.25 M. Two hundred µL of a 10% $ZnCl_2$ solution was added to the sample. The pH was adjusted to 5.49 with concentrated ammonium hydroxide. The solution was stirred at +5° C. for 15 minutes and then stood at +5° C. for seven days to allow solid formation to occur.

The reaction mixture was transferred to a centrifuge tube and centrifuged at 2600 RPM for 20 minutes. The solution was decanted and the solid was washed with 10 mL cold DI $H_2O$. This solution was centrifuged at 2600 RPM for 20 minutes before the $H_2O$ was decanted. The water washes were repeated two additional times. The sample was then washed with 10 mL 200 proof cold EtOH and centrifuged at 2600 RPM for 20 minutes before the EtOH was decanted. Two more EtOH washes were carried out the same way before the sample was placed on the lyophilizer to dry for four days.

9.1.7 T-Type Zn Complex of HIM2 at Neutral pH (5 g Scale)

A HIM2 solution at approximately 10 g/L was prepared to a final pH ~3 with 10% HCl. Two mililiters of a 10% $ZnCl_2$ solution was added to the sample. The pH was adjusted to 7.05 with concentrated ammonium hydroxide. The solution was stirred at room temperature overnight to allow solid formation to occur.

The milky Zn-HIM2 reaction mixture (500 mL) was added, in parts, to a 350 mL fine-fritted (4.5-5 um) disc funnel (ChemGlass CG1402-28, 90 mm diameter). The filtrate was collected in a side-arm flask while applying vacuum for about 4-6 hours. As an option, the cake may be washed with 100 mL cold 1% $ZnCl_2$ and the filtrate collected separately. The cake was washed with 100 mL ice-cold water, and the filtrate was again collected. The cake was also washed with an additional 100 mL ice-cold 100% ethanol and the filtrate was collected once again. The final wash of the cake was 100 mL of fresh ice-cold water and the final filtrate collected. The cake was dried under vacuum and/or air-dried over 12-18 hours. After drying, the cake was scraped off the funnel, weighed, and moisture/protein contents were measured via HPLC. The collected filtrates from the various wash steps were also analyzed using HPLC to determine the concentration of the lost Zn-HIM2 during the process. The filtration yielded a 2.5% w/w Zn content with an overall yield of 98%.

9.1.8 T-Type Zn Complex of HIM2 at Neutral pH (500 mg Scale)

A HIM2 solution at approximately 10 g/L was prepared to a final pH ~3 with 10% HCl. Two hundred µL of a 10% $ZnCl_2$ solution was added to the sample. The pH was adjusted to 7.06 with concentrated ammonium hydroxide. The solution was stirred at +5 for 15 minutes and then stood at +5 for two days to allow solid formation to occur.

The reaction mixture was transferred to a centrifuge tube and centrifuged at 2800 RPM for 15 minutes. The solution was decanted and the solid was washed with 10 mL cold DI $H_2O$. This solution was centrifuged at 2800 RPM for 15 minutes before the $H_2O$ was decanted. The water washes were repeated two additional times. The sample was then washed with 10 mL 200 proof cold EtOH and centrifuged at 2600 RPM for 20 minutes before the EtOH was decanted. Two more EtOH washes were carried out the same way before the sample was placed on the lyophilizer to dry for two days.

9.1.9

Results for T-type Solid Compositions

| Reaction | Observations | Solubility (mg/mL) | % w/w Zn |
|---|---|---|---|
| 9.1.1 | No solid formed | N/A | N/A |
| 9.1.2 | White solid | NEM | NEM |
| 9.1.3 | White solid | NEM | NEM |
| 9.1.4 | White solid | NEM | 0.53 |
| 9.1.5 | White solid | 146 | 0.66 |
| 9.1.6 | White solid | 109 | 0.55 |
| 9.1.7 | White solid | ND | 2.50 |
| 9.1.8 | White solid | ND | 1.63 |

NEM = Not enough material
ND = No data

9.2 Preparation and Analysis of R-Type Solids

9.2.1 R-Type Zn Complex of HIM2 with Phenol at 2 g/L

A HIM2 solution at approximately 2 g/L was prepared to a final pH ~3 with glacial acetic acid. Thirty three microliters of liquefied phenol was added to a 10 mL aliquot of the above solution. The pH was adjusted to 5.89 with concentrated ammonium hydroxide. One hundred sixty μL of a 10% w/w $ZnCl_2$ solution was added to the sample. The solution was stirred at room temperature for 15 minutes and then stood at room temperature for three days to allow more precipitate to form.

The reaction mixture was transferred to a centrifuge tube and centrifuged at 3400 RPM for 15 minutes. The supernatant was decanter and the solid was washed with 5 mL cold DI water. This solution was centrifuged at 3200 RPM for 15 minutes before the $H_2O$ was decanted. The sample was then washed with 5 mL 200 proof cold EtOH and centrifuged at 3200 RPM for 15 minutes before the EtOH was decanted. Again the sample was washed with 5 mL of cold EtOH, however, it was not centrifuged. The solid was allowed to settle to the bottom of the tube and then placed in the speed vacuum to dry.

9.2.2 Preparation of R-Type Zn Complex of HIM2 at 20 g/L

A HIM2 solution at approximately 20 g/L was prepared to a final pH ~3 with 10% HCl. Sixty six μL of liquefied phenol was added to a 10 mL aliquot of the above solution. The pH was adjusted to 6.43 with concentrated ammonium hydroxide. Three hundred twenty μL of a 10% $ZnCl_2$ solution was added to the sample. The solution was stirred at room temperature for 15 minutes and then stood at room temperature for four days to allow more precipitate to form.

The reaction mixture was transferred to a centrifuge tube and centrifuged at 2600 RPM for 20 minutes. The solution was decanted and the solid was washed with 5 mL cold DI $H_2O$. This solution was centrifuged at 2600 RPM for 20 minutes before the $H_2O$ was decanted and the solid was washed with another 5 mL cold DI $H_2O$. Again, the sample was centrifuged at 2600 RPM for 20 minutes before the $H_2O$ was decanted. The sample was washed with 5 mL 200 proof cold EtOH and centrifuged at 2600 RPM for 20 minutes before the EtOH was decanted. The sample was lyophilized for three days.

9.2.3 Preparation of R-Type Zn Complex of HIM2 at 30 g/L

A HIM2 solution at approximately 30 g/L was prepared to a final pH ~3 with 10% HCl. Ninety nine microliters of liquefied phenol was added to a 10 mL aliquot of the above solution. The pH was adjusted to 6.47 with concentrated ammonium hydroxide. Then, 480 μL of a 10% $ZnCl_2$ solution was added to the sample. The solution was stirred at room temperature for 15 minutes and then stood at room temperature for four days to allow more precipitate to form.

The reaction mixture was transferred to a centrifuge tube and centrifuged at 2600 RPM for 20 minutes. The solution was decanted and the solid was washed with 5 mL cold DI $H_2O$. This solution was centrifuged at 2600 RPM for 20 minutes before the $H_2O$ was decanted and the solid was washed with another 5 mL cold DI $H_2O$. Again, the sample was centrifuged at 2600 RPM for 20 minutes before the $H_2O$ was decanted. The sample was washed with 5 mL 200 proof cold EtOH and centrifuged at 2600 RPM for 20 minutes before the EtOH was decanted. The sample was lyophilized for three days.

Figure 4:
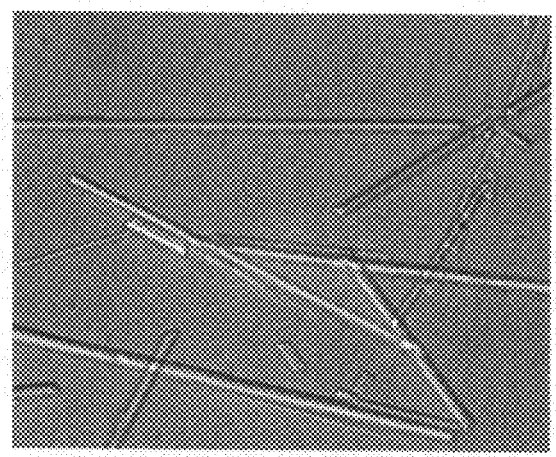

FIG. 4 shows solid grown for 4 days. The picture was taken using a Zeiss Axiovert microscope. The average length of the crystals is approximately 9.7 μM.

9.2.4 Preparation of R-Type Zn Complex of HIM2 at 50 g/L

A HIM2 solution at approximately 50 g/L was prepared to a final pH ~3 with 10% HCl. One hundred sixty five microliters of liquefied phenol was added to a 10 mL aliquot of the above solution. The pH was adjusted to 6.82 with concentrated ammonium hydroxide. Eight hundred μL of a 10% $ZnCl_2$ solution was added to the sample. The solution was stirred at room temperature for 15 minutes and then stood at room temperature for four days to allow more precipitate to form.

The reaction mixture was transferred to a centrifuge tube and centrifuged at 2600 RPM for 20 minutes. The solution was decanted, and the solid was washed with 5 mL cold DI $H_2O$. This solution was centrifuged at 2600 RPM for 20 minutes before the $H_2O$ was decanted and the solid was washed with another 5 mL cold DI $H_2O$. Again, the sample was centrifuged at 2600 RPM for 20 minutes before the $H_2O$ was decanted. The sample was washed with 5 mL 200 proof cold EtOH and centrifuged at 2600 RPM for 20 minutes before the EtOH was decanted. The sample was lyophilized for three days.

9.2.5 Preparation of R-Type Zn Complex of HIM2 at 1 g Scale

A HIM2 solution at approximately 10 g/L was prepared to a final pH ~3 with 10% HCl. One hundred sixty five microliters of liquefied phenol was added to a 50 mL aliquot of the above solution. The pH was adjusted to 6.42 with concentrated ammonium hydroxide. Eight hundred μL of a 10% $ZnCl_2$ solution was added to the sample. The solution was stirred at room temperature for 15 minutes and then stood at room temperature for seven days to allow more precipitate to form.

The reaction mixture was transferred to a centrifuge tube and centrifuged at 2600 RPM for 20 minutes. The solution was decanted and the solid was washed with 10 mL cold DI $H_2O$. This solution was centrifuged at 2600 RPM for 20 minutes before the $H_2O$ was decanted. Two more water washes occurred the same way. The sample was then washed with 10 mL 200 proof cold EtOH and centrifuged at 2600 RPM for 20 minutes before the EtOH was decanted. Two more EtOH washes were carried out the same way before the sample was placed on the lyophilizer for four days.

9.2.6 R-Type Zn Complex of HIM2 at 5 g Scale

A HIM2 solution at approximately 10 g/L was prepared to a final pH ~3 with 10% HCl. Fifteen hundred microliters of liquefied phenol was added to 450 mL of the above solution. The pH was adjusted to 7.1 with concentrated ammonium hydroxide. Eighteen hundred μL of a 10% $ZnCl_2$ solution was added to the sample. The solution was stirred at room temperature for 15 minutes and then stood at room temperature overnight to allow more precipitate to form.

The reaction performed above was split into three filtration trials. In trial one, the reaction mixture was filtered through a fine fritted funnel and then washed with a 1% ZnCl2 solution. The material was dried overnight via vacuum filtration. The second trial was filtered over a medium fritted filter which also contained filter paper. The substance was then washed with ethanol and water and dried overnight via vacuum filtration. Finally, the third trial was filtered through a fine fritted funnel, washed with a 1% ZnCl2 solution and also washed with ethanol and water. This material was also dried overnight under vacuum filtration.

|  | Trial 1 (fine-frit, ZnCl2 wash, not H₂O/EtOH wash) | Trial 2 (filter paper, medium frit, EtOH/H₂0 wash) | Trial 3 (fine-frit, EtOH/H₂O washes) |
|---|---|---|---|
| Yield | 74% | 93% | 58% |
| w/w % Zn | 1.99 | 2.83 | 2.06% |
| w/w % Phenol | 0.033 | 0.45 | 1.28 |

9.2.7 R-Type Zn Complex of HIM2 at Neutral pH

A HIM2 solution at approximately 10 g/L was prepared to a final pH ~3 with 10% HCl. One hundred sixty five microliters of liquefied phenol was added to 50 mL of the above solution. Then, two hundred microliters of a 10% $ZnCl_2$ solution was added to the sample. The pH was adjusted to 7.18 with concentrated ammonium hydroxide. The solution sat at room temperature for two days to allow precipitate to form.

The reaction mixture was transferred to a centrifuge tube and centrifuged at 2800 RPM for 20 minutes. However, the material did not settle to the bottom of the tube initially and was therefore, centrifuged for about 2 hours. The solution was decanted and the solid was washed with 5 mL cold DI $H_2O$. This solution was centrifuged at 2800 RPM for 60 minutes before the $H_2O$ was decanted. The water wash was repeated two more times. The sample was then washed with 5 mL 200 proof cold EtOH and centrifuged at 2800 RPM for 60 minutes before the EtOH was decanted. Two more EtOH washes were carried out the same way. Material was cloudy after the third EtOH wash and was placed in the refrigerator overnight to allow the reactions to settle more. The solvent was decanted and the material was placed on the lyophilizer for 2 days.

9.2.8

| Results for R-type Solid Compositions | | | | |
|---|---|---|---|---|
| Reaction | Observations | Solubility (mg/mL) | % w/w Zn | Phenol |
| 9.2.1 | White solid | NEM | NEM | NEM |
| 9.2.2 | White solid | 44.75 | 1.21 | 0.097 |
| 9.2.3 | White solid | 50.49 | 1.74 | 0.41 |
| 9.2.4 | White solid | 36.24 | 2.32 | 0.52 |
| 9.2.5 | White solid | 47.7 | 1.06 | 0.16 |
| 9.2.6 | White solid | ND | See above | See above |
| 9.2.7 | White solid | ND | 1.74 | 1.62 |

NEM = Not enough material
ND = No data

9.3 Preparation and Analysis of Protamine Solids

9.3.1 Preparation of T-Type Zn Complex of HIM2 with Protamine at Acidic pH

Protamine was added to a 10 g/L stock solution of HIM2 that had a final pH ~3 with 10% HCl. Glacial acetic acid was added to a 10 mL aliquot (100 mg protein) of the above solution to a final concentration of 0.25 M. Two hundred microliters of a 10% $ZnCl_2$ solution was added to the sample. The pH was adjusted with concentrated ammonium hydroxide to a pH ~5. The solution was stirred at +5° C. for 15 minutes and then stood at +5° C. for two days to allow solid formation to occur.

The reaction mixture was transferred to a centrifuge tube and centrifuged at 2600 RPM for 20 minutes. The solution was decanted and the solid was washed with 10 mL cold DI $H_2O$. This solution was centrifuged at 2600 RPM for 20 minutes before the $H_2O$ was decanted. Two more $H_2O$ washed occurred the same way. The sample was then washed with 10 mL 200 proof cold EtOH and centrifuged at 2600 RPM for 20 minutes before the EtOH was decanted. Two more EtOH washes were carried out the same way before the sample was placed on the lyophilizer for two days.

9.3.2 Preparation of T-Type Zn Complex of HIM2 with Protamine at Neutral pH A HIM2 solution at approximately 30 g/L was prepared to a final pH ~3 with 10% HCl. One milliliter of glacial acetic acid was added to a 50 mL aliquot (1.5 g protein) of the above solution. Six hundred microliters of a 10% $ZnCl_2$ solution was added to the reaction followed by the addition of 225 milligrams of protamine. The pH was adjusted to 6.95 with concentrated ammonium hydroxide and the reaction stood for two days at +5° C. to allow solid formation to occur.

The reaction mixture was transferred to a centrifuge tube and centrifuged at 2600 RPM for 20 minutes. The solution was decanted and the solid was washed with 10 mL cold DI $H_2O$. This solution was centrifuged at 2600 RPM for 20 minutes before the $H_2O$ was decanted. Two more $H_2$? washed occurred the same way. The sample was then washed with 10 mL 200 proof cold EtOH and centrifuged at 2600 RPM for 20 minutes before the EtOH was decanted. Two more EtOH washes were carried out the same way before the sample was placed on the lyophilizer for three days

9.3.3 Preparation of R-Type Zn Complex of HIM2 with Protamine at Acidic pH

A HIM2 solution at approximately 10 g/L was prepared to a final pH ~3 with 10% HCl. Liquified phenol (2.48 mL) was added to a 150 mL aliquot (1.5 g protein) of the above solution. The pH of the reaction was adjusted with concentrated ammonium hydroxide to a pH ~6.57. Twelve microliters of a 10% $ZnCl_2$ solution was added to the reaction followed by the addition of 225 milligrams of protamine. The reaction mixture stirred at room temperature for 15 minutes before it stood for two days at room temperature to allow solid formation to occur.

The reaction mixture was transferred to a centrifuge tube and centrifuged at 2800 RPM for 15 minutes. The solution was decanted and the solid was washed with 50 mL cold DI $H_2$?. This solution was centrifuged at 2800 RPM for 15 minutes before the $H_2O$ was decanted. Two more $H_2O$ washed occurred the same way. The sample was then washed with 10 mL 200 proof cold EtOH and centrifuged at 2800 RPM for 15 minutes before the EtOH was decanted. Two more EtOH washes were carried out the same way before the sample was placed on the lyophilizer for two days.

9.3.4 Preparation of R-Type Zn Complex of HIM2 with Protamine at Neutral pH A HIM2 solution at approximately 10 g/L was prepared to a final pH ~3 with 10% HCl. Liquefied phenol (495 mL) was added to 150 mL reaction. Then, 600 mililiters of a 10% $ZnCl_2$ solution was added to reaction followed by the addition of 75 mg protamine. The pH was adjusted with concentrated ammonium hydroxide to a pH of 7.01. The reaction stood for three days at room temperature to allow solid formation.

The reaction mixture was transferred to a centrifuge tube and centrifuged at 2800 RPM for 15 minutes. The solution was decanted and the solid was washed with 50 mL cold DI $H_2O$. This solution was centrifuged at 2800 RPM for 15 minutes before the $H_2O$ was decanted. Two more H2O washes occurred the same way. The sample was then washed with 50 mL 200 Proof cold EtOH and centrifuged at 2800 RPM for 15 minutes before the EtOH was decanted. Two more EtOH washes were carried out the same way before the sample was placed on the lyophilizer for two days.

Results for Protamine Solid Compositions

| Reaction | Observations | Solubility (mg/mL) | % w/w Zn | Phenol |
|---|---|---|---|---|
| 9.3.1 | White solid | ND | 0.66 | N/A |
| 9.3.2 | White solid | ND | 2.47 | N/A |
| 9.3.3 | White solid | 36.78 | 1.22 | 9.87 |
| 9.3.4 | White solid | NEM | NEM | NEM |

NEM = Not enough material
ND = No data

9.4 Preparation and Analysis of Complexes of Insulin Compound Diconjugates

9.4.1 T-Type Zn Complex at A1 and B29 Insulin Compound Diconjugate

An insulin compound diconjugate having a modifying moiety —$C(O)(CH_2)_5(OCH_2CH_2)_7OCH_3$ coupled at B29 and A1 of human insulin (DICON-1) was added to solution at approximately 10 g/L and prepared to a final pH 3.15 with 10% HCl. Glacial acetic acid was added to a 3.75 mL aliquot of the above solution to a final concentration of 0.25 M. Then 15 µL of a 10% $ZnCl_2$ solution was added to the sample. The pH was adjusted to 4.90 with concentrated ammonium hydroxide. The solution stirred for 15 minutes at +5° C. and then stood for six days at +5° C. to allow solid formation (yielded a white solid).

9.4.2 R-Type Zn Complex at A1 and B29 Insulin Compound Diconjugate

DICON-1 was added to solution at approximately 10 g/L and prepared to a final pH 3.15 with 10% HCl. About 12 µL of liquefied phenol was added to a 3.75 mL aliquot of the above solution. The pH was adjusted to 5.75 with concentrated ammonium hydroxide. Sixty µL of a 10% $ZnCl_2$ solution was added to the sample. The solution was stirred at room temperature for 15 minutes and then stood at room temperature for six days to allow more precipitate to form (yielded a white solid).

The reaction mixture was transferred to a centrifuge tube and centrifuged at 2600 RPM for 20 minutes. The solution was decanted and the solid was washed with 5 mL cold DI $H_2O$. This solution was centrifuged at 2600 RPM for 20 minutes before the $H_2O$ was decanted and the solid was washed with another 5 mL cold DI $H_2O$. Again, the sample was centrifuged at 2600 RPM for 20 minutes before the $H_2O$ was decanted. The sample was washed with 5 mL 200 proof cold EtOH and centrifuged at 2600 RPM for 20 minutes before the EtOH was decanted. The sample was lyophilized for six days.

9.4.3 Diconjugate B1, B29 (10 mg/mL)

DICON-1 was added to solution at approximately 10 g/L and 33 µL of liquified phenol was added. The pH was adjusted to 5.34 with concentrated ammonium hydroxide. Then 160 µL of a 10% $ZnCl_2$ solution was added to the sample. The solution stood at room temperature for two weeks to allow solid formation to occur (yielded a white solid).

The reaction mixture was transferred to a centrifuge tube and centrifuged at 2800 RPM for 15 minutes. The solution was decanted and the solid was washed three times with 5 mL cold DI $H_2O$. The solution was centrifuged for 15 minutes at 2800 RPM and decanted after each wash. The sample was then washed three times with 5 mL 200 proof cold EtOH. Again the sample was centrifuged at 2600 RPM for 15 minutes and decanted after each wash. The sample was lyophilized for two days.

9.4.4 Diconjugate B1, B29 (20 mg/mL)

DICON-1 was added to solution at approximately 20 g/L and 66 microliters of liquified phenol was added. The pH was adjusted to 7.65 with concentrated ammonium hydroxide. Then 320 µL of a 10% $ZnCl_2$ solution was added to the sample. The solution stood at room temperature for two weeks to allow solid formation to occur (yielded a white solid).

The reaction mixture was transferred to a centrifuge tube and centrifuged at 2800 RPM for 15 minutes. The solution was decanted and the solid was washed three times with 5 mL cold DI $H_2O$. The solution was centrifuged for 15 minutes at 2800 RPM and decanted after each wash. The sample was then washed three times with 5 mL 200 proof cold EtOH. Again the sample was centrifuged at 2600 RPM for 15 minutes and decanted after each wash. The sample was lyophilized for two days.

9.5 Preparation and Analysis of T-Type IN105 Solids

9.5.1 T-Type Zn Complex of IN105 Monoconjugate (10 g/L Concentration)

A IN105 solution at approximately 10 g/L (100 mg) was prepared having a final pH ~3 with 10% HCl. 50 µL of a 10% w/w $ZnCl_2$ solution was added to the sample. The pH was adjusted to 7.52 with concentrated ammonium hydroxide. The cloudy solution was stirred and then allowed to stand for five days at room temperature to allow solid formation.

The reaction mixture was transferred to a centrifuge tube and centrifuged at 2900 RPM for 15 minutes. The solution was decanted and the solid was washed with 3×10 mL cold DI water. This solution was centrifuged at 2900 RPM for 10 minutes before the water was decanted and the solids were washed with another portion of cold DI water. The sample then was washed with 3×10 mL 200 proof cold EtOH and centrifuged at 2900 RPM for 10 minutes before the EtOH was decanted. The sample was vacuum dried to provide white solid (90 mg).

9.5.2 T-Type Zn Complex of IN105 Monoconjugate (1 g Scale)

A IN105 solution at approximately 10 g/L (1 g) was prepared to a final pH ~3 with 10% HCl. Five hundred µL of a 10% $ZnCl_2$ solution was added to the sample. The pH was adjusted to ~7.4 with concentrated ammonium hydroxide.

The cloudy solution was stirred for 15 minutes and then allowed to stand at room temperature for ~2 days before filtration.

The reaction mixture was filtered through sintered glass funnel (fine) under house vacuum. The sintered glass funnel with filtered material was placed under vacuum in a glass dessicator over night to result a white fine powder (900 mg).

9.5.3 T-Type Zn Complex of IN105 Monoconjugate at Neutral pH (5 g Scale)

A IN105 solution at approximately 10 g/L (5 g, lot# Nobex040706L) was prepared to a final pH ~3 with 10% HCl. Two mL of a 10% $ZnCl_2$ solution was added to the sample. The pH was adjusted to ~7.4 with concentrated ammonium hydroxide. The cloudy solution was then allowed to stand at room temperature overnight to allow solid formation before filtration.

The reaction performed above was split into 4×50 mL centrifuge tubes and initially centrifuged at 3200 RPM for a total 2 hours. The material was then centrifuged at 9000 RPM for 20 minutes and stored at 5° C. over night. The supernatant was decanted and the solid was washed with 10 mL cold DI $H_2O$ from each tube. The tubes were inverted and centrifuged at 3200 RPM for ~1 hour before the $H_2O$ was decanted and the solids were washed with another 10 mL cold DI $H_2O$. Again, the sample was centrifuged at 3200 RPM for ~1 hour before the $H_2O$ was decanted. The sample was washed with 2×10 mL 200 proof cold EtOH and centrifuged at 3200 RPM for 1 hour before the EtOH was decanted. The sample was vacuum dried for two days to give 1.64 g (lot# Nobex040730L-A) of white powder.

| Results for T-type IN105 Solid Compositions | | | |
| --- | --- | --- | --- |
| Reaction | Observations | Solubility (mg/mL) in a pH of about 7.4, 0.1M phosphate buffer | % w/w Zn |
| 9.5.1 | White solid | 80-85 | 0.0 |
| 9.5.2 | White solid | 10-20 | 1.67 |
| 9.5.3 | White solid | ND | 1.88 |

9.6 Preparation and Analysis of R-Type IN105 Solids

9.6.1 R-Type Zn Complex at IN105 Conjugate with Phenol at Neutral pH

A IN105 solution at approximately 10 g/L (500 mg) was prepared to a final pH ~3 with 10% HCl. Two hundred μL of 10% $ZnCl_2$ and 165 μL of liquefied phenol was added to the above solution. The pH was adjusted to 7.37 with concentrated ammonium hydroxide. The cloudy solution sat at room temperature for 2 days to allow solid formation before filtration.

The reaction mixture was filtered through sintered glass funnel (fine) under house vacuum. The sintered glass funnel with filtered material was placed in under vacuum in a glass dessicator over night to result in a white fine powder (440 mg).

9.6.2 R-Type Zn Complex of IN105 Conjugate at 5 g Scale

A IN105 solution at approximately 10 g/L (4.2 g, lot# Nobex040706L) was prepared to a final pH ~3 with 10% HCl. 1.5 liquefied phenol and 1.8 mL of 10% ZnCl2 solution was added to the above solution. The pH was adjusted to ~7.4 with concentrated ammonium hydroxide. The very cloudy solution stood at room temperature overnight to allow more precipitate to form.

The reaction performed above was split into 4×50 mL centrifuge tubes and initially centrifuged at 3200 RPM for 2 hours. The material was then centrifuged at 9000 RPM for 20 minutes and stored at 5° C. over night. The supernatant was decanted and the solid was washed with 10 mL cold DI $H_2O$ from each tube. The tubes were inverted and centrifuged at 3200 RPM for ~1 hour before the $H_2O$ was decanted and the solids were washed with another 10 mL cold DI $H_2O$. Again, the sample was centrifuged at 3200 RPM for ~1 hour before the $H_2O$ was decanted. The sample was washed with 2×10 mL 200 proof cold EtOH and centrifuged at 3200 RPM for 1 hour before the EtOH was decanted. The sample was vacuum dried for 2 days to give 2.34 g of white powder.

| Results for R-Type IN105 Solid Compositions | | | | |
| --- | --- | --- | --- | --- |
| Reaction | Observations | Solubility (mg/mL)* | % w/w Zn | % w/w Phenol |
| 9.6.1 | White solid | ND | 1.85 | 2.37 |
| 9.6.2 | White solid | 10-25 | 1.71 | 2.66 |

ND = No data
*In a pH of about 7.4 phosphate buffer

9.7 Preparation and Analysis of Protamine IN105 Solids

9.7.1 Preparation of R-Type Zn Complex of IN105 Monoconjugate with Protamine at Acidic pH A IN105 solution at approximately 10 g/L is prepared to a final pH ~3 with 10% HCl. Liquified phenol (248 uL) is added to a 15 mL aliquot (150 mg protein) of the above solution. The pH of the reaction is adjusted with concentrated ammonium hydroxide to a pH ~6.50. One microliter of a 10% $ZnCl_2$ solution is added to the reaction followed by the addition of 22.5 milligrams of protamine. The reaction mixture is stirred at room temperature for 15 minutes before it stood for two days at room temperature to allow solid formation to occur.

The reaction mixture is transferred to a centrifuge tube and centrifuged at 2800 RPM for 15 minutes. The solution is decanted and the solid is washed with 5 mL cold DI $H_2O$. This solution is centrifuged at 2800 RPM for 15 minutes before the $H_2O$ is decanted. Two more $H_2O$ wash is occurred the same way. The sample is then washed with 10 mL 200 proof cold EtOH and centrifuged at 2800 RPM for 15 minutes before the EtOH is decanted. Two more EtOH washes are carried out the same way before the sample is vacuum dried over two days.

9.7.2 Preparation of R-Type Zn Complex of IN105 Conjugate With Protamine at Neutral pH A IN105 solution at approximately 10 g/L is prepared to a final pH ~3 with 10% HCl. Liquefied phenol (49.5 uL) is added to 15 mL reaction. Then, 60 microliters of a 10% $ZnCl_2$ solution is added to reaction followed by the addition of 7.5 mg protamine. The pH is adjusted with concentrated ammonium hydroxide to a pH of 7.00. The reaction is allowed to stand for three days at room temperature to allow solid formation.

The reaction mixture is transferred to a centrifuge tube and centrifuged at 2800 RPM for 15 minutes. The solution is decanted and the solid was washed with 5.0 mL cold DI $H_2O$. This solution is centrifuged at 2800 RPM for 15 minutes before the $H_2O$ is decanted. Two more $H_2O$ washes are occurred the same way. The sample is then washed with 50 mL 200 Proof cold EtOH and centrifuged at 2800 RPM for 15 minutes before the EtOH is decanted. Two more EtOH washes are carried out the same way before the sample is vacuum dried over two days.

9.7.3 Preparation of R-Type Crystalline Zn Complex of IN105

A crude 15 mg/mL IN105 solution containing 25% organic was pH adjusted to 3.47 using 1M HCl. Solid phenol was melted in a 40-60° C. water bath and 0.218 mL was added to reaction flask. Then 0.4 mL of 4% acidified aqueous $ZnCl_2$ solution was added to reaction. The pH of the solution was adjusted with 1M NaOH to a final pH of 6.6. While adjusting the pH, 10 mL aliquots were pulled at the following pH values: 4.8, 5.0, 5.2, 5.4, 5.6, 5.8, 6.0, 6.2, 6.4 and 6.6. The samples were allowed to sit without stirring for 24 hours. Needle-like crystals were observed under a microscope.

Figure 5:
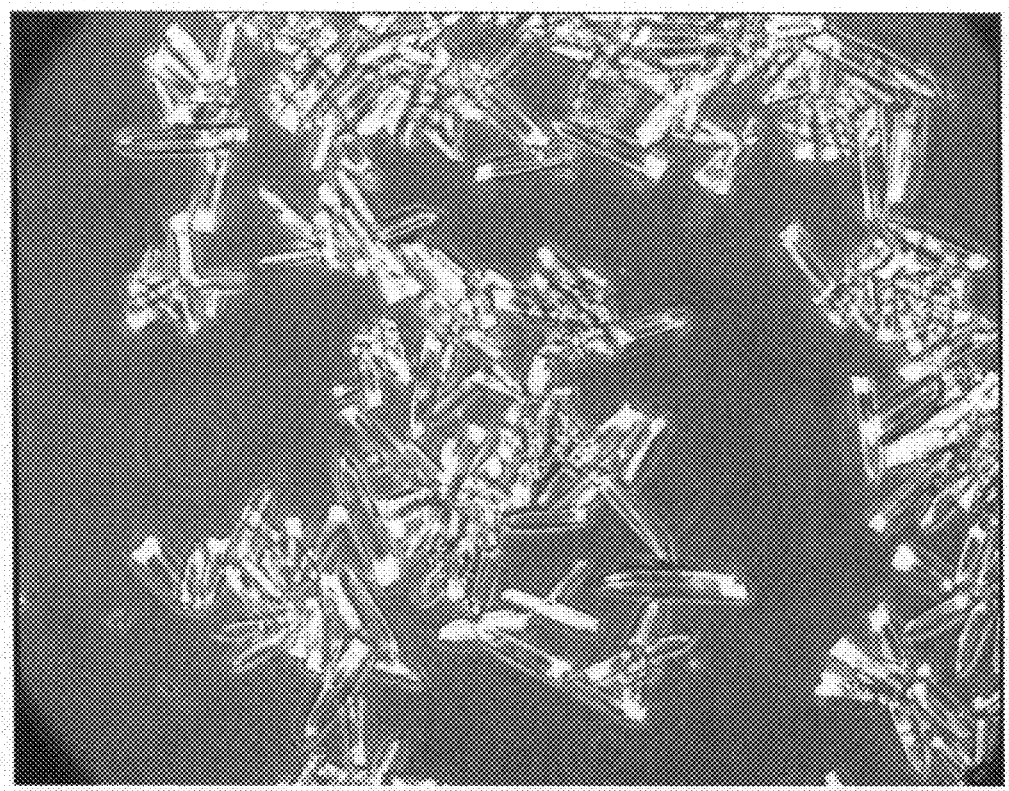

9.7.4 Preparation of R-Type Crystalline Zn Complex of IN105 Containing 30% Organic A fresh 15 mg/mL solution of $MPEG_3$ propionyl insulin compound was prepared in 250 mM ammonium acetate buffer and the pH was adjusted to 2.81 with 1M HCl. Liquefied phenol, 0.040 mL, and 95% EtOH, 4.25 mL, were added to the solution. Then, 0.400 mL of a 4% acidified $ZnCl_2$ solution was added to the reaction mixture. The pH of the solution was adjusted from 3.7 to 5.4 using 50% $NH_4OH$ and pulling 1 mL aliquots at each of the following desired pH: 4.0, 4.2, 4.4, 4.6, 4.8, 5.0, 5.2, 5.4. The samples were allowed to sit without stirring for 24 hours. The microscope pictures taken after 24 hours showed needle-like crystals (see FIG. 5) from the pH range 4.0 to 5.2.

9.7.5 Preparation of R-Type Crystalline Zn Complex of IN105 in 100 mM Ammonium Acetate Buffer (30, 20 and 10% EtOH)

A fresh 15 mg/mL solution of $MPEG_3$ propionyl insulin compound was prepared in 100 mM ammonium acetate buffer and the pH was adjusted to 2.8 with 5M HCl. Liquefied phenol, 0.040 mL, and 95% EtOH, 4.25 mL, were added to the solution. Then, 0.400 mL of a 4% acidified $ZnCl_2$ solution was added to the reaction mixture. The pH of the solution was adjusted from 2.9 to 5.6 using 5M $NH_4OH$ and pulling 0.5 mL aliquots at each of the following desired pH: 4.2, 4.4, 4.6, 4.8, 5.0, 5.2, 5.4, 5.6. The samples were allowed to sit without stirring for 24 hours. The microscope pictures taken after 24 hours showed needle-like crystals from the pH range 4.4 to 4.8.

A fresh 15 mg/mL solution of $MPEG_3$ propionyl insulin compound was prepared in 100 mM ammonium acetate buffer and the pH was adjusted to 2.8 with 5M HCl. Liquefied phenol, 0.040 mL, and 95% EtOH, 2.25 mL, were added to the solution. Then, 0.400 mL of a 4% acidified $ZnCl_2$ solution was added to the reaction mixture. The pH of the solution was adjusted from 2.9 to 5.6 using 5M $NH_4OH$ and pulling 0.5 mL aliquots at each of the following desired pH: 4.2, 4.4, 4.6, 4.8, 5.0, 5.2, 5.4, 5.6. The samples were allowed to sit without stirring for 24 hours. The microscope pictures taken after 24 hours showed circle-like crystals from the pH range 4.8 to 5.4.

A fresh 15 mg/mL solution of $MPEG_3$ propionyl insulin compound was prepared in 100 mM ammonium acetate buffer and the pH was adjusted to 2.8 with 5M HCl. Liquefied phenol, 0.040 mL, and 95% EtOH, 1.15 mL, were added to the solution. Then, 0.400 mL of a 4% acidified $ZnCl_2$ solution was added to the reaction mixture. The pH of the solution was adjusted from 2.8 to 5.6 using 5M $NH_4OH$ and pulling 0.5 mL aliquots at each of the following desired pH: 4.2, 4.4, 4.6, 4.8, 5.0, 5.2, 5.4, 5.6. The samples were allowed to sit without stirring for 24 hours. The microscope pictures taken after 24 hours showed needle-like crystals from the pH range 5.0 to 5.6.

9.7.6 Preparation of R-Type Crystalline Zn Complex of IN105 in 20% Organic with 0.1 and 0.2% Phenol A fresh 15 mg/mL solution of $MPEG_3$ propionyl insulin compound was prepared in 100 mM ammonium acetate buffer and the pH was adjusted to 3.0 with 5M HCl. Liquefied phenol, 0.010 mL, and 95% EtOH, 2.5 mL, were added to the solution. Then, 0.400 mL of a 4% acidified $ZnCl_2$ solution was added to the reaction mixture. The pH of the solution was adjusted from 3.2 to 5.6 using 5M $NH_4OH$ and pulling 0.5 mL aliquots at each of the following desired pH: 4.2, 4.4, 4.6, 4.8, 5.0, 5.2, 5.4, 5.6. The samples were allowed to sit without stirring for 24 hours. The microscope pictures taken after 24 hours showed circle-like crystals from the pH range 4.4 to 5.4.

A fresh 15 mg/mL solution of $MPEG_3$ propionyl insulin compound was prepared in 100 mM ammonium acetate buffer and the pH was adjusted to 3.0 with 5M HCl. Liquefied phenol, 0.020 mL, and 95% EtOH, 2.5 mL, were added to the solution. Then, 0.400 mL of a 4% acidified $ZnCl_2$ solution was added to the reaction mixture. The pH of the solution was adjusted from 3.3 to 5.6 using 5M $NH_4OH$ and pulling 0.5 mL aliquots at each of the following desired pH: 4.2, 4.4, 4.6, 4.8, 5.0, 5.2, 5.4, 5.6. The samples were allowed to sit without stirring for 24 hours. The microscope pictures taken after 24 hours showed circle-like crystals from the pH range 4.4 to 5.2.

9.7.7 Preparation of R-Type Crystalline Zn Complex of IN105 at 8.0 gram Scale, pH 4.8 and Room Temperature A fresh 15 mg/mL solution of $MPEG_3$ propionyl insulin compound was prepared in 250 mM ammonium acetate buffer and the pH was adjusted to 2.0 with 5M HCl. Liquefied phenol, 2.13 mL, and 95% EtOH, 225 mL, were added to the solution. Then, 21.3 mL of a 4% acidified $ZnCl_2$ solution was added to the reaction mixture. The pH of the solution was adjusted to 4.8 using 5M $NH_4OH$. The solution was allowed to sit without stirring for 24 hours before the crystals were harvested. Needle-like crystals were observed at the T=0 microscope picture.

The crystals were harvested by splitting the reaction mixture into 6×250 mL centrifuge tubes. The tubes were spun at 10,000 RPM for 8 minutes at 10° C. before the supernatant was decanted. Then, to each tube, was added 10 mL cold $H_2O$ before consolidating the 6 tubes into 2 tubes. The centrifuge process was repeated once more with cold water and twice more with cold EtOH. The crystals were then dried with a desktop lyophilizer for 2 days. The procedure produced 93% yield (w/w) relative to the starting material.

9.7.8 Preparation of R-Type Crystalline Zn Complex of IN105 at 1.5 gram Scale, pH 4.8 and Room Temperature A fresh solution of MPEG3 Propionyl Insulin compound (IN105) was prepared by dissolving 1.52 g of solid IN105 in 100 mL of 250 mM ammonium acetate pH 7.5. The solution was adjusted to pH 2.8 using 5M HCl/5M $NH_4OH$. Solid phenol was melted in a 40-60° C. warm water bath. 400 μL of melted phenol and 42.5 mL of 95% EtOH were added to the reaction flask. Then 4 mL of 4% acidified aqueous $ZnCl_2$ was added to the reaction flask. The resulting solution was then adjusted to pH 4.8 using 5M $NH_4OH$. The reaction was then allowed to sit without stirring for 48 hours before crystals were harvested. Needle-like crystal formation was observed after 21 hours via microscope.

The crystals were harvested by splitting of the reaction slurry among 4×50 mL centrifuge tubes. The tubes were spun initially at 1000 RPM for 8 min. The supernatant was then decanted. The crystals in each tube were washed with 1×5 mL aliquot of ice-cold $H_2O$ then spun at 3000 RPM for 8 min. The supernatant was then decanted. Repeated the washing/spinning procedure with 1×5 mL aliquot of ice-cold $H_2O$ then with 1×5 mL aliquot of ice-cold EtOH. The crystals were then dried in a vacuum dessicator overnight. The procedure produced 73% yield (w/w) relative to the starting material.

9.7.9 Preparation of R-Type Crystalline Zn Complex of IN105 at 1.5 gram Scale, pH 4.4 and Room Temperature A fresh solution of MPEG3 Propionyl Insulin compound (IN105) was prepared by dissolving 1.50 g of solid IN105 in 100 mL of 250 mM ammonium acetate pH 7.5. The solution was adjusted to pH 2.6 using 5M HCl. Solid phenol was melted in a 40-60° C. warm water bath. 400 μL of melted phenol and 42.5 mL of 95% EtOH were added to the reaction flask. Then 4 mL of 4% acidified aqueous $ZnCl_2$ was added to the reaction flask. The resulting solution was then adjusted to pH 4.4 using 5M $NH_4OH$. The reaction was then allowed to sit without stirring for 22 hours before crystals were harvested. A mixture of needle-like crystal formation and precipitate was observed after 2 hours via microscope. The reaction mixture appeared to be completely crystalline after 21 hours via microscope.

The crystals were harvested by transferring the reaction slurry to a 1×250 mL centrifuge tube. The tube was spun initially at 10,000 RPM for 8 min. The supernatant was then decanted. The crystals were washed with 1×20 mL aliquot of ice-cold $H_2O$ then spun at 10,000 RPM for 8 min. The supernatant was then decanted. Repeated the washing/spinning procedure with 1×20 mL aliquot of ice-cold $H_2O$ then with 2×20 mL aliquots of ice-cold EtOH and a final 1×20 mL aliquot of ice-cold $H_2O$. The crystals were then dried in a vacuum dessicator overnight. The procedure produced 67% yield (w/w) relative to the starting material.

9.7.10 Preparation of R-Type Crystalline Zn Complex of IN105 at 8.0 Gram Scale, pH 4.8 and Room Temperature A fresh solution of MPEG3 Propionyl Insulin compound (IN105) was prepared by dissolving 7.98 g of solid IN105 in 533 mL of 250 mM ammonium acetate pH 7.5. The solution was adjusted to pH 2.4 using 5M HCl. Solid phenol was melted in a 40-60° C. warm water bath. 2.13 mL of melted phenol and 225 mL of 95% EtOH were added to the reaction flask. Then 21.3 mL of 4% acidified aqueous $ZnCl_2$ was added to the reaction flask. The resulting solution was then adjusted to pH 4.8 using 5M $NH_4OH$. The reaction was then allowed to sit without stirring for 21 hours before crystals were harvested. The reaction mixture appeared to be completely crystalline after 2 hours via microscope.

The crystals were harvested by splitting the reaction slurry among 6×250 mL centrifuge tubes. The tubes were spun initially at 10,000 RPM for 8 min. The supernatant was then decanted. The crystals in each tube were washed with 1×10 mL aliquots of ice-cold $H_2O$ then spun at 10,000 RPM for 8 min. The supernatant was then decanted Repeated the washing/spinning procedure with 1×10 mL aliquot of ice-cold $H_2O$ then with 2×10 mL aliquots of ice-cold EtOH and a final 1×10 mL aliquot of ice-cold $H_2O$. The crystals were then dried in a vacuum dessicator for 2 days. The procedure produced 87% yield (w/w) relative to the starting material.

9.7.11 Preparation of R-Type Crystalline Zn Complex of IN105 at 10.0 Gram Scale, pH 4.8 and Room Temperature A fresh solution of MPEG3 Propionyl Insulin compound (IN105) was prepared by dissolving 10.06 g of solid IN105 in 670 mL of 250 mM ammonium acetate pH 7.5. The solution was adjusted to pH 2.6 using 5M HCl. Solid phenol was melted in a 40-60° C. warm water bath. 2.7 mL of melted phenol and 285 mL of 95% EtOH were added to the reaction flask. Then 27 mL of 4% acidified aqueous $ZnCl_2$ was added to the reaction flask. The resulting solution was then adjusted to pH 4.8 using 5M $NH_4OH$. The reaction was then allowed to sit without stirring for 21 hours before crystals were harvested. The reaction mixture appeared to be completely crystalline after 2.5 hours via microscope.

The crystals were harvested by splitting the reaction slurry among 6×250 mL centrifuge tubes. The tubes were spun initially at 10° C., 10,000 RPM for 8 min. The supernatant was then decanted. The crystals in each tube were washed with 1×10 mL aliquots of ice-cold $H_2O$, and consolidated into 2×250 mL centrifuge tubes then spun at 10° C., 10,000 RPM for 8 min. The supernatant was then decanted Repeated the washing/spinning procedure with 1×30 mL aliquot of ice-cold $H_2O$ then with 2×30 mL aliquots of ice-cold EtOH and a final 1×30 mL aliquot of ice-cold $H_2O$. The crystals were then dried using a benchtop lyophilizer for 3 days. The procedure produced 89% yield (w/w) relative to the starting material.

9.8 Preparation and Analysis of Crystalline Zn Complex of HIM2 Using Organic Solvent

9.8.1 Preparation of R-Type Zn Complexes of HIM2

A fresh 15 mg/mL solution of HIM2 was prepared in 250 mM ammonium acetate buffer and the pH was adjusted to 2.95 with 5M HCl. Liquefied phenol, 40 uL, and 95% EtOH, 3.5 mL, were added to the solution. Then, 600 uL of a 4% acidified $ZnCl_2$ solution was added to the reaction mixture.

Figure 6:
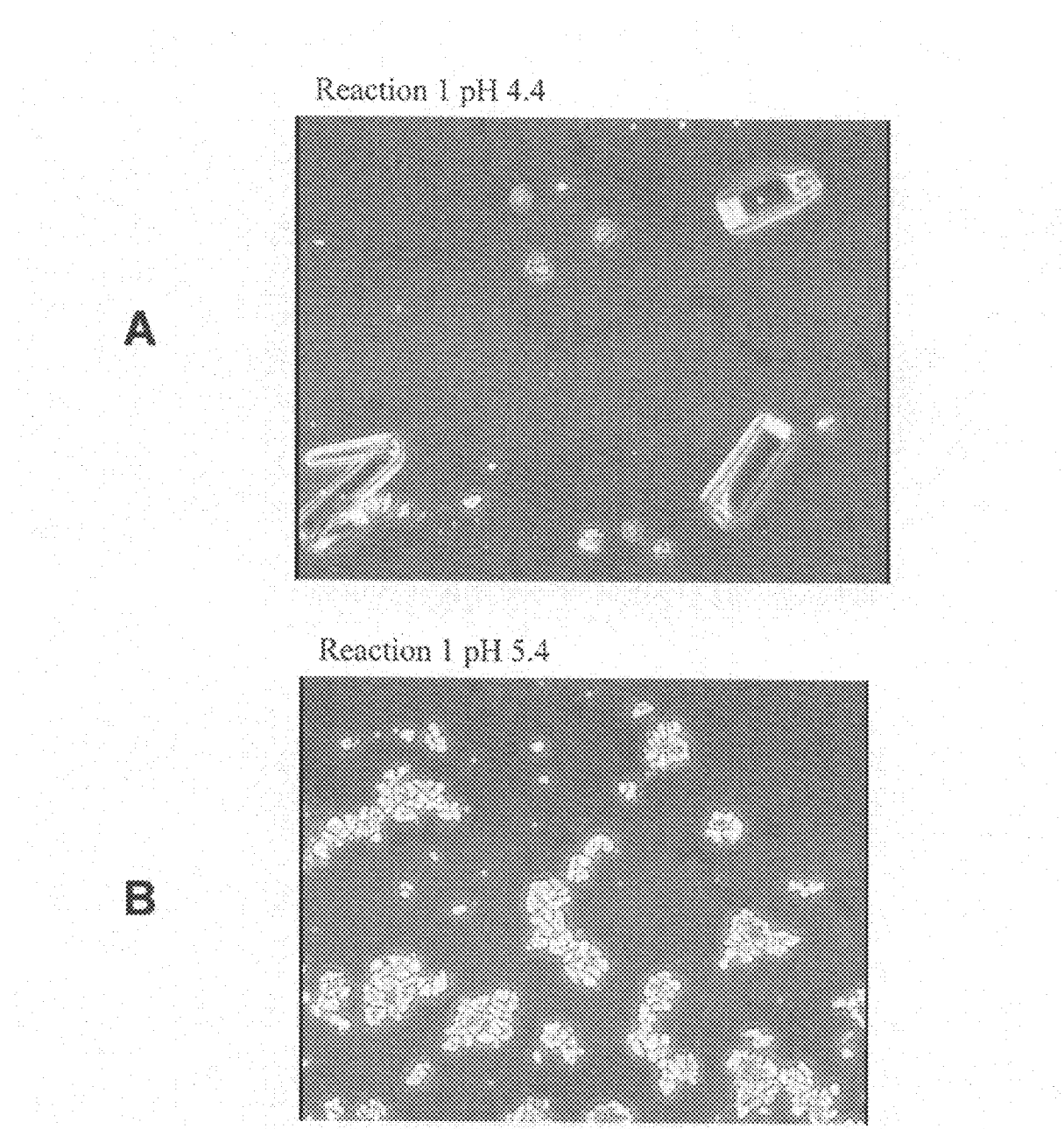

The pH of the solution was adjusted from 3.14 to 6.0 using 5M NH$_4$OH and pulling 500 uL aliquots at each of the following desired pH: 4.2, 4.4 (See FIG. 6A), 4.6, 4.8, 5.0, 5.2, 5.4 (See FIG. 6B), 5.6, 5.8, 6.0. The samples were allowed to sit without stirring for 24 hours. The microscope pictures taken after 24 hours showed needle-like crystals at pH 4.4. The pH range from 4.6-6.0 show large, crystalline like solids of various shapes and sizes.

Figure 7:
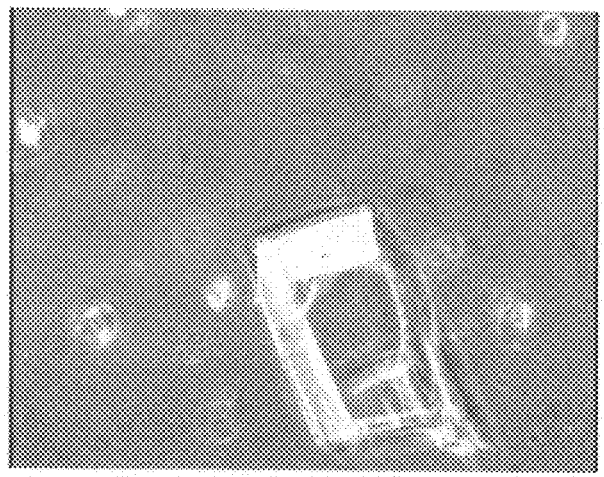
Figure 7:
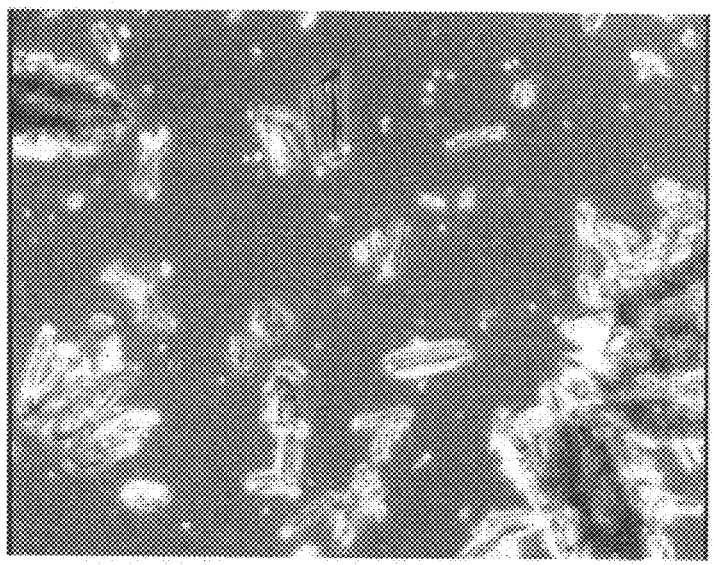

A fresh 15 mg/mL solution of HIM2 was prepared in 250 mM ammonium acetate buffer and the pH was adjusted to 2.95 with 5M HCl. Liquefied phenol, 40 uL, and 95% EtOH, 3.5 mL, were added to the solution. Then, 400 uL of a 4% acidified ZnCl$_2$ solution was added to the reaction mixture. The pH of the solution was adjusted from 3.22 to 6.0 using 5M NH$_4$OH and pulling 500 uL aliquots at each of the following desired pH: 4.2, 4.4, 4.6, 4.8, 5.0, 5.2 (See FIG. 7A), 5.4, 5.6, 5.8, 6.0. The samples were allowed to sit without stirring for 24 hours. The microscope pictures taken after 24 hours show crystalline-like solids from pH 4.2-6.0 of various shapes and sizes.

A fresh 15 mg/mL solution of HIM2 was prepared in 250 mM ammonium acetate buffer and the pH was adjusted to 2.95 with 5M HCl. Liquefied phenol, 40 uL, and 95% EtOH, 3.5 mL, were added to the solution. Then, 200 uL of a 4% acidified ZnCl$_2$ solution was added to the reaction mixture. The pH of the solution was adjusted from 3.19 to 6.0 using 5M NH$_4$OH and pulling 500 uL aliquots at each of the following desired pH: 4.2, 4.4, 4.6, 4.8, 5.0 (See FIG. 7B), 5.2, 5.4, 5.6, 5.8, 6.0. The samples were allowed to sit without stirring for 24 hours. The microscope pictures taken after 24 hours showed crystalline-like solids from pH 4.4-4.6 of various shapes and sizes. The pH range of 4.8-5.2 show more uniform, needle-like crystals.

Figure 8:
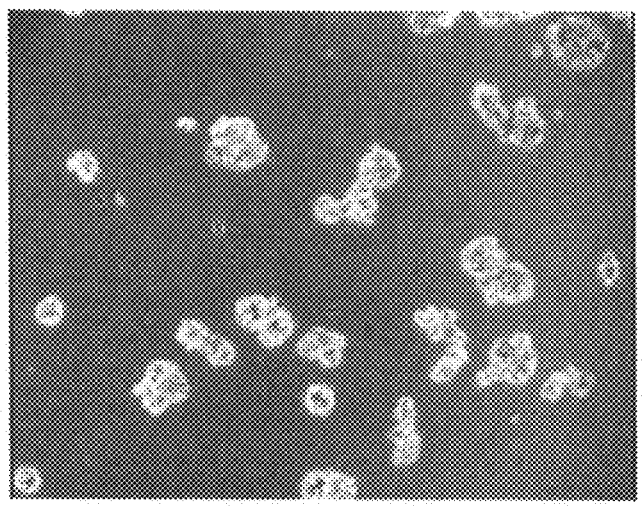
Figure 8:

A fresh 15 mg/mL solution of HIM2 was prepared in 250 mM ammonium acetate buffer and the pH was adjusted to 2.95 with 5M HCl. Liquefied phenol, 40 uL, and 95% EtOH, 2.6 mL, were added to the solution. Then, 600 uL of a 4% acidified ZnCl$_2$ solution was added to the reaction mixture. The pH of the solution was adjusted from 3.04 to 6.0 using 5M NH$_4$OH and pulling 500 uL aliquots at each of the following desired pH: 4.2, 4.4, 4.6, 4.8, 5.0, 5.2, 5.4 (See FIG. 8A), 5.6, 5.8, 6.0. The samples were allowed to sit without stirring for 24 hours. The microscope pictures taken after 24 hours showed flat, snowflake-like crystals from pH 4.6-5.4.

A fresh 15 mg/mL solution of HIM2 was prepared in 250 mM ammonium acetate buffer and the pH was adjusted to 2.95 with 5M HCl. Liquefied phenol, 40 uL, and 95% EtOH, 2.6 mL, were added to the solution. Then, 400 uL of a 4% acidified ZnCl$_2$ solution was added to the reaction mixture. The pH of the solution was adjusted from 3.05 to 6.0 using 5M NH$_4$OH and pulling 500 uL aliquots at each of the following desired pH: 4.2, 4.4, 4.6, 4.8, 5.0 (See FIG. 8B), 5.2, 5.4, 5.6, 5.8, 6.0. The samples were allowed to sit without stirring for 24 hours. The microscope pictures taken after 24 hours showed needle-like crystals at pH5.0, crystal-like solids at pH5.2 and flat, snowflake-like crystals at pH5.4.

Figure 9:
Figure 9:
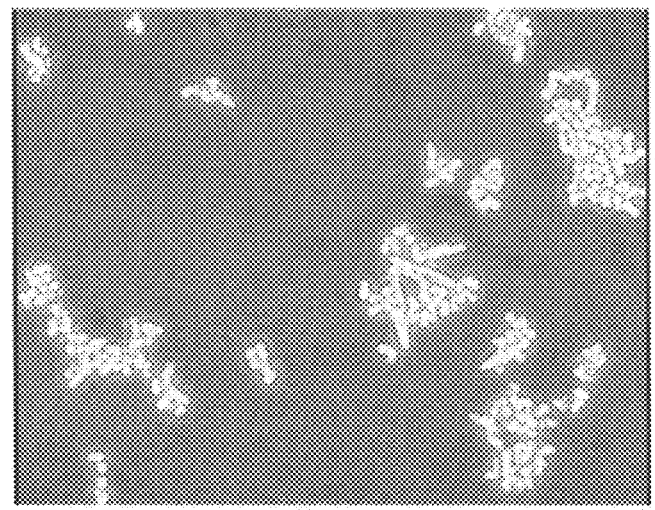

Rxn 6 A fresh 15 mg/mL solution of HIM2 was prepared in 250 mM ammonium acetate buffer and the pH was adjusted to 2.95 with 5M HCl. Liquefied phenol, 40 uL, and 95% EtOH, 2.6 mL, were added to the solution. Then, 200 uL of a 4% acidified ZnCl$_2$ solution was added to the reaction mixture. The pH of the solution was adjusted from 3.09 to 6.0 using 5M NH$_4$OH and pulling 500 uL aliquots at each of the following desired pH: 4.2, 4.4, 4.6, 4.8 (See FIG. 9A), 5.0, 5.2, 5.4, 5.6, 5.8, 6.0. The samples were allowed to sit without stirring for 24 hours. The microscope pictures taken after 24 hours showed needle-like crystals and crystal like solid at pH4.8-5.6.

A fresh 15 mg/mL solution of HIM2 was prepared in 250 mM ammonium acetate buffer and the pH was adjusted to 2.76 with 5M HCl. Liquefied phenol, 40 uL, and 95% EtOH, 4.25 mL, were added to the solution. Then, 250 uL of a 4% acidified ZnCl$_2$ solution was added to the reaction mixture. The pH of the solution was adjusted from 2.97 to 5.8 using 5M NH$_4$OH and pulling 500 uL aliquots at each of the following desired pH: 4.4, 4.6, 4.8, 5.0, 5.2, 5.4, 5.6, 5.8. The samples were allowed to sit without stirring for 24 hours. The microscope pictures taken after 24 hours showed crystal-like precipitation from pH 4.6-5.8

A fresh 15 mg/mL solution of HIM2 was prepared in 250 mM ammonium acetate buffer and the pH was adjusted to 2.76 with 5M HCl. Liquefied phenol, 40 uL, and 95% EtOH, 4.25 mL, were added to the solution. Then, 200 uL of a 4% acidified ZnCl$_2$ solution was added to the reaction mixture. The pH of the solution was adjusted from 3.06 to 5.8 using 5M NH$_4$OH and pulling 500 uL aliquots at each of the following desired pH: 4.4, 4.6, 4.8, 5.0, 5.2, 5.4 (See FIG. 9B), 5.6, 5.8. The samples were allowed to sit without stirring for 24 hours. The microscope pictures taken after 24 hours showed crystal-like precipitation from pH 4.6-5.6.

A fresh 15 mg/mL solution of HIM2 was prepared in 250 mM ammonium acetate buffer and the pH was adjusted to 2.76 with 5M HCl. Liquefied phenol, 40 uL, and 95% EtOH, 4.25 mL, were added to the solution. Then, 150 uL of a 4% acidified ZnCl$_2$ solution was added to the reaction mixture. The pH of the solution was adjusted from 3.09 to 5.8 using 5M NH$_4$OH and pulling 500 uL aliquots at each of the following desired pH: 4.4, 4.6, 4.8, 5.0, 5.2, 5.4, 5.6, 5.8. The samples were allowed to sit without stirring for 24 hours. The microscope pictures taken after 24 hours showed crystals of various sizes and shapes from pH 5.0-5.2.

Figure 10:
Figure 10:
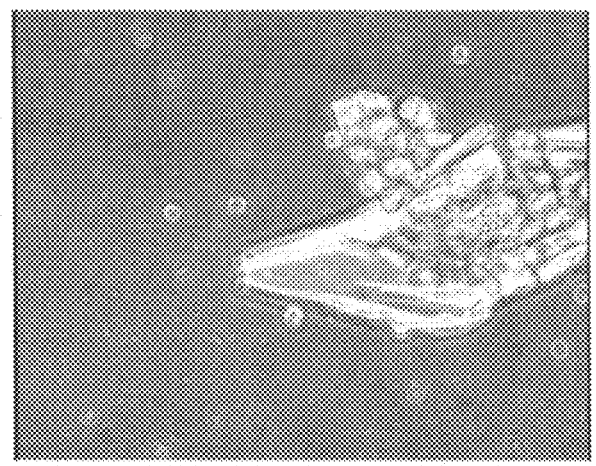

A fresh 15 mg/mL solution of HIM2 was prepared in 250 mM ammonium acetate buffer and the pH was adjusted to 2.76 with 5M HCl. Liquefied phenol, 40 uL, and 95% EtOH, 4.25 mL, were added to the solution. Then, 100 uL of a 4% acidified ZnCl$_2$ solution was added to the reaction mixture. The pH of the solution was adjusted from 3.09 to 5.8 using 5M NH$_4$OH and pulling 500 uL aliquots at each of the following desired pH: 4.4, 4.6, 4.8, 5.0 (See FIG. 10A), 5.2, 5.4 (See FIG. 10B), 5.6, 5.8. The samples were allowed to sit without stirring for 24 hours. The microscope pictures taken after 24 hours showed needle-like crystals at pH 5.0 and various shapes and sizes of crystalline material from pH 5.2-5.6.

A fresh 15 mg/mL solution of HIM2 was prepared in 250 mM ammonium acetate buffer and the pH was adjusted to 2.76 with 5M HCl. Liquefied phenol, 20 uL, and 95% EtOH, 4.25 mL, were added to the solution. Then, 250 uL of a 4% acidified ZnCl$_2$ solution was added to the reaction mixture. The pH of the solution was adjusted from 3.08 to 5.8 using 5M NH$_4$OH and pulling 500 uL aliquots at each of the following desired pH: 4.4, 4.6, 4.8, 5.0, 5.2, 5.4, 5.6, 5.8. The samples were allowed to sit without stirring for 24 hours. The microscope pictures taken after 24 hours showed crystal-like precipitation from pH 4.8-5.8.

A fresh 15 mg/mL solution of HIM2 was prepared in 250 mM ammonium acetate buffer and the pH was adjusted to 2.76 with 5M HCl. Liquefied phenol, 20 uL, and 95% EtOH, 4.25 mL, were added to the solution. Then, 200 uL of a 4% acidified ZnCl$_2$ solution was added to the reaction mixture. The pH of the solution was adjusted from 3.05 to 5.8 using 5M NH$_4$OH and pulling 500 uL aliquots at each of the following desired pH: 4.4, 4.6, 4.8, 5.0, 5.2, 5.4, 5.6, 5.8. The samples were allowed to sit without stirring for 24 hours. The microscope pictures taken after 24 hours showed very little crystal-like solids.

A fresh 15 mg/mL solution of HIM2 was prepared in 250 mM ammonium acetate buffer and the pH was adjusted to 2.76 with 5M HCl. Liquefied phenol, 20 uL, and 95% EtOH, 4.25 mL, were added to the solution. Then, 200 uL of a 4% acidified $ZnCl_2$ solution was added to the reaction mixture. The pH of the solution was adjusted from 3.05 to 5.8 using 5M $NH_4OH$ and pulling 500 uL aliquots at each of the following desired pH: 4.4, 4.6, 4.8, 5.0, 5.2, 5.4, 5.6, 5.8. The samples were allowed to sit without stirring for 24 hours. The microscope pictures taken after 24 hours showed very little crystal-like solids.

A fresh 15 mg/mL solution of HIM2 was prepared in 250 mM ammonium acetate buffer and the pH was adjusted to 2.76 with 5M HCl. Liquefied phenol, 20 uL, and 95% EtOH, 4.25 mL, were added to the solution. Then, 100 uL of a 4% acidified $ZnCl_2$ solution was added to the reaction mixture. The pH of the solution was adjusted from 3.06 to 5.8 using 5M $NH_4OH$ and pulling 500 uL aliquots at each of the following desired pH: 4.4, 4.6, 4.8, 5.0, 5.2, 5.4, 5.6, 5.8. The samples were allowed to sit without stirring for 24 hours. The microscope pictures taken after 24 hours showed very little crystal-like solids.

9.9 Co-Crystallization of HIM2 and IN105 with Zinc

9.9.1 Preparation of R-Type Co-Crystallized Zn Complexes of HIM2 and IN105

9.9.2 50:50 (HIM2:IN105)

A fresh solution of HIM2 and IN105 was prepared by dissolving 37.3 mg HIM2 and 36.4 mg IN105 in 4 mL of 250 mM ammonium acetate pH 7.5. The solution was adjusted to pH 2.84 using 5M HCl. Solid phenol was melted in a 40-60° C. warm water bath. 16 μL of melted phenol and 1.75 mL of 95% EtOH were added to the reaction flask. Then, 80 μL of 4% acidified aqueous $ZnCl_2$ was added to the reaction flask. The pH of the solution was then adjusted from 3.19 to 5.60 using 5M $NH_4OH$ and pulling 0.500 mL aliquots at each of the following desired pH: 4.4, 4.6, 4.8, 5.0, 5.2, 5.4 and 5.6. The samples were allowed to sit without stirring for 4 hours. The microscope pictures taken after 4 hours show various sizes and shapes of crystals from the pH range 4.4 to 5.6.

Figure 11:
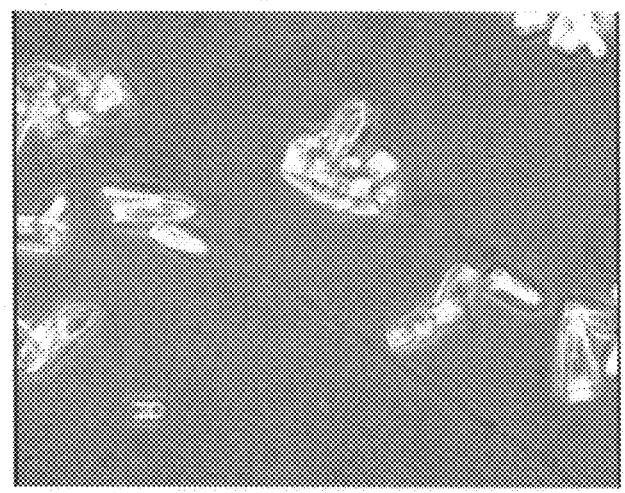
Figure 11:
Figure 12:
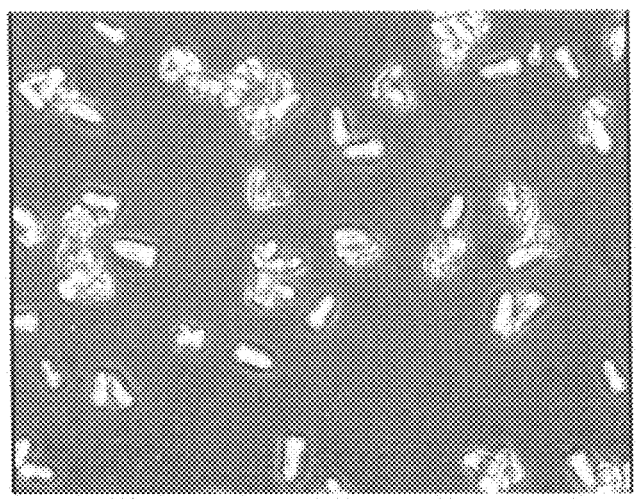
Figure 12:
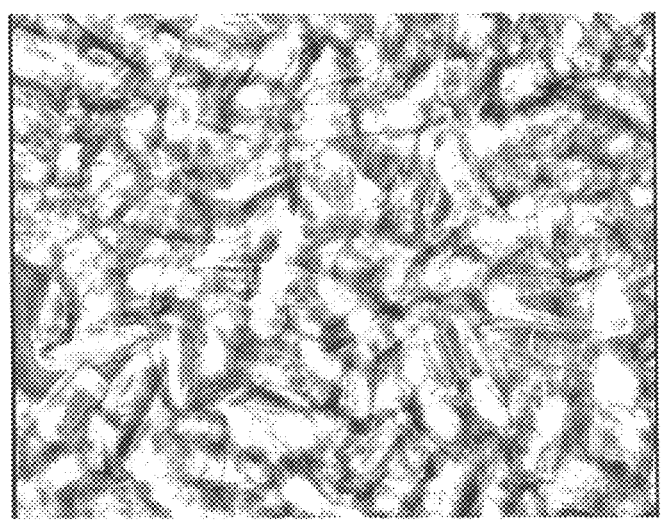

A fresh solution of HIM2 and IN105 was prepared by dissolving 37.1 mg HIM2 and 35.9 mg IN105 in 4 mL of 250 mM ammonium acetate pH 7.5. The solution was adjusted to pH 3.03 using 5M HCl. Solid phenol was melted in a 40-60° C. warm water bath. 16 μL of melted phenol and 1.75 mL of 95% EtOH were added to the reaction flask. Then, 40 uL of 4% acidified aqueous $ZnCl_2$ was added to the reaction flask. The pH of the solution was then adjusted from 3.38 to 5.60 using 5M $NH_4OH$ and pulling 0.500 mL aliquots at each of the following desired pH: 4.4, 4.6, 4.8, 5.0 (See FIG. 11A), 5.2 (See FIG. 11B), 5.4 and 5.6 (See FIG. 12A). The samples were allowed to sit without stirring for 4 hours. The microscope pictures taken after 4 hours show mostly short, needle-like crystals from the pH range 4.6 to 5.6.

9.9.3 70:30 (HIM2:IN105)

A fresh solution of HIM2 and IN105 was prepared by dissolving 53.4 mg HIM2 and 23.2 mg IN105 in 4 mL of 250 mM ammonium acetate pH 7.5. The solution was adjusted to pH 2.62 using 5M HCl. Solid phenol was melted in a 40-60° C. warm water bath. 16 μL of melted phenol and 1.75 mL of 95% EtOH were added to the reaction flask. Then, 80 uL of 4% acidified aqueous $ZnCl_2$ was added to the reaction flask. The pH of the solution was then adjusted from 3.02 to 5.60 using 5M $NH_4OH$ and pulling 0.500 mL aliquots at each of the following desired pH: 4.4, 4.6, 4.8, 5.0, 5.2 (See FIG. 12B), 5.4 and 5.6. The samples were allowed to sit without stirring for 1 hour. The microscope pictures taken after 1 hour show various sizes and shapes of crystal-like precipitation from the pH range 4.4 to 5.6.

Figure 13:
Figure 13:
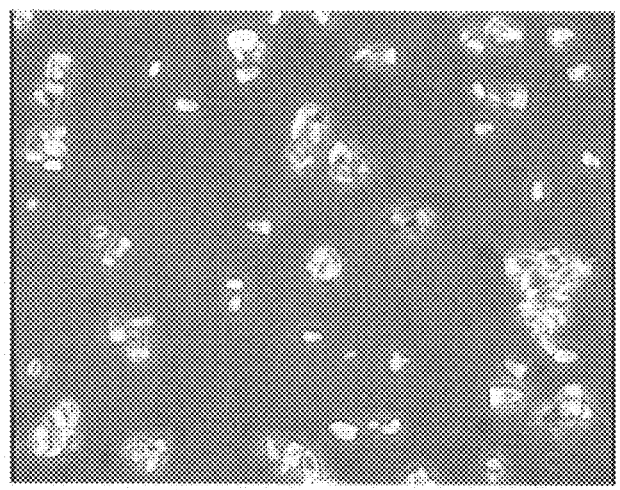

A fresh solution of HIM2 and IN105 was prepared by dissolving 53.6 mg HIM2 and 24.5 mg IN105 in 4 mL of 250 mM ammonium acetate pH 7.5. The solution was adjusted to pH 2.89 using 5M HCl. Solid phenol was melted in a 40-60° C. warm water bath. 16 μL of melted phenol and 1.75 mL of 95% EtOH were added to the reaction flask. Then, 40 uL of 4% acidified aqueous $ZnCl_2$ was added to the reaction flask. The pH of the solution was then adjusted from 3.28 to 5.60 using 5M $NH_4OH$ and pulling 0.500 mL aliquots at each of the following desired pH: 4.4, 4.6, 4.8, 5.0, 5.2 (See FIG. 13A), 5.4 and 5.6. The samples were allowed to sit without stirring for 1 hour. The microscope pictures taken after 1 hour show mostly various sizes and shapes of crystal-like precipitation from the pH range 4.6 to 4.8 and many, short, needle-like crystals from the pH range 5.0 to 5.4.

9.9.4 30:70 (HIM2:IN105)

A fresh solution of HIM2 and IN105 was prepared by dissolving 23.3 mg HIM2 and 54.7 mg IN105 in 4 mL of 250 mM ammonium acetate pH 7.5. The solution was adjusted to pH 2.84 using 5M HCl. Solid phenol was melted in a 40-60° C. warm water bath. 16 μL of melted phenol and 1.75 mL of 95% EtOH were added to the reaction flask. Then, 80 μL of 4% acidified aqueous $ZnCl_2$ was added to the reaction flask. The pH of the solution was then adjusted from 3.27 to 5.60 using 5M $NH_4OH$ and pulling 0.500 mL aliquots at each of the following desired pH: 4.4, 4.6, 4.8, 5.0, 5.2, 5.4 and 5.6. The samples were allowed to sit without stirring for 1 hour. The microscope pictures taken after 1 hour show mostly various sizes and shapes of crystal-like precipitation from the pH range 4.4 to 5.0 and few, needle-like crystals from the pH range 5.2 to 5.6.

A fresh solution of HIM2 and IN105 was prepared by dissolving 24.8 mg HIM2 and 54.9 mg IN105 in 4 mL of 250 mM ammonium acetate pH 7.5. The solution was adjusted to pH 3.09 using 5M HCl. Solid phenol was melted in a 40-60° C. warm water bath. 16 μL of melted phenol and 1.75 mL of 95% EtOH were added to the reaction flask. Then, 40 μL of 4% acidified aqueous $ZnCl_2$ was added to the reaction flask. The pH of the solution was then adjusted from 3.47 to 5.60 using 5M $NH_4OH$ and pulling 0.500 mL aliquots at each of the following desired pH: 4.4, 4.6, 4.8, 5.0, 5.2, 5.4 and 5.6 (See FIG. 13B). The samples were allowed to sit without stirring for 1 hour. The microscope pictures taken after 1 hour show mostly various circular sizes of crystal-like precipitation from the pH range 4.4 to 5.0 and crystals various shapes and sizes from the pH range 5.2 to 5.6.

9.9.5 Preparation of R-Type Co-Crystallized Zn Complexes of HIM2 and IN105

9.9.6 50:50 (HIM2:IN105)

A fresh solution of HIM2 and IN105 was prepared by dissolving 37.4 mg HIM2 and 35.9 mg IN105 in 4 mL of 250 mM ammonium acetate pH 7.5. The solution was adjusted to pH 2.60 using 5M HCl. Solid phenol was melted in a 40-60° C. warm water bath. 16 μL of melted phenol and 1.75 mL of 95% EtOH were added to the reaction flask. Then, 40 uL of 4% acidified aqueous $ZnCl_2$ was added to the reaction flask. The pH of the solution was then adjusted from 2.15 to 5.60 using 5M $NH_4OH$ and pulling 0.500 mL aliquots at each of the following desired pH: 4.4, 4.6, 4.8, 5.0, 5.2, 5.4 and 5.6. The samples were allowed to sit without stirring for 24 hours. The microscope pictures taken after 24 hours showed crystal solids of various shapes and sizes from pH=4.6-5.6.

9.9.7 70:30 (HIM2:IN105)

Figure 14:
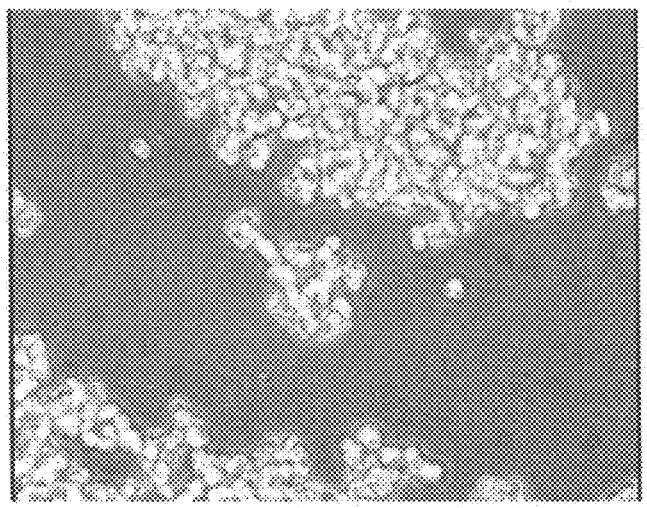
Figure 14:
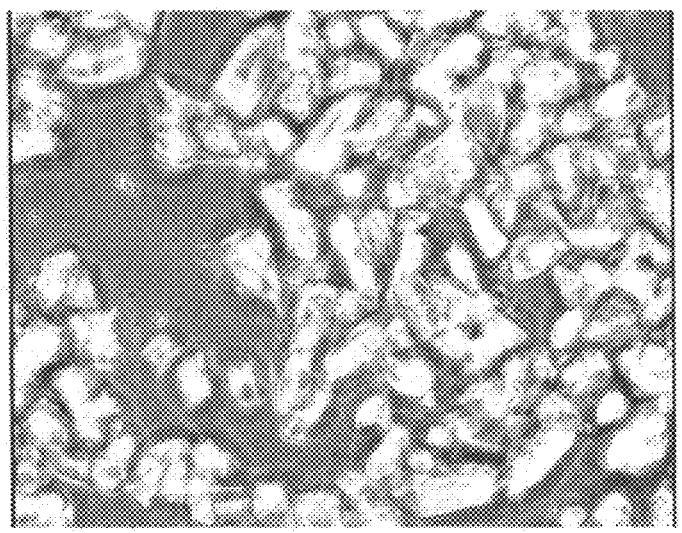

A fresh solution of HIM2 and IN105 was prepared by dissolving 57.0 mg HIM2 and 24.5 mg IN105 in 4 mL of 250 mM ammonium acetate pH 7.5. The solution was adjusted to pH 2.43 using 5M HCl. Solid phenol was melted in a 40-60° C. warm water bath. 16 μL of melted phenol and 1.75 mL of 95% EtOH were added to the reaction flask. Then, 40 uL of 4% acidified aqueous $ZnCl_2$ was added to the reaction flask. The pH of the solution was then adjusted from 2.92 to 5.60 using 5M $NH_4OH$ and pulling 0.500 mL aliquots at each of the following desired pH: 4.4, 4.6 (See FIG. 14A), 4.8, 5.0, 5.2, 5.4 and 5.6. The samples were allowed to sit without stirring for 24 hours. The microscope pictures taken after 24 hours showed needle-like crystals from pH 5.0-5.2.

9.9.8 30:70 (HIM2:IN105)

A fresh solution of HIM2 and IN105 was prepared by dissolving 24.1 mg HIM2 and 53.8 mg IN105 in 4 mL of 250 mM ammonium acetate pH 7.5. The solution was adjusted to pH 2.35 using 5M HCl. Solid phenol was melted in a 40-60° C. warm water bath. 16 μL of melted phenol and 1.75 mL of 95% EtOH were added to the reaction flask. Then, 40 μL of 4% acidified aqueous $ZnCl_2$ was added to the reaction flask. The pH of the solution was then adjusted from 2.60 to 5.60 using 5M $NH_4OH$ and pulling 0.500 mL aliquots at each of the following desired pH: 4.4, 4.6, 4.8, 5.0 (See FIG. 14B), 5.2, 5.4 and 5.6. The samples were allowed to sit without stirring for 24 hours. The microscope pictures taken after 24 hours showed needle-like crystals from pH 5.0-5.2.

9.9.9 Preparation of R-Type Co-Crystallized Zn Complexes of HIM2 and Human Insulin

9.9.10 50:50 (HIM2:Insulin)

Figure 15:
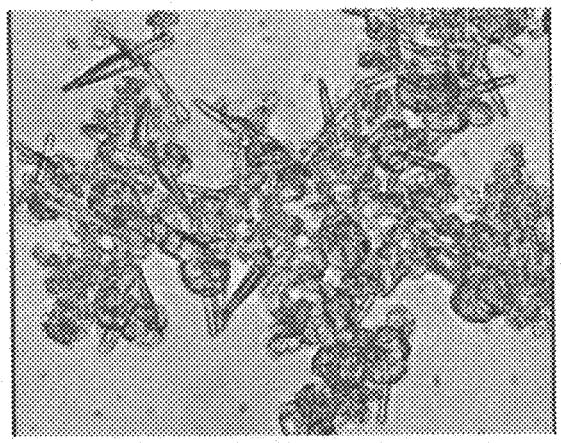
Figure 15:
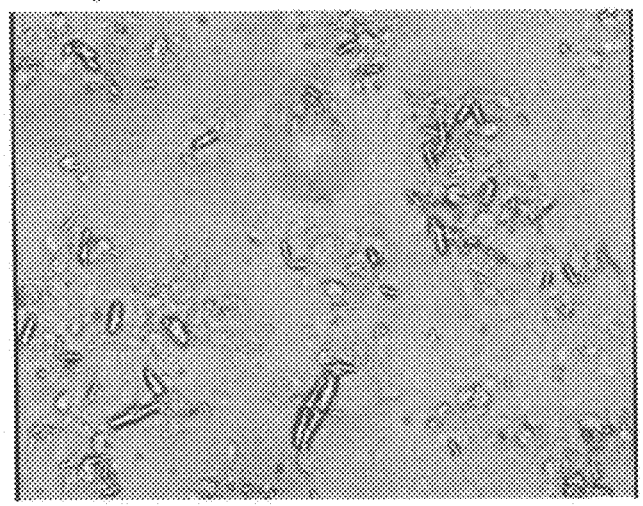

A fresh solution of HIM2 and Insulin was prepared by dissolving 39.2 mg HIM2 and 36.7 mg Insulin in 4 mL of 250 mM ammonium acetate pH 7.5. The solution was adjusted to pH 2.53 using 5M HCl. Solid phenol was melted in a 40-60° C. warm water bath. 16 μL of melted phenol and 1.75 mL of 95% EtOH were added to the reaction flask. Then, 40 uL of 4% acidified aqueous $ZnCl_2$ was added to the reaction flask. The pH of the solution was then adjusted from 2.82 to 5.60 using 5M $NH_4OH$ and pulling 0.500 mL aliquots at each of the following desired pH: 4.4, 4.6, 4.8, 5.0, 5.2 (See FIG. 15A), 5.4 and 5.6. The samples were allowed to sit without stirring for 24 hours. The microscope pictures taken after 24 hours showed various shapes and sizes of crystal-like solid from pH 5.2 and 5.4. Many tiny, needle-like crystals were observed at pH 5.6.

9.9.11 70:30 (HIM2:Insulin)

A fresh solution of HIM2 and Insulin was prepared by dissolving 56.5 mg HIM2 and 20.2 mg Insulin in 4 mL of 250 mM ammonium acetate pH 7.5. The solution was adjusted to pH 3.23 using 5M HCl. Solid phenol was melted in a 40-60° C. warm water bath. 16 μL of melted phenol and 1.75 mL of 95% EtOH were added to the reaction flask. Then, 40 uL of 4% acidified aqueous $ZnCl_2$ was added to the reaction flask. The pH of the solution was then adjusted from 2.82 to 5.60 using 5M $NH_4OH$ and pulling 0.500 mL aliquots at each of the following desired pH: 4.4, 4.6, 4.8, 5.0, 5.2, 5.4 and 5.6. The samples were allowed to sit without stirring for 24 hours. The microscope pictures taken after 24 hours showed various shapes and sizes of crystal-like solid from pH 5.2 and 5.6.

9.9.12 30:70 (HIM2:Insulin)

A fresh solution of HIM2 and Insulin was prepared by dissolving 21.8 mg HIM2 and 49.2 mg Insulin in 4 mL of 250 mM ammonium acetate pH 7.5. The solution was adjusted to pH 3.23 using 5M HCl. Solid phenol was melted in a 40-60° C. warm water bath. 16 μL of melted phenol and 1.75 mL of 95% EtOH were added to the reaction flask. Then, 40 uL of 4% acidified aqueous $ZnCl_2$ was added to the reaction flask. The pH of the solution was then adjusted from 2.93 to 5.60 using 5M $NH_4OH$ and pulling 0.500 mL aliquots at each of the following desired pH: 4.4, 4.6, 4.8, 5.0, 5.2, 5.4 (See FIG. 15B) and 5.6. The samples were allowed to sit without stirring for 24 hours. The microscope pictures taken after 24 hours showed flat, snowflake-like crystals at pH 4.8. At pH 5.0, there was a mix of needle-like and snowflake-like crystals. From pH 5.2-5.6 there were many tiny, needle-like crystals observed.

10 AQUEOUS SOLUBILITY OF Zn COMPLEXES

Two hundred microliters of 0.1M Phosphate Buffer Saline (PBS, filtered, pH=7.4) was added to a 1 mL conical reaction vial. To this vial, a small amount of sample was added slowly until saturation is observed. Periodically, the solution was vortexed. Upon saturation, the vial was placed in a small centrifuge tube and the sample was centrifuged at 2000 RPM for 3 min at RT. After centrifugation, 10 μL of the sample was removed from the supernatant and diluted in 490 μL buffer (0.1M PBS). This diluted sample was analyzed via HPLC to determine its' concentration.

| Conjugate | Solubility | Zn | Phenol |
|---|---|---|---|
| IN105 | ~26 mg/mL | N/A | N/A |
| ZnIN105 | 15 mg/mL-20 mg/mL | 0.44% | 0.76% |
| ZnIN105 | ~24 mg/mL | 0.61% | 1.11% |
| ZnIN105 | 15 mg/mL-20 mg/mL | 0.63% | 1.04% |

11 IN VITRO ENZYME RESISTANCE EXAMPLES FOR Zn IN105 COMPLEXES insulin compound conjugates (IN105) were provided in 10 mM sodium phosphate buffer (a pH of about 7.4) and their concentrations were determined by HPLC (the solutions are diluted with buffer so that equimolar comparisons can be made between parent and conjugates ~0.6 mg/mL). Lyophilized chymotrypsin enzyme was resuspended in 1 mM HCl to a concentration of 7.53 U/mL. A 1.53 mL aliquot of each sample was added to sample tubes and 0.850 mL into control tubes. Samples were tested in duplicate along with four control tubes per sample. Aliquots were incubated at 37° C. in a thermomixer for 15 minutes. Then 17 μL of chymotrypsin enzyme was added to each sample tube. Five μL of 1 mM HCl was added to each control tube. Immediately following the additions, 200 μL was removed from the sample and the control tubes and placed into 50 μL of 1% TFA previously aliquoted out into centrifuge tubes. This sample serves as T=0.

The sampling procedure for Insulin compound (Zn free), IN105 (Zn free) and Insulin compound (regular insulin compound) was repeated at the following intervals: 0, 2, 5, 8, 12, 15, and 30 minutes. The control procedure was repeated at the following intervals: 0, 8, 15, 30 minutes. For T-type and R-type samples, the procedure was repeated at the following intervals: 0, 5, 8, 12, 30, 40 and 60 minutes. The control procedure for the Zn complexes was repeated at the following intervals: 0, 12, 40 and 60 minutes. Samples were stored at −20° C. until analysis can occur via HPLC. HPLC was performed to determine percent degradation relative to the respective T=0 minute for each digest. The natural log of the percent remaining was plotted versus time and a linear regression run for each digest. The half life was calculated using the equation: $t_{1/2}$:=−0.693/slope.

| Results at 0.6 mg/ml protein: | | | |
|---|---|---|---|
| Sample | T half | Zinc content | Phenol content |
| Insulin compound (zinc free) | 4.9 mins | 0.0 | — |
| IN105 (zinc free) | 12.5 mins | 0.0 | — |
| IN105 (zinc free) | 11.1 mins | 0.0 | — |
| Insulin compound, USP (Regular insulin compound) | 11.6 mins | 0.3 to 1% w/w | — |
| IN105 (R-type zinc complex) | 55.3 mins | 1.85% w/w | 2.37% w/w |
| IN105 (T-type zinc complex) | 54.8 mins | 1.88% w/w | — |

12 FORMULATIONS EXAMPLES

12.1 Liquid Formulation Examples

| Buffer Solution for R6 type Zn-HIM2 Buffer Study | |
|---|---|
| Components | Amount in 1 mL solution |
| Dibasic Sodium Phosphate | 1.88 mg |
| Insulin component | 3.7 mg (100 units) |
| Glycerol | 16.0 mg |
| Phenol (or m-Cresol) | 3.0 mg |
| Zinc | 0.037 mg (1% w/w of insulin)* |
| pH | 7.4 to 7.8** |

*Adjustment of the amount of Zinc to 0.037 mg/ml per 3.7 mg/ml insulin by adding Zinc chloride and to be based the zinc content in the Zinc HIM2 solid.
**pH may be adjusted with HCl 10% and/or sodium hydroxide 10%

12.1.2 Preparation of Capric Acid/Lauric Acid Formulation Oral Liquid Diluent We transferred approximately 60% of the required sterile water volume into a suitable container. We added the appropriate amount (as indicated in the table below) of tromethamine, trolamine, citric acid anhydrous, and sodium hydroxide pellets to the container and mixed well until dissolved. We adjusted the temperature to 21-25° C. (or room temperature) and measured the pH of the liquid. We adjusted the pH to 7.7-7.9 as necessary using 1N sodium hydroxide or 1N hydrochloric acid. We then adjusted the temperature to 45-50° C. by warming on a hotplate and maintained this temperature. We then added the capric acid to the warm solution and mixed until the capric acid was dissolved. We adjusted the temperature to 21-25° C. (or room temperature) and measured the pH of the liquid. As needed, we adjusted the pH to 7.7-7.9 using 1N sodium hydroxide or 1N hydrochloric acid. We then mixed the solution for 5 minutes. We added appropriate amount of sterile water to equal 100% of the required volume and mixed well.

| Component | Percentage (% w/v) |
|---|---|
| Tromethamine | 4.24 |
| Trolamine | 5.22 |
| Citric Acid Anhydrous | 6.72 |
| Sodium Hydroxide Pellets | 1.88 |
| Capric Acid | 0.50 |
| Lauric Acid | 0.50 |
| Sodium Hydroxide, 1N | As Needed to Adjust pH 7.7-7.9 |
| Hydrochloric Acid, 1N | As Needed to Adjust pH 7.7-7.9 |
| Sterile Water | Dilute to Required Volume |

IN105, HIM2 or ZnHIM2 was weighed out in amounts necessary to achieve appropriate concentration for dosing studies, e.g., 1 mg IN105 (of protein) was weighed out and combined with 1 mL of formulation to yield a 1 mg/mL IN105 in formulation.

12.1.3 Preparation of Oleic acid/capric Acid/Lauric Acid/Cholate Formulation Oral Liquid Diluent An oral liquid formulation of R-type Zn HIM2 was prepared having the components shown in the following table:

| Component | Percentage (% w/v) |
|---|---|
| Tromethamine | 4.24 |
| Trolamine | 5.22 |
| Citric Acid Anhydrous | 6.72 |
| Sodium Hydroxide Pellets | 1.88 |
| Sodium Cholate | 3.00 |
| Oleic Acid | 1.00 |
| Capric Acid | 0.50 |
| Lauric Acid | 0.50 |
| Sucralose Solution, 25% | 0.80 |
| Strawberry Flavor | 0.40 |
| Sodium Hydroxide, 1N | As Needed to Adjust pH 7.7-7.9 |
| Hydrochloric Acid, 1N | As Needed to Adjust pH 7.7-7.9 |
| Sterile Water | Dilute to Required Volume |

Oral liquid samples were prepared to contain 1 mg/mL protein equivalent of R-type Zn HIM2 (ZnHIM2-R). The ZnHIM2-R was removed from the Freezer (−20° C.), placed in a dessicator and allowed to come to room temperature. A 1 mg/mL protein equivalent of ZnHIM2-R was prepared in oral liquid diluent solution as follows. 6.4 mg of ZnHIM2-R was weighed. Then, 5.0 mL of oral liquid diluent was transferred into the container and gently swirled to mix. The solution took approximately 45 minutes to dissolve. The resulting solution was a suspension (cloudy appearance). Prior to dosing, the solution was gently swirled for 60 seconds to ensure the solution was a homogeneous solution. For ZnHIM2-R, the protein content was 78.6%, 1 mg/mL protein equivalent, quantity=5 mL. Amount of ZnHIM2-R=(1 mg/mL)/

(0.786)}×(5.0 mL)=6.4 mg. ZnHIM2-R Concentration=(6.4 mg)/(5.0 mL)=1.28 mg/mL (equivalent to 1 mg/mL adjusted for protein content).

12.1.4 Preparation of Capric Acid Liquid Formulations

We transferred approximately 60% of the required sterile water volume into a suitable container. We added the appropriate amount (as indicated in the table below) of tromethamine, trolamine, citric acid anhydrous, and sodium hydroxide pellets to the container and mixed well until dissolved. We adjusted the temperature to 21-25° C. (or room temperature) and measured the pH of the liquid. We adjusted the pH to 7.7-7.9 as necessary using 1N sodium hydroxide or 1N hydrochloric acid. We then adjusted the temperature to 45-50° C. by warming on a hotplate and maintained this temperature. We then added the capric acid to the warm solution and mixed until the capric acid was dissolved. We adjusted the temperature to 21-25° C. (or room temperature) and measured the pH of the liquid. As needed, we adjusted the pH to 7.7-7.9 using 1N sodium hydroxide or 1N hydrochloric acid. We then mixed the solution for 5 minutes. We added appropriate amount of sterile water to equal 100% of the required volume and mixed well.

| Component | % w/v |
| --- | --- |
| Tromethamine | 4.24 |
| Trolamine | 5.22 |
| Citric Acid Anhydrous | 6.72 |
| Sodium Hydroxide Pellets | 1.88 |
| Capric Acid | 0.9, 1.5, 3.0 or 6.0 |
| Sodium Hydroxide, 1N | As Needed to Adjust pH |
| Hydrochloric Acid, 1N | As Needed to Adjust pH |
| Sterile Water | To Required Volume |

IN105 was weighed out in amounts necessary to achieve appropriate concentration for dosing studies, e.g., 1 mg IN105 (of protein) was weighed out and combined with 1 mL of formulation to yield a 1 mg/mL IN105 in formulation.

12.1.5 Caprate and/or Laurate in Phosphate Buffer Liquid Formulations

Preparation of 100 mM Sodium Phosphate Buffer, pH 7.8 or 8.2. We transferred 1.17 grams of Monosodium Phosphate Monohydrate to a 1-L flask. Approximately 500 mL of sterile water was added and mixed well until dissolved. We then added 24.58 grams of Sodium Phosphate Dibasic Heptahydrate and mixed well until dissolved. Diluted to volume with sterile water and mixed well. Filtered through a 0.22 µm filter. We adjusted the pH to 7.8 or 8.2 with 1N HCl or 1N NaOH.

For IN105, we transferred 60% of the appropriate volume of the phosphate buffer pH 7.8 or 8.2 into a suitable container. We then added an amount of caprate calculated to produce 3% w/v of the final solution and mixed well until dissolved. We then adjusted the pH to 7.8 or 8.2 with 1N HCl or 1N NaOH. We diluted to the appropriate volume (e.g., 100 mL) with phosphate buffer pH 7.8 or 8.2.

| Component | % w/v |
| --- | --- |
| Sodium Caprate | 3.0 |
| 100 mM Sodium Phosphate Buffer, pH 7.8 or 8.2 | QS to 100% |

For BN-054, we weighed 400 grams of 100 mM Sodium Phosphate Buffer, pH 7.8 in a suitable container. We added 9.7 grams of Sodium Caprate and 11.1 grams Sodium Laurate and mixed well until dissolved. We added appropriate amount of 100 mM Sodium Phosphate Buffer, pH 7.8, to equal a net weight of 500 grams.

| Component | % w/w |
| --- | --- |
| Sodium Caprate | 1.94 |
| Sodium Laurate | 2.22 |
| 100 mM Sodium Phosphate Buffer, pH 7.8 | QS to 100% |

12.1.6 Liquid Formulation with Arginine or Trolamine

Preparation of 100 mM Sodium Phosphate Buffer, pH 7.8. We transferred 1.17 grams of Monosodium Phosphate Monohydrate to a 1-L flask. Approximately 500 mL of sterile water was added and mixed well until dissolved. We then added 24.58 grams of Sodium Phosphate Dibasic Heptahydrate and mixed well until dissolved. Diluted to volume with sterile water and mixed well. Filtered through a 0.22 µm filter. We adjusted the pH to 7.8 with 1N HCl or 1N NaOH.

We transferred 60% of the appropriate volume of the phosphate buffer pH 7.8 into a suitable container. We added the appropriate amount (as indicated in the table below) of arginine or trolamine to the container and mixed well until dissolved. We then added an amount of caprate calculated to produce 3% w/v of the final solution and mixed well until dissolved. We then adjusted the pH to 7.8 with 1N HCl or 1N NaOH. We diluted to the appropriate volume (e.g., 100 mL) with phosphate buffer pH 7.8.

| Component | % w/v |
| --- | --- |
| Sodium Caprate | 3.0 |
| Arginine or Trolamine | 0.4 or 1.2 |
| 100 mM Sodium Phosphate Buffer, pH 7.8 | QS to 100% |

IN105 was weighed out in amounts necessary to achieve appropriate concentration for dosing studies, e.g., 1 mg IN105 (of protein) was weighed out and combined with 1 mL of formulation to yield a 1 mg/mL IN105 in formulation.

12.1.7 Liquid Formulation with Caprylic Acid

We transferred approximately 60% of the required sterile water volume into a suitable container. We added the appropriate amount (as indicated in the table below) of tromethamine, trolamine, citric acid anhydrous, and sodium hydroxide pellets to the container and mixed well until dissolved. We adjusted the temperature to 21-25° C. (or room temperature) and measured the pH of the liquid. We adjusted the pH to 7.7-7.9 as necessary using 1N sodium hydroxide or 1N hydrochloric acid. We then adjusted the temperature to 45-50° C. by warming on a hotplate and maintained this temperature. We then added the caprylic acid to the warm solution and mixed until the caprylic acid was dissolved. We adjusted the temperature to 21-25° C. (or room temperature) and measured the pH of the liquid. As needed, we adjusted the pH to 7.7-7.9 using 1N sodium hydroxide or 1N hydrochloric acid. We then mixed the solution for 5 minutes. We added appropriate amount of sterile water to equal 100% of the required volume and mixed well.

| Component | % w/v |
|---|---|
| Tromethamine | 4.24 |
| Trolamine | 5.22 |
| Citric Acid Anhydrous | 6.72 |
| Sodium Hydroxide Pellets | 1.88 |
| Caprylic Acid | 3.0 |
| Sodium Hydroxide, 1N | As Needed to Adjust pH |
| Hydrochloric Acid, 1N | As Needed to Adjust pH |
| Sterile Water | To Required Volume |

IN105 was weighed out in amounts necessary to achieve appropriate concentration for dosing studies, e.g., 1 mg IN105 (of protein) was weighed out and combined with 1 mL of formulation to yield a 1 mg/mL IN105 in formulation.

12.1.8 Liquid Formulation with Linoleic Acid

Preparation of 100 mM Sodium Phosphate Buffer, pH 7.8. We transferred 1.17 grams of Monosodium Phosphate Monohydrate to a 1-L flask. Approximately 500 mL of sterile water was added and mixed well until dissolved. We then added 24.58 grams of Sodium Phosphate Dibasic Heptahydrate and mixed well until dissolved. Diluted to volume with sterile water and mixed well. Filtered through a 0.22 µm filter. We adjusted the pH to 7.8 with 1N HCl or 1N NaOH.

We transferred 60% of the appropriate volume of the phosphate buffer pH 7.8 into a suitable container. We then added an amount of linoleic acid sodium salt calculated to produce 3% w/v of the final solution and mixed well until dissolved. We then adjusted the pH to 7.8 with 1N HCl or 1N NaOH. We diluted to the appropriate volume (e.g., 100 mL) with phosphate buffer pH 7.8.

| Component | % w/v |
|---|---|
| Linoleic Acid Sodium Salt | 3.0 |
| 100 mM Sodium Phosphate Buffer, pH 7.8 | QS to 100% |

12.1.9 Preparation of Capric Acid and Lauric Acid Liquid Formulations

We transferred approximately 60% of the required sterile water volume into a suitable container. We added the appropriate amount (as indicated in the table below) of tromethamine, trolamine, citric acid anhydrous, and sodium hydroxide pellets to the container and mixed well until dissolved. We adjusted the temperature to 21-25° C. (or room temperature) and measured the pH of the liquid. We adjusted the pH to 7.7-7.9 as necessary using 1N sodium hydroxide or 1N hydrochloric acid. We then adjusted the temperature to 45-50° C. by warming on a hotplate and maintained this temperature. We then added the capric acid and/or lauric acid to the warm solution and mixed until the capric acid and/or lauric acid were dissolved. We adjusted the temperature to 21-25° C. (or room temperature) and measured the pH of the liquid. As needed, we adjusted the pH to 7.7-7.9 using 1N sodium hydroxide or 1N hydrochloric acid. We then mixed the solution for 5 minutes. We added appropriate amount of sterile water to equal 100% of the required volume and mixed well.

| Component | % w/v |
|---|---|
| Tromethamine | 4.24 |
| Trolamine | 5.22 |
| Citric Acid Anhydrous | 6.72 |
| Sodium Hydroxide Pellets | 1.88 |
| Capric Acid | 0, 0.1 or 0.9 |
| Lauric Acid | 0, 0.9 or 0.1 |
| Sodium Hydroxide, 1N | As Needed to Adjust pH |
| Hydrochloric Acid, 1N | As Needed to Adjust pH |
| Sterile Water | To Required Volume |

IN105 was weighed out in amounts necessary to achieve appropriate concentration for dosing studies, e.g., 1 mg IN105 (of protein) was weighed out and combined with 1 mL of formulation to yield a 1 mg/mL IN105 in formulation.

12.2 Solid Dosage Formulation Examples

12.2.1 Preparation and Dissolution Profile of Caprate/Laurate Solid Dosage Formulation Using Nobex-IN105-[854]

Transfer approximately 58 mg of sodium caprate, 57 mg of sodium laurate, 286 mg mannitol, 30 mg of sodium starch glycolate, and 6 mg (protein) of Nobex-IN105 onto a piece of weigh paper and blend thoroughly. Transfer the blend to the press and compress at approximately 350 psi to form a tablet.

| Solid Dosage Form (Tablets) Formulation Nobex-IN105-[854] 58 mg Caprate and 57 mg Laurate per Tablet | |
|---|---|
| Component | mg per Tablet |
| Sodium Caprate | 58 |
| Sodium Laurate | 57 |
| Mannitol | 286 |
| Explotab (sodium starch glycolate) | 30 |
| Nobex-IN105 (protein) | 6 |

The dissolution testing was carried out using a USP apparatus 2 dissolution unit. The medium was water, paddle speed 50 rpm, and the medium volume was 500 mL. The dissolution samples were analyzed HPLC using a gradient system. The mobile phases were water with 0.1% TFA (mobile phase A) and acetonitrile with 0.1% TFA (mobile phase B). The gradient utilized was: 0 minutes 100% mobile phase A, 11 minutes 65% mobile phase A, 15 minutes 20% mobile phase A, 16 minutes 20% mobile phase A, 17 minutes 100% mobile phase A. The wavelength was 214 nm and column was a C18 (150×2 mm). The following tables and graphs summarize the dissolution data obtained for the dissolution testing of Nobex-Zn-IN105 Tablets Formulation [854] containing 6 mg Zn-IN105 (protein), 286 mg Mannitol, 58 mg Sodium Caprate, 57 mg Sodium Laurate, and 30 mg sodium starch glycolate (Explotab):

| Sample Time (Minutes) | Vessel 1 (% Dissolved) | Vessel 2 (% Dissolved) | Average (% Dissolved) |
|---|---|---|---|
| Data Summary for the Dissolution Profile of Nobex-Zn-IN105 Tablets [854], % IN105 Dissolved ||||
| 5 | 71 | 72 | 72 |
| 10 | 86 | 94 | 90 |
| 15 | 87 | 96 | 92 |
| 30 | 89 | 96 | 93 |
| 45 | 90 | 96 | 93 |
| 60 | 87 | 96 | 92 |
| Data Summary for the Dissolution Profile of Nobex-Zn-IN105 Tablets [854], % Caprate Dissolved ||||
| 5 | 98 | 93 | 96 |
| 10 | 102 | 104 | 103 |
| 15 | 101 | 104 | 103 |
| 30 | 102 | 105 | 104 |
| 45 | 102 | 104 | 103 |
| 60 | 102 | 105 | 104 |
| Data Summary for the Dissolution Profile of Nobex-Zn-IN105 Tablets [854], % Laurate Dissolved ||||
| 5 | 72 | 75 | 74 |
| 10 | 90 | 89 | 90 |
| 15 | 91 | 90 | 91 |
| 30 | 88 | 91 | 90 |
| 45 | 89 | 91 | 90 |
| 60 | 91 | 90 | 91 |

| Sample Time (Minutes) | Vessel 1 (% Dissolved) | Vessel 2 (% Dissolved) | Average (% Dissolved) |
|---|---|---|---|
| Data Summary for the Dissolution Profile of Nobex-Zn-IN105 Tablets [856], % IN105 Dissolved ||||
| 5 | 43 | 31 | 37 |
| 10 | 66 | 53 | 60 |
| 15 | 81 | 72 | 77 |
| 30 | 98 | 97 | 98 |
| 45 | 98 | 99 | 99 |
| 60 | 96 | 98 | 97 |
| Data Summary for the Dissolution Profile of Nobex-Zn-IN105 Tablets [856], % Caprate Dissolved ||||
| 5 | 36 | 32 | 34 |
| 10 | 68 | 57 | 63 |
| 15 | 89 | 79 | 84 |
| 30 | 105 | 103 | 104 |
| 45 | 105 | 103 | 104 |
| 60 | 105 | 104 | 105 |
| Data Summary for the Dissolution Profile of Nobex-Zn-IN105 Tablets [856], % Laurate Dissolved ||||
| 5 | 35 | 25 | 30 |
| 10 | 61 | 44 | 53 |
| 15 | 74 | 61 | 68 |
| 30 | 93 | 88 | 91 |
| 45 | 93 | 91 | 92 |
| 60 | 93 | 92 | 93 |

12.2.2 Solid Dosage Form (Tablet) Formulation Preparation 143 mg Caprate and 140 mg Laurate Per Tablet Preparation of Formulation Nobex-IN105-18561

Transfer approximately 143 mg of sodium caprate, 140 mg of sodium laurate, 150 mg mannitol, 30 mg of sodium starch glycolate, and 6 mg (protein) of Nobex-IN105 onto a piece of weigh paper and blend thoroughly. Transfer the blend to the press and compress at approximately 350 psi to form a tablet.

| Solid Dosage Form (Tablets) Formulation Nobex-IN105-[856] 143 mg Caprate and 140 mg Laurate per Tablet ||
|---|---|
| Component | mg per Tablet |
| Sodium Caprate | 143 |
| Sodium Laurate | 140 |
| Mannitol | 150 |
| Explotab (sodium starch glycolate) | 30 |
| Nobex-IN105 (protein) | 6 |

The dissolution testing was carried out using a USP apparatus 2 dissolution unit. The medium was water, paddle speed 50 rpm, and the medium volume was 500 mL. The dissolution samples were analyzed by HPLC using a gradient system. The mobile phases were water with 0.1% TFA (mobile phase A) and acetonitrile with 0.1% TFA (mobile phase B). The gradient utilized was: 0 minutes 100% mobile phase A, 11 minutes 65% mobile phase A, 15 minutes 20% mobile phase A, 16 minutes 20% mobile phase A, 17 minutes 100% mobile phase A. The wavelength was 214 nm and column was a C18 (150×2 mm). The following tables and graphs summarize the dissolution data obtained for the dissolution testing of Nobex-Zn-IN105 Tablets containing 6 mg Zn-IN105 (protein), 150 mg Mannitol, 143 mg Sodium Caprate, 140 mg Sodium Laurate, and 30 mg sodium starch glycolate (Explotab):

12.2.3 Solid Dosage Form (Tablet) Formulation Preparation 143 mg Caprate Per Tablet Preparation of Formulation Nobex-IN105-[859]

Transfer approximately 143 mg of sodium caprate, 150 mg mannitol, 30 mg of sodium starch glycolate, and 6 mg (protein) of Nobex-IN105 onto a piece of weigh paper and blend thoroughly. Transfer the blend to the press and compress at approximately 350 psi to form a tablet.

| Solid Dosage Form (Tablets) Formulation Nobex-IN105-[859] 143 mg Caprate per Tablet ||
|---|---|
| Component | mg per Tablet |
| Sodium Caprate | 143 |
| Mannitol | 150 |
| Explotab (sodium starch glycolate) | 30 |
| Nobex-IN105 (protein) | 6 |

The dissolution testing was carried out using a USP apparatus 2 dissolution unit. The medium was water, paddle speed 50 rpm, and the medium volume was 500 mL. The dissolution samples were analyzed by HPLC using a gradient system. The mobile phases were water with 0.1% TFA (mobile phase A) and acetonitrile with 0.1% TFA (mobile phase B). The gradient utilized was: 0 minutes 100% mobile phase A, 11 minutes 65% mobile phase A, 15 minutes 20% mobile phase A, 16 minutes 20% mobile phase A, 17 minutes 100% mobile phase A. The wavelength was 214 nm and column was a C18 (150×2 mm). The following tables and graphs summarize the dissolution data obtained for the dissolution testing of Nobex-Zn-IN105 Tablets containing 6 mg Zn-IN105 (protein), 150 mg Mannitol, 143 mg Sodium Caprate, and 30 mg sodium starch glycolate (Explotab):

| Sample Time (Minutes) | Vessel 1 (% Dissolved) | Vessel 2 (% Dissolved) | Average (% Dissolved) |
|---|---|---|---|
| Data Summary for the Dissolution Profile of Nobex-Zn-IN105 Tablets [859], % IN105 Dissolved | | | |
| 5 | 11 | 26 | 19 |
| 10 | 63 | 58 | 61 |
| 15 | 84 | 80 | 82 |
| 30 | 86 | 88 | 87 |
| 45 | 88 | 88 | 88 |
| 60 | 87 | 89 | 88 |
| Data Summary for the Dissolution Profile of Nobex-Zn-IN105 Tablets [859], % Caprate Dissolved | | | |
| 5 | 61 | 43 | 52 |
| 10 | 93 | 72 | 83 |
| 15 | 99 | 95 | 97 |
| 30 | 99 | 100 | 100 |
| 45 | 99 | 100 | 100 |
| 60 | 99 | 100 | 100 |

| Sample Time (Minutes) | Vessel 1 (% Dissolved) | Vessel 2 (% Dissolved) | Average (% Dissolved) |
|---|---|---|---|
| Data Summary for the Dissolution Profile of Nobex-Zn-IN105 Tablets [860], % IN105 Dissolved | | | |
| 5 | 28 | 19 | 24 |
| 10 | 53 | 44 | 49 |
| 15 | 70 | 68 | 69 |
| 30 | 92 | 90 | 91 |
| 45 | 92 | 92 | 92 |
| 60 | 92 | 93 | 93 |
| Data Summary for the Dissolution Profile of Nobex-Zn-IN105 Tablets [860], % Caprate Dissolved | | | |
| 5 | 29 | 35 | 32 |
| 10 | 52 | 66 | 59 |
| 15 | 70 | 84 | 77 |
| 30 | 99 | 99 | 99 |
| 45 | 99 | 99 | 99 |
| 60 | 99 | 100 | 100 |

12.2.4 Solid Dosage Form (Tablet) Formulation Preparation 286 mg Caprate Per Tablet Preparation Formulation Nobex-IN105-[860]

Transfer approximately 286 mg of sodium caprate, 150 mg mannitol, 30 mg of sodium starch glycolate, and 6 mg (protein) of Nobex-IN105 onto a piece of weigh paper and blend thoroughly. Transfer the blend to the press and compress at approximately 350 psi to form a tablet.

| Solid Dosage Form (Tablets) Formulation Nobex-IN105-[860] 286 mg Caprate per Tablet | |
|---|---|
| Component | mg per Tablet |
| Sodium Caprate | 286 |
| Mannitol | 150 |
| Explotab (sodium starch glycolate) | 30 |
| Nobex-IN105 (protein) | 6 |

The dissolution testing was carried out using a USP apparatus 2 dissolution unit. The medium was water, paddle speed 50 rpm, and the medium volume was 500 mL. The dissolution samples were analyzed by HPLC using a gradient system. The mobile phases were water with 0.1% TFA (mobile phase A) and acetonitrile with 0.1% TFA (mobile phase B). The gradient utilized was: 0 minutes 100% mobile phase A, 11 minutes 65% mobile phase A, 15 minutes 20% mobile phase A, 16 minutes 20% mobile phase A, 17 minutes 100% mobile phase A. The wavelength was 214 nm and column was a C18 (150×2 mm). The following tables and graphs summarize the dissolution data obtained for the dissolution testing of Nobex-Zn-IN105 Tablets containing 6 mg Zn-IN105 (protein), 150 mg Mannitol, 286 mg Sodium Caprate, and 30 mg sodium starch glycolate (Explotab):

12.2.5 Solid Dosage Form (Tablet) Formulation Preparation 100 mg Caprate Per Tablet Preparation of Formulation Nobex-IN105-[861]

Transfer approximately 100 mg of sodium caprate, 150 mg mannitol, 25 mg of sodium starch glycolate, and 6 mg (protein) of Nobex-IN105 onto a piece of weigh paper and blend thoroughly. Transfer the blend to the press and compress at approximately 350 psi to form a tablet.

| Solid Dosage Form (Tablets) Formulation Nobex-IN105-[861] 100 mg Caprate per Tablet | |
|---|---|
| Component | mg per Tablet |
| Sodium Caprate | 100 |
| Mannitol | 150 |
| Explotab (sodium starch glycolate) | 25 |
| Nobex-IN105 (protein) | 6 |

The dissolution testing was carried out using a USP apparatus 2 dissolution unit. The medium was water, paddle speed 50 rpm, and the medium volume was 500 mL. The dissolution samples were analyzed by HPLC using a gradient system. The mobile phases were water with 0.1% TFA (mobile phase A) and acetonitrile with 0.1% TFA (mobile phase B). The gradient utilized was: 0 minutes 100% mobile phase A, 11 minutes 65% mobile phase A, 15 minutes 20% mobile phase A, 16 minutes 20% mobile phase A, 17 minutes 100% mobile phase A. The wavelength was 214 nm and column was a C18 (150×2 mm). The following tables and graphs summarize the dissolution data obtained for the dissolution testing of Nobex-Zn-IN105 Tablets containing 6 mg Zn-IN105 (protein), 150 mg Mannitol, 100 mg Sodium Caprate, and 25 mg sodium starch glycolate (Explotab):

| Sample Time (Minutes) | Vessel 1 (% Dissolved) | Vessel 2 (% Dissolved) | Average (% Dissolved) |
|---|---|---|---|
| Data Summary for the Dissolution Profile of Nobex-Zn-IN105 Tablets [861], % IN105 Dissolved ||||
| 5 | 77 | 41 | 59 |
| 10 | 94 | 84 | 89 |
| 15 | 96 | 90 | 93 |
| 30 | 95 | 91 | 93 |
| 45 | 95 | 91 | 93 |
| 60 | 97 | 89 | 93 |
| Data Summary for the Dissolution Profile of Nobex-Zn-IN105 Tablets [861], % Caprate Dissolved ||||
| 5 | 97 | 77 | 87 |
| 10 | 101 | 99 | 100 |
| 15 | 101 | 103 | 102 |
| 30 | 101 | 103 | 102 |
| 45 | 101 | 104 | 103 |
| 60 | 101 | 104 | 103 |

12.2.6 Solid Dosage Form (Tablet) Formulation Preparation 150 mg Caprate Per Tablet Preparation of Formulation Nobex-IN105-[862]

Transfer approximately 150 mg of sodium caprate, 150 mg mannitol, 25 mg of croscarmellose sodium, and 6 mg (protein) of Nobex-IN105 onto a piece of weigh paper and blend thoroughly. Transfer the blend to the press and compress at approximately 350 psi to form a tablet.

| Solid Dosage Form (Tablets) Formulation Nobex-IN105-[862] 150 mg Caprate per Tablet ||
|---|---|
| Component | mg per Tablet |
| Sodium Caprate | 150 |
| Mannitol | 150 |
| Explotab (Croscarmellose Sodium) | 25 |
| Nobex-IN105 (protein) | 6 |

The dissolution testing was carried out using a USP apparatus 2 dissolution unit. The medium was water, paddle speed 50 rpm, and the medium volume was 500 mL. The dissolution samples were analyzed by HPLC using a gradient system. The mobile phases were water with 0.1% TFA (mobile phase A) and acetonitrile with 0.1% TFA (mobile phase B). The gradient utilized was: 0 minutes 100% mobile phase A, 11 minutes 65% mobile phase A, 15 minutes 20% mobile phase A, 16 minutes 20% mobile phase A, 17 minutes 100% mobile phase A. The wavelength was 214 nm and column was a C18 (150×2 mm). The following tables and graphs summarize the dissolution data obtained for the dissolution testing of Nobex-Zn-IN105 Tablets containing 6 mg Zn-IN105 (protein), 150 mg Mannitol, 150 mg Sodium Caprate, and 25 mg Croscarmellose Sodium (Explotab):

| Sample Time (Minutes) | Vessel 1 (% Dissolved) | Vessel 2 (% Dissolved) | Average (% Dissolved) |
|---|---|---|---|
| Data Summary for the Dissolution Profile of Nobex-Zn-IN105 Tablets [862], % IN105 Dissolved ||||
| 5 | 76 | 41 | 59 |
| 10 | 93 | 87 | 90 |
| 15 | 95 | 99 | 97 |
| 30 | 96 | 98 | 97 |
| 45 | 97 | 98 | 98 |
| 60 | 98 | 97 | 98 |
| Data Summary for the Dissolution Profile of Nobex-Zn-IN105 Tablets [862], % Caprate Dissolved ||||
| 5 | 84 | 51 | 68 |
| 10 | 98 | 88 | 93 |
| 15 | 98 | 97 | 98 |
| 30 | 98 | 98 | 98 |
| 45 | 98 | 98 | 98 |
| 60 | 98 | 98 | 98 |

13 IN VITRO ENZYME RESISTANCE EXAMPLES insulin compound conjugates (HIM2) were provided in 10 mM sodium phosphate buffer (a pH of about 7.4) and their concentrations are determined by HPLC (the solutions are diluted with buffer so that equimolar comparisons can be made between parent and conjugates ~0.6 mg/mL). Lyophilized chymotrypsin enzyme was resuspended in 1 mM HCl to a concentration of 7.53 U/mL. A 1.53 mL aliquot of each sample was added to sample tubes and 0.850 mL into control tubes. Samples were tested in duplicate along with four control tubes per sample. Aliquots were incubated at 37° C. in a thermomixer for 15 minutes. Then 17 µL of chymotrypsin enzyme was added to each sample tube. Five µL of 1 mM HCl was added to each control tube. Immediately following the additions, 200 µL was removed from the sample and the control tubes and placed into 50 µL of 1% TFA previously aliquoted out into centrifuge tubes. This sample serves as T=0.

The sampling procedure for Insulin (Zn free), HIM2 (Zn free) and Insulin (regular insulin compound) was repeated at the following intervals: 0, 2, 5, 8, 12, 15, and 30 minutes. The control procedure was repeated at the following intervals: 0, 8, 15, 30 minutes. For T-type and R-type samples, the procedure was repeated at the following intervals: 0, 5, 8, 12, 30, 40 and 60 minutes. The control procedure for the Zn complexes was repeated at the following intervals: 0, 12, 40 and 60 minutes. Samples were stored at −20° C. until analysis can occur via HPLC. HPLC was performed to determine percent degradation relative to the respective T=0 minute for each digest. The natural log of the percent remaining was plotted versus time and a linear regression run for each digest. The half life was calculated using the equation: $t_{1/2}$: =−0.693/slope.

| Sample | T half | Zinc content | Phenol content |
|---|---|---|---|
| Results at 0.6 mg/ml protein | | | |
| Insulin (zinc free) | 7-9 mins | — | — |
| HIM2 (zinc free) | 12-15 mins | — | — |
| Insulin, USP (Regular insulin compound) | 26-29 mins | 0.3 to 1% w/w | — |
| HIM2 (R-type zinc complex) | 51-78 mins | 1.1% w/w | 0.1 to 0.25% w/w |
| HIM2 (T-type zinc complex) | 51 mins | 0.55% w/w | — |
| HIM2 (R-type zinc/protamine complex) | 95-120 mins | 2.0 to 2.1% w/w | 5.3 to 6.2% w/w |
| DICON-1 (R-type complex) | 24-26 mins | ND | ND |
| Results at 0.3 mg/mL protein | | | |
| Insulin (zinc free) | 4-5 mins | — | — |
| HIM2 (zinc free) | 7-9 mins | — | — |
| Insulin, USP (regular insulin compound) | 7-8 mins | 0.4 to 1% w/w | — |
| HIM2 (R-type zinc complex) | 19-21 mins | 1.1% w/w | 0.1 to 0.25% w/w |
| HIM2 (T-type zinc complex) | 12-15 mins | 0.55% w/w | — |

14 IN VIVO EXAMPLES

14.1 Extended Mouse Blood Glucose Assay (MBGA)

Six paired-dose groups of 5 male CF-1 mice (Charles River Laboratories; 25-30 g) received subcutaneous injections of either the insulin compound conjugate (test article) or recombinant human insulin. The test article was reconstituted with phosphate buffer (0.01M, a pH of about 7.4) containing 0.1% w/w bovine serum albumin and dosed at 100, 66.6, 43.3, 30, 20, and 13.3 µg/kg. Insulin was reconstituted with phosphate buffer (0.01 M, a pH of about 7.4) containing 0.1% w/w bovine serum albumin and dosed at 50, 33.3, 21.7, 15, 10, and 6.7 µg/kg. After receiving a subcutaneous dose in the pocket formed by the thigh and groin, animals were returned to their cages for 30 minutes at room temperature and then were quickly anesthetized and terminally bled. Blood samples were collected in heparin tubes for glucose assay. If glucose assay was delayed, the tubes were stored in ice water and re-warmed to room temperature before assay.

Plasma glucose was measured with a glucometer (e.g., One Touch® Basic; Lifescan), which was calibrated at the beginning of each day of use according to the manufacturer's instructions. The potency of the insulin compound conjugate was then calculated relative to the standard curve that was generated for the recombinant human insulin response. Calculations were based upon the assumption that recombinant human insulin has a potency of 27.4 IU/mg.

Figure 16:
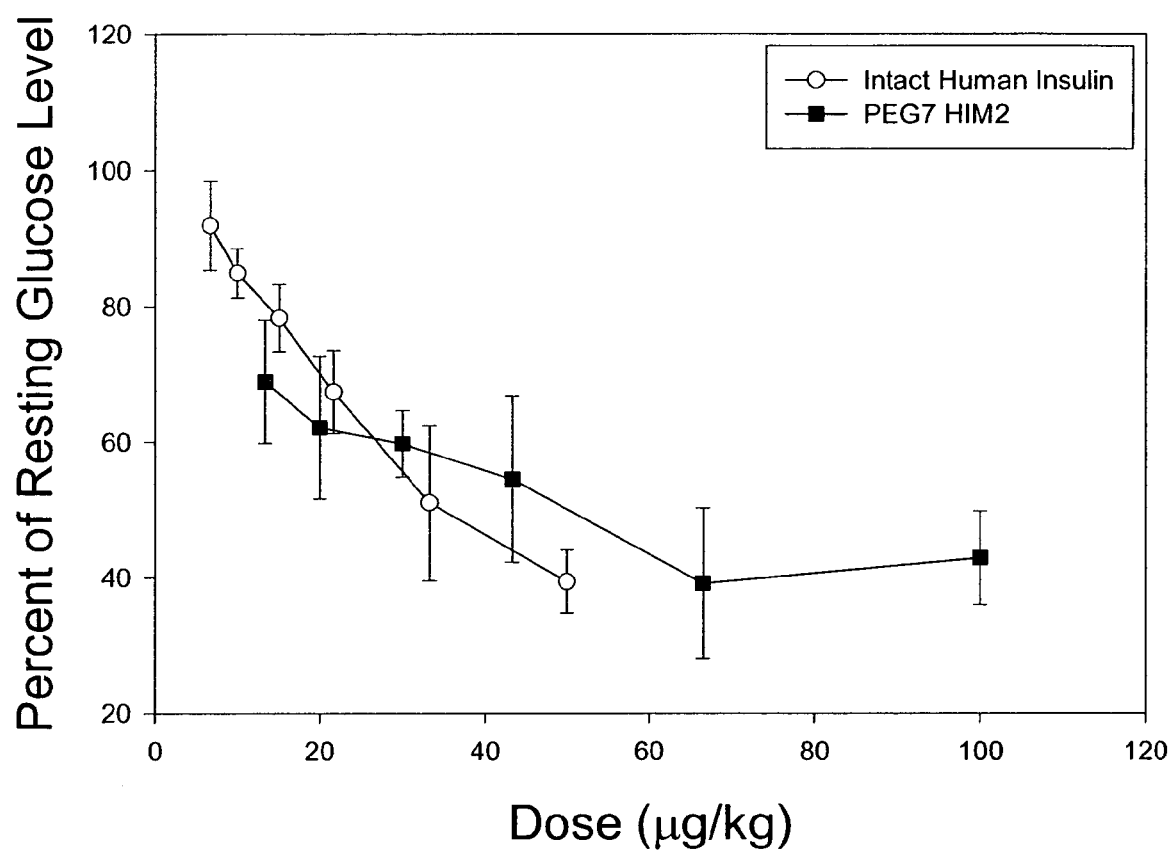
Figure 17:
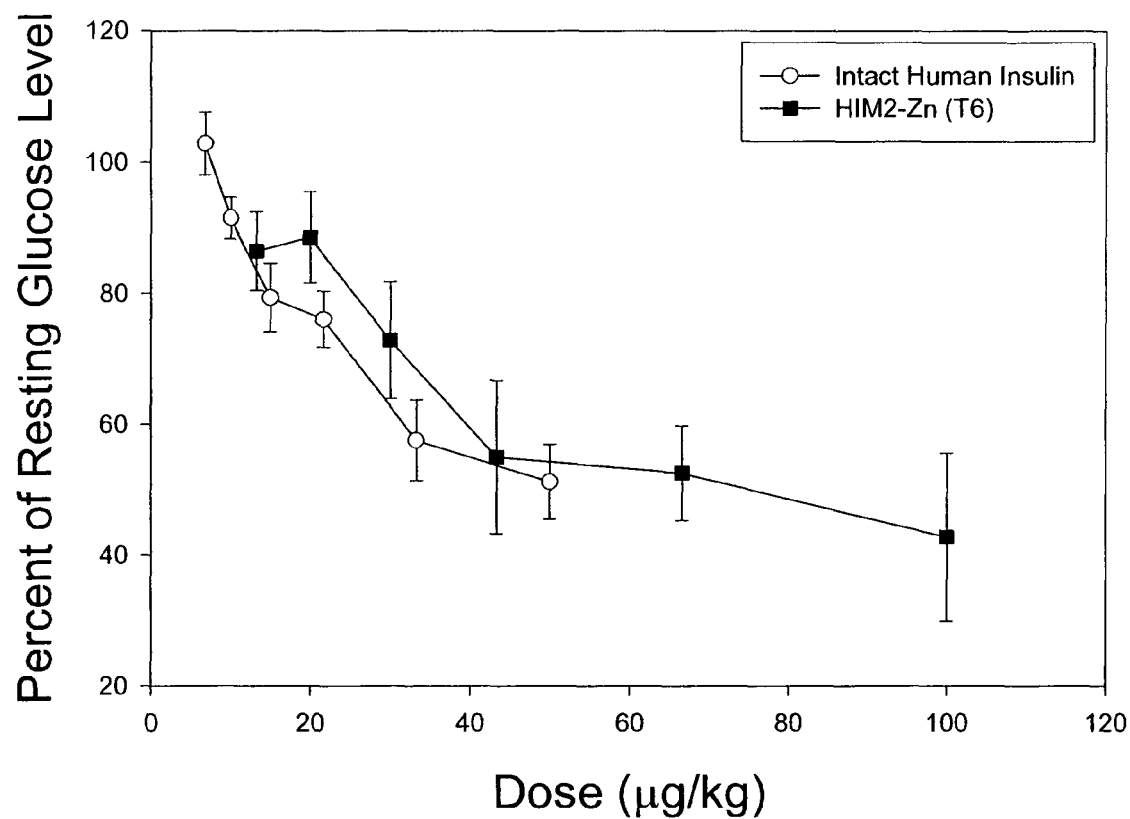
Figure 18:
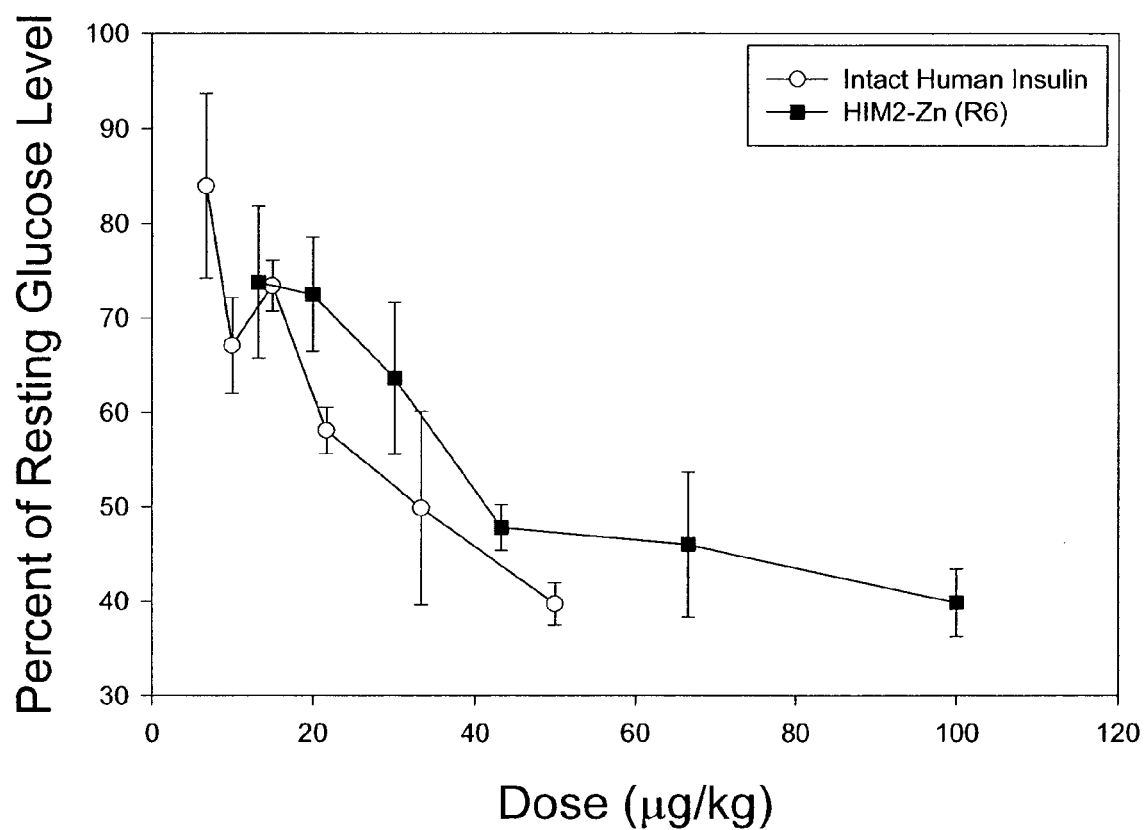
Figure 19:
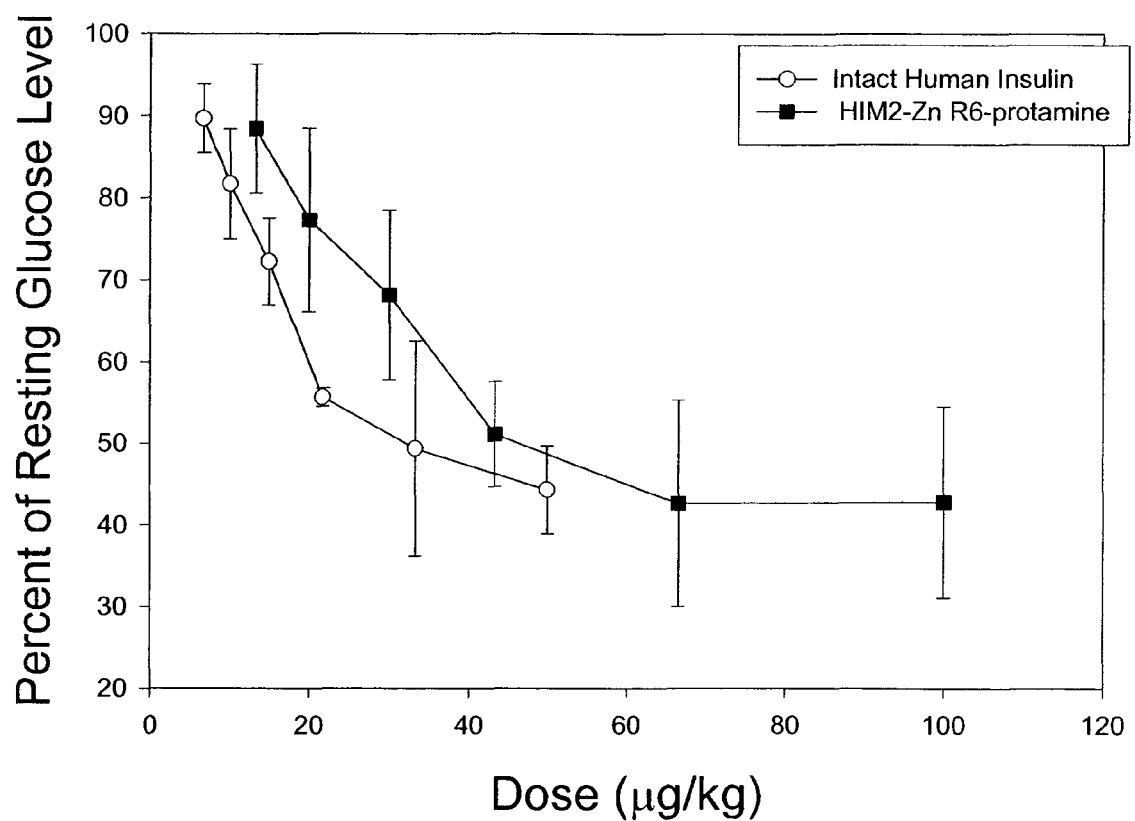
Figure 20:
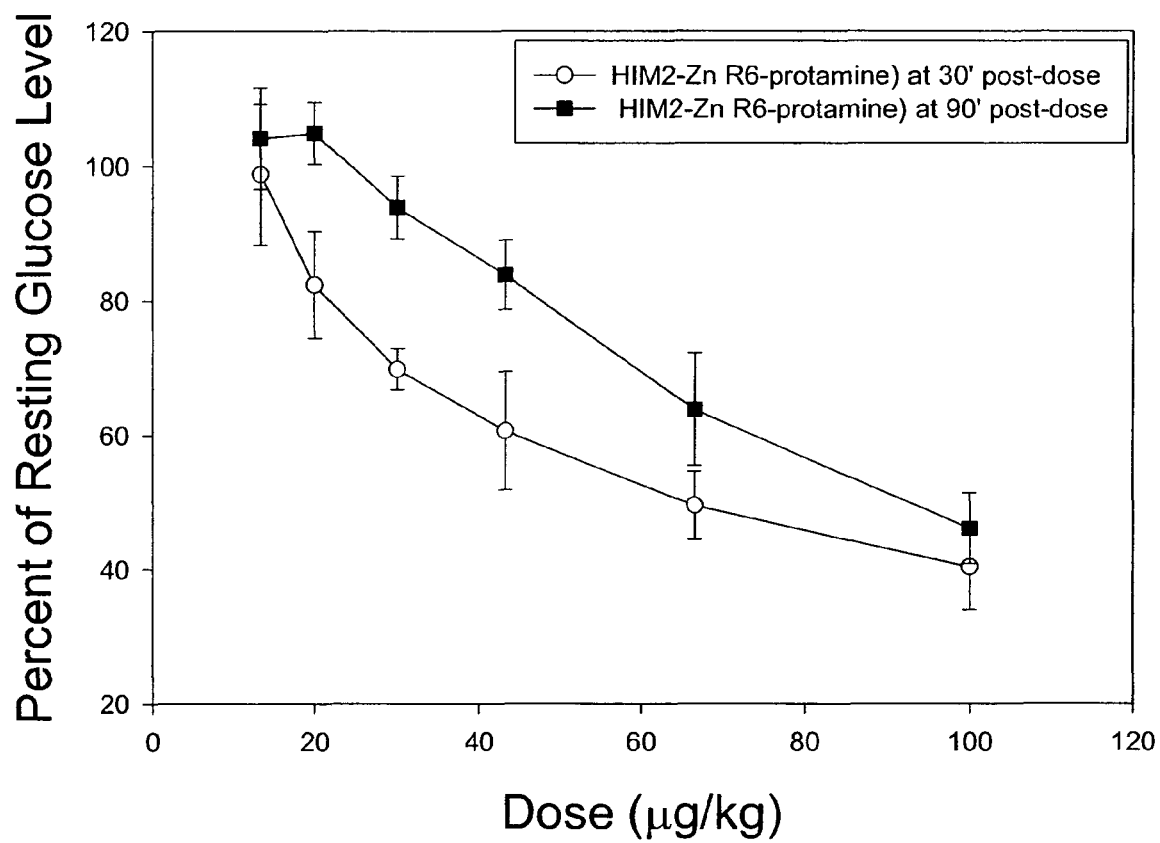
Figure 21:
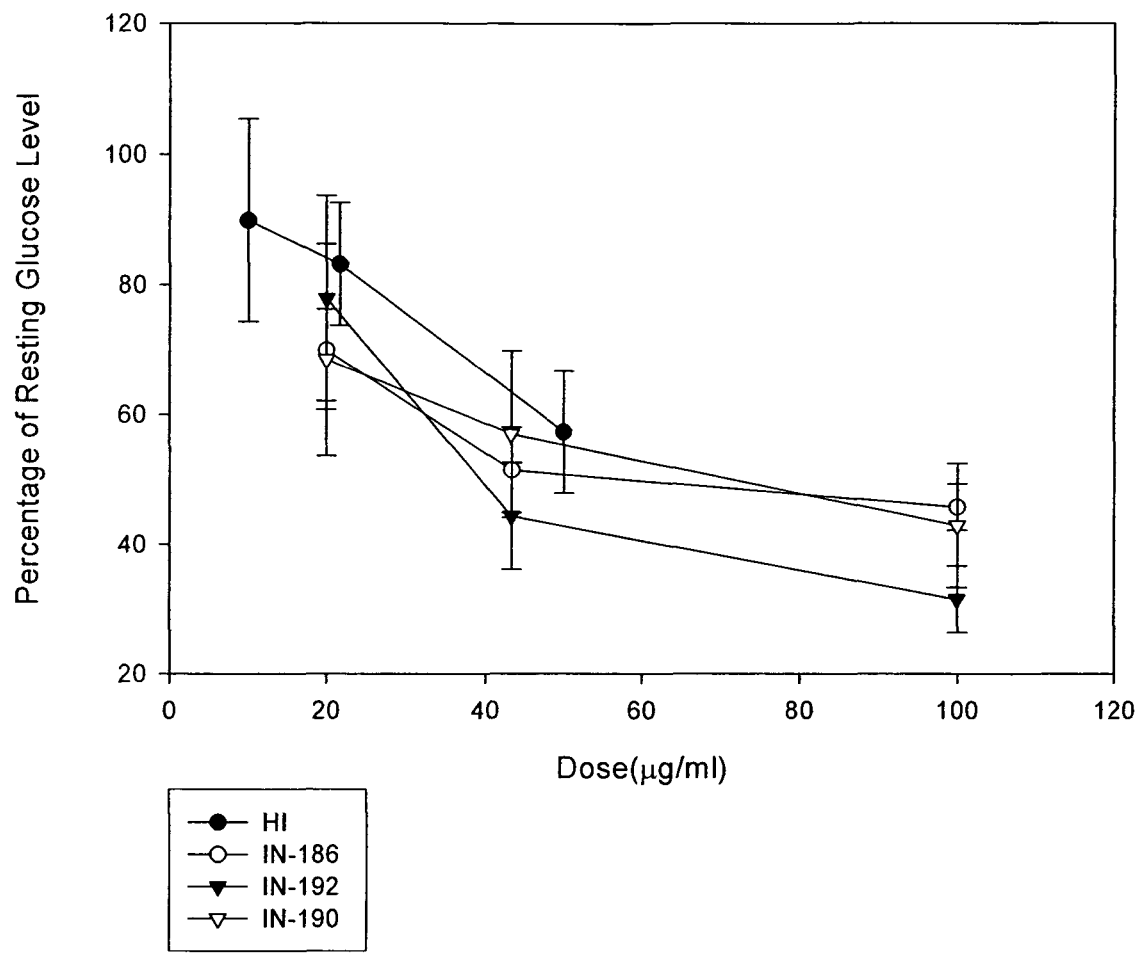
FIGS. 21-24 show MBGA biopotency profiles for IN-186, IN-192, IN-190, IN-191, IN-189, IN-178, IN-193, IN-194, IN-185, IN-196 and IN-197.
Figure 22:
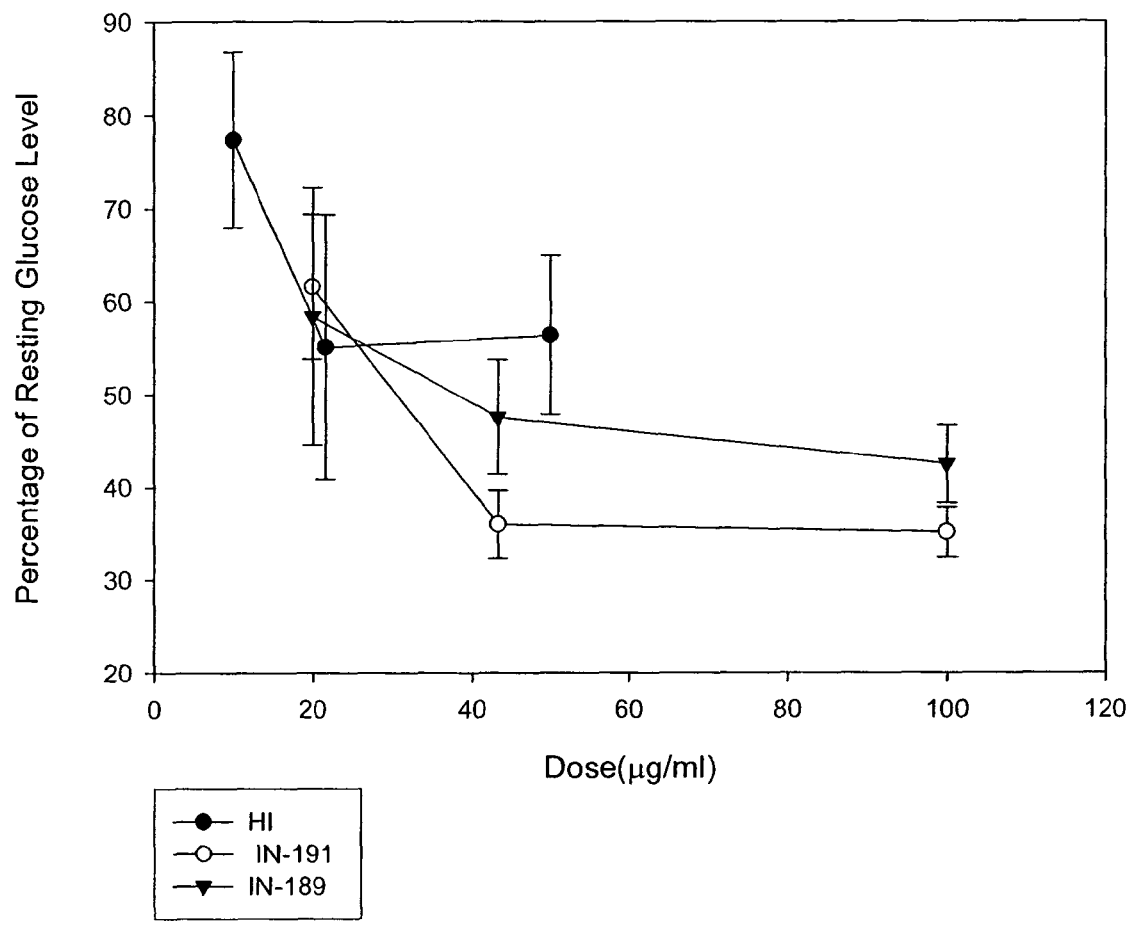
Figure 23:
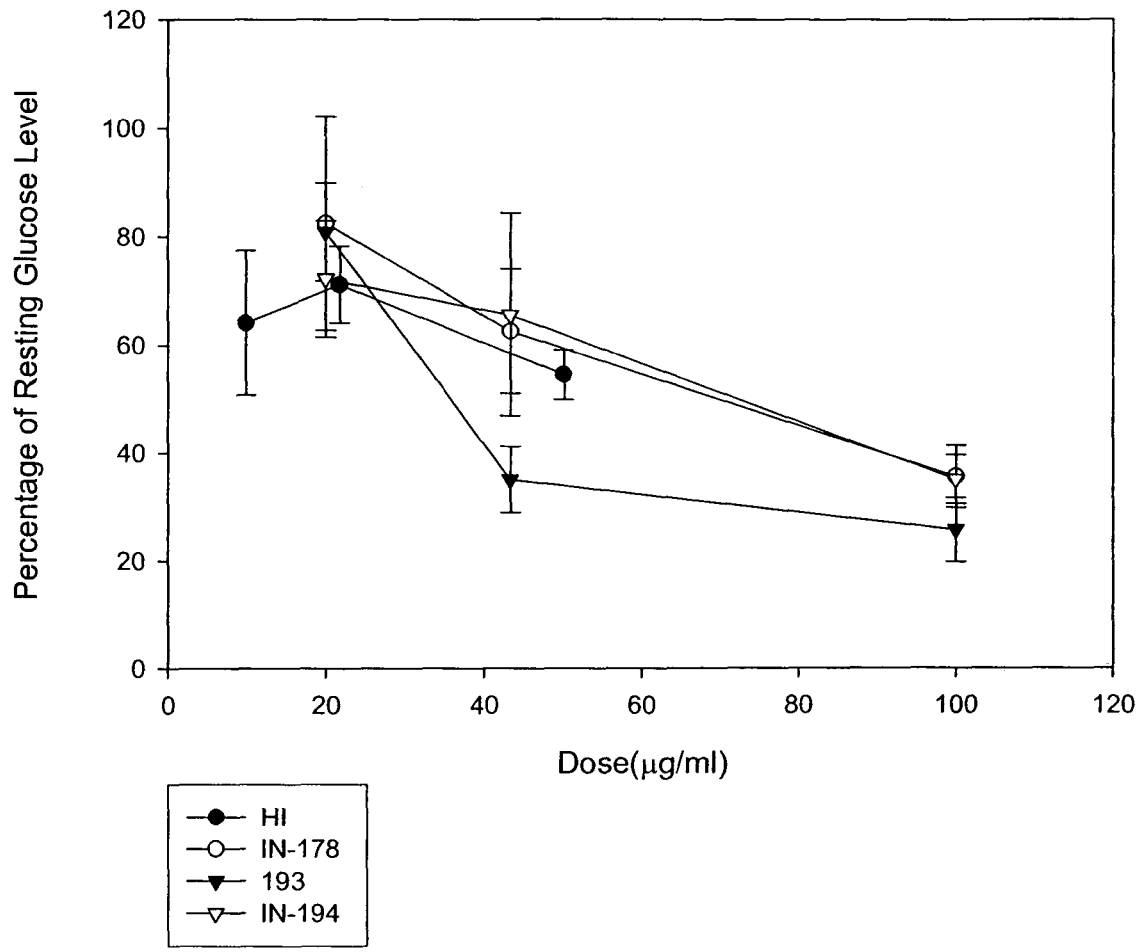
Figure 24:
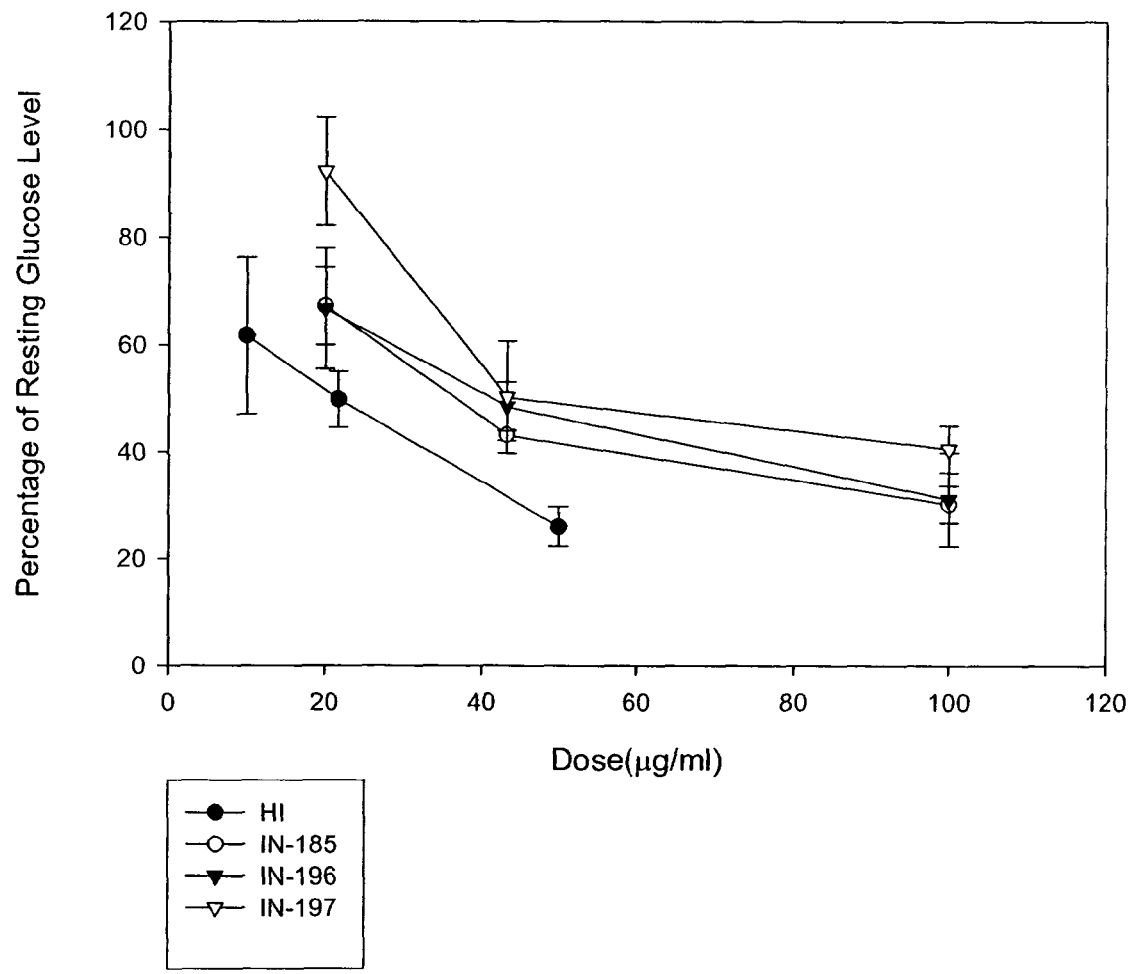

Results are shown in FIGS. 16-20. FIG. 16 shows MBGA biopotency profiles for HIM2. FIG. 17 shows MBGA biopotency profiles for Zn-HIM2 insulin compound product R-type. FIG. 18 shows MBGA biopotency profiles for Zn-HIM2 insulin compound product T-type. FIG. 19 shows MBGA biopotency profiles for Zn-HIM2 insulin compound product with protamine. FIG. 20 shows glucose lowering effect of R-type protamine complex at 30 and 90 minutes post dose. These results show that the biopotency of HIM2 is not significantly reduced by complexation with $Zn^{++}$. The R-type protamine complex (see FIG. 17) shows greater glucose reduction at 30 minutes than 90 minutes.

Further, FIGS. 21-24 show MBGA biopotency profiles for IN-186, IN-192, IN-190, IN-191, IN-189, IN-178, IN-193, IN-194, IN-185, IN-196 and IN-197 having structures as follows:

B1 monoconjugate, IN-186:

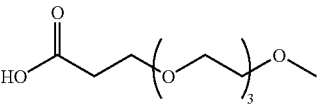

B29 monoconhugate, IN-194:

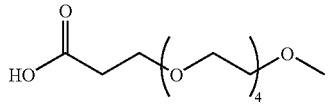

B29 monoconjugate, IN-197:

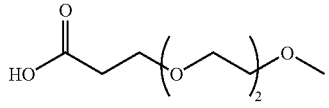

B29 monoconjugate, IN-178:

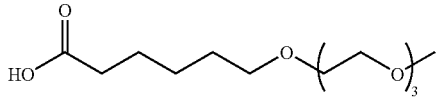

-continued

B29 monoconjugate, IN-190:

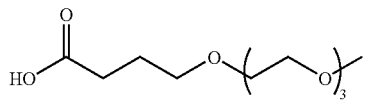

B29 monoconjugate, IN-196:

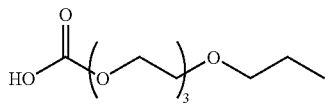

B29 monoconjugate, IN-191:

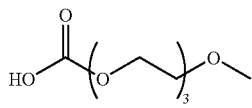

B29 monoconjugate, IN-189:

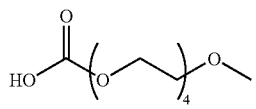

14.2 Dog Clamp Studies

14.2.1 Initial HIM2 Studies

Dogs (n=3 or 6) were prepared surgically (isoflurane anesthesia) by placing a catheter in a femoral artery. The animals were allowed to recover for 16-17 days after which they were fasted overnight and studied in the conscious state. After a 60 min equilibration period, there was a 20 min control period after which the drug was given by mouth. $Zn^{++}$-HIM2 R-type Insulin compound was tested in a buffer solution, prepared as shown in Example Error! Reference source not found. In addition, R-type and NPH-type complexes were tested in oral liquid formulation that contains caprate acid and laurate acid, prepared as shown in Example Error! Reference source not found.

All 3 test samples were tested at only one dose level (the dose level were identified based on the previous experimental results). The plasma glucose level was then be clamped at a euglycemic value by infusion of D-20 through a leg vein for 4 h. Blood samples (4 ml) were taken at −20, 0, 5, 10, 20, 30, 45, 90, 120, 180 and 240 min for measurement of glucose, insulin compound and C-peptide. Arterial blood samples were obtained as required to clamp the plasma glucose level. A total of 72 ml of blood was taken in each experiment.

The following measurements were performed: glucose infusion rate, insulin compound concentration, C-peptide concentration, and plasma C-peptide levels (to allow an estimation of endogenous insulin compound release). The glucose infusion rate required to maintain euglycemia provides an index of insulin compound action.

Following the experiment the free end of the catheter was buried subcutaneously and the dogs were allowed to recover for two weeks prior to another study in which a different test article was used. Animals were randomized to dose and used a total of 3 times. Total number of dogs was 6.

Figure 25:
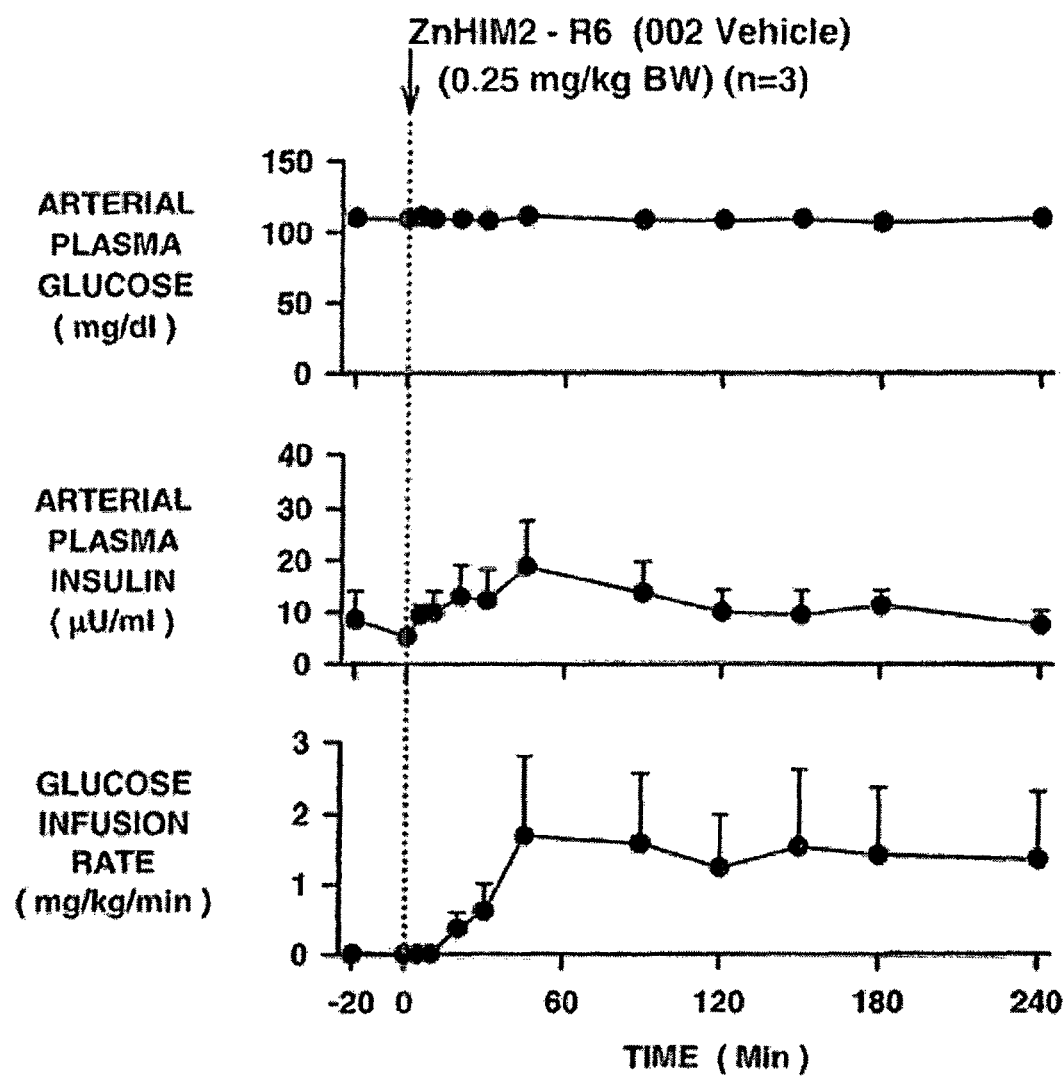
FIGS. 25 and 26 show dog clamp study results for Zn-HIM2 complexes of the invention.
Figure 26:
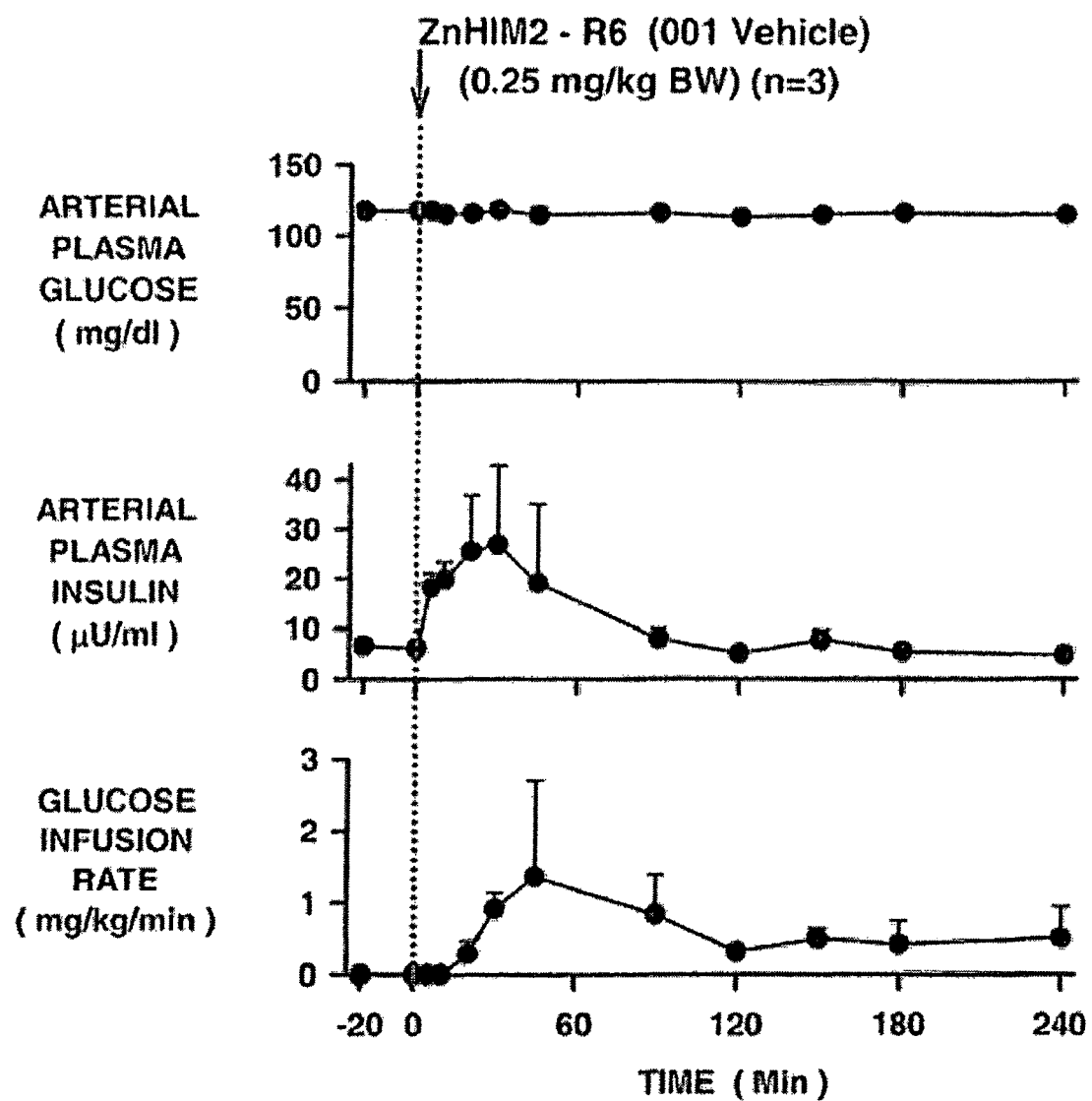

FIGS. 25 and 26 show the results.

14.2.2 Initial IN105 Studies

The study was conducted on six (6) overnight fasted conscious mongrel dogs which had been fed a diet of 34% protein, 46% carbohydrate, 14.5% fat and 5.5% fiber based on dry weight. Each animal had a silastic catheter inserted into the femoral artery as described elsewhere (1) approximately three weeks prior to the experiment. On the day of experiment the catheter was removed from its subcutaneous pocket under local anesthesia. Test article: Nobex-IN105 (Lot.# KJ-173-095 & KJ-173-116) was provided in the oral fatty acid formulation (Nobex-IN-[753]-040422) at a concentration of 1.0 mg/ml. Each dog received 0.25 mg/kg oral dose of Nobex-IN105 (1.0 mg/ml@0.25 ml/kg dosing volume). Nobex-IN105 was given at t=0 and glucose (D-20) was infused through a cephalic vein in order to maintain euglycemia. Arterial blood samples were drawn for the measurement of insulin and glucose as previously described (1). After the experiment was completed, the arterial catheter was buried subcutaneously as it was during the initial surgery.

During the experiment, one dog vomited immediately after the dosing and only a portion of the dose administered. Therefore, the results from this experiment were reported with and without the data obtained from this dog.

Figure 27:
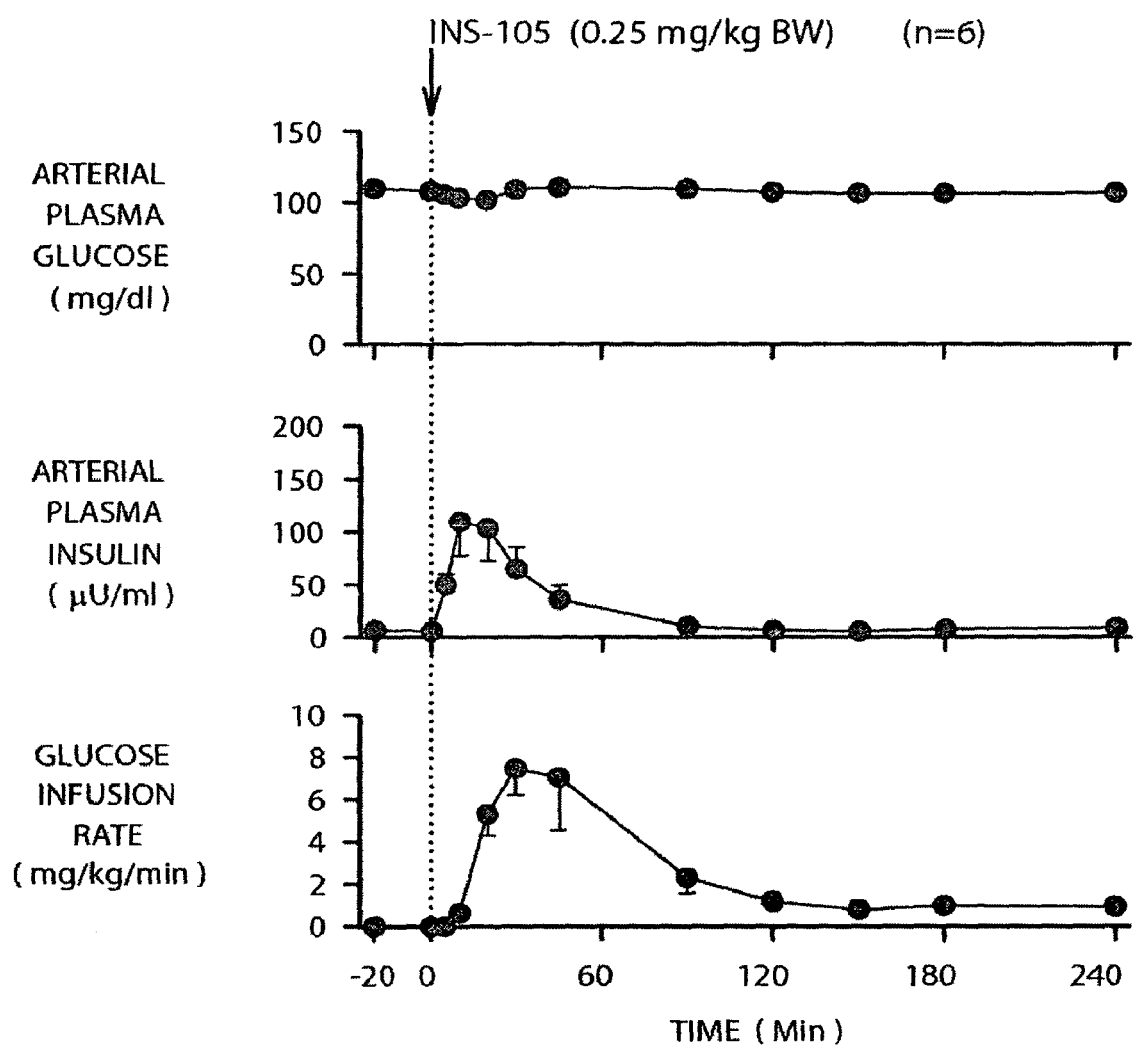
FIGS. 27 and 28 show dog clamp study results for Zn-IN105 complexes of the invention.
Figure 28:
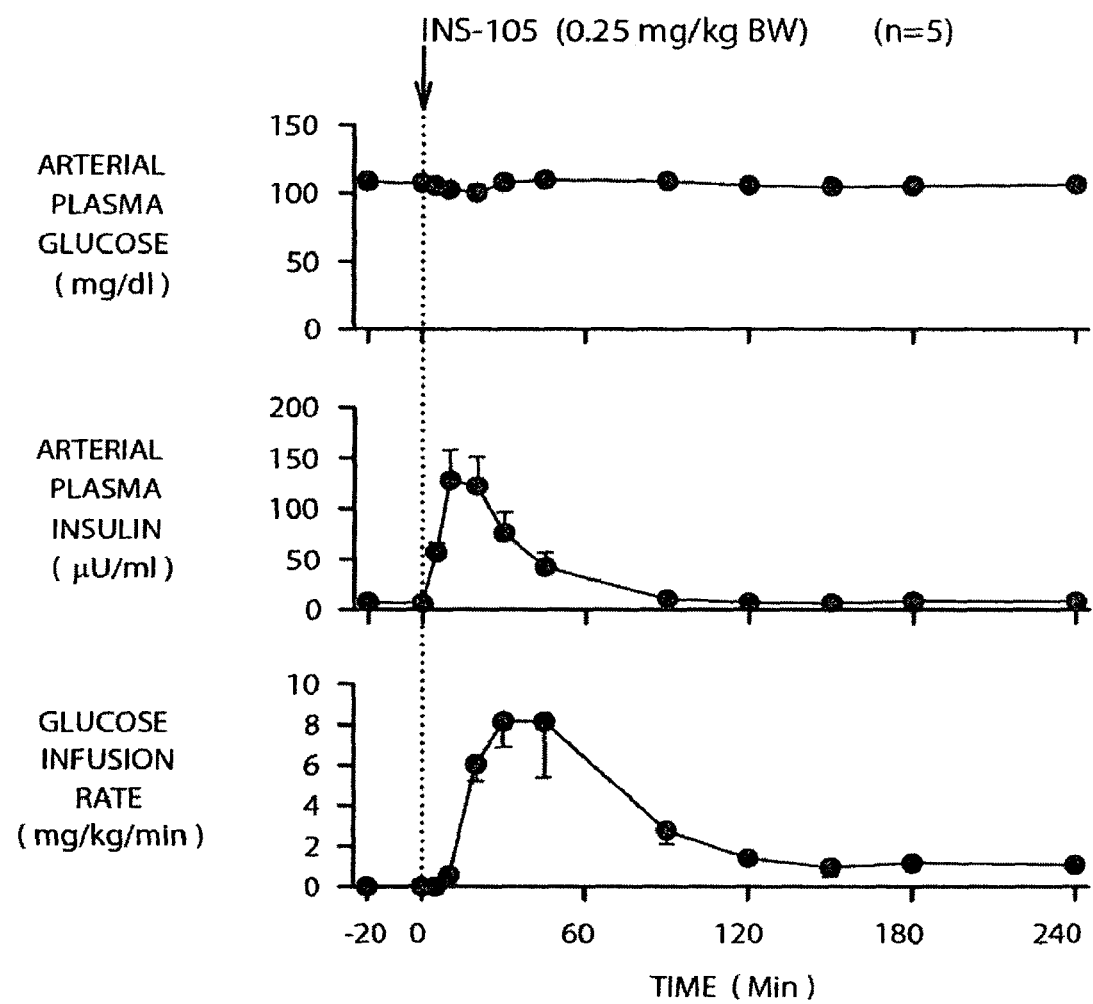

Arterial plasma insulin levels rose in all six dogs, including outlier (Oral-2i), following the oral administration of Nobex-IN105. Mean arterial insulin rose from 6.0±1.4 µU/ml (6.3±1.7 µU/ml, n=5) to a peak of 109.4±31.4 µU/ml (127.8±30.1 µU/ml, n=5) at 10 min post-administration and then fell so that by 150 min all dogs returned to baseline insulin levels (FIGS. 27 and 28).

Euglycemia was maintained by glucose infusion. The glucose infusion rate required to maintain euglycemia as greatest in the animals with larger rise in arterial insulin (FIGS. 27 and 28). Mean Area-Under-The-Glucose Infusion Rate Curve (AUC0-240) was 578.5±144.5 mg/kg/min (669.4±137.7 mg/kg/min, n=5).

14.2.3 Solid Formulations

Formulation screening studies using the glucose-clamp model were conducted on overnight fasted conscious mongrel dogs which had been fed a diet of 34% protein, 46% carbohydrate, 14.5% fat and 5.5% fiber, based on dry weight. Each animal had a silastic catheter inserted into the femoral artery as described elsewhere (reference 1) approximately three weeks prior to the experiment. On the day of experiment the catheter was removed from its subcutaneous pocket under local anesthesia. The test article contained 1.0 mg/mL Zn IN105 in different liquid formulations or 5-6 mg of IN105 per capsule or tablet. Each dog in every experiment received an oral liquid dose of approximately 0.25 mg/kg or a capsule or tablet containing 5 or 6 mg of IN105 twice in succession, the first at t=0 and the second at t=120 minutes. Glucose (D-20) was infused through a cephalic vein in order to maintain euglycemia. In some cases study time was extended after dosing where the effect lasted beyond 120 minutes. Arterial blood samples were drawn for the measurement of insulin, glucose and C-peptide as previously described (reference 1). After the experiment was completed, the arterial catheter was replaced into the subcutaneous tissue.

Formulations, both solution and solid dosage forms, ware prepared with different levels of fatty acids, buffers, diluents and disintegrants. To minimize variables, the liquid and the solid formulations contained consistent levels of IN105 and each excipient (Capric, Lauric, Caprylic, Myristic, Linoleic), thus varying only the relative amounts of fatty acid content, buffer, diluents (mannitol or micro crystalline cellulose), and/or disintegrant (Explotab). The glucose infusion rate and IN105 absorption (plasma insulin immuno-reactivity) data were evaluated and compared with each dosed formulation.

Initially, experiments were carried out to simplify and refine the optimized liquid formulation (reference 2) to a liquid formulation that would be more readily converted to a solid dosage form. This was carried out by substituting the free fatty acid with the corresponding sodium salt (e.g. capric acid replaced by sodium caprate) as well as removing the buffer components (citric acid, trolamine, tromethamine, sodium hydroxide) that were deemed to be no longer required. Additionally, the effect of other fatty acids such as linoleic, caprylic and myristic acids and the amino acid, arginine, were examined for their effects on the absorption of IN105.

After an initial set of prototype screens using one to two dogs per experiments few prototype formulations were selected and tested in additional dogs to better determine the variability and consistency between formulations and individual animals.

A dissolution method was developed and dissolution studies were carried out on a variety of candidate formulations to evaluate dissolution profiles of IN105 and the fatty acids contents.

RESULTS

Figure 29:
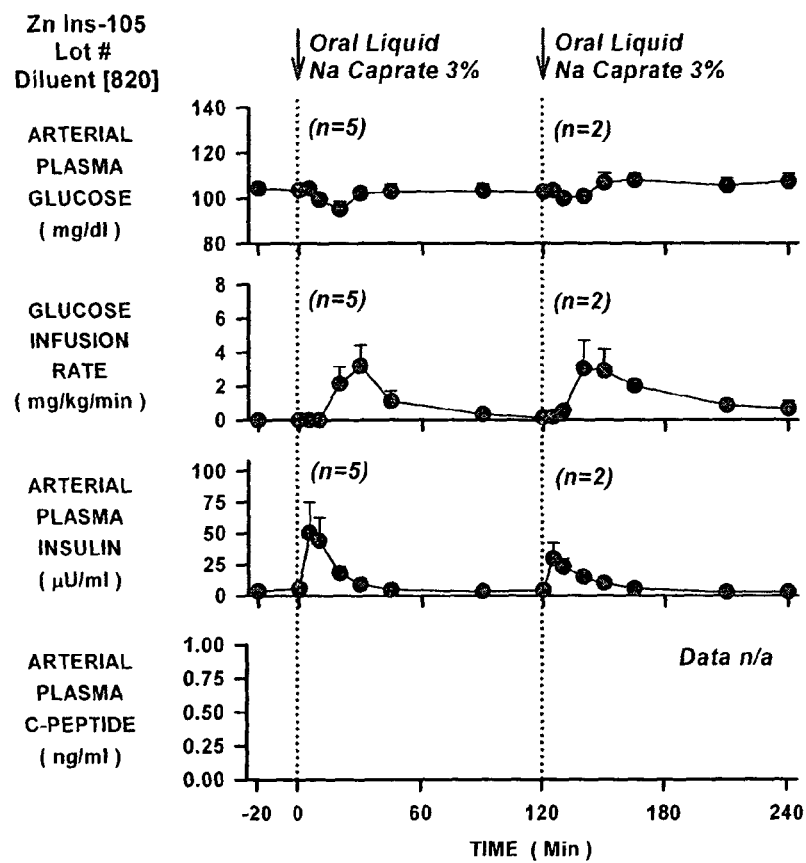
FIGS. 29 and 30 show dog clamp study results for dogs dosed with IN105 in 3% w/v capric acid sodium salt in a phosphate buffer without additional excipients.
Figure 30:
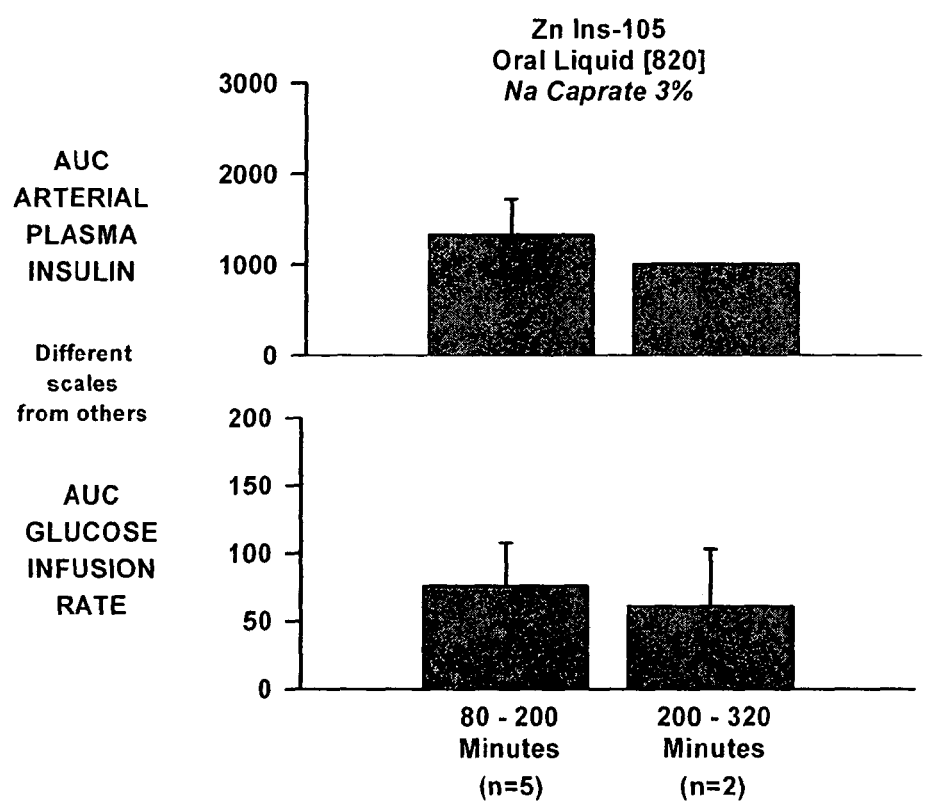

In the initial experiments, dogs dosed with IN105 in 3% w/v capric acid sodium salt in a phosphate buffer without additional excipients, showed (FIGS. 29-30) a similar response compared to the optimized liquid formulation containing 3% w/v capric acid in Trolamine/Citric acid/Tromethamine/Sodium Hydroxide buffer. This demonstrated that the sodium salt of the fatty acid form behaves comparably to the acid form and that the additional buffer components did not contribute to the formulation.

In separate studies evaluating alternative fatty acids substituting 3% caprate with either 3% caprylic acid or 3% linoleic acid, neither of the alternatives exhibited significant effects. The use of caprylic acid resulted in the need for low to moderate levels of glucose while the use of linoleic acid did not result in requiring any glucose infusion suggesting lack of effect. Both formulations showed relatively low levels of arterial insulin. A liquid formulation containing arginine showed relatively no benefit on GIR or IN105 levels.

In the primary studies, solid formulations were evaluated as both powder blend filled into hard gelatin capsules and tablets compressed by hand using a Carver Press. The capsules, powder blend of 6 mg of IN105 (insulin equivalent, 0.25 mg/Kg) with 57 mg of caprate/57 mg laurate showed no significant effect in the first dosing up to 120 mins, and in the second dosing a significant effect was observed with the GIR concurrent with IN105 absorption where the levels were well above the base line form 0 to 120 mins. This data suggests a variable but potential delayed response in IN105 in the capsule dosage form. Dissolution was only slightly delayed with the capsule relative to the tablets although there may be little to no in-vitro/in-vivo correlation.

In the initial prototype tablet screening studies, tablets containing 6 mg of IN105 and 150 mg Mannitol, 30 mg sodium starch glycolate with 143 mg Caparte with or without 143 mg laurate showed significantly higher GIR and IN105 absorption than the same tablets with 54 mg Caprate or/and 54 mg Laurate (FIGS. 31, 32, and 33). This suggests a reasonable dose response of higher GIR and IN105 levels relative to increasing levels of caprate and laurate. The tables showed an early and consistent GIR response time to the IN105 filled capsules. Additionally, the IN105 tablets showed an arterial plasma rise in insulin in all dogs dosed.

In a series of final studies, three prototype tablet formulations (Formulation [856] contained 143 mg caprate and 140 mg laurate, [860] contained 286 mg caprate, and [862]] contained 150 mg caprate] were selected for evaluation in 5 dogs (3 different dogs for each formulation) to assess the consistency of performance (FIGS. 34-37). Arterial plasma insulin levels rose in all 3 dogs and at all 18 doses (3 dogs×3 tablets×2 doses each) with corresponding GIR response following the oral administration of 6 mg (Insulin equivalent) of IN105 formulated in the tablets containing either 150 mg or 280 mg caprate or 143 mg/140 mg caprate/laurate (FIGS. 31-32 and 38-42). The c-peptide levels (ng/ml), with 150 mg and 280 mg caprate tablets, the average (n=2), showed a decrease from an initial level of 0.30±0.05 to 0.22±0.02 during the first dosing and 0.1±0.05 to 0.02±0.0 in the second dosing, and with 140 mg/140 mg caprate/laurate tablets, showed 0.21±0.05 to 0.05±0.02 during the fist dosing and 0.18±0.05 to 0.18±0.01. This is indicative of suppression of C-peptide secretion from the pancreas as result of the exogenous IN105 insulin.

All three prototype tablet formulations of IN105 showed consistent levels of IN105 absorption and resultant glucose infusion rate among doses and within and between dogs, including on different days During the final studies, in which sets of 6 dogs were utilized, one dog (dog #3) experienced less response with all liquid and solid dosages. To more accurately represent the results, the data is presented with and without results from dog #3. Data from dogs that did not receive a complete dose (bad gavage, vomiting, etc) or had endogenous insulin are omitted.

Dissolution study: Representative samples of tablets and capsules were subject to dissolution testing (described above).

Discussion

These studies demonstrate that the prototype IN105 tablet containing caprate or caprate and laurate sodium salts with mannitol and the disintegrant sodium starch glycolate and containing 6 mg IN105 (approximately 0.25 mg/kg) delivered orally resulted in significant and consistent elevation of arterial plasma insulin that required glucose infusion to preserve euglycemia.

These prototype tablets resulted in IN105 levels and GIR rates at least as good and likely to be better than the liquid formulations containing comparable levels of caprate or laurate. The prototype tablets forms maintain the absorption profile of the oral liquid formulation. The relative oral bio-efficacy of the selected prototype tablet formulations (e.g., 280 mg and 150 mg caprate containing tablets, n=6, AUC for GIR=496±117 and 500±275) appears to be better than liquid formulations (e.g., 3% w/v capric acid liquid formulation, n=5, AUC for GIR=182±92 and 198±119).

The data suggests that the tablets containing sodium caprate as the only fatty acid along with mannitol and the disintegrant, sodium starch glycolate would be useful in the further development of solid dosage forms for use in clinical studies. Data also suggest that Insulin levels following the oral administration of IN105 in the selected prototype caprate tablets forms (sodium caprate at either 150 mg or 286 mg) peaked steadily with a typical Tmax at around 20 min post-dose and a $C_{max}$ of about 59.0±20.1 and 62.9.±25.4 μUnits/ml, in both doses. The plasma insulin levels remained elevated close to the Cmax level for 10-15 minutes and above basal levels throughout 120 min following each dose. The GIR required maintaining euglycemia using these tablets reached Tmax at or around 30 to 40 min in both doses and GIR Cmax reached an average of 8.4±1.99 and 7.41±2.18 mg/kg/min. The tablet dosage forms required higher GIR Cmax (7.4-8.4 vs. 4.5-5.4) and required glucose infusion for a longer duration (100-120 mins vs. 60-90 min) to maintain euglycemia then the optimized liquid formulation.

In comparison with arterial plasma insulin levels of historical SQ and inhaled insulin, it appears that these prototype tablets provide maximum insulin levels similar to SQ and inhaled delivery and resembles an insulin profile comparable to that of inhaled insulin (FIGS. 34-37).

The prototype tablet experiments suggests the selected prototype tablets are suitable as solid dosage formulations for further evaluation of IN105 with future development to focus on producing a clinical formulation that can be produced using a tablet press.

This specification is divided into sections with subject for ease of reference only. Sections and subject headings are not intended to limit the scope of the invention. The embodiments described herein are for the purpose of illustrating the many aspects and attributes of the invention and are not intended to limit the scope of the invention.

We claim:

1. A solid complex comprising:
   an insulin compound conjugate comprising an insulin compound conjugated to a modifying moiety, wherein the modifying moiety comprises from 2 to 10 PEG subunits ($OCH_2$—$CH_2$) forming a PEG component coupled to a lipophilic component, where the lipophilic component is selected from the group consisting of alkyls, fatty acids and linear or branched lipids, and either the PEG component or the lipophilic component is coupled to the insulin compound at the B29 amino acid residue; and
   a cation, wherein the cation is a divalent cation selected from the group consisting of $Zn^{++}$, $Mn^{++}$, $Ca^{++}$, $Fe^{++}$, $Ni^{++}$, $Cu^{++}$, $Co^{++}$ and $Mg^{++}$; where the insulin compound conjugate is complexed with the cation, and wherein the solid complex is a crystalline solid or a rod shaped crystal.

2. The complex of claim 1 where the insulin compound conjugate comprises an insulin compound analog.

3. The complex of claim 2 where the insulin compound analog is human insulin with $Lys^{28}$ and $Pro^{29}$.

4. The complex of claim 2 where the insulin compound analog is a native proinsulin compound.

5. The complex of claim 2 where the insulin compound analog is an artificial proinsulin compound.

6. The complex of claim 2 where the insulin compound analog is a miniproinsulin compound comprising a C-peptide having 5 or less amino acids.

7. The complex of claim 2 where the insulin compound analog is a native proinsulin compound having a leader peptide which is cleavable or non-cleavable.

8. The complex of claim 2 where the insulin compound analog is an artificial proinsulin compound having a leader peptide which is cleavable or non-cleavable.

9. The complex of claim 2 where the insulin compound analog is a miniproinsulin compound comprising:
   a C-peptide having 5 or less amino acids;
   a leader peptide which is cleavable or non-cleavable.

10. The complex of claim 2 where the insulin compound analog is a pre-proinsulin compound comprising proinsulin compound and a leader peptide or a carrier protein joined at the C-terminus or N-terminus of the proinsulin compound.

11. The complex of claim 2 where the insulin compound analog is a single chain insulin compound precursor comprising insulin compound A-chain-B-chain, where the A chain and/or B chain may be truncated at the point of attachment to the other by 1, 2 or 3 amino acids.

12. The complex of claim 2 where the insulin compound analog is an insulin compound comprising a leader peptide or a carrier protein.

13. A solid complex comprising:
   an insulin compound conjugate comprising an insulin compound conjugated to a modifying moiety, wherein the modifying moiety comprises ($OCH_2$—$CH_2$) PEG subunits forming a PEG component coupled to a lipophilic component, where the lipophilic component is selected from the group consisting of alkyls, fatty acids and linear or branched lipids, and either the PEG component or the lipophilic component is coupled to the insulin compound at the B29 amino acid residue; and
   a cation, wherein the cation is a divalent cation selected from the group consisting of $Zn^{++}$, $Mn^{++}$, $Ca^{++}$, $Fe^{++}$, $Ni^{++}$, $Cu^{++}$, $Co^{++}$ and $Mg^{++}$;
   where the insulin compound conjugate is complexed with the cation, where the modifying moiety is selected to render the insulin compound conjugate more water soluble than a corresponding unconjugated insulin compound, and wherein the solid complex is a crystalline solid or a rod shaped crystal.

14. The complex of claim 13 where the modifying moiety is selected to render the insulin compound conjugate more amphiphilic than a corresponding unconjugated insulin compound.

15. The complex of claim 13 where the modifying moiety is selected to render the insulin compound conjugate at least 1.05, 1.25, 1.5, 1.75, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 times more soluble than a corresponding unconjugated insulin compound in an aqueous solution at a pH of about 7.4.

16. The complex of claim 13 where the modifying moiety is selected to render an insulin compound conjugate having a solubility that exceeds about 1 g/L, 2 g/L, 3 g/L, 4 g/L, 5 g/L, 10 g/L, 15 g/L, 20 g/L, 25 g/L, 50 g/L, 75 g/L, 100 g/L, 125 g/L, or 150 g/L at a pH ranging from about 4 to about 8.

17. The complex of claim 1 where the water solubility of the insulin compound conjugate is decreased by the addition of zinc.

18. The complex of claim 1 where the relative lipophilicity of the insulin compound conjugate relative to the corresponding parent insulin compound is 1 or less than 1.

19. The complex of claim 18, wherein:
   (a) $k_{rel} = (t_{conjugate} - t_0)/(t_{human} - t_0)$;
   (b) relative lipophilicity is measured on an LiChroSorb RP18 (5 µm, 250×4 mm) high performance liquid chromatography column by isocratic elution at 40° C.
   (c) the following mixtures are used as eluents:
      (i) 0.1M sodium phosphate buffer at pH 7.3 containing 10% acetonitrile, and
      (ii) 50% acetonitrile in water;
   (d) void time ($t_0$) is identified by injecting 0.1 mM sodium nitrate;
   (e) retention time for human insulin is adjusted to at least $2t_0$ by varying the ratio between the mixtures of (c)(i) and (c)(ii).

20. The complex of claim 1 where the modifying moiety is coupled to one or more amino groups on the insulin compound.

21. The complex of claim 1 where a modifying moiety is coupled at the carboxy terminus of the A-chain and/or a modifying moiety is coupled at the carboxy terminus of the B-chain of the insulin compound.

22. The complex of claim 1 where a modifying moiety is coupled at the N-terminus of a leader peptide which is coupled to the B-chain of the insulin compound.

23. The complex of claim 1 where the cation comprises $Zn^{++}$.

24. The complex of claim 1 where the cation is greater than about 90, 95, 99, or 99.9% $Zn^{++}$.

25. The complex of claim 1 where molar ratio of insulin compound conjugate to cation is between about 1:1 and about 1:100, about 1:2 and about 1:12, or about 1:2 and about 1:7.

26. The complex of claim 13 where resistance of the complexed insulin compound conjugate to chymotrypsin degradation is greater than the chymotrypsin degradation of a corresponding uncomplexed insulin compound conjugate.

27. The complex of claim 13 where resistance of the complexed insulin compound conjugate to chymotrypsin degradation is greater than the chymotrypsin degradation of a corresponding complexed but unconjugated insulin compound.

28. The complex of claim 1 where the insulin compound conjugate consists of human insulin coupled at B29 to a modifying moiety having a structure:

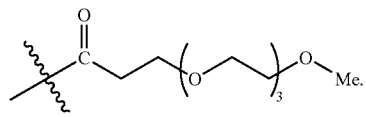

29. The complex of claim 13 where the modifying moiety has a formula:

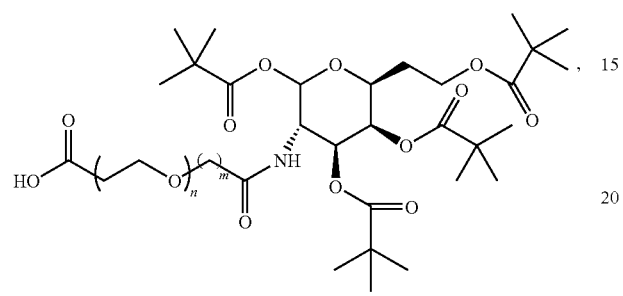
(Formula IX)

where m is 1, 2, 3, 4, 5, 6, 7, 8, 9, 10, 11, 12, 13, 14, 15, 16, 17, 18, 19 or 20 and n is 1, 2, 3, 4, 5, 6, 7, 8, 9, 10, 11, 12, 13, 14, 15, 16, 17, 18, 19 or 20.

30. The complex of claim 13 where the modifying moiety has a formula:

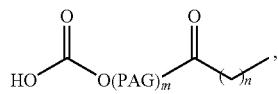
(Formula X)

where PAG is a PAG moiety having m subunits and m is 1, 2, 3, 4, 5, 6, 7, 8, 9, 10, 11, 12, 13, 14, 15, 16, 17, 18, 19 or 20 and n is 1, 2, 3, 4, 5, 6, 7, 8, 9, 10, 11, 12, 13, 14, 15, 16, 17, 18, 19 or 20.

31. The complex of claim 1 where the modifying moiety has a structure:

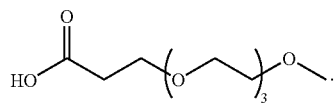

32. The complex of claim 1 where the modifying moiety has a structure:

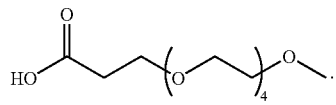

33. The complex of claim 1 where the modifying moiety has a structure:

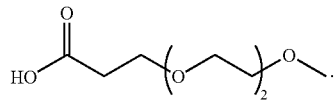

34. The complex of claim 1 where the modifying moiety has a structure:

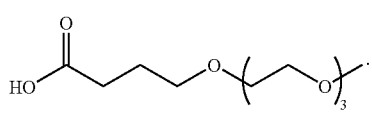

35. The complex of claim 1 where the modifying moiety has a structure:

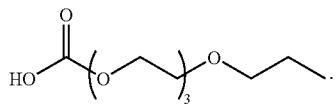

36. The complex of claim 1 where the modifying moiety has a structure:

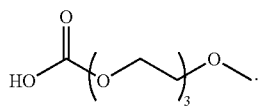

37. The complex of claim 1 where the modifying moiety has a structure:

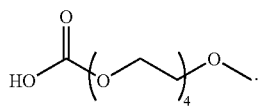

38. The complex of claim 1 where the modifying moiety has a structure:

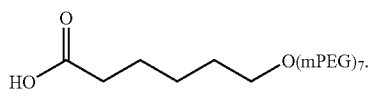

39. The complex of claim 1 where the modifying moiety has a structure:

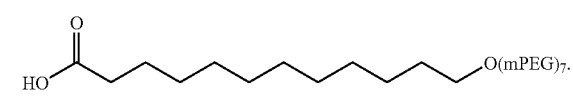

40. The complex of claim 1 where the modifying moiety has a structure:

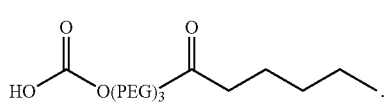

41. The complex of claim 1 where the modifying moiety has a structure:

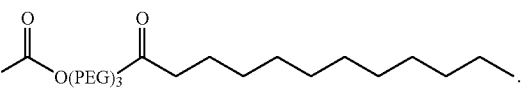

42. The complex of claim 1 where the modifying moiety has a structure:

HO-C(=O)-O(PEG)₄-(CH₂)₁₄-CH₃.

43. The complex of claim 1 where the modifying moiety has a structure:

HO-C(=O)-O(PEG)₆-(CH₂)₁₄-CH₃.

44. The complex of claim 1 where the modifying moiety has a structure:

HO-C(=O)-(CH₂)₄-NH-C(=O)-O-CH(CH₂-OMPEG₄)-MPEGO₄.

45. The complex of claim 1 where the modifying moiety has a structure:

HO-C(=O)-O-CH₂CH₂-O-CH₂CH₂-O-CH₂CH₂-O-(CH₂)₄-C(=O)-NH-[sugar with three pivaloyl groups].

46. A complex mixture comprising the complex of claim 1.
47. A solid mixture comprising the complex of claim 1.
48. A hybrid complex comprising the complex of claim 1.
49. A co-crystal comprising the complex of claim 1.
50. A composition comprising the complex of claim 1 wherein the composition is provided as a lyophilized powder.
51. The complex of claim 13 in a mixture having a pharmaceutically acceptable level of purity.
52. A composition comprising:
   a first complex according to the complex of claim 1; and
   a second complex selected from a group consisting of a conjugated insulin compound or unconjugated insulin compound.
53. The composition of claim 52 where the first complex and second complex is provided as a solid.
54. The composition of claim 52 where:
   the second complex is provided as an amorphous solid.
55. The composition of claim 52 where the complex of where the first complex and second complex is provided as a crystalline solid.
56. The composition of claim 52 further comprising a third complex comprising:

an insulin compound conjugate comprising an insulin compound coupled to a third modifying moiety, and
a cation component, where the insulin compound conjugate is complexed with the cation.
57. The composition of claim 52 where the first complex and second complex comprise different insulin compounds.
58. The composition of claim 52 where:
   the first complex and second complex comprise different insulin compound conjugates, and
   one of the complexes comprises a lipophilic insulin compound conjugate and the other of the complexes comprises a hydrophilic insulin compound conjugate.
59. The composition of claim 52 where:
   the first complex and second complex comprise different insulin compound conjugates, and
   one of the complexes has a circulation half-life of from about 1 to about 4 hours; and
   the other of the complexes has a circulation half-life that is greater than the circulation half-life of the first complex.
60. The composition of claim 52 where:
   the first complex and second complex comprise different insulin compound conjugates, and
   one of the complexes has a rapid-acting profile; and
   the other of the complexes has a medium-to-long acting profile.
61. The composition of claim 52 where:
   the first complex and second complex comprise different insulin compound conjugates, and
   one of the complexes has profile suitable for basal insulin compound control; and the other of the complexes has a profile suitable for post-prandial glucose control.

62. The composition of claim 52 where the composition is a crystal exhibiting one or more of the following characteristics: substantially homogenous dissolution, a single in vivo dissolution curve, and/or a single peak pharmacodynamic profile.

63. The composition of claim 52 where the composition is a co-crystal of HIM2 and insulin compound.

64. The composition of claim 52 where the composition is a co-crystal of HIM2 and IN105.

65. The composition of claim 52 where the composition is a co-crystal of IN105 and insulin compound.

66. The composition of claim 52 where the composition is a co-crystal which has a PK/PD profile suitable for post-prandial glucose control.

67. The composition of claim 52 where the composition is a co-crystal which has a PK/PD profile suitable for overnight basal insulin compound control.

68. A composition comprising the complex of claim 1 in the form of a crystalline solid having irregular morphology.

69. A composition comprising the complex of claim 1 in the form of a crystalline solid having an average diameter ranging from about 0.5 to about 40 μm.

70. A composition comprising the complex of claim 1 and one or more additional pharmaceutically acceptable components.

71. The complex of claim 13 where in a dried state, the solid comprises:
greater than about 96% w/w insulin compound conjugate, and
from about 0.05 to about 4% w/w $Zn^{++}$.

72. The complex of claim 13 where in a dried state, the solid comprises:
greater than about 91% w/w insulin compound conjugate, from about 0.3 to about 4% w/w $Zn^{++}$, and further comprises
from about 0.2 to about 5% w/w phenol.

73. The complex of claim 13 where in a dried state, the solid comprises:
from about 0.1 to about 2% w/w $Zn^{++}$, and further comprises
from about 0.08 to about 1% w/w phenol.

74. The complex of claim 13 where the solid is greater than about 90, 95, or 99% crystalline.

75. A pharmaceutical composition comprising the complex of claim 1 and a pharmaceutically acceptable carrier.

76. The pharmaceutical composition of claim 75 further comprising a stabilizing agent.

77. The pharmaceutical composition of claim 76 where the stabilizing agent is a phenolic compound.

78. The pharmaceutical composition of claim 76 where the stabilizing agent is selected from the group consisting of phenol, m-cresol and paraben.

79. A method of treating diabetes comprising administering to a subject in need thereof a pharmaceutically acceptable amount of a complex of claim 1.

80. The method of claim 79 where the composition is administered orally.

81. The complex of claim 1, wherein the complex is an R-type complex, an NPH-type complex, a T-type complex, an R-type Zn complex, or T-type Zn complex.

82. The complex of claim 81, wherein the R-type Zn complex or T-type Zn complex further comprises protamine.

* * * * *

UNITED STATES PATENT AND TRADEMARK OFFICE
CERTIFICATE OF CORRECTION

PATENT NO. : 7,875,700 B2
APPLICATION NO. : 11/184668
DATED : January 25, 2011
INVENTOR(S) : Balasingam Radhakrishnan et al.

Page 1 of 1

It is certified that error appears in the above-identified patent and that said Letters Patent is hereby corrected as shown below:

Column 105, lines 4-8, claim 28: replace with the following:

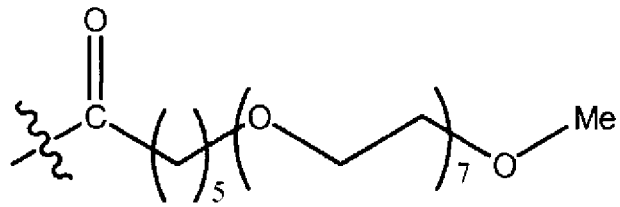

Signed and Sealed this
Seventeenth Day of April, 2012

David J. Kappos
*Director of the United States Patent and Trademark Office*